US010017825B2

(12) United States Patent
Scully et al.

(10) Patent No.: US 10,017,825 B2
(45) Date of Patent: Jul. 10, 2018

(54) COMPOSITIONS AND METHODS FOR CHARACTERIZING A DNA REPAIR VARIANT POLYPEPTIDE

(71) Applicant: BETH ISRAEL DEACONESS MEDICAL CENTER, INC., Boston, MA (US)

(72) Inventors: Ralph Scully, Boston, MA (US); Nicholas A. Willis, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 14/941,769

(22) Filed: Nov. 16, 2015

(65) Prior Publication Data

US 2016/0160291 A1 Jun. 9, 2016

Related U.S. Application Data

(60) Provisional application No. 62/080,875, filed on Nov. 17, 2014.

(51) Int. Cl.

| | |
|---|---|
| ***C12Q 1/68*** | (2018.01) |
| ***C12Q 1/6886*** | (2018.01) |
| ***C12N 15/90*** | (2006.01) |

(52) U.S. Cl.

CPC ......... *C12Q 1/6886* (2013.01); *C12N 15/907* (2013.01); *C12Q 2600/106* (2013.01); *C12Q 2600/156* (2013.01)

(58) Field of Classification Search

None

See application file for complete search history.

(56) References Cited

PUBLICATIONS

Willis, Nicholas A., et al., "BRCA1 controls homologous recombination at Tus / Ter-stalled mammalian replication forks," Nature, vol. 510, pp. 556-559 (2014).

Chandramouly, Gurushankar, et al., "BRCA1 and CtIP suppress long-tract gene conversion between sister chromatids," Nature Communications, vol. 4, Article 2404 (2013).

*Primary Examiner* — Antonio Galisteo Gonzalez

(74) *Attorney, Agent, or Firm* — Melissa Hunter-Ensor; Greenberg Traurig, LLP

(57) ABSTRACT

As described below, the present invention provides quantitative homologous recombination assays developed to characterize the pathogenicity DNA repair polypeptides (e.g., BRCA1, BRCA2, Rad51) and provide urgently needed functional information on the significance of DNA repair variants of uncertain significance (VUS) alleles. The invention also provides a method of generating site-specific recombination at a genomic locus or site-specific genome editing by inhibiting replication at the genomic locus, e.g., involving contacting the genomic locus with polypeptides that specifically bind target sequences at the genomic locus.

6 Claims, 39 Drawing Sheets

RFP+
<0.01%
GFP+ RFP+
<0.01%
GFP+
<0.01%
Control
RFP+
0.045%
GFP+ RFP+
0.37%
GFP+
6.52%
I-SceI

FIG. 18A

LTGC reporter vector-I-SceI

CCCCGCGGCAGGCCCTCCGAGCGTGGTGGAGCCGTTCTGTGAGACAGCCGGGTACG
AGTCGTGACGCTGGAAGGGGCAAGCGGGTGGTGGGCAGGAATGCGGTCCGCCCTGC
AGCAACCGGAGGGGGAGGGAGAAGGGAGCGGAAAAGTCTCCACCGGACGCGGCCA
TGGCTCGGGGGGGGGGGGGCAGCGGAGGASCGCTTCCGGCCGACGTCTCGTCGCTG
ATTGGCTTYTTTCCTCCCGCCGTGTGTGAAAACACAAATGGCGTGTTTTGGTTGGCG
TAAGGCGCCTGTCAGTTAACGGCAGCCGGAGTGCGCAGCCGCCGGCAGCCTCGCTC
TGCCCACTGGGTGGGGCGGGAGGTAGGTGGGGTGAGGCGAGCTGNACGTGCGGGCG
CGGTCGGCCTCTGGCGGGGCGGGGGAGGGGAGGGAGGGTCAGCGAAAGTAGCTCG
CGCGCGAGCGGCCGCCCACCCTCCCCTTCCTCTGGGGGAGTCGTTTTACCCGCCGCC
GGCCGGGCCTCGTCGTCTGATTGGCTCTCGGGGCCCAGAAAACTGGCCCTTGCCATT
GGCTCGTGTTCGTGCAAGTTGAGTCCATCCGCCGGCCAGCGGGGGCGGCGAGGAGG
CGCTCCCAGGTTCCGGCCCTCCCCTCGGCCCCGCGCCGCAGAGTCTGGCCGCGCGCC
CCTGCGCAACGTGGCAGGAAGCGCGCGCTGGGGGCGGGGACGGGCAGTAGGGCTG
AGCGGCTGCGGGGCGGGTGCAAGCACGTTTCCGACTTGAGTTGCCTCAAGAGGGGC
GTGCTGAGCCAGACCTCCATCGCGCACTCCGGGGAGTGGAGGGAAGGAGCGAGGGC
TCAGTTGGGCTGTTTTGGAGGCAGGAAGCACTTGCTCTCCCAAAGTCGCTCTGAGTT
GTTATCAGTAAGGGAGCTGCAGTGGAGTAGGCGGGGAGAAGGCCGCACCCTTCTCC
GGAGGGGGGAGGGGAGTGTTGCAATACCTTTCTGGGAGTTCTCTGCTGCCTCCTGGC
TTCTGAGGACCGCCCTGGGCCTGGGAGAATCCCTTGCCCCCTCTTCCCCTCGTGATCT
GCAACTCCAGTCTTTCTAGCCTTAATTAAGGGATCTGTAGGGCGCAGTAGTCCAGGG
TTTCCTTGATGATGTCATACTTATCCTGTCCCTTTTTTTTCCACAGCTCGCGGTTGAGG
ACAAACTCTTCGCGGTCTTTCCAGTGGGGATCGACGGTATCGTAGAGTCGAGGCCGC
TCTAGAACTAGTGGATCTACCATGACCGAGTACAAGCCCACGGTGCGCCTCGCCACC
CGCGACGACGTCCCCCGGGCCGTACGCACCCTCGCCGCCGCGTTCGCCGACTACCCC
GCCACGCGCCACACCGTCGACCCGGACCGCCACATCGAGCGGGTCACCGAGCTGCA
AGAACTCTTCCTCACGCGCGTCGGGCTCGACATCGGCAAGGTGTGGGTCGCGGACG
ACGGCGCCGCGGTGGCGGTCTGGACCACGCCGGAGAGCGTCGAAGCGGGGGCGGT
GTTCGCCGAGATCGGCCCGCGCATGGCCGAGTTGAGCGGTTCCCGGCTGGCCGCGC
AGCAACAGATGGAAGGCCTCCTGGCGCCGCACCGGCCCAAGGAGCCCGCGTGGTTC
CTGGCCACCGTCGGCGTCTCGCCCGACCACCAGGGCAAGGGTCTGGGCAGCGCCGT
CGTGCTCCCCGGAGTGGAGGCGGCCGAGCGCGCCGGGGTGCCCGCCTTCCTGGAGA
CCTCCGCGCCCCGCAACCTCCCCTTCTACGAGCGGCTCGGCTTCACCGTCACCGCCG
ACGTCGAGTGCCCGAAGGACCGCGCGACCTGGTGCATGACCCGCAAGCCCGGTGCC
TGACTCGACCCTAGGGGGAGGCTAACTGAAACACGGAAGGAGACAATACCGGAAG
GAACCCGCGCTATGACGGCAATAAAAAGACAGAATAAAACGCACGGTGTTGGGTCG
TTTGTTCATAAACGCGGGGTTCGGTCCCAGGGCTGGCACTCTGTCGATACCCCACCG
AGACCCCATTGGGGCCAATACGCCCGCGTTTCTTCCTTTTCCCCACCCCACCCCCCA
AGTTCGGGTGAAGGCCCAGGGCTCGCAGCCAACGTCGGGGCGGCAGGCCCTGCCAT
AGCCTCAGGTTACTCGGATCTCGACCTCGAGGGGCCCCCGCGGGTGGGGAAGATCT
CGGGGTGCCCATCCTGGTCGAGCTGGACGGCGACGTAAACGGCCACAAGTTCAGCG
TGTCCGGCGAGGGCGAGGGCGATGCCACCTACGGCAAGCTGACCCTGAAGTTCATC
TGCACCACCGGCAAGCTGCCCGTGCCCTGGCCCACCCTCGTGACCACCCTGACCTAC
GGCGTGCAGTGCTTCAGCCGCTACCCCGACCACATGAAGCAGCACGACTTCTTCAAG
TCCGCCATGCCCGAAGGCTACGTCCAGGAGCGCACCATCTTCTTCAAGGACGACGG

FIG. 18B

CAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTG
GAGTACAACTACAACAGCCACAACGTCTATATCATGGCCGACAAGCAGAAGAACGG
CATCAAGGTGAACTTCAAGATCCGCCACAACATCGAGGACGGCAGCGTGCAGCTCG
CCGACCACTACCAGCAGAACACCCCCATCGGCGACGGCCCCGTGCTGCTGCCCGAC
AACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGACGA
GCTGTACAAGTAAAGCGGCCGCGACTCTAGATCATAATCAGCCATACCACATTTGTA
GAGGTTTTACTTGCTTTAAAAAACCTCCCACACCTCCCCCTGAACCTGAAACATAAA
ATGAATGCAATTGTTGTTGTTAACTTGTTTATTGCAGCTTATAATGGTTACAAATAAA
GCAATAGCATCACAAATTTCACAAATAAAGCATTTTTTTCACTGCATTCTAGTTGTG
GTTTGTCCAAACTCATCAATGTCGGGATCCCGCCAATTGTCTAGATTTCTCTAATCAC
TTTTTTTTCAAGGCAATCAGGGTATATTATATTGTACTTCAGCACAGTTTTAGAGAAC
AATTGTTATAATTAAATGATAAGGTAGAATATTTCTGCATATAAATTCTGGCTGGCG
TGGAAATATTCTTATTGGTAGAAACAACTACATCCTGGTCATCATCCTGCCTTTCTCT
TTATGGTTACAATGATATACACTGTTTGAGATGAGGATAAAATACTCTGAGTCCAAA
CCGGGCCCCTCTGCTAACCATGTTCATGCCTTCTTCTTTTTCCTACAGGACTCCTCCC
TGCAGGACGGCGAGTTCATCTACAAGGTGAAGCTGCGCGGCACCAACTTCCCCTCC
GACGGCCCCGTAATGCAGAAGAAGACCATGGGCTGGGAGGCCTCCTCCGAGCGGAT
GTACCCCGAGGACGGCGCCCTGAAGGGCGAGATCAAGATGAGGCTGAAGCTGAAG
GACGGTGGCCACTACGACGCCGAGGTCAAGACCACCTACATGGCCAAGAAGCCCGT
GCAGCTGCCCGGCGCCTACAAGACCGACATCAAGCTGGACATCACCTCCCACAACG
AGGACTACACCATCGTGGAACAGTACGAGCGCGCCGAGGGCCGCCACTCCACCGGC
GGTATGGATGAACTCTATAAATAAGCACGGGCCCTATTCTATAGTGTCACCTAAATG
CTAGAGCTCGCTGATCAGCCTCGACTGTGCCTTCTAGTTGCCAGCCATCTGTTGTTTG
CCCCTCCCCCGTGCCTTCCTTGACCCTGGAAGGTGCCACTCCCACTGTCCTTTCCTAA
TAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTG
GGGAGGATCTGTGTGGAAAGTCCCCAGGCTCCCCAGGCAGGCAGAAGTATGCAAAG
CATGCATCTCAATTAGTCAGCAACCAGGTGTGGAAAGTCCCCAGGCTCCCCAGCAG
GCAGAAGTATGCAAAGCATGCATCTCAATTAGTCAGCAACCATAGTCCCGCCCCTA
ACTCCGCCCATCCCGCCCCTAACTCCGCCCAGTTCCGCCCATTCTCCGCCCCATGGCT
GACTAATTTTTTTTATTTATGCAGAGGCCGAGGCCGCCTCTGCCTCTGAGCTATTCCA
GAAGTAGTGAGGAGGCTTTTTTGGAGGCCTAGGCTTTTGCAAAAAGCTCCCGGGAG
CTTGTATATCCATTTTCGGATAAGCTTAACTAAACCATGGTATCAAAAGGTGAAGAA
AACAATATGGCAGTCATCAAGGAGTTCATGCGCTTCAAGGTGCGCATGGAGGGCTC
CGTGAACGGCCACGAGTTCGAGATCGAGGGCGAGGGCGAGGGCCGCCCCTACGAG
GGCACCCAGACCGCCAAGCTGAAGGTGACCGAGGGTGGCCCCCTGCCCTTCGCCTG
GGACATCCTGTCCCCTCAGTTCATGTACGGCTCCAAGGCCTACGTGAAGCACCCCGC
CGACATCCCCGACTACTTGAAGCTGTCCTTCCCCGAGGGCTTCAAGTGGGAGCGCGT
GATGAACTTCGAGGACGGCGGCGTGGTGACCGTGACCCAGGTGAGTTTGGGGACCC
TTGATTGTTCTTTCTTTTTCGCTATTGTAAAATTCATGTTATATGGAGGGGGCAAAGT
TTTCAGGGTGTTGTTTAGAATGGGAAGATGTCCCTTGTATCACCATGGACCCTCATG
ATAATTTTGTTTCTTTCACTTTCTACTCTGTTGACAACCATTGTCTCCTCTTATTTTCTT
TTCATTTTCTGTAACTTTTTCGTTAAACTTTAGCTTGCATTTGTAACGAATTTTTAAAT
TCACTTTTGTTTATTTGTCAGATTGTAAGTACCGGGACCCGGAATTCTACCGGGTAG

FIG. 18C

GGGAGGCGCTTTTCCCAAGGCAGTCTGGAGCATGCGCTTTAGCAGCCCCGCTGGCAC
TTGGCGCTACACAAGTGGCCTCTGGCCTCGCACACATTCCACATCCACCGGTAGCGC
CAACCGGCTCCGTTCTTTGGTGGCCCCTTCGCGCCACTTCTACTCCTCCCCTAGTCAG
GAAGTTTCCCCCAGCAAGCTCGCGTCGTGCAGGACGTGACAAATGGAAGTAGCACG
TCTCACTAGTCTCGTGCAGATGGACAGCACCGCTGAGCAATGGAAGCGGGTAGGCC
TTTGGGGCAGCGGCCAATAGCAGCTTTGTTCCTTCGCTTTCTGGGCTCAGAGGCTGG
GAAGGGGTGGGTCCGGGGGCGGGCTCAGGGGCGGGCTCAGGGGCGGGCGGGCGCC
CGAAGGTCCTCCCGAGGCCCGGCATTCTGCACGCTTCAAAAGCGCACGTCTGCCGCG
CTGTTCTCCTCTTCCTCATCTCCGGGCCTTTCGACCTGCAGCCCAAGCTCTAGCGCTA
CCGGTCGCCACCATGGTGAGCAAGGGCGAGGAGCTGTTCACCGGGGTGGTGCCCAT
CCTGGTCGAGCTGGACGGCGACGTAAACGGCCACAAGTTCAGCGTGTCCGGCGAGG
GCGAGGGCGATGCCACCTACGGCAAGCTGACCCTGAAGTTCATCTGCACCACCGGC
AAGCTGCCCGTGCCCTGGCCCACCCTCGTGACCACCCTGACCTACGGCGTGCAGTGC
TTCAGCCGCTACCCCGACCACATGAAGCAGCACGACTTCTTCAAGTCCGCCATGCCC
GAAGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAAGG
GCATCGTAGGGATAACAGGGTAATCAAGGAGGACGGCAACATCCTGGGGCACAAGC
TGGAGTACAACTACAACAGCCACAACGTCTATATCATGGCCGACAAGCAGAAGAAC
GGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGC
GATCACATGGTCCTGCTGGAGTTCGTGACCGCCGCCGGGATCACTCTCGGCATGGAC
GAGCTGTACAAGTAAAGCGGCCGCGACTCTAGATCATAATCAGCCATACCACATTTG
TAGAGGTTTTACTTGCTTTAAAAAACCTCCCACACCTCCCCCTGAACCTGAAACATA
AAATGAATGCAATTGTTGTTGTTAACTTGTTTATTGCAGCTTATAATGGTTACAAATA
AAGCAATAGCATCACAAATTTCACAAATAAAGCATTTTTTTCACTGCATTCTAGTTG
TGGTTTGTCCAAACTCATCAATGTCGGATGGCCGCGCTGGGGATGCGGTGGGCTCTA
TGGCTTATGAGGCGGAAAGAACCAGCTGGGGCTCGATCCTCTAGTTGGCGCGCCGG
CTAGAAGATGGGCGGGAGTCTTCTGGGCAGGCTTAAAGGCTAACCTGGTGTGTGGG
CGTTGTCCTGCAGGGGAATTGAACAGGTGTAAAATTGGAGGGACAAGACTTCCCAC
AGATTTTCGGTTTTGTCGGGAAGTTTTTTAATAGGGGCAAATAGGAAAATGGAGGAT
AGGAGTCATCTGGGGTTTATGCAGCAAAACTACAGGTATATTGCTTGTATCCGCCTC
GGAGATTTCCATGAGGAGATAAAGACATGTCACCCGAGTTTATACTCTCCTGCTTAG
ATCCTACTACAGTATGAAATACAGTGTYGCGAGGTAGACTATGTAAGCAGATTTAAT
CATTTTAAAGAGCCCAGTACTTCATATCCATTTCTCCCGCTCCTTCTGCAGCCTTATC
AAAAGGTATTTAGAACACTCATTTTAGCCCCATTTTCATTTATTATACTGGCTTATCC
AACCCCTAGACAGAGCATTGGCATTTTCCCTTTCCTGATCTTAGAAGTCTGATGACTC
ATGAAACCAGACAGATTAGTTACATACACCACAAATCGAGGCTGTAGCTGGGGCCT
CAACACTGCAGTTCTTTTATAACTCCTTAGTACACTTTTTGTTGATCCTTTGCCTTGAT
CCTTAATTTTCAGTGTCTATCACCTCTCCCGTCAGGTGGTGTTCCACATTTGGGCCTA
TTCTCAGTCCAGGGAGTTTTACAACAATAGATGTATTGAGAATCCAACCTAAAGCTT
AACTTTCCACTCCCATGAATGCCTCTCTCCTTTTTCTCCATTATAACTGAGCTATWAC
CATTAATGGTTTCAGGTGGATGTCTCCTCCCCCAATATACCTGATGTATCTACATATT
GCCAGGCTGATATTTTAAGACATWAAAGGTATATTTCATTATTGAGCCACATGGTAT
TGATTACTGCTACTAAAATTTTGTCATTGTACACATCTGTAAAAGGTGGTTCCTTTTG
GAATGCAAAGTTCAGGTGTTTGTTGTCTTTCCTGACCTAAGGTCTTGTGAGCTTGTAT

FIG. 18D

TTTTTCTATTTAAGCAGTGCTTTCTCTTGGACTGGCTTGACTCATGGCATTCTACACG
TTATTGCTGGTCTAAATGTGATTTTGCCAAGCTTCTTCAGGACCTATAATTTTGCTTG
ACTTGTAGCCAAACACAAGTAAAATGATTAAGCAACAAATGTATTTGTGAAGCTTG
GTTTTTAGGTTGTTGTGTTGTGTGTGCTTGTGCTCTATAATAATACTATCCAGGGGCT
GGAGAGGTGGCTCGGAGTTCAAGAGCACAGACTGCTCTTCCAGAAGTCCTGAGTTC
AATTCCCAGCAACCACATGGTGGCTCACAACCATCTGTAATGGGATCTGATGCCCTC
TTCTGGTGTGTCTGAAGACCACAAGTGTATTCACATTAAATAAATAATCCTCCTTCTT
CTTCTTTTTTTTTTTTAAAGAGAATWCTGTCTCCAGTAGAATTACTGAAGTAATGAA
ATACTTTGTGTTTGTTCCAATATGGWAGCCAATAATCAAATACTCTTWAGCACTGGA
AATGTACCAAGGAACTATTTTATTTAAGTGWACTGTGGACAGAGGAGCCATAACTG
CAGACTTGTGGGATACAGAAGACCAATGCAGACTTAATGTCTTTCTCTTACACTAA
GCAATAAAGAAATAAAAATTGAACTTCTAGTATCCTATTTGTTAAACTGCTAGCTTT
ACTAACTTTTGTGCTTCATCTATACAAAGCTGAAAGCTAAGTCTGCAGCCATTACTA
AACATGAAAGCAAGTAATGATAATTTTGGATTTCAAAAATGTAGGGCCAGAGTTTA
GCCAGCCAGTGGTGGTGCTTGCCTTTATGCCTTAATCCCAGCACTCTGGAGGCAGAG
ACAGGCAGATCTCTGAGTTTGAGCCCAGCCTGGTCTACACATCAAGTTCTATCTAGG
ATAGCCAGGAATACACACAGAAACCCTGTTGGGGAGGGGGGCTCTGAGATTTCATA
AAATTATAATTGAAGCATTCCCTAATGAGCCACTATGGATGTGGCTAAATCCGTCTA
CCTTTCTGATGAGATTTGGGTATTATTTTTTCTGTCTCTGCTGTTGGTTGGGTCTTTTG
ACACTGTGGGCTTTCTTAAAGCCTCCTTCCCTGCCATGTGGTCTCTTGTTTGCTACTA
ACTTCCCATGGCTTAAATGGCATGGCTTTTTGCCTTCTAAGGGCAGCTGCTGAGWTT
TGCAGCCTGATTTCCAGGGTGGGGTTGGGAAATCTTTCAAACACTAAAATTGTCCTT
TAATTTTTTTTTAAAAAAATGGGTTATATAATAAACCTCATAAAATAGTTATGAGGAG
TGAGGTGGACTAATATTAATGAGTCCCTCCCCTATAAAAGAGCTATTAAGGCTTTTT
GTCTTATACTAACTTTTTTTTTAAATGTGGTATCTTTAGAACCAAGGGTCTTAGAGTT
TTAGTATACAGAAACTGTTGCATCGCTTAATCAGATTTTCTAGTTTCAAATCCAGAG
AATCCAAATTCTTCACAGCCAAAGTCAAATTAAGAATTTCTGACTTTAATGTTATTTG
CTACTGTGAATATAAAATGATAGCTTTTCCTGAGGCAGGGTCTCACTATGTATCTCT
GCCTGATCTGCAACAAGATATGTAGACTAAAGTTCTGCCTGCTTTTGTCTCCTGAAT
ACTAAGGTTAAAATGTAGTAATACTTTTGGAACTTGCAGGTCAGATTCTTTTATAGG
GGACACACTAAGGGAGCTTGGGTGATAGTTGGTAAATGTGTTTAAGTGATGAAAAC
TTGAATTATTATCACCGCAACCTACTTTTTAAAAAAAAAAGCCAGGCCTGTTAGAGC
ATGCTAAGGGATCCCTAGGACTTGCTGAGCACACAAGAGTAGTACTTGGCAGGCTC
CTGGTGAGAGCATATTTCAAAAAACAAGGCAGACAACCAAGAAACTACAGTAAGGT
TACCTGTCTTTAACCATCTGCATATACACAGGGATATTAAAATATTCCAAATAATAT
TTCATTCAAGTTTTCCCCCATCAAATTGGGACATGGATTTCTCCGGTGAATAGGCAG
AGTTGGAAACTAAACAAATGTTGGTTTTGTGATTTGTGAAATTGTTTTCAAGTGATA
GTTAAAGCCCATGAGATACAGAACAAAGCTGCTATTTCGAGGTCTCTTGGTTATACT
CAGAAGCACTTCTTTGGGTTTCCCTGCACTATCCTGATCATGTGCTAGGCCTWCCTT
AGGCTGATTGTTGTTCAAATAACTTAAGTTTCCTGTCAGGTGATGTCATATGATTTCA
TATATCAAGGCAAAACATGTTATATATGTTAAACATTTGKACTTAATGTGAAAGTTA
GGTCTTTGTGGGTTTTGATTTTAATTTCAAAACCTGAGCTAAATAAGTCATTTTACAT
GTCTTACATTTGGTGAATTGTATATTGTGGTTTGCAGGCAAGACTCTCTGACCTAGTA
ACCCTCCTATAGAGCACTTTGCTGGGTCACAAGTCTAGGAGTCAAGCATTTCACCTT
GAAGTTGAGACGTTTTGTTAGTGTATACTAGTTATATGTTGGAGGACATGTTTATCC
AGAAGATATTCAGGACTATTTTGACTGGGCTAAGGAATTGATTCTGATTAGCACTG

FIG. 18E

TTAGTGAGCATTGAGTGGCCTTTAGGCTTGAATTGGAGTCACTTGTATATCTCAAAT
AATGCTGGCCTTTTTTWAAAAGCCCTTGTTCTTTATCACCCTGTTTTCTACATAATTT
TTGTTCAAAGAAATACTTGTTTGGATCTCCTTTTGACAACAATAGCATGTTTTCAAGC
CATATTTTTTTTCCTTTTTTTTTTTTTTTTTGGTTTTTCGAGACAGGGTTTCTCTGTATA
GCCCTGGCTGTCCTGGAACTCACTTTGTAGACCAGGCTGGCCTCGAACTCAGAAATC
CGCCTGCCTCTGCCTCCTGAGTGCCGGGATTAAAGGCGTGCACCACCACGCCTGGCT
AAGTTGGATATTTTGTATATAACTATAACCAATACTAACTCCACTGGGTGGATTTTTA
ATTCAGTCAGTAGTCTTAAGTGGTCTTTATTGGCCCTTATTAAAATCTACTGTTCACT
CTAACAGAGGCTGTTGGACTAGTGGSACTAAGCAACTTCCTACGGATATACTAGCAG
ATAAGGGTCAGGGATAGAAACTAGTCTAGCGTTTTGTATACCTACCAGCTTATACTA
CCTTGTTCTGATAGAAATATTTAGGACATCTAGCTTATCGATCCGTCGACGGTATCG
ATAAGCTTGATATCGAATTCTACCGGGTAGGGGAGGCGCTTTTCCAAGGCAGTCTGA
GCATGCGCTTAGCAGCCCCGCTGGCACTTGGCGCTACACAAGTGGCCTYTGGCCTCG
CACACATTCCACATCCACCGGTAGGCGCCAACCGGCTCCGTTCTTTGGTGGCCCCTT
CGCGCCACCTTCTWCTCCTCCCCTAGTCAGGAAGTTCCCCCCCGCCCCGCAGCTCGC
GTCGTSAGGACGTGACAAATGGAAGTAGCACGTCTCACTAGTCTCGTCAGATGGACA
GCACCGCTGAGCAATGGAAGCGGGTAGGCCTTTGGGGCAGCGGCCAATAGCAGCTT
TGCTCCTTCGCTTTCTGGGCTCAGAGGCTGGGAAGGGGTGGGTCCGGGGGCGGGCTC
AGGGGCGGGCTCAGGGGCGGGGCGGGCGCCCGAAGGTCCTCCGGAGGCCCGGCATT
CTGCACGCTTCAAAAGCGCACGTCTGCCGCGCTGTTCTCCTCTTCCTCATCTCCGGGC
CTTTCGACCTGCAGGTCCTCGCCATGGATCCTGATGATGTTGTTATTCTTCTAATCTT
TTGTATGGAAAACTTTTCTTCGTACCACGGGACTAAACCTGGTTATGTAGATTCCATT
CAAAAAGGTATACAAAAGCCAAAATCTGGTACACAAGGAAATTATGACGATGATTG
GAAAGGGTTTTATAGTACCGACAATAAATACGACGCTGCGGGATACTCTGTAGATA
ATGAAAACCCGCTCTCTGGAAAAGCTGGAGGCGTGGTCAAAGTGACGTATCCAGGA
CTGACGAAGGTTCTCGCACTAAAAGTGGATAATGCCGAAACTATTAAGAAAGAGTT
AGGTTTAAGTCTCACTGAACCGTTGATGGAGCAAGTCGGAACGGAAGAGTTTATCA
AAAGGTTCGGTGATGGTGCTTCGCGTGTAGTGCTCAGCCTTCCCTTCGCTGAGGGGA
GTTCTAGCGTTGAATATATTAATAACTGGGAACAGGCGAAAGCGTTAAGCGTAGAA
CTTGAGATTAATTTTGAAACCCGTGGAAAACGTGGCCAAGATGCGATGTATGAGTAT
ATGGCTCAAGCCTGTGCAGGAAATCGTGTCAGGCGATCTCTTTGTGAAGGAACCTTA
CTTCTGTGGTGTGACATAATTGGACAAACTACCTACAGAGATTTAAAGCTCTAAGGT
AAATATAAAATTTTTAAGTGTATAATGTGTTAAACTACTGATTCTAATTGTTTGTGTA
TTTTAGATTCCAACCTATGGAACTGATGAATGGGAGCAGTGGTGGAATGCAGATCCT
AGAGCTCGCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGG
GATGCGGTGGGCTCTATGGCTTCTGAGGCGGAAAGAACCAGCTGGGGCTCGACCTC
GAGGGGGGGCCCGGTACCCAGCTTTTGTTCCCTTTAGTGAGGGTTAATTGCGCGCTT
GGCGTAATCATGGTCATAGCTGTTTCCTGTGTGAAATTGTTATCCGCTCACAATTCCA
CACAACATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAAACCTGTC
GTGCCAGCTGCATTAATGAATCGGCCAACGCGCGGGGAGAGGCGGTTTGCGTATTG
GGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATA

FIG. 18F

ACGCAGGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGTCATGA
GATTATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAGTG
AGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCG
GAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAG
CTCCGGTTCCCAACGATCAAGGCGAGTTACATGATCCCCCATGTTGTGCAAAAAAGC
GGTTAGCTCCTTCGGTCCTCCGATCGTTGTCAGAAGTAAGTTGGCCGCAGTGTTATC
ACTCATGGTTATGGCAGCACTGCATAATTCTCTTACTGTCATGCCATCCGTAAGATG
CTTTTCTGTGACTGGTGAGTACTCAACCAAGTCATTCTGAGAATAGTGTATGCGGCG
ACCGAGTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAG
CATCTTTTACTTTCACCAGCGTTTCTGGGTGAGCAAAAACAGGAAGGCAAAATGCCG
CAAAAAAGGGAATAAGGGCGACACGGAAATGTTGAATACTCATACTCTTCCTTTTTC
AATATTATTGAAGCATTTATCAGGGTTATTGTCTCATGAGCGGATACATATTTGAAT
GTATTTAGAAAAATAAACAAATAGGGGTTCCGCGCACATTTCCCCGAAAAGTGCCA
CCTAAATTGTAAGCGTTAATATTTTGTTAAAATTCGCGTTAAATTTTTGTTAAATCAG
CTCATTTTTTAACCAATAGGCCGAAATCGGCAAAATCCCTTATAAATCAAAAGAATA
GACCGAGATAGGGTTGAGTGTTGTTCCAGTTTGGAACAAGAGTCCACTATTAAAGA
ACGTGGACTCCAACGTCAAAGGGCGAAAAACCGTCTATCAGGGCGATGGCCCACTA
CGTGAACCATCACCCTAATCAAGTTTTTTGGGGTCGAGGTGCCGTAAAGCACTAAAT
CGGAACCCTAAAGGGAGCCCCCGATTTAGAGCTTGACGGGGAAAGCCGGCGAACGT
GGCGAGAAAGGAAGGGAAGAAAGCGAAAGGAGCGGGCGCTAGGGCGCTGGCAAGT
GTAGCGGTCACGCTGCGCGTAACCACCACACCCGCCGCGCTTAATGCGCCGCTACA
GGGCGCGTCCCATTCGCCATTCAGGCTGCGCAACTGTTGGGAAGGGCGATCGGTGC
GGGCCTCTTCGCTATTACGCCAGCTGGCGAAAGGGGGATGTGCTGCAAGGCGATTA
AGTTGGGTAACGCCAGGGTTTTCCCAGTCACGACGTTGTAAAACGACGGCCAGTGA
GCGCGCGTAATACGACTCACTATAGGGCGAATTGGAGCT

FIG. 19A

Tus expression vector

GACGGATCGGGAGATCTCCCGATCCCCTATGGTCGACTCTCAGTACAATCTGCTCTG
ATGCCGCATAGTTAAGCCAGTATCTGCTCCCTGCTTGTGTGTTGGAGGTCGCTGAGT
AGTGCGCGAGCAAAATTTAAGCTACAACAAGGCAAGGCTTGACCGACAATTGCATG
AAGAATCTGCTTAGGGTTAGGCGTTTTGCGCTGCTTCGCGATGTACGGGCCAGATAT
ACGCGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATA
GTAACGCCAATAGGGACTTTCCATTGACGTCAATGGGTGGACTATTTACGGTAAACT
GCCCACTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTT
CCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCC
ACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGG
GAGGTCTATATAAGCAGAGCTCTCTGGCTAACTAGAGAACCCACTGCTTACTGGCTT
ATCGAAATTAATACGACTCACTATAGGGAGACCCAAGCTAGAGTCGATCCTGAGAA
CTTCAGGGTGAGTTTGGGGACCCTTGATTGTTCTTTCTTTTTCGCTATTGTAAAATTC
ATGTTATATGGAGGGGGCAAAGTTTTCAGGGTGTTGTTTAGAATGGGAAGATGTCCC
TTGTATCACCATGGACCCTCATGATAATTTTGTTTCTTTCACTTTCTACTCTGTTGACA
ACCATTGTCTCCTCTTATTTTCTTTTCATTTTCTGTAACTTTTTCGTTAAACTTTAGCTT
GCATTTGTAACGAATTTTTAAATTCACTTTTGTTTATTTGTCAGATTGTAAGTACTTTC
TCTAATCACTTTTTTTTCAAGGCAATCAGGGTATATTATATTGTACTTCAGCACAGTT
TTAGAGAACAATTGTTATAATTAAATGATAAGGTAGAATATTTCTGCATATAAATTC
TGGCTGGCGTGGAAATATTCTTATTGGTAGAAACAACTACATCCTGGTCATCATCCT
GCCTTTCTCTTTATGGTTACAATGATATACACTGTTTGAGATGAGGATAAAATACTCT
GAGTCCAAACCGGGCCCCTCTGCTAACCATGTTCATGCCTTCTTCTTTTTCCTACAGC
TCCTGGGCAACGTGCTGGTTTGTGCTGTCGACCCCAAGCTGGCCGCTCGAGCCACCA
TGGAACAAAAGCTGATTTCTGAAGAAGACTTGGCTAGCGAACAAAAGCTGATTTCT
GAAGAAGACTTGGAACAAAAGCTGATTTCTGAAGAAGACTTGACCGGTATGCCAAA
AAAGAAGAGAAAGGTATTAGGATCCATGGCCAGATACGACCTGGTGGACAGGCTGA
ACACCACCTTCAGGCAGATGGAGCAGGAGCTGGCCATCTTCGCCGCTCACCTGGAG
CAGCACAAGCTGCTGGTGGCCCGGGTGTTCTCCCTGCCTGAGGTGAAGAAGGAGGA
TGAGCACAACCCACTGAATCGCATCGAGGTGAAGCAGCACCTGGGCAACGATGCTC
AGAGCCTGGCTCTGCGCCACTTCAGGCACCTGTTCATCCAGCAGCAGTCCGAGAACC
GCTCTTCCAAGGCCGCTGTGAGGCTGCCAGGAGTGCTGTGCTACCAGGTGGACAAC
CTGTCCCAGGCCGCCCTGGTGTCTCACATCCAGCACATCAACAAGCTGAAGACCACA
TTCGAGCACATCGTGACCGTGGAGTCCGAGCTGCCAACCGCGGCCCGGTTCGAGTG
GGTGCACAGACACCTGCCAGGCCTGATCACACTGAACGCTTACAGGACCCTGACCG
TGCTGCACGATCCTGCTACCCTGAGATTTGGATGGGCCAACAAGCACATCATCAAGA
ACCTGCACAGAGACGAGGTGCTGGCCCAGCTGGAGAAGAGCCTGAAGAGCCCCAG
GTCTGTGGCTCCCTGGACCAGGGAGGAGTGGCAGAGAAAGCTGGAGCGCGAGTACC
AGGACATCGCCGCCCTGCCCCAGAACGCCAAGCTGAAGATCAAGAGACCTGTGAAG
GTGCAGCCAATCGCCAGAGTGTGGTACAAGGGCGACCAGAAGCAGGTGCAGCACGC
CTGCCCCACACCACTGATCGCCCTGATCAATCGGGACAACGGCGCCGGAGTGCCAG

FIG. 19B

ACGTGGGAGAGCTGCTGAACTACGACGCCGATAATGTGCAGCACCGCTACAAGCCC
CAGGCCCAGCCCCTGCGGCTGATCATCCCACGGCTGCACCTGTACGTGGCTGACTGA
TGAGAATTCTGCAGATATCCATCACACTGGCGGCCCTAGAGGGCCCTATTCTATAGT
GTCACCTAAATGCTAGAGCTCGCTGATCAGCCTCGACTGTGCCTTCTAGTTGCCAGC
CATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGACAATA
GCAGGCATGCTGGGGATGCGGTGGGCTCTATGGCTTCTGAGGCGGAAAGAACCAGC
TGGGGCTCTAGGGGGTATCCCCACGCGCCCTGTAGCGGCGCATTAAGCGCGGCGGG
TGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAA
ATCGGGGCATCCCTTTAGGGTTCCGATTTAGTGCTTTACGGCACCTCGACCCCAAAA
AACTTGATTAGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGGAAC
AACACTCAACCCTATCTCGGTCTATTCTTTTGATTTATAAGGGATTTTGGGGATTTCG
GCCTATTGGTTAAAAAATGAGCTGATTTAACAAAAATTTAACGCGAATTAATTCTGT
GGAATGTGTGTCAGTTAGGGTGTGGAAAGTCCCCAGGCTCCCCAGGCAGGCAGAAG
TATGCAAAGCATGCATCTCAATTAGTCAGCAACCAGGTGTGGAAAGTCCCCAGGCTC
CCCAGCAGGCAGAAGTATGCAAAGCATGCATCTCAATTAGTCAGCAACCATAGTCC
CGCCCCTAACTCCGCCCATCCCGCCCCTAACTCCGCCCAGTTCCGCCCATTCTCCGCC
CCATGGCTGACTAATTTTTTTTATTTATGCAGAGGCCGAGGCCGCCTCTGCCTCTGAG
CTATTCCAGAAGTAGTGAGGAGGCTTTTTTGGAGGCCTAGGCTTTTGCAAAAAGCTC
CCGGGAGCTTGTATATCCATTTTCGGATCTGATCAAGAGACAGGATGAGGATCGTTT
CGCATGATTGAACAAGATGGATTGCACGCAGGTTCTCCGGCCGCTTGGGTGGAGAG
GCTATTCGGCTATGACTGGGCACAACAGACAATCGGCTGCTCTGATGCCGCCGTGTT
CCGGCTGTCAGCGCAGGGGCGCCCGGTTCTTTTTGTCAAGACCGACCTGTCCGGTGC
CCTGAATGAACTGCAGGACGAGGCAGCGCGGCTATCGTGGCTGGCCACGACGGGCG
TTCCTTGCGCAGCTGTGCTCGACGTTGTCACTGAAGCGGGAAGGGACTGGCTGCTAT
TGGGCGAAGTGCCGGGGCAGGATCTCCTGTCATCTCACCTTGCTCCTGCCGAGAAAG
TATCCATCATGGCTGATGCAATGCGGCGGCTGCATACGCTTGATCCGGCTACCTGCC
CATTCGACCACCAAGCGAAACATCGCATCGAGCGAGCACGTACTCGGATGGAAGCC
GGTCTTGTCGATCAGGATGATCTGGACGAAGAGCATCAGGGGCTCGCGCCAGCCGA
ACTGTTCGCCAGGCTCAAGGCGCGCATGCCCGACGGCGAGGATCTCGTCGTGACCC
ATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCC
GTGATATTGCTGAAGAGCTTGGCGGCGAATGGGCTGACCGCTTCCTCGTGCTTTACG
GTATCGCCGCTCCCGATTCGCAGCGCATCGCCTTCTATCGCCTTCTTGACGAGTTCTT
CTGAGCGGGACTCTGGGGTTCGAAATGACCGACCAAGCGACGCCCAACCTGCCATC
ACGAGATTTCGATTCCACCGCCGCCTTCTATGAAAGGTTGGGCTTCGGAATCGTTTT
CCGGGACGCCGGCTGGATGATCCTCCAGCGCGGGGATCTCATGCTGGAGTTCTTCGC
CCACCCCAACTTGTTTATTGCAGCTTATAATGGTTACAAATAAAGCAATAGCATCAC
AAATTTCACAAATAAAGCATTTTTTTCACTGCATTCTAGTTGTGGTTTGTCCAAACTC
ATCAATGTATCTTATCATGTCTGTATACCGTCGACCTCTAGCTAGAGCTTGGCGTAAT
CATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCGTGCCAGC

FIG. 19C

TGCATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGA
AAGAACATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCC
GCCTTTCTCCCTTCGGGAAGCGTGGCGCTTTCTCAATGCTCACGCTGTAGGTATCTCA
GTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACGGG
GTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAG
ATAACTACGATACGGGAGGGCTTACCATCTGGCCCCAGTGCTGCAATGATACCGCG
AGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATG
GTTATGGCAGCACTGCATAATTCTCTTACTGTCATGCCATCCGTAAGATGCTTTTCTG
TGACTGGTGAGTACTCAACCAAGTCATTCTGAGAATAGTGTATGCGGCGACCGAGTT
GCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAG
AAAAATAAACAAATAGGGGTTCCGCGCACATTTCCCCGAAAAGTGCCACCTGACGT
C

FIG. 20A

**6x*Ter* array reporter plasmid**

CCCCGCGGCAGGCCCTCCGAGCGTGGTGGAGCCGTTCTGTGAGACAGCCGGGTACG
AGTCGTGACGCTGGAAGGGGCAAGCGGGTGGTGGGCAGGAATGCGGTCCGCCCTGC
AGCAACCGGAGGGGGAGGGAGAAGGGAGCGGAAAAGTCTCCACCGGACGCGGCCA
TGGCTCGGGGGGGGGGGGGCAGCGGAGGASCGCTTCCGGCCGACGTCTCGTCGCTG
ATTGGCTTYTTTTCCTCCCGCCGTGTGTGAAAACACAAATGGCGTGTTTTGGTTGGCG
TAAGGCGCCTGTCAGTTAACGGCAGCCGGAGTGCGCAGCCGCCGGCAGCCTCGCTC
TGCCCACTGGGTGGGGCGGGAGGTAGGTGGGGTGAGGCGAGCTGNACGTGCGGGCG
CGGTCGGCCTCTGGCGGGGCGGGGGAGGGGAGGGAGGGTCAGCGAAAGTAGCTCG
CGCGCGAGCGGCCGCCCACCCTCCCCTTCCTCTGGGGGAGTCGTTTTACCCGCCGCC
GGCCGGGCCTCGTCGTCTGATTGGCTCTCGGGGCCCAGAAAACTGGCCCTTGCCATT
GGCTCGTGTTCGTGCAAGTTGAGTCCATCCGCCGGCCAGCGGGGGCGGCGAGGAGG
CGCTCCCAGGTTCCGGCCCTCCCCTCGGCCCCGCGCCGCAGAGTCTGGCCGCGCGCC
CCTGCGCAACGTGGCAGGAAGCGCGCGCTGGGGGCGGGGACGGGCAGTAGGGCTG
AGCGGCTGCGGGGCGGGTGCAAGCACGTTTCCGACTTGAGTTGCCTCAAGAGGGGC
GTGCTGAGCCAGACCTCCATCGCGCACTCCGGGGAGTGGAGGGAAGGAGCGAGGGC
TCAGTTGGGCTGTTTTGGAGGCAGGAAGCACTTGCTCTCCCAAAGTCGCTCTGAGTT
GTTATCAGTAAGGGAGCTGCAGTGGAGTAGGCGGGGAGAAGGCCGCACCCTTCTCC
GGAGGGGGGAGGGGAGTGTTGCAATACCTTTCTGGGAGTTCTCTGCTGCCTCCTGGC
TTCTGAGGACCGCCCTGGGCCTGGGAGAATCCCTTGCCCCCTCTTCCCCTCGTGATCT
GCAACTCCAGTCTTTCTAGCCTTAATTAAGGGATCTGTAGGGCGCAGTAGTCCAGGG
TTTCCTTGATGATGTCATACTTATCCTGTCCCTTTTTTTTCCACAGCTCGCGGTTGAGG
ACAAACTCTTCGCGGTCTTTCCAGTGGGGATCGACGGTATCGTAGAGTCGAGGCCGC
TCTAGAACTAGTGGATCTACCATGACCGAGTACAAGCCCACGGTGCGCCTCGCCACC
CGCGACGACGTCCCCCGGGCCGTACGCACCCTCGCCGCCGCGTTCGCCGACTACCCC
GCCACGCGCCACACCGTCGACCCGGACCGCCACATCGAGCGGGTCACCGAGCTGCA
AGAACTCTTCCTCACGCGCGTCGGGCTCGACATCGGCAAGGTGTGGGTCGCGGACG
ACGGCGCCGCGGTGGCGGTCTGGACCACGCCGGAGAGCGTCGAAGCGGGGGCGGT
GTTCGCCGAGATCGGCCCGCGCATGGCCGAGTTGAGCGGTTCCCGGCTGGCCGCGC
AGCAACAGATGGAAGGCCTCCTGGCGCCGCACCGGCCCAAGGAGCCCGCGTGGTTC
CTGGCCACCGTCGGCGTCTCGCCCGACCACCAGGGCAAGGGTCTGGGCAGCGCCGT
CGTGCTCCCCGGAGTGGAGGCGGCCGAGCGCGCCGGGGTGCCCGCCTTCCTGGAGA
CCTCCGCGCCCCGCAACCTCCCCTTCTACGAGCGGCTCGGCTTCACCGTCACCGCCG
ACGTCGAGTGCCCGAAGGACCGCGCGACCTGGTGCATGACCCGCAAGCCCGGTGCC
TGACTCGACCCTAGGGGGAGGCTAACTGAAACACGGAAGGAGACAATACCGGAAG
GAACCCGCGCTATGACGGCAATAAAAAGACAGAATAAAACGCACGGTGTTGGGTCG
TTTGTTCATAAACGCGGGGTTCGGTCCCAGGGCTGGCACTCTGTCGATACCCCACCG
AGACCCCATTGGGGCCAATACGCCCGCGTTTCTTCCTTTTCCCCACCCCACCCCCCA
AGTTCGGGTGAAGGCCCAGGGCTCGCAGCCAACGTCGGGGCGGCAGGCCCTGCCAT
AGCCTCAGGTTACTCGGATCTCGACCTCGAGACGCGTGCCCCCACTCCACAATTTCA
AAAAAAAGAGTGGCCACTTGTCTTTGTTTATGGGCCCCATTGGCGTGGAGCCCCGTT
TAATTTTCGGGGGTGTTAGAGACAACCAGTGGAGTCCGCTGCTGTCGGCGTCCACTC
TCTTTCCCCTTGTTACAAATAGAGTGTAACAACATGGTTCACCTGTCTTGGTCCCTGC
CTGGGACACATCTTAATAACCCCAGTATCATATTGCACTAGGATTATGTGTTGCCCA
TAGCCATAAATTCGTGTGAGATGGACATCCAGTCTTTACGGCTTGTCCCCACCCCAT
GGATTTCTATTGTTAAAGATATTCAGAATGTTTCATTCCTACACTAGTATTTATTGCC

FIG. 20B

CAAGGGGTTTGTGAGGGTTATATTGGTGTCATAGCACAATGCCACCACTGAACCCCC
CGTCCAAATTTTATTCTGGGGGCGTCACCTGAAACCTTGTTTTCGAGCACCTCACATA
CACCTTACTGTTCACAACTCAGCAGTTATTCTATTAGCTAAACGAAGGAGAATGAAG
AAGCAGGCGAAGATTCAGGAGAGTTCACTGCCCGCTCCTTGATCTTCAGCCACTGCC
CTTGTGACTAAAATGGTTCACTACCCTCGTGGAATCCTGACCCCATGTAAATAAAAC
CGTGACAGCTCATGGGGTGGGAGATATCGCTGTTCCTTAGGACCCTTTTACTAACCC
TAATTCGATAGCATATGCTTCCCGTTGGGTAACATATGCTATTGAATTAGGGTTAGT
CTGGATAGTATATACTACTACCCGGGAAGCATATGCTACCCGTTTAGGGTTAACAAG
GGGGCCTTATAAACACTATTGCTAATGCCCTCTTGAGGGTCCGCTTATCGGTAGCTA
CACAGGCCCCTCTGATTGACGTTGGTGTAGCCTCCCGTAGTCTTCCTGGGCCCCTGG
GAGGTACATGTCCCCCAGCATTGGTGTAAGAGCTTCAGCCAAGAGTTACACATAAA
GGTACGTACCAGTCTTCGAAAGATCTCGGGGTGCCCATCCTGGTCGAGCTGGACGGC
GACGTAAACGGCCACAAGTTCAGCGTGTCCGGCGAGGGCGAGGGCGATGCCACCTA
CGGCAAGCTGACCCTGAAGTTCATCTGCACCACCGGCAAGCTGCCCGTGCCCTGGCC
CACCCTCGTGACCACCCTGACCTACGGCGTGCAGTGCTTCAGCCGCTACCCCGACCA
CATGAAGCAGCACGACTTCTTCAAGTCCGCCATGCCCGAAGGCTACGTCCAGGAGC
GCACCATCTTCTTCAAGGACGACGGCAACTACAAGACCCGCGCCGAGGTGAAGTTC
GAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATA
TCATGGCCGACAAGCAGAAGAACGGCATCAAGGTGAACTTCAAGATCCGCCACAAC
ATCGAGGACGGCAGCGTGCAGCTCGCCGACCACTACCAGCAGAACACCCCCATCGG
CGACGGCCCCGTGCTGCTGCCCGACAACCACTACCTGAGCACCCAGTCCGCCCTGAG
CAAAGACCCCAACGAGAAGCGCGATCACATGGTCCTGCTGGAGTTCGTGACCGCCG
CCGGGATCACTCTCGGCATGGACGAGCTGTACAAGTAAAGCGGCCGCGACTCTAGA
TCATAATCAGCCATACCACATTTGTAGAGGTTTTACTTGCTTTAAAAAACCTCCCAC
ACCTCCCCCTGAACCTGAAACATAAAATGAATGCAATTGTTGTTGTTAACTTGTTTAT
TGCAGCTTATAATGGTTACAAATAAAGCAATAGCATCACAAATTTCACAAATAAAG
CATTTTTTTCACTGCATTCTAGTTGTGGTTTGTCCAAACTCATCAATGTCGGGATCCC
GCCAATTGTCTAGATTTCTCTAATCACTTTTTTTTCAAGGCAATCAGGGTATATTATA
TTGTACTTCAGCACAGTTTTAGAGAACAATTGTTATAATTAAATGATAAGGTAGAAT
ATTTCTGCATATAAATTCTGGCTGGCGTGGAAATATTCTTATTGGTAGAAACAACTA
CATCCTGGTCATCATCCTGCCTTTCTCTTTATGGTTACAATGATATACACTGTTTGAG
ATGAGGATAAAATACTCTGAGTCCAAACCGGGCCCCTCTGCTAACCATGTTCATGCC
TTCTTCTTTTTCCTACAGGACTCCTCCCTGCAGGACGGCGAGTTCATCTACAAGGTGA
AGCTGCGCGGCACCAACTTCCCCTCCGACGGCCCCGTAATGCAGAAGAAGACCATG
GGCTGGGAGGCCTCCTCCGAGCGGATGTACCCCGAGGACGGCGCCCTGAAGGGCGA
GATCAAGATGAGGCTGAAGCTGAAGGACGGTGGCCACTACGACGCCGAGGTCAAGA
CCACCTACATGGCCAAGAAGCCCGTGCAGCTGCCCGGCGCCTACAAGACCGACATC
AAGCTGGACATCACCTCCCACAACGAGGACTACACCATCGTGGAACAGTACGAGCG
CGCCGAGGGCCGCCACTCCACCGGCGGTATGGATGAACTCTATAAATAAGCACGGG
CCCTATTCTATAGTGTCACCTAAATGCTAGAGCTCGCTGATCAGCCTCGACTGTGCCT
TCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGAT
TGGGAAGACAATAGCAGGCATGCTGGGGAGGATCTGTGTGGAAAGTCCCCAGGCTC
CCCAGGCAGGCAGAAGTATGCAAAGCATGCATCTCAATTAGTCAGCAACCAGGTGT

FIG. 20C

GGAAAGTCCCCAGGCTCCCCAGCAGGCAGAAGTATGCAAAGCATGCATCTCAATTA
GTCAGCAACCATAGTCCCGCCCCTAACTCCGCCCATCCCGCCCCTAACTCCGCCCAG
TTCCGCCCATTCTCCGCCCCATGGCTGACTAATTTTTTTTATTTATGCAGAGGCCGAG
GCCGCCTCTGCCTCTGAGCTATTCCAGAAGTAGTGAGGAGGCTTTTTTGGAGGCCTA
GGCTTTTGCAAAAAGCTCCCGGGAGCTTGTATATCCATTTTCGGATAAGCTTAACTA
AACCATGGTATCAAAAGGTGAAGAAAACAATATGGCAGTCATCAAGGAGTTCATGC
GCTTCAAGGTGCGCATGGAGGGCTCCGTGAACGGCCACGAGTTCGAGATCGAGGGC
GAGGGCGAGGGCCGCCCCTACGAGGGCACCCAGACCGCCAAGCTGAAGGTGACCG
AGGGTGGCCCCCTGCCCTTCGCCTGGGACATCCTGTCCCCTCAGTTCATGTACGGCT
CCAAGGCCTACGTGAAGCACCCCGCCGACATCCCCGACTACTTGAAGCTGTCCTTCC
CCGAGGGCTTCAAGTGGGAGCGCGTGATGAACTTCGAGGACGGCGGCGTGGTGACC
GTGACCCAGGTGAGTTTGGGGACCCTTGATTGTTCTTTCTTTTTCGCTATTGTAAAAT
TCATGTTATATGGAGGGGGCAAAGTTTTCAGGGTGTTGTTTAGAATGGGAAGATGTC
CCTTGTATCACCATGGACCCTCATGATAATTTTGTTTCTTTCACTTTCTACTCTGTTGA
CAACCATTGTCTCCTCTTATTTTCTTTTCATTTTCTGTAACTTTTTCGTTAAACTTTAG
CTTGCATTTGTAACGAATTTTTAAATTCACTTTTGTTTATTTGTCAGATTGTAAGTAC
CGGGACCCGGAATTCTACCGGGTAGGGGAGGCGCTTTTCCCAAGGCAGTCTGGAGC
ATGCGCTTTAGCAGCCCCGCTGGCACTTGGCGCTACACAAGTGGCCTCTGGCCTCGC
ACACATTCCACATCCACCGGTAGCGCCAACCGGCTCCGTTCTTTGGTGGCCCCTTCG
CGCCACTTCTACTCCTCCCCTAGTCAGGAAGTTTCCCCCAGCAAGCTCGCGTCGTGC
AGGACGTGACAAATGGAAGTAGCACGTCTCACTAGTCTCGTGCAGATGGACAGCAC
CGCTGAGCAATGGAAGCGGGTAGGCCTTTGGGGCAGCGGCCAATAGCAGCTTTGTT
CCTTCGCTTTCTGGGCTCAGAGGCTGGGAAGGGGTGGGTCCGGGGGCGGGCTCAGG
GGCGGGCTCAGGGGCGGGCGGGCGCCCGAAGGTCCTCCCGAGGCCCGGCATTCTGC
ACGCTTCAAAAGCGCACGTCTGCCGCGCTGTTCTCCTCTTCCTCATCTCCGGGCCTTT
CGACCTGCAGCCCAAGCTCTAGCGCTACCGGTCGCCACCATGGTGAGCAAGGGCGA
GGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTG
ACCCTGAAGTTCATCTGCACCACCGGCAAGCTGCCCGTGCCCTGGCCCACCCTCGTG
ACCACCCTGACCTACGGCGTGCAGTGCTTCAGCCGCTACCCCGACCACATGAAGCA
GCACGACTTCTTCAAGTCCGCCATGCCCGAAGGCTACGTCCAGGAGCGCACCATCTT
CTTCAAGGACGACGGCAACTACAAGACCCGCGCCGAGGTGAAGTTCGAGGGCGACA
CCCTGGTGAACCGCATCGAGCTGAAGGGCATCGTAGGGATAACGCTCATATATCGA
TAATAAGTATGTTGTAACTAAAGTCGTGAAATAAGTATGTTGTAACTAAAGTCTTAC
AATAAGTATGTTGTAACTAAAGTGTATACCTTTCCGGATAGGGATAACGCTCATATA
TCGATAATAAGTATGTTGTAACTAAAGTCGTGAAATAAGTATGTTGTAACTAAAGTC
TTACAATAAGTATGTTGTAACTAAAGTGTATACCTTTCCGGATAGGGATAACAGGGT
AATCAAGGAGGACGGCAACATCCTGGGGCACAAGCTGGAGTACAACTACAACAGCC
ACAACGTCTATATCATGGCCGACAAGCAGAAGAACGGCATCAAGGTGAACTTCAAG
ATCCGCCACAACATCGAGGACGGCAGCGTGCAGCTCGCCGACCACTACCAGCAGAA
CACCCCCATCGGCGACGGCCCCGTGCTGCTGCCCGACAACCACTACCTGAGCACCCA
GTCCGCCCTGAGCAAAGACCCCAACGAGAAGCGCGATCACATGGTCCTGCTGGAGT
TCGTGACCGCCGCCGGGATCACTCTCGGCATGGACGAGCTGTACAAGTAAAGCGGC
CGCGACTCTAGATCATAATCAGCCATACCACATTTGTAGAGGTTTTACTTGCTTTAA
AAAACCTCCCACACCTCCCCCTGAACCTGAAACATAAAATGAATGCAATTGTTGTTG
TTAACTTGTTTATTGCAGCTTATAATGGTTACAAATAAAGCAATAGCATCACAAATT

FIG. 20D

TCACAAATAAAGCATTTTTTTCACTGCATTCTAGTTGTGGTTTGTCCAAACTCATCAA
TGTCGGATGGCCGCGCTGGGGATGCGGTGGGCTCTATGGCTTATGAGGCGGAAAGA
ACCAGCTGGGGCTCGATCCTCTAGTTGGCGCGCCGGCTAGAAGATGGGCGGGAGTC
TTCTGGGCAGGCTTAAAGGCTAACCTGGTGTGTGGGCGTTGTCCTGCAGGGGAATTG
AACAGGTGTAAAATTGGAGGGACAAGACTTCCCACAGATTTTCGGTTTTGTCGGGAA
GTTTTTTAATAGGGGCAAATAGGAAAATGGAGGATAGGAGTCATCTGGGGTTTATG
CAGCAAAACTACAGGTATATTGCTTGTATCCGCCTCGGAGATTTCCATGAGGAGATA
AAGACATGTCACCCGAGTTTATACTCTCCTGCTTAGATCCTACTACAGTATGAAATA
CAGTGTYGCGAGGTAGACTATGTAAGCAGATTTAATCATTTTAAAGAGCCCAGTACT
TCATATCCATTTCTCCCGCTCCTTCTGCAGCCTTATCAAAAGGTATTTAGAACACTCA
TTTTAGCCCCATTTTCATTTATTATACTGGCTTATCCAACCCCTAGACAGAGCATTGG
CATTTTCCCTTTCCTGATCTTAGAAGTCTGATGACTCATGAAACCAGACAGATTAGTT
ACATACACCACAAATCGAGGCTGTAGCTGGGGCCTCAACACTGCAGTTCTTTTATAA
CTCCTTAGTACACTTTTTGTTGATCCTTTGCCTTGATCCTTAATTTTCAGTGTCTATCA
CCTCTCCCGTCAGGTGGTGTTCCACATTTGGGCCTATTCTCAGTCCAGGGAGTTTTAC
AACAATAGATGTATTGAGAATCCAACCTAAAGCTTAACTTTCCACTCCCATGAATGC
CTCTCTCCTTTTTCTCCATTATAACTGAGCTATWACCATTAATGGTTTCAGGTGGATG
TCTCCTCCCCCAATATACCTGATGTATCTACATATTGCCAGGCTGATATTTTAAGACA
TWAAAGGTATATTTCATTATTGAGCCACATGGTATTGATTACTGCTACTAAAATTTT
GTCATTGTACACATCTGTAAAAGGTGGTTCCTTTTGGAATGCAAAGTTCAGGTGTTT
GTTGTCTTTCCTGACCTAAGGTCTTGTGAGCTTGTATTTTTTCTATTTAAGCAGTGCTT
TCTCTTGGACTGGCTTGACTCATGGCATTCTACACGTTATTGCTGGTCTAAATGTGAT
TTTGCCAAGCTTCTTCAGGACCTATAATTTTGCTTGACTTGTAGCCAAACACAAGTA
AAATGATTAAGCAACAAATGTATTTGTGAAGCTTGGTTTTTAGGTTGTTGTGTTGTGT
GTGCTTGTGCTCTATAATAATACTATCCAGGGGCTGGAGAGGTGGCTCGGAGTTCAA
GAGCACAGACTGCTCTTCCAGAAGTCCTGAGTTCAATTCCCAGCAACCACATGGTGG
CTCACAACCATCTGTAATGGGATCTGATGCCCTCTTCTGGTGTGTCTGAAGACCACA
AGTGTATTCACATTAAATAAATAATCCTCCTTCTTCTTCTTTTTTTTTTTTTAAAGAGA
ATWCTGTCTCCAGTAGAATTACTGAAGTAATGAAATACTTTGTGTTTGTTCCAATAT
GGWAGCCAATAATCAAATACTCTTWAGCACTGGAAATGTACCAAGGAACTATTTTA
TTTAAGTGWACTGTGGACAGAGGAGCCATAACTGCAGACTTGTGGGATACAGAAGA
CCAATGCAGACTTAATGTCTTTTCTCTTACACTAAGCAATAAAGAAATAAAAATTGA
ACTTCTAGTATCCTATTTGTTAAACTGCTAGCTTTACTAACTTTTGTGCTTCATCTATA
CAAAGCTGAAAGCTAAGTCTGCAGCCATTACTAAACATGAAAGCAAGTAATGATAA
TTTTGGATTTCAAAAATGTAGGGCCAGAGTTTAGCCAGCCAGTGGTGGTGCTTGCCT
TTATGCCTTAATCCCAGCACTCTGGAGGCAGAGACAGGCAGATCTCTGAGTTTGAGC
CCAGCCTGGTCTACACATCAAGTTCTATCTAGGATAGCCAGGAATACACACAGAAA
CCCTGTTGGGGAGGGGGGCTCTGAGATTTCATAAAATTATAATTGAAGCATTCCCTA
ATGAGCCACTATGGATGTGGCTAAATCCGTCTACCTTTCTGATGAGATTTGGGTATT
ATTTTTTCTGTCTCTGCTGTTGGTTGGGTCTTTTGACACTGTGGGCTTTCTTAAAGCCT
CCTTCCCTGCCATGTGGTCTCTTGTTTGCTACTAACTTCCCATGGCTTAAATGGCATG
GCTTTTTGCCTTCTAAGGGCAGCTGCTGAGWTTTGCAGCCTGATTTCCAGGGTGGGG
TTGGGAAATCTTTCAAACACTAAAATTGTCCTTTAATTTTTTTTTAAAAAATGGGTTA
TATAATAAACCTCATAAAATAGTTATGAGGAGTGAGGTGGACTAATATTAATGAGTC
CCTCCCCTATAAAAGAGCTATTAAGGCTTTTTGTCTTATACTAACTTTTTTTTTAAAT
GTGGTATCTTTAGAACCAAGGGTCTTAGAGTTTAGTATACAGAAACTGTTGCATCG

FIG. 20E

CTTAATCAGATTTTCTAGTTTCAAATCCAGAGAATCCAAATTCTTCACAGCCAAAGT
CAAATTAAGAATTTCTGACTTTAATGTTATTTGCTACTGTGAATATAAAATGATAGCT
TTTCCTGAGGCAGGGTCTCACTATGTATCTCTGCCTGATCTGCAACAAGATATGTAG
ACTAAAGTTCTGCCTGCTTTTGTCTCCTGAATACTAAGGTTAAAATGTAGTAATACTT
TTGGAACTTGCAGGTCAGATTCTTTTATAGGGGACACACTAAGGGAGCTTGGGTGAT
AGTTGGTAAATGTGTTTAAGTGATGAAAACTTGAATTATTATCACCGCAACCTACTT
TTTAAAAAAAAAAGCCAGGCCTGTTAGAGCATGCTAAGGGATCCCTAGGACTTGCT
GAGCACACAAGAGTAGTACTTGGCAGGCTCCTGGTGAGAGCATATTTCAAAAAACA
AGGCAGACAACCAAGAAACTACAGTAAGGTTACCTGTCTTTAACCATCTGCATATAC
ACAGGGATATTAAAATATTCCAAATAATATTTCATTCAAGTTTTCCCCCATCAAATT
GGGACATGGATTTCTCCGGTGAATAGGCAGAGTTGGAAACTAAACAAATGTTGGTTT
TGTGATTTGTGAAATTGTTTTCAAGTGATAGTTAAAGCCCATGAGATACAGAACAAA
GCTGCTATTTCGAGGTCTCTTGGTTATACTCAGAAGCACTTCTTTGGGTTTCCCTGCA
CTATCCTGATCATGTGCTAGGCCTWCCTTAGGCTGATTGTTGTTCAAATAACTTAAG
TTTCCTGTCAGGTGATGTCATATGATTTCATATATCAAGGCAAAACATGTTATATATG
TTAAACATTTGKACTTAATGTGAAAGTTAGGTCTTTGTGGGTTTTGATTTTAATTTCA
AAACCTGAGCTAAATAAGTCATTTTACATGTCTTACATTTGGTGAATTGTATATTGTG
GTTTGCAGGCAAGACTCTCTGACCTAGTAACCCTCCTATAGAGCACTTTGCTGGGTC
ACAAGTCTAGGAGTCAAGCATTTCACCTTGAAGTTGAGACGTTTTGTTAGTGTATAC
TAGTTATATGTTGGAGGACATGTTTATCCAGAAGATATTCAGGACTATTTTTGACTG
GGCTAAGGAATTGATTCTGATTAGCACTGTTAGTGAGCATTGAGTGGCCTTTAGGCT
TGAATTGGAGTCACTTGTATATCTCAAATAATGCTGGCCTTTTTTWAAAAGCCCTTG
TTCTTTATCACCCTGTTTTCTACATAATTTTTGTTCAAAGAAATACTTGTTTGGATCTC
CTTTTGACAACAATAGCATGTTTTCAAGCCATATTTTTTTTCCTTTTTTTTTTTTTTTT
GGTTTTTCGAGACAGGGTTTCTCTGTATAGCCCTGGCTGTCCTGGAACTCACTTTGTA
GACCAGGCTGGCCTCGAACTCAGAAATCCGCCTGCCTCTGCCTCCTGAGTGCCGGGA
TTAAAGGCGTGCACCACCACGCCTGGCTAAGTTGGATATTTTGTATATAACTATAAC
CAATACTAACTCCACTGGGTGGATTTTTAATTCAGTCAGTAGTCTTAAGTGGTCTTTA
TTGGCCCTTATTAAAATCTACTGTTCACTCTAACAGAGGCTGTTGGACTAGTGGSACT
AAGCAACTTCCTACGGATATACTAGCAGATAAGGGTCAGGGATAGAAACTAGTCTA
GCGTTTTGTATACCTACCAGCTTATACTACCTTGTTCTGATAGAAATATTTAGGACAT
CTAGCTTATCGATCCGTCGACGGTATCGATAAGCTTGATATCGAATTCTACCGGGTA
GGGGAGGCGCTTTTCCAAGGCAGTCTGAGCATGCGCTTAGCAGCCCCGCTGGCACTT
GGCGCTACACAAGTGGCCTYTGGCCTCGCACACATTCCACATCCACCGGTAGGCGCC
AACCGGCTCCGTTCTTTGGTGGCCCCTTCGCGCCACCTTCTWCTCCTCCCCTAGTCAG
GAAGTTCCCCCCCGCCCCGCAGCTCGCGTCGTSAGGACGTGACAAATGGAAGTAGC
ACGTCTCACTAGTCTCGTCAGATGGACAGCACCGCTGAGCAATGGAAGCGGGTAGG
CCTTTGGGGCAGCGGCCAATAGCAGCTTTGCTCCTTCGCTTTCTGGGCTCAGAGGCT
GGGAAGGGGTGGGTCCGGGGGCGGGCTCAGGGGCGGGCTCAGGGGCGGGGCGGGC
GCCCGAAGGTCCTCCGGAGGCCCGGCATTCTGCACGCTTCAAAAGCGCACGTCTGCC
GCGCTGTTCTCCTCTTCCTCATCTCCGGGCCTTTCGACCTGCAGGTCCTCGCCATGGA
TCCTGATGATGTTGTTATTCTTCTAATCTTTTGTATGGAAAACTTTTCTTCGTACCACG
GGACTAAACCTGGTTATGTAGATTCCATTCAAAAAGGTATACAAAAGCCAAAATCT
GGTACACAAGGAAATTATGACGATGATTGGAAAGGGTTTTATAGTACCGACAATAA
ATACGACGCTGCGGGATACTCTGTAGATAATGAAAACCCGCTCTCTGGAAAAGCTG
GAGGCGTGGTCAAAGTGACGTATCCAGGACTGACGAAGGTTCTCGCACTAAAAGTG

FIG. 20F

GATAATGCCGAAACTATTAAGAAAGAGTTAGGTTTAAGTCTCACTGAACCGTTGATG
GAGCAAGTCGGAACGGAAGAGTTTATCAAAAGGTTCGGTGATGGTGCTTCGCGTGT
AGTGCTCAGCCTTCCCTTCGCTGAGGGGAGTTCTAGCGTTGAATATATTAATAACTG
GGAACAGGCGAAAGCGTTAAGCGTAGAACTTGAGATTAATTTTGAAACCCGTGGAA
AACGTGGCCAAGATGCGATGTATGAGTATATGGCTCAAGCCTGTGCAGGAAATCGT
GTCAGGCGATCTCTTTGTGAAGGAACCTTACTTCTGTGGTGTGACATAATTGGACAA
ACTACCTACAGAGATTTAAAGCTCTAAGGTAAATATAAAATTTTTAAGTGTATAATG
TGTTAAACTACTGATTCTAATTGTTTGTGTATTTTAGATTCCAACCTATGGAACTGAT
GAATGGGAGCAGTGGTGGAATGCAGATCCTAGAGCTCGCTGATCAGCCTCGACTGT
GCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGA
GGATTGGGAAGACAATAGCAGGCATGCTGGGGATGCGGTGGGCTCTATGGCTTCTG
AGGCGGAAAGAACCAGCTGGGGCTCGACCTCGAGGGGGGGCCCGGTACCCAGCTTT
TGTTCCCTTTAGTGAGGGTTAATTGCGCGCTTGGCGTAATCATGGTCATAGCTGTTTC
CTGTGTGAAATTGTTATCCGCTCACAATTCCACACAACATACGAGCCGGAAGCATAA
AGTGTAAAGCCTGGGGTGCCTAATGAGTGAGCTAACTCACATTAATTGCGTTGCGCT
CACTGCCCGCTTTCCAGTCGGGAAACCTGTCGTGCCAGCTGCATTAATGAATCGGCC
AACGCGCGGGGAGAGGCGGTTTGCGTATTGGGCGCTCTTCCGCTTCCTCGCTCACTG
ACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAA
GGCCAGCAAAAGGCCAGGAACCGTAAAAAGGCCGCGTTGCTGGCGTTTTTCCATAG
GCTCCGCCCCCCTGACGAGCATCACAAAAATCGACGCTCAAGTCAGAGGTGGCGAA
ACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGGCAGCA
GCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCT
GCTGAAGCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGA
GTTACATGATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGCACTGCAT
AATTCTCTTACTGTCATGCCATCCGTAAGATGCTTTTCTGTGACTGGTGAGTACTCAA
CCAAGTCATTCTGAGAATAGTGTATGCGGCGACCGAGTTGCTCTTGCCCGGCGTCAA

FIG. 20G

TACGGGATAATACCGCGCCACATAGCAGAACTTTAAAAGTGCTCATCATTGGAAAA
CGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGT
TATTGTCTCATGAGCGGATACATATTTGAATGTATTTAGAAAAATAAACAAATAGGG
GTTCCGCGCACATTTCCCCGAAAAGTGCCACCTAAATTGTAAGCGTTAATATTTTGTT
AAAATTCGCGTTAAATTTTTGTTAAATCAGCTCATTTTTTAACCAATAGGCCGAAATC
GGCAAAATCCCTTATAAATCAAAAGAATAGACCGAGATAGGGTTGAGTGTTGTTCC
AGTTTGGAACAAGAGTCCACTATTAAAGAACGTGGACTCCAACGTCAAAGGGCGAA
AAACCGTCTATCAGGGCGATGGCCCACTACGTGAACCATCACCCTAATCAAGTTTTT
TGGGGTCGAGGTGCCGTAAAGCACTAAATCGGAACCCTAAAGGGAGCCCCCGATTT
AGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACC
ACACCCGCCGCGCTTAATGCGCCGCTACAGGGCGCGTCCCATTCGCCATTCAGGCTG
CGCAACTGTTGGGAAGGGCGATCGGTGCGGGCCTCTTCGCTATTACGCCAGCTGGCG
AAAGGGGGATGTGCTGCAAGGCGATTAAGTTGGGTAACGCCAGGGTTTTCCCAGTC
ACGACGTTGTAAAACGACGGCCAGTGAGCGCGCGTAATACGACTCACTATAGGGCG
AATTGGAGCT

SEQUENCE LISTING

```
<160> NUMBER OF SEQ ID NOS: 55

<210> SEQ ID NO 1
<211> LENGTH: 1863
<212> TYPE: PRT
<213> ORGANISM: Homo sapiens

<400> SEQUENCE: 1

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240
```

```
Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
```

```
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu  Glu Asn Phe Glu Glu  His Ser Met
        995                 1000                1005

Ser Pro  Glu Arg Glu Met Gly  Asn Glu Asn Ile Pro  Ser Thr Val
    1010                1015                1020

Ser Thr  Ile Ser Arg Asn Asn  Ile Arg Glu Asn Val  Phe Lys Glu
    1025                1030                1035

Ala Ser  Ser Ser Asn Ile Asn  Glu Val Gly Ser Ser  Thr Asn Glu
    1040                1045                1050

Val Gly  Ser Ser Ile Asn Glu  Ile Gly Ser Ser Asp  Glu Asn Ile
    1055                1060                1065

Gln Ala  Glu Leu Gly Arg Asn  Arg Gly Pro Lys Leu  Asn Ala Met
    1070                1075                1080
```

```
Leu Arg  Leu Gly Val Leu Gln  Pro Glu Val Tyr Lys  Gln Ser Leu
    1085                 1090                 1095

Pro Gly  Ser Asn Cys Lys His  Pro Glu Ile Lys Lys  Gln Glu Tyr
    1100                 1105                 1110

Glu Glu  Val Val Gln Thr Val  Asn Thr Asp Phe Ser  Pro Tyr Leu
    1115                 1120                 1125

Ile Ser  Asp Asn Leu Glu Gln  Pro Met Gly Ser Ser  His Ala Ser
    1130                 1135                 1140

Gln Val  Cys Ser Glu Thr Pro  Asp Asp Leu Leu Asp  Asp Gly Glu
    1145                 1150                 1155

Ile Lys  Glu Asp Thr Ser Phe  Ala Glu Asn Asp Ile  Lys Glu Ser
    1160                 1165                 1170

Ser Ala  Val Phe Ser Lys Ser  Val Gln Lys Gly Glu  Leu Ser Arg
    1175                 1180                 1185

Ser Pro  Ser Pro Phe Thr His  Thr His Leu Ala Gln  Gly Tyr Arg
    1190                 1195                 1200

Arg Gly  Ala Lys Lys Leu Glu  Ser Ser Glu Glu Asn  Leu Ser Ser
    1205                 1210                 1215

Glu Asp  Glu Glu Leu Pro Cys  Phe Gln His Leu Leu  Phe Gly Lys
    1220                 1225                 1230

Val Asn  Asn Ile Pro Ser Gln  Ser Thr Arg His Ser  Thr Val Ala
    1235                 1240                 1245

Thr Glu  Cys Leu Ser Lys Asn  Thr Glu Glu Asn Leu  Leu Ser Leu
    1250                 1255                 1260

Lys Asn  Ser Leu Asn Asp Cys  Ser Asn Gln Val Ile  Leu Ala Lys
    1265                 1270                 1275

Ala Ser  Gln Glu His His Leu  Ser Glu Glu Thr Lys  Cys Ser Ala
    1280                 1285                 1290

Ser Leu  Phe Ser Ser Gln Cys  Ser Glu Leu Glu Asp  Leu Thr Ala
    1295                 1300                 1305

Asn Thr  Asn Thr Gln Asp Pro  Phe Leu Ile Gly Ser  Ser Lys Gln
    1310                 1315                 1320

Met Arg  His Gln Ser Glu Ser  Gln Gly Val Gly Leu  Ser Asp Lys
    1325                 1330                 1335

Glu Leu  Val Ser Asp Asp Glu  Glu Arg Gly Thr Gly  Leu Glu Glu
    1340                 1345                 1350

Asn Asn  Gln Glu Glu Gln Ser  Met Asp Ser Asn Leu  Gly Glu Ala
    1355                 1360                 1365

Ala Ser  Gly Cys Glu Ser Glu  Thr Ser Val Ser Glu  Asp Cys Ser
    1370                 1375                 1380

Gly Leu  Ser Ser Gln Ser Asp  Ile Leu Thr Thr Gln  Gln Arg Asp
    1385                 1390                 1395

Thr Met  Gln His Asn Leu Ile  Lys Leu Gln Gln Glu  Met Ala Glu
    1400                 1405                 1410

Leu Glu  Ala Val Leu Glu Gln  His Gly Ser Gln Pro  Ser Asn Ser
    1415                 1420                 1425

Tyr Pro  Ser Ile Ile Ser Asp  Ser Ser Ala Leu Glu  Asp Leu Arg
    1430                 1435                 1440

Asn Pro  Glu Gln Ser Thr Ser  Glu Lys Ala Val Leu  Thr Ser Gln
    1445                 1450                 1455

Lys Ser  Ser Glu Tyr Pro Ile  Ser Gln Asn Pro Glu  Gly Leu Ser
    1460                 1465                 1470
```

```
Ala Asp Lys Phe Glu Val Ser Ala Asp Ser Ser Thr Ser Lys Asn
    1475                1480                1485

Lys Glu Pro Gly Val Glu Arg Ser Ser Pro Ser Lys Cys Pro Ser
    1490                1495                1500

Leu Asp Asp Arg Trp Tyr Met His Ser Cys Ser Gly Ser Leu Gln
    1505                1510                1515

Asn Arg Asn Tyr Pro Ser Gln Glu Glu Leu Ile Lys Val Val Asp
    1520                1525                1530

Val Glu Glu Gln Gln Leu Glu Glu Ser Gly Pro His Asp Leu Thr
    1535                1540                1545

Glu Thr Ser Tyr Leu Pro Arg Gln Asp Leu Glu Gly Thr Pro Tyr
    1550                1555                1560

Leu Glu Ser Gly Ile Ser Leu Phe Ser Asp Asp Pro Glu Ser Asp
    1565                1570                1575

Pro Ser Glu Asp Arg Ala Pro Glu Ser Ala Arg Val Gly Asn Ile
    1580                1585                1590

Pro Ser Ser Thr Ser Ala Leu Lys Val Pro Gln Leu Lys Val Ala
    1595                1600                1605

Glu Ser Ala Gln Ser Pro Ala Ala Ala His Thr Thr Asp Thr Ala
    1610                1615                1620

Gly Tyr Asn Ala Met Glu Glu Ser Val Ser Arg Glu Lys Pro Glu
    1625                1630                1635

Leu Thr Ala Ser Thr Glu Arg Val Asn Lys Arg Met Ser Met Val
    1640                1645                1650

Val Ser Gly Leu Thr Pro Glu Glu Phe Met Leu Val Tyr Lys Phe
    1655                1660                1665

Ala Arg Lys His His Ile Thr Leu Thr Asn Leu Ile Thr Glu Glu
    1670                1675                1680

Thr Thr His Val Val Met Lys Thr Asp Ala Glu Phe Val Cys Glu
    1685                1690                1695

Arg Thr Leu Lys Tyr Phe Leu Gly Ile Ala Gly Gly Lys Trp Val
    1700                1705                1710

Val Ser Tyr Phe Trp Val Thr Gln Ser Ile Lys Glu Arg Lys Met
    1715                1720                1725

Leu Asn Glu His Asp Phe Glu Val Arg Gly Asp Val Val Asn Gly
    1730                1735                1740

Arg Asn His Gln Gly Pro Lys Arg Ala Arg Glu Ser Gln Asp Arg
    1745                1750                1755

Lys Ile Phe Arg Gly Leu Glu Ile Cys Cys Tyr Gly Pro Phe Thr
    1760                1765                1770

Asn Met Pro Thr Asp Gln Leu Glu Trp Met Val Gln Leu Cys Gly
    1775                1780                1785

Ala Ser Val Val Lys Glu Leu Ser Ser Phe Thr Leu Gly Thr Gly
    1790                1795                1800

Val His Pro Ile Val Val Val Gln Pro Asp Ala Trp Thr Glu Asp
    1805                1810                1815

Asn Gly Phe His Ala Ile Gly Gln Met Cys Glu Ala Pro Val Val
    1820                1825                1830

Thr Arg Glu Trp Val Leu Asp Ser Val Ala Leu Tyr Gln Cys Gln
    1835                1840                1845

Glu Leu Asp Thr Tyr Leu Ile Pro Gln Ile Pro His Ser His Tyr
    1850                1855                1860
```

<210> SEQ ID NO 2
<211> LENGTH: 7224
<212> TYPE: DNA
<213> ORGANISM: Homo sapiens

<400> SEQUENCE: 2
gtaccttgat ttcgtattct gagaggctgc tgcttagcgg tagccccttg gtttccgtgg 60
caacggaaaa gcgcgggaat tacagataaa ttaaaactgc gactgcgcgg cgtgagctcg 120
ctgagacttc ctggacgggg gacaggctgt ggggtttctc agataactgg gcccctgcgc 180
tcaggaggcc ttcaccctct gctctgggta aagttcattg gaacagaaag aaatggattt 240
atctgctctt cgcgttgaag aagtacaaaa tgtcattaat gctatgcaga aaatcttaga 300
gtgtcccatc tgtctggagt tgatcaagga acctgtctcc acaaagtgtg accacatatt 360
ttgcaaattt tgcatgctga aacttctcaa ccagaagaaa gggccttcac agtgtccttt 420
atgtaagaat gatataacca aaaggagcct acaagaaagt acgagattta gtcaacttgt 480
tgaagagcta ttgaaaatca tttgtgcttt tcagcttgac acaggtttgg agtatgcaaa 540
cagctataat tttgcaaaaa aggaaaataa ctctcctgaa catctaaaag atgaagtttc 600
tatcatccaa agtatgggct acagaaaccg tgccaaaaga cttctacaga gtgaacccga 660
aaatccttcc ttgcaggaaa ccagtctcag tgtccaactc tctaaccttg gaactgtgag 720
aactctgagg acaaagcagc ggatacaacc tcaaaagacg tctgtctaca ttgaattggg 780
atctgattct tctgaagata ccgttaataa ggcaacttat tgcagtgtgg gagatcaaga 840
attgttacaa atcacccctc aaggaaccag ggatgaaatc agtttggatt ctgcaaaaaa 900
ggctgcttgt gaattttctg agacggatgt aacaaatact gaacatcatc aacccagtaa 960
taatgatttg aacaccactg agaagcgtgc agctgagagg catccagaaa agtatcaggg 1020
tagttctgtt tcaaacttgc atgtggagcc atgtggcaca aatactcatg ccagctcatt 1080
acagcatgag aacagcagtt tattactcac taaagacaga atgaatgtag aaaaggctga 1140
attctgtaat aaaagcaaac agcctggctt agcaaggagc caacataaca gatgggctgg 1200
aagtaaggaa acatgtaatg ataggcggac tcccagcaca gaaaaaaagg tagatctgaa 1260
tgctgatccc ctgtgtgaga gaaaagaatg gaataagcag aaactgccat gctcagagaa 1320
tcctagagat actgaagatg ttccttggat aacactaaat agcagcattc agaaagttaa 1380
tgagtggttt tccagaagtg atgaactgtt aggttctgat gactcacatg atggggagtc 1440
tgaatcaaat gccaaagtag ctgatgtatt ggacgttcta aatgaggtag atgaatattc 1500
tggttcttca gagaaaatag acttactggc cagtgatcct catgaggctt taatatgtaa 1560
aagtgaaaga gttcactcca aatcagtaga gagtaatatt gaagacaaaa tatttgggaa 1620
aacctatcgg aagaaggcaa gcctccccaa cttaagccat gtaactgaaa atctaattat 1680
aggagcattt gttactgagc cacagataat acaagagcgt cccctcacaa ataaattaaa 1740
gcgtaaaagg agacctacat caggccttca tcctgaggat tttatcaaga aagcagattt 1800
ggcagttcaa aagactcctg aaatgataaa tcagggaact aaccaaacgg agcagaatgg 1860
tcaagtgatg aatattacta atagtggtca tgagaataaa acaaaaggtg attctattca 1920
gaatgagaaa aatcctaacc caatagaatc actcgaaaaa gaatctgctt tcaaaacgaa 1980
agctgaacct ataagcagca gtataagcaa tatggaactc gaattaaata tccacaattc 2040
aaaagcacct aaaaagaata ggctgaggag gaagtcttct accaggcata ttcatgcgct 2100
tgaactagta gtcagtagaa atctaagccc acctaattgt actgaattgc aaattgatag 2160

```
ttgttctagc agtgaagaga taaagaaaaa aaagtacaac caaatgccag tcaggcacag   2220
cagaaaccta caactcatgg aaggtaaaga acctgcaact ggagccaaga agagtaacaa   2280
gccaaatgaa cagacaagta aaagacatga cagcgatact ttcccagagc tgaagttaac   2340
aaatgcacct ggttctttta ctaagtgttc aaataccagt gaacttaaag aatttgtcaa   2400
tcctagcctt ccaagagaag aaaaagaaga gaaactagaa acagttaaag tgtctaataa   2460
tgctgaagac cccaaagatc tcatgttaag tggagaaagg gttttgcaaa ctgaaagatc   2520
tgtagagagt agcagtattt cattggtacc tggtactgat tatggcactc aggaaagtat   2580
ctcgttactg gaagttagca ctctagggaa ggcaaaaaca gaaccaaata aatgtgtgag   2640
tcagtgtgca gcatttgaaa accccaaggg actaattcat ggttgttcca aagataatag   2700
aaatgacaca gaaggcttta agtatccatt gggacatgaa gttaaccaca gtcgggaaac   2760
aagcatagaa atggaagaaa gtgaacttga tgctcagtat ttgcagaata cattcaaggt   2820
ttcaaagcgc cagtcatttg ctccgttttc aaatccagga aatgcagaag aggaatgtgc   2880
aacattctct gcccactctg ggtccttaaa gaaacaaagt ccaaaagtca cttttgaatg   2940
tgaacaaaag gaagaaaatc aaggaaagaa tgagtctaat atcaagcctg tacagacagt   3000
taatatcact gcaggctttc ctgtggttgg tcagaaagat aagccagttg ataatgccaa   3060
atgtagtatc aaaggaggct ctaggttttg tctatcatct cagttcagag gcaacgaaac   3120
tggactcatt actccaaata aacatggact tttacaaaac ccatatcgta taccaccact   3180
ttttcccatc aagtcatttg ttaaaactaa atgtaagaaa aatctgctag aggaaaactt   3240
tgaggaacat tcaatgtcac ctgaaagaga aatgggaaat gagaacattc caagtacagt   3300
gagcacaatt agccgtaata acattagaga aaatgttttt aaagaagcca gctcaagcaa   3360
tattaatgaa gtaggttcca gtactaatga agtgggctcc agtattaatg aaataggttc   3420
cagtgatgaa aacattcaag cagaactagg tagaaacaga gggccaaaat tgaatgctat   3480
gcttagatta ggggttttgc aacctgaggt ctataaacaa agtcttcctg gaagtaattg   3540
taagcatcct gaaataaaaa agcaagaata tgaagaagta gttcagactg ttaatacaga   3600
tttctctcca tatctgattt cagataactt agaacagcct atgggaagta gtcatgcatc   3660
tcaggtttgt tctgagacac ctgatgacct gttagatgat ggtgaaataa aggaagatac   3720
tagttttgct gaaaatgaca ttaaggaaag ttctgctgtt tttagcaaaa gcgtccagaa   3780
aggagagctt agcaggagtc ctagcccttt cacccataca catttggctc agggttaccg   3840
aagaggggcc aagaaattag agtcctcaga agagaactta tctagtgagg atgaagagct   3900
tccctgcttc caacacttgt tatttggtaa agtaaacaat ataccttctc agtctactag   3960
gcatagcacc gttgctaccg agtgtctgtc taagaacaca gaggagaatt tattatcatt   4020
gaagaatagc ttaaatgact gcagtaacca ggtaatattg gcaaaggcat ctcaggaaca   4080
tcaccttagt gaggaaacaa aatgttctgc tagcttgttt tcttcacagt gcagtgaatt   4140
ggaagacttg actgcaaata caaacaccca ggatcctttc ttgattggtt cttccaaaca   4200
aatgaggcat cagtctgaaa gccagggagt tggtctgagt gacaaggaat tggtttcaga   4260
tgatgaagaa agaggaacgg gcttggaaga aaataatcaa gaagagcaaa gcatggattc   4320
aaacttaggt gaagcagcat ctgggtgtga gagtgaaaca agcgtctctg aagactgctc   4380
agggctatcc tctcagagtg acattttaac cactcagcag agggatacca tgcaacataa   4440
cctgataaag ctccagcagg aaatggctga actagaagct gtgttagaac agcatgggag   4500
ccagccttct aacagctacc cttccatcat aagtgactct tctgcccttg aggacctgcg   4560
```

```
aaatccagaa caaagcacat cagaaaaagc agtattaact tcacagaaaa gtagtgaata   4620
ccctataagc cagaatccag aaggcctttc tgctgacaag tttgaggtgt ctgcagatag   4680
ttctaccagt aaaaataaag aaccaggagt ggaaaggtca tccccttcta aatgcccatc   4740
attagatgat aggtggtaca tgcacagttg ctctgggagt cttcagaata gaaactaccc   4800
atctcaagag gagctcatta aggttgttga tgtggaggag caacagctgg aagagtctgg   4860
gccacacgat ttgacggaaa catcttactt gccaaggcaa gatctagagg gaacccctta   4920
cctggaatct ggaatcagcc tcttctctga tgaccctgaa tctgatcctt ctgaagacag   4980
agccccagag tcagctcgtg ttggcaacat accatcttca acctctgcat tgaaagttcc   5040
ccaattgaaa gttgcagaat ctgcccagag tccagctgct gctcatacta ctgatactgc   5100
tgggtataat gcaatggaag aaagtgtgag cagggagaag ccagaattga cagcttcaac   5160
agaaagggtc aacaaaagaa tgtccatggt ggtgtctggc ctgaccccag aagaatttat   5220
gctcgtgtac aagtttgcca gaaaacacca catcacttta actaatctaa ttactgaaga   5280
gactactcat gttgttatga aaacagatgc tgagtttgtg tgtgaacgga cactgaaata   5340
ttttctagga attgcgggag gaaaatgggt agttagctat ttctgggtga cccagtctat   5400
taaagaaaga aaaatgctga atgagcatga ttttgaagtc agaggagatg tggtcaatgg   5460
aagaaaccac caaggtccaa agcgagcaag agaatcccag gacagaaaga tcttcagggg   5520
gctagaaatc tgttgctatg ggcccttcac caacatgccc acagatcaac tggaatggat   5580
ggtacagctg tgtggtgctt ctgtggtgaa ggagctttca tcattcaccc ttggcacagg   5640
tgtccaccca attgtggttg tgcagccaga tgcctggaca gaggacaatg gcttccatgc   5700
aattgggcag atgtgtgagg cacctgtggt gacccgagag tgggtgttgg acagtgtagc   5760
actctaccag tgccaggagc tggacaccta cctgataccc cagatccccc acagccacta   5820
ctgactgcag ccagccacag gtacagagcc acaggacccc aagaatgagc ttacaaagtg   5880
gcctttccag gccctgggag ctcctctcac tcttcagtcc ttctactgtc ctggctacta   5940
aatattttat gtacatcagc ctgaaaagga cttctggcta tgcaagggtc ccttaaagat   6000
tttctgcttg aagtctccct tggaaatctg ccatgagcac aaaattatgg taatttttca   6060
cctgagaaga ttttaaaacc atttaaacgc caccaattga gcaagatgct gattcattat   6120
ttatcagccc tattctttct attcaggctg ttgttggctt agggctggaa gcacagagtg   6180
gcttggcctc aagagaatag ctggtttccc taagtttact tctctaaaac cctgtgttca   6240
caaaggcaga gagtcagacc cttcaatgga aggagagtgc ttgggatcga ttatgtgact   6300
taaagtcaga atagtccttg ggcagttctc aaatgttgga gtggaacatt ggggaggaaa   6360
ttctgaggca ggtattagaa atgaaaagga aacttgaaac ctgggcatgg tggctcacgc   6420
ctgtaatccc agcactttgg gaggccaagg tgggcagatc actggaggtc aggagttcga   6480
aaccagcctg gccaacatgg tgaaacccca tctctactaa aaatacagaa attagccggt   6540
catggtggtg gacacctgta atcccagcta ctcaggtggc taaggcagga gaatcacttc   6600
agcccgggag gtggaggttg cagtgagcca agatcatacc acggcactcc agcctgggtg   6660
acagtgagac tgtggctcaa aaaaaaaaaa aaaaaaagga aaatgaaact agaagagatt   6720
tctaaaagtc tgagatatat ttgctagatt tctaaagaat gtgttctaaa acagcagaag   6780
attttcaaga accggtttcc aaagacagtc ttctaattcc tcattagtaa taagtaaaat   6840
gtttattgtt gtagctctgg tatataatcc attcctctta aaatataaga cctctggcat   6900
```

```
gaatatttca tatctataaa atgacagatc ccaccaggaa ggaagctgtt gctttctttg   6960

aggtgatttt tttcctttgc tccctgttgc tgaaaccata cagcttcata aataattttg   7020

cttgctgaag gaagaaaaag tgtttttcat aaacccatta tccaggactg tttatagctg   7080

ttggaaggac taggtcttcc ctagcccccc cagtgtgcaa gggcagtgaa gacttgattg   7140

tacaaaatac gttttgtaaa tgttgtgctg ttaacactgc aaataaactt ggtagcaaac   7200

acttccaaaa aaaaaaaaaa aaaa                                          7224


<210> SEQ ID NO 3
<211> LENGTH: 3418
<212> TYPE: PRT
<213> ORGANISM: Homo sapiens

<400> SEQUENCE: 3

Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
            20                  25                  30

Glu Glu Leu Ser Ser Glu Ala Pro Pro Tyr Asn Ser Glu Pro Ala Glu
        35                  40                  45

Glu Ser Glu His Lys Asn Asn Asn Tyr Glu Pro Asn Leu Phe Lys Thr
    50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val
    130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
    210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
    290                 295                 300

Glu Asp Ser Phe Ser Leu Cys Phe Ser Lys Cys Arg Thr Lys Asn Leu
305                 310                 315                 320
```

```
Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
        355                 360                 365

Asn Val Ala His Gln Lys Pro Phe Glu Ser Gly Ser Asp Lys Ile Ser
    370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
        435                 440                 445

Ile Ser Ser Leu Pro Lys Ser Glu Lys Pro Leu Asn Glu Glu Thr Val
    450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
            500                 505                 510

Lys Glu Thr Phe Asn Ala Ser Phe Ser Gly His Met Thr Asp Pro Asn
        515                 520                 525

Phe Lys Lys Glu Thr Glu Ala Ser Glu Ser Gly Leu Glu Ile His Thr
    530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
            580                 585                 590

Ala Ile His Asp Glu Thr Phe Tyr Lys Gly Lys Lys Ile Pro Lys Asp
        595                 600                 605

Gln Lys Ser Glu Leu Ile Asn Cys Ser Ala Gln Phe Glu Ala Asn Ala
    610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
        675                 680                 685

Lys Glu Ala Lys Cys Asn Lys Glu Lys Leu Gln Leu Phe Ile Thr Pro
    690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Glu Val Leu Ala Ala
                725                 730                 735
```

-continued

```
Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
        755                 760                 765

Leu Ile Leu Thr Pro Thr Ser Lys Asp Val Leu Ser Asn Leu Val Met
    770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
        835                 840                 845

Val Gln Phe Asn Gln Asn Thr Asn Leu Arg Val Ile Gln Lys Asn Gln
    850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
        915                 920                 925

Leu Tyr Gly Asp Thr Gly Asp Lys Gln Ala Thr Gln Val Ser Ile Lys
    930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile  Ser Asn His Ser Phe  Gly Gly Ser
        995                 1000                 1005

Phe Arg  Thr Ala Ser Asn Lys  Glu Ile Lys Leu Ser  Glu His Asn
    1010                 1015                 1020

Ile Lys  Lys Ser Lys Met Phe  Phe Lys Asp Ile Glu  Glu Gln Tyr
    1025                 1030                 1035

Pro Thr  Ser Leu Ala Cys Val  Glu Ile Val Asn Thr  Leu Ala Leu
    1040                 1045                 1050

Asp Asn  Gln Lys Lys Leu Ser  Lys Pro Gln Ser Ile  Asn Thr Val
    1055                 1060                 1065

Ser Ala  His Leu Gln Ser Ser  Val Val Val Ser Asp  Cys Lys Asn
    1070                 1075                 1080

Ser His  Ile Thr Pro Gln Met  Leu Phe Ser Lys Gln  Asp Phe Asn
    1085                 1090                 1095

Ser Asn  His Asn Leu Thr Pro  Ser Gln Lys Ala Glu  Ile Thr Glu
    1100                 1105                 1110

Leu Ser  Thr Ile Leu Glu Glu  Ser Gly Ser Gln Phe  Glu Phe Thr
    1115                 1120                 1125

Gln Phe  Arg Lys Pro Ser Tyr  Ile Leu Gln Lys Ser  Thr Phe Glu
    1130                 1135                 1140

Val Pro  Glu Asn Gln Met Thr  Ile Leu Lys Thr Thr  Ser Glu Glu
```

```
    1145                1150                1155

Cys Arg  Asp Ala Asp Leu His  Val Ile Met Asn Ala  Pro Ser Ile
    1160                1165                1170

Gly Gln  Val Asp Ser Ser Lys  Gln Phe Glu Gly Thr  Val Glu Ile
    1175                1180                1185

Lys Arg  Lys Phe Ala Gly Leu  Leu Lys Asn Asp Cys  Asn Lys Ser
    1190                1195                1200

Ala Ser  Gly Tyr Leu Thr Asp  Glu Asn Glu Val Gly  Phe Arg Gly
    1205                1210                1215

Phe Tyr  Ser Ala His Gly Thr  Lys Leu Asn Val Ser  Thr Glu Ala
    1220                1225                1230

Leu Gln  Lys Ala Val Lys Leu  Phe Ser Asp Ile Glu  Asn Ile Ser
    1235                1240                1245

Glu Glu  Thr Ser Ala Glu Val  His Pro Ile Ser Leu  Ser Ser Ser
    1250                1255                1260

Lys Cys  His Asp Ser Val Val  Ser Met Phe Lys Ile  Glu Asn His
    1265                1270                1275

Asn Asp  Lys Thr Val Ser Glu  Lys Asn Asn Lys Cys  Gln Leu Ile
    1280                1285                1290

Leu Gln  Asn Asn Ile Glu Met  Thr Thr Gly Thr Phe  Val Glu Glu
    1295                1300                1305

Ile Thr  Glu Asn Tyr Lys Arg  Asn Thr Glu Asn Glu  Asp Asn Lys
    1310                1315                1320

Tyr Thr  Ala Ala Ser Arg Asn  Ser His Asn Leu Glu  Phe Asp Gly
    1325                1330                1335

Ser Asp  Ser Ser Lys Asn Asp  Thr Val Cys Ile His  Lys Asp Glu
    1340                1345                1350

Thr Asp  Leu Leu Phe Thr Asp  Gln His Asn Ile Cys  Leu Lys Leu
    1355                1360                1365

Ser Gly  Gln Phe Met Lys Glu  Gly Asn Thr Gln Ile  Lys Glu Asp
    1370                1375                1380

Leu Ser  Asp Leu Thr Phe Leu  Glu Val Ala Lys Ala  Gln Glu Ala
    1385                1390                1395

Cys His  Gly Asn Thr Ser Asn  Lys Glu Gln Leu Thr  Ala Thr Lys
    1400                1405                1410

Thr Glu  Gln Asn Ile Lys Asp  Phe Glu Thr Ser Asp  Thr Phe Phe
    1415                1420                1425

Gln Thr  Ala Ser Gly Lys Asn  Ile Ser Val Ala Lys  Glu Ser Phe
    1430                1435                1440

Asn Lys  Ile Val Asn Phe Phe  Asp Gln Lys Pro Glu  Glu Leu His
    1445                1450                1455

Asn Phe  Ser Leu Asn Ser Glu  Leu His Ser Asp Ile  Arg Lys Asn
    1460                1465                1470

Lys Met  Asp Ile Leu Ser Tyr  Glu Glu Thr Asp Ile  Val Lys His
    1475                1480                1485

Lys Ile  Leu Lys Glu Ser Val  Pro Val Gly Thr Gly  Asn Gln Leu
    1490                1495                1500

Val Thr  Phe Gln Gly Gln Pro  Glu Arg Asp Glu Lys  Ile Lys Glu
    1505                1510                1515

Pro Thr  Leu Leu Gly Phe His  Thr Ala Ser Gly Lys  Lys Val Lys
    1520                1525                1530

Ile Ala  Lys Glu Ser Leu Asp  Lys Val Lys Asn Leu  Phe Asp Glu
    1535                1540                1545
```

```
Lys Glu  Gln Gly Thr Ser Glu  Ile Thr Ser Phe Ser  His Gln Trp
    1550                 1555                 1560

Ala Lys  Thr Leu Lys Tyr Arg  Glu Ala Cys Lys Asp  Leu Glu Leu
    1565                 1570                 1575

Ala Cys  Glu Thr Ile Glu Ile  Thr Ala Ala Pro Lys  Cys Lys Glu
    1580                 1585                 1590

Met Gln  Asn Ser Leu Asn Asn  Asp Lys Asn Leu Val  Ser Ile Glu
    1595                 1600                 1605

Thr Val  Val Pro Pro Lys Leu  Leu Ser Asp Asn Leu  Cys Arg Gln
    1610                 1615                 1620

Thr Glu  Asn Leu Lys Thr Ser  Lys Ser Ile Phe Leu  Lys Val Lys
    1625                 1630                 1635

Val His  Glu Asn Val Glu Lys  Glu Thr Ala Lys Ser  Pro Ala Thr
    1640                 1645                 1650

Cys Tyr  Thr Asn Gln Ser Pro  Tyr Ser Val Ile Glu  Asn Ser Ala
    1655                 1660                 1665

Leu Ala  Phe Tyr Thr Ser Cys  Ser Arg Lys Thr Ser  Val Ser Gln
    1670                 1675                 1680

Thr Ser  Leu Leu Glu Ala Lys  Lys Trp Leu Arg Glu  Gly Ile Phe
    1685                 1690                 1695

Asp Gly  Gln Pro Glu Arg Ile  Asn Thr Ala Asp Tyr  Val Gly Asn
    1700                 1705                 1710

Tyr Leu  Tyr Glu Asn Asn Ser  Asn Ser Thr Ile Ala  Glu Asn Asp
    1715                 1720                 1725

Lys Asn  His Leu Ser Glu Lys  Gln Asp Thr Tyr Leu  Ser Asn Ser
    1730                 1735                 1740

Ser Met  Ser Asn Ser Tyr Ser  Tyr His Ser Asp Glu  Val Tyr Asn
    1745                 1750                 1755

Asp Ser  Gly Tyr Leu Ser Lys  Asn Lys Leu Asp Ser  Gly Ile Glu
    1760                 1765                 1770

Pro Val  Leu Lys Asn Val Glu  Asp Gln Lys Asn Thr  Ser Phe Ser
    1775                 1780                 1785

Lys Val  Ile Ser Asn Val Lys  Asp Ala Asn Ala Tyr  Pro Gln Thr
    1790                 1795                 1800

Val Asn  Glu Asp Ile Cys Val  Glu Glu Leu Val Thr  Ser Ser Ser
    1805                 1810                 1815

Pro Cys  Lys Asn Lys Asn Ala  Ala Ile Lys Leu Ser  Ile Ser Asn
    1820                 1825                 1830

Ser Asn  Asn Phe Glu Val Gly  Pro Pro Ala Phe Arg  Ile Ala Ser
    1835                 1840                 1845

Gly Lys  Ile Val Cys Val Ser  His Glu Thr Ile Lys  Lys Val Lys
    1850                 1855                 1860

Asp Ile  Phe Thr Asp Ser Phe  Ser Lys Val Ile Lys  Glu Asn Asn
    1865                 1870                 1875

Glu Asn  Lys Ser Lys Ile Cys  Gln Thr Lys Ile Met  Ala Gly Cys
    1880                 1885                 1890

Tyr Glu  Ala Leu Asp Asp Ser  Glu Asp Ile Leu His  Asn Ser Leu
    1895                 1900                 1905

Asp Asn  Asp Glu Cys Ser Thr  His Ser His Lys Val  Phe Ala Asp
    1910                 1915                 1920

Ile Gln  Ser Glu Glu Ile Leu  Gln His Asn Gln Asn  Met Ser Gly
    1925                 1930                 1935
```

```
Leu Glu  Lys Val Ser Lys Ile  Ser Pro Cys Asp Val  Ser Leu Glu
    1940                 1945                 1950

Thr Ser  Asp Ile Cys Lys Cys  Ser Ile Gly Lys Leu  His Lys Ser
    1955                 1960                 1965

Val Ser  Ser Ala Asn Thr Cys  Gly Ile Phe Ser Thr  Ala Ser Gly
    1970                 1975                 1980

Lys Ser  Val Gln Val Ser Asp  Ala Ser Leu Gln Asn  Ala Arg Gln
    1985                 1990                 1995

Val Phe  Ser Glu Ile Glu Asp  Ser Thr Lys Gln Val  Phe Ser Lys
    2000                 2005                 2010

Val Leu  Phe Lys Ser Asn Glu  His Ser Asp Gln Leu  Thr Arg Glu
    2015                 2020                 2025

Glu Asn  Thr Ala Ile Arg Thr  Pro Glu His Leu Ile  Ser Gln Lys
    2030                 2035                 2040

Gly Phe  Ser Tyr Asn Val Val  Asn Ser Ser Ala Phe  Ser Gly Phe
    2045                 2050                 2055

Ser Thr  Ala Ser Gly Lys Gln  Val Ser Ile Leu Glu  Ser Ser Leu
    2060                 2065                 2070

His Lys  Val Lys Gly Val Leu  Glu Glu Phe Asp Leu  Ile Arg Thr
    2075                 2080                 2085

Glu His  Ser Leu His Tyr Ser  Pro Thr Ser Arg Gln  Asn Val Ser
    2090                 2095                 2100

Lys Ile  Leu Pro Arg Val Asp  Lys Arg Asn Pro Glu  His Cys Val
    2105                 2110                 2115

Asn Ser  Glu Met Glu Lys Thr  Cys Ser Lys Glu Phe  Lys Leu Ser
    2120                 2125                 2130

Asn Asn  Leu Asn Val Glu Gly  Gly Ser Ser Glu Asn  Asn His Ser
    2135                 2140                 2145

Ile Lys  Val Ser Pro Tyr Leu  Ser Gln Phe Gln Gln  Asp Lys Gln
    2150                 2155                 2160

Gln Leu  Val Leu Gly Thr Lys  Val Ser Leu Val Glu  Asn Ile His
    2165                 2170                 2175

Val Leu  Gly Lys Glu Gln Ala  Ser Pro Lys Asn Val  Lys Met Glu
    2180                 2185                 2190

Ile Gly  Lys Thr Glu Thr Phe  Ser Asp Val Pro Val  Lys Thr Asn
    2195                 2200                 2205

Ile Glu  Val Cys Ser Thr Tyr  Ser Lys Asp Ser Glu  Asn Tyr Phe
    2210                 2215                 2220

Glu Thr  Glu Ala Val Glu Ile  Ala Lys Ala Phe Met  Glu Asp Asp
    2225                 2230                 2235

Glu Leu  Thr Asp Ser Lys Leu  Pro Ser His Ala Thr  His Ser Leu
    2240                 2245                 2250

Phe Thr  Cys Pro Glu Asn Glu  Glu Met Val Leu Ser  Asn Ser Arg
    2255                 2260                 2265

Ile Gly  Lys Arg Arg Gly Glu  Pro Leu Ile Leu Val  Gly Glu Pro
    2270                 2275                 2280

Ser Ile  Lys Arg Asn Leu Leu  Asn Glu Phe Asp Arg  Ile Ile Glu
    2285                 2290                 2295

Asn Gln  Glu Lys Ser Leu Lys  Ala Ser Lys Ser Thr  Pro Asp Gly
    2300                 2305                 2310

Thr Ile  Lys Asp Arg Arg Leu  Phe Met His His Val  Ser Leu Glu
    2315                 2320                 2325

Pro Ile  Thr Cys Val Pro Phe  Arg Thr Thr Lys Glu  Arg Gln Glu
```

```
    2330                2335                2340

Ile Gln  Asn Pro Asn Phe Thr  Ala Pro Gly Gln Glu  Phe Leu Ser
    2345                2350                2355

Lys Ser  His Leu Tyr Glu His  Leu Thr Leu Glu Lys  Ser Ser Ser
    2360                2365                2370

Asn Leu  Ala Val Ser Gly His  Pro Phe Tyr Gln Val  Ser Ala Thr
    2375                2380                2385

Arg Asn  Glu Lys Met Arg His  Leu Ile Thr Thr Gly  Arg Pro Thr
    2390                2395                2400

Lys Val  Phe Val Pro Pro Phe  Lys Thr Lys Ser His  Phe His Arg
    2405                2410                2415

Val Glu  Gln Cys Val Arg Asn  Ile Asn Leu Glu Glu  Asn Arg Gln
    2420                2425                2430

Lys Gln  Asn Ile Asp Gly His  Gly Ser Asp Asp Ser  Lys Asn Lys
    2435                2440                2445

Ile Asn  Asp Asn Glu Ile His  Gln Phe Asn Lys Asn  Asn Ser Asn
    2450                2455                2460

Gln Ala  Ala Ala Val Thr Phe  Thr Lys Cys Glu Glu  Glu Pro Leu
    2465                2470                2475

Asp Leu  Ile Thr Ser Leu Gln  Asn Ala Arg Asp Ile  Gln Asp Met
    2480                2485                2490

Arg Ile  Lys Lys Lys Gln Arg  Gln Arg Val Phe Pro  Gln Pro Gly
    2495                2500                2505

Ser Leu  Tyr Leu Ala Lys Thr  Ser Thr Leu Pro Arg  Ile Ser Leu
    2510                2515                2520

Lys Ala  Ala Val Gly Gly Gln  Val Pro Ser Ala Cys  Ser His Lys
    2525                2530                2535

Gln Leu  Tyr Thr Tyr Gly Val  Ser Lys His Cys Ile  Lys Ile Asn
    2540                2545                2550

Ser Lys  Asn Ala Glu Ser Phe  Gln Phe His Thr Glu  Asp Tyr Phe
    2555                2560                2565

Gly Lys  Glu Ser Leu Trp Thr  Gly Lys Gly Ile Gln  Leu Ala Asp
    2570                2575                2580

Gly Gly  Trp Leu Ile Pro Ser  Asn Asp Gly Lys Ala  Gly Lys Glu
    2585                2590                2595

Glu Phe  Tyr Arg Ala Leu Cys  Asp Thr Pro Gly Val  Asp Pro Lys
    2600                2605                2610

Leu Ile  Ser Arg Ile Trp Val  Tyr Asn His Tyr Arg  Trp Ile Ile
    2615                2620                2625

Trp Lys  Leu Ala Ala Met Glu  Cys Ala Phe Pro Lys  Glu Phe Ala
    2630                2635                2640

Asn Arg  Cys Leu Ser Pro Glu  Arg Val Leu Leu Gln  Leu Lys Tyr
    2645                2650                2655

Arg Tyr  Asp Thr Glu Ile Asp  Arg Ser Arg Arg Ser  Ala Ile Lys
    2660                2665                2670

Lys Ile  Met Glu Arg Asp Asp  Thr Ala Ala Lys Thr  Leu Val Leu
    2675                2680                2685

Cys Val  Ser Asp Ile Ile Ser  Leu Ser Ala Asn Ile  Ser Glu Thr
    2690                2695                2700

Ser Ser  Asn Lys Thr Ser Ser  Ala Asp Thr Gln Lys  Val Ala Ile
    2705                2710                2715

Ile Glu  Leu Thr Asp Gly Trp  Tyr Ala Val Lys Ala  Gln Leu Asp
    2720                2725                2730
```

```
Pro Pro  Leu Leu Ala Val Leu  Lys Asn Gly Arg Leu  Thr Val Gly
    2735                 2740                 2745

Gln Lys  Ile Ile Leu His Gly  Ala Glu Leu Val Gly  Ser Pro Asp
    2750                 2755                 2760

Ala Cys  Thr Pro Leu Glu Ala  Pro Glu Ser Leu Met  Leu Lys Ile
    2765                 2770                 2775

Ser Ala  Asn Ser Thr Arg Pro  Ala Arg Trp Tyr Thr  Lys Leu Gly
    2780                 2785                 2790

Phe Phe  Pro Asp Pro Arg Pro  Phe Pro Leu Pro Leu  Ser Ser Leu
    2795                 2800                 2805

Phe Ser  Asp Gly Gly Asn Val  Gly Cys Val Asp Val  Ile Ile Gln
    2810                 2815                 2820

Arg Ala  Tyr Pro Ile Gln Trp  Met Glu Lys Thr Ser  Ser Gly Leu
    2825                 2830                 2835

Tyr Ile  Phe Arg Asn Glu Arg  Glu Glu Glu Lys Glu  Ala Ala Lys
    2840                 2845                 2850

Tyr Val  Glu Ala Gln Gln Lys  Arg Leu Glu Ala Leu  Phe Thr Lys
    2855                 2860                 2865

Ile Gln  Glu Glu Phe Glu Glu  His Glu Glu Asn Thr  Thr Lys Pro
    2870                 2875                 2880

Tyr Leu  Pro Ser Arg Ala Leu  Thr Arg Gln Gln Val  Arg Ala Leu
    2885                 2890                 2895

Gln Asp  Gly Ala Glu Leu Tyr  Glu Ala Val Lys Asn  Ala Ala Asp
    2900                 2905                 2910

Pro Ala  Tyr Leu Glu Gly Tyr  Phe Ser Glu Glu Gln  Leu Arg Ala
    2915                 2920                 2925

Leu Asn  Asn His Arg Gln Met  Leu Asn Asp Lys Lys  Gln Ala Gln
    2930                 2935                 2940

Ile Gln  Leu Glu Ile Arg Lys  Ala Met Glu Ser Ala  Glu Gln Lys
    2945                 2950                 2955

Glu Gln  Gly Leu Ser Arg Asp  Val Thr Thr Val Trp  Lys Leu Arg
    2960                 2965                 2970

Ile Val  Ser Tyr Ser Lys Lys  Glu Lys Asp Ser Val  Ile Leu Ser
    2975                 2980                 2985

Ile Trp  Arg Pro Ser Ser Asp  Leu Tyr Ser Leu Leu  Thr Glu Gly
    2990                 2995                 3000

Lys Arg  Tyr Arg Ile Tyr His  Leu Ala Thr Ser Lys  Ser Lys Ser
    3005                 3010                 3015

Lys Ser  Glu Arg Ala Asn Ile  Gln Leu Ala Ala Thr  Lys Lys Thr
    3020                 3025                 3030

Gln Tyr  Gln Gln Leu Pro Val  Ser Asp Glu Ile Leu  Phe Gln Ile
    3035                 3040                 3045

Tyr Gln  Pro Arg Glu Pro Leu  His Phe Ser Lys Phe  Leu Asp Pro
    3050                 3055                 3060

Asp Phe  Gln Pro Ser Cys Ser  Glu Val Asp Leu Ile  Gly Phe Val
    3065                 3070                 3075

Val Ser  Val Val Lys Lys Thr  Gly Leu Ala Pro Phe  Val Tyr Leu
    3080                 3085                 3090

Ser Asp  Glu Cys Tyr Asn Leu  Leu Ala Ile Lys Phe  Trp Ile Asp
    3095                 3100                 3105

Leu Asn  Glu Asp Ile Ile Lys  Pro His Met Leu Ile  Ala Ala Ser
    3110                 3115                 3120
```

```
Asn Leu  Gln Trp Arg Pro Glu  Ser Lys Ser Gly Leu  Leu Thr Leu
    3125                 3130                 3135

Phe Ala  Gly Asp Phe Ser Val  Phe Ser Ala Ser Pro  Lys Glu Gly
    3140                 3145                 3150

His Phe  Gln Glu Thr Phe Asn  Lys Met Lys Asn Thr  Val Glu Asn
    3155                 3160                 3165

Ile Asp  Ile Leu Cys Asn Glu  Ala Glu Asn Lys Leu  Met His Ile
    3170                 3175                 3180

Leu His  Ala Asn Asp Pro Lys  Trp Ser Thr Pro Thr  Lys Asp Cys
    3185                 3190                 3195

Thr Ser  Gly Pro Tyr Thr Ala  Gln Ile Ile Pro Gly  Thr Gly Asn
    3200                 3205                 3210

Lys Leu  Leu Met Ser Ser Pro  Asn Cys Glu Ile Tyr  Tyr Gln Ser
    3215                 3220                 3225

Pro Leu  Ser Leu Cys Met Ala  Lys Arg Lys Ser Val  Ser Thr Pro
    3230                 3235                 3240

Val Ser  Ala Gln Met Thr Ser  Lys Ser Cys Lys Gly  Glu Lys Glu
    3245                 3250                 3255

Ile Asp  Asp Gln Lys Asn Cys  Lys Lys Arg Arg Ala  Leu Asp Phe
    3260                 3265                 3270

Leu Ser  Arg Leu Pro Leu Pro  Pro Pro Val Ser Pro  Ile Cys Thr
    3275                 3280                 3285

Phe Val  Ser Pro Ala Ala Gln  Lys Ala Phe Gln Pro  Pro Arg Ser
    3290                 3295                 3300

Cys Gly  Thr Lys Tyr Glu Thr  Pro Ile Lys Lys Lys  Glu Leu Asn
    3305                 3310                 3315

Ser Pro  Gln Met Thr Pro Phe  Lys Lys Phe Asn Glu  Ile Ser Leu
    3320                 3325                 3330

Leu Glu  Ser Asn Ser Ile Ala  Asp Glu Glu Leu Ala  Leu Ile Asn
    3335                 3340                 3345

Thr Gln  Ala Leu Leu Ser Gly  Ser Thr Gly Glu Lys  Gln Phe Ile
    3350                 3355                 3360

Ser Val  Ser Glu Ser Thr Arg  Thr Ala Pro Thr Ser  Ser Glu Asp
    3365                 3370                 3375

Tyr Leu  Arg Leu Lys Arg Arg  Cys Thr Thr Ser Leu  Ile Lys Glu
    3380                 3385                 3390

Gln Glu  Ser Ser Gln Ala Ser  Thr Glu Glu Cys Glu  Lys Asn Lys
    3395                 3400                 3405

Gln Asp  Thr Ile Thr Thr Lys  Lys Tyr Ile
    3410                 3415
```

<210> SEQ ID NO 4
<211> LENGTH: 11386
<212> TYPE: DNA
<213> ORGANISM: Homo sapiens

<400> SEQUENCE: 4

```
gtggcgcgag cttctgaaac taggcggcag aggcggagcc gctgtggcac tgctgcgcct     60

ctgctgcgcc tcgggtgtct tttgcggcgg tgggtcgccg ccgggagaag cgtgagggga    120

cagatttgtg accggcgcgg tttttgtcag cttactccgg ccaaaaaaga actgcacctc    180

tggagcggac ttatttacca agcattggag gaatatcgta ggtaaaaatg cctattggat    240

ccaaagagag gccaacattt tttgaaattt ttaagacacg ctgcaacaaa gcagatttag    300

gaccaataag tcttaattgg tttgaagaac tttcttcaga agctccaccc tataattctg    360
```

```
aacctgcaga agaatctgaa cataaaaaca acaattacga accaaaccta tttaaaactc    420
cacaaaggaa accatcttat aatcagctgg cttcaactcc aataatattc aaagagcaag    480
ggctgactct gccgctgtac caatctcctg taaaagaatt agataaattc aaattagact    540
taggaaggaa tgttcccaat agtagacata aaagtcttcg cacagtgaaa actaaaatgg    600
atcaagcaga tgatgtttcc tgtccacttc taaattcttg tcttagtgaa agtcctgttg    660
ttctacaatg tacacatgta acaccacaaa gagataagtc agtggtatgt gggagtttgt    720
ttcatacacc aaagtttgtg aagggtcgtc agacaccaaa acatatttct gaaagtctag    780
gagctgaggt ggatcctgat atgtcttggt caagttcttt agctacacca cccaccctta    840
gttctactgt gctcatagtc agaaatgaag aagcatctga aactgtattt cctcatgata    900
ctactgctaa tgtgaaaagc tatttttcca atcatgatga aagtctgaag aaaaatgata    960
gatttatcgc ttctgtgaca gacagtgaaa acacaaatca aagagaagct gcaagtcatg   1020
gatttggaaa aacatcaggg aattcattta aagtaaatag ctgcaaagac cacattggaa   1080
agtcaatgcc aaatgtccta gaagatgaag tatatgaaac agttgtagat acctctgaag   1140
aagatagttt ttcattatgt ttttctaaat gtagaacaaa aaatctacaa aaagtaagaa   1200
ctagcaagac taggaaaaaa attttccatg aagcaaacgc tgatgaatgt gaaaaatcta   1260
aaaaccaagt gaaagaaaaa tactcatttg tatctgaagt ggaaccaaat gatactgatc   1320
cattagattc aaatgtagca aatcagaagc cctttgagag tggaagtgac aaaatctcca   1380
aggaagttgt accgtctttg gcctgtgaat ggtctcaact aaccctttca ggtctaaatg   1440
gagcccagat ggagaaaata cccctattgc atatttcttc atgtgaccaa aatatttcag   1500
aaaaagacct attagacaca gagaacaaaa gaaagaaaga ttttcttact tcagagaatt   1560
ctttgccacg tatttctagc ctaccaaaat cagagaagcc attaaatgag gaaacagtgg   1620
taaataagag agatgaagag cagcatcttg aatctcatac agactgcatt cttgcagtaa   1680
agcaggcaat atctggaact tctccagtgg cttcttcatt tcagggtatc aaaaagtcta   1740
tattcagaat aagagaatca cctaaagaga ctttcaatgc aagtttttca ggtcatatga   1800
ctgatccaaa ctttaaaaaa gaaactgaag cctctgaaag tggactggaa atacatactg   1860
tttgctcaca gaaggaggac tccttatgtc caaatttaat tgataatgga agctggccag   1920
ccaccaccac acagaattct gtagctttga agaatgcagg tttaatatcc actttgaaaa   1980
agaaaacaaa taagtttatt tatgctatac atgatgaaac atcttataaa ggaaaaaaaa   2040
taccgaaaga ccaaaaatca gaactaatta actgttcagc ccagtttgaa gcaaatgctt   2100
ttgaagcacc acttacattt gcaaatgctg attcaggttt attgcattct tctgtgaaaa   2160
gaagctgttc acagaatgat tctgaagaac caactttgtc cttaactagc tcttttggga   2220
caattctgag gaaatgttct agaaatgaaa catgttctaa taatacagta atctctcagg   2280
atcttgatta taaagaagca aaatgtaata aggaaaaact acagttattt attaccccag   2340
aagctgattc tctgtcatgc ctgcaggaag gacagtgtga aaatgatcca aaaagcaaaa   2400
aagtttcaga tataaaagaa gaggtcttgg ctgcagcatg tcacccagta caacattcaa   2460
aagtggaata cagtgatact gactttcaat cccagaaaag tcttttatat gatcatgaaa   2520
atgccagcac tcttatttta actcctactt ccaaggatgt tctgtcaaac ctagtcatga   2580
tttctagagg caaagaatca tacaaaatgt cagacaagct caaaggtaac aattatgaat   2640
ctgatgttga attaaccaaa aatattccca tggaaaagaa tcaagatgta tgtgctttaa   2700
```

-continued

```
atgaaaatta taaaaacgtt gagctgttgc cacctgaaaa atacatgaga gtagcatcac   2760
cttcaagaaa ggtacaattc aaccaaaaca caaatctaag agtaatccaa aaaaatcaag   2820
aagaaactac ttcaatttca aaaataactg tcaatccaga ctctgaagaa cttttctcag   2880
acaatgagaa taattttgtc ttccaagtag ctaatgaaag gaataatctt gctttaggaa   2940
atactaagga acttcatgaa acagacttga cttgtgtaaa cgaacccatt ttcaagaact   3000
ctaccatggt tttatatgga gacacaggtg ataaacaagc aacccaagtg tcaattaaaa   3060
aagatttggt ttatgttctt gcagaggaga acaaaaatag tgtaaagcag catataaaaa   3120
tgactctagg tcaagattta aaatcggaca tctccttgaa tatagataaa ataccagaaa   3180
aaaataatga ttacatgaac aaatgggcag gactcttagg tccaatttca aatcacagtt   3240
ttggaggtag cttcagaaca gcttcaaata aggaaatcaa gctctctgaa cataacatta   3300
agaagagcaa aatgttcttc aaagatattg aagaacaata tcctactagt ttagcttgtg   3360
ttgaaattgt aaataccttg gcattagata atcaaaagaa actgagcaag cctcagtcaa   3420
ttaatactgt atctgcacat ttacagagta gtgtagttgt ttctgattgt aaaaatagtc   3480
atataacccc tcagatgtta ttttccaagc aggattttaa ttcaaaccat aatttaacac   3540
ctagccaaaa ggcagaaatt acagaacttt ctactatatt agaagaatca ggaagtcagt   3600
ttgaatttac tcagtttaga aaaccaagct acatattgca gaagagtaca tttgaagtgc   3660
ctgaaaacca gatgactatc ttaaagacca cttctgagga atgcagagat gctgatcttc   3720
atgtcataat gaatgcccca tcgattggtc aggtagacag cagcaagcaa tttgaaggta   3780
cagttgaaat taaacggaag tttgctggcc tgttgaaaaa tgactgtaac aaaagtgctt   3840
ctggttattt aacagatgaa aatgaagtgg ggtttagggg cttttattct gctcatggca   3900
caaaactgaa tgtttctact gaagctctgc aaaaagctgt gaaactgttt agtgatattg   3960
agaatattag tgaggaaact tctgcagagg tacatccaat aagtttatct tcaagtaaat   4020
gtcatgattc tgttgtttca atgtttaaga tagaaaatca taatgataaa actgtaagtg   4080
aaaaaaataa taaatgccaa ctgatattac aaaataatat tgaaatgact actggcactt   4140
ttgttgaaga aattactgaa aattacaaga gaaatactga aaatgaagat aacaaatata   4200
ctgctgccag tagaaattct cataacttag aatttgatgg cagtgattca agtaaaaatg   4260
atactgtttg tattcataaa gatgaaacgg acttgctatt tactgatcag cacaacatat   4320
gtcttaaatt atctggccag tttatgaagg agggaaacac tcagattaaa gaagatttgt   4380
cagatttaac tttttggaa gttgcgaaag ctcaagaagc atgtcatggt aatacttcaa   4440
ataaagaaca gttaactgct actaaaacgg agcaaaatat aaaagatttt gagacttctg   4500
atacattttt tcagactgca agtgggaaaa atattagtgt cgccaaagag tcatttaata   4560
aaattgtaaa tttctttgat cagaaaccag aagaattgca taacttttcc ttaaattctg   4620
aattacattc tgacataaga aagaacaaaa tggacattct aagttatgag gaaacagaca   4680
tagttaaaca caaaatactg aaagaaagtg tcccagttgg tactggaaat caactagtga   4740
ccttccaggg acaacccgaa cgtgatgaaa agatcaaaga acctactcta ttgggttttc   4800
atacagctag cgggaaaaaa gttaaaattg caaaggaatc tttggacaaa gtgaaaaacc   4860
tttttgatga aaaagagcaa ggtactagtg aaatcaccag ttttagccat caatgggcaa   4920
agaccctaaa gtacagagag gcctgtaaag accttgaatt agcatgtgag accattgaga   4980
tcacagctgc cccaaagtgt aaagaaatgc agaattctct caataatgat aaaaaccttg   5040
tttctattga gactgtggtg ccacctaagc tcttaagtga taatttatgt agacaaactg   5100
```

```
aaaatctcaa aacatcaaaa agtatctttt tgaaagttaa agtacatgaa aatgtagaaa   5160
aagaaacagc aaaaagtcct gcaacttgtt acacaaatca gtccccttat tcagtcattg   5220
aaaattcagc cttagctttt tacacaagtt gtagtagaaa aacttctgtg agtcagactt   5280
cattacttga agcaaaaaaa tggcttagag aaggaatatt tgatggtcaa ccagaaagaa   5340
taaatactgc agattatgta ggaaattatt tgtatgaaaa taattcaaac agtactatag   5400
ctgaaaatga caaaaatcat ctctccgaaa aacaagatac ttatttaagt aacagtagca   5460
tgtctaacag ctattcctac cattctgatg aggtatataa tgattcagga tatctctcaa   5520
aaaataaact tgattctggt attgagccag tattgaagaa tgttgaagat caaaaaaaca   5580
ctagtttttc caaagtaata tccaatgtaa aagatgcaaa tgcataccca caaactgtaa   5640
atgaagatat ttgcgttgag gaacttgtga ctagctcttc accctgcaaa aataaaaatg   5700
cagccattaa attgtccata tctaatagta ataattttga ggtagggcca cctgcattta   5760
ggatagccag tggtaaaatc gtttgtgttt cacatgaaac aattaaaaaa gtgaaagaca   5820
tatttacaga cagtttcagt aaagtaatta aggaaaacaa cgagaataaa tcaaaaattt   5880
gccaaacgaa aattatggca ggttgttacg aggcattgga tgattcagag gatattcttc   5940
ataactctct agataatgat gaatgtagca cgcattcaca taaggttttt gctgacattc   6000
agagtgaaga aattttacaa cataaccaaa atatgtctgg attggagaaa gtttctaaaa   6060
tatcaccttg tgatgttagt ttggaaactt cagatatatg taaatgtagt atagggaagc   6120
ttcataagtc agtctcatct gcaaatactt gtgggatttt tagcacagca agtggaaaat   6180
ctgtccaggt atcagatgct tcattacaaa acgcaagaca agtgttttct gaaatagaag   6240
atagtaccaa gcaagtcttt tccaaagtat tgtttaaaag taacgaacat tcagaccagc   6300
tcacaagaga agaaaatact gctatacgta ctccagaaca tttaatatcc caaaaaggct   6360
tttcatataa tgtggtaaat tcatctgctt tctctggatt tagtacagca agtggaaagc   6420
aagtttccat tttagaaagt tccttacaca aagttaaggg agtgttagag gaatttgatt   6480
taatcagaac tgagcatagt cttcactatt cacctacgtc tagacaaaat gtatcaaaaa   6540
tacttcctcg tgttgataag agaaacccag agcactgtgt aaactcagaa atggaaaaaa   6600
cctgcagtaa agaatttaaa ttatcaaata acttaaatgt tgaaggtggt tcttcagaaa   6660
ataatcactc tattaaagtt tctccatatc tctctcaatt tcaacaagac aaacaacagt   6720
tggtattagg aaccaaagtg tcacttgttg agaacattca tgttttggga aaagaacagg   6780
cttcacctaa aaacgtaaaa atggaaattg gtaaaactga aactttttct gatgttcctg   6840
tgaaaacaaa tatagaagtt tgttctactt actccaaaga ttcagaaaac tactttgaaa   6900
cagaagcagt agaaattgct aaagctttta tggaagatga tgaactgaca gattctaaac   6960
tgccaagtca tgccacacat tctcttttta catgtcccga aaatgaggaa atggttttgt   7020
caaattcaag aattggaaaa agaagaggag agccccttat cttagtggga gaaccctcaa   7080
tcaaaagaaa cttattaaat gaatttgaca ggataataga aaatcaagaa aaatccttaa   7140
aggcttcaaa aagcactcca gatggcacaa taaaagatcg aagattgttt atgcatcatg   7200
tttctttaga gccgattacc tgtgtaccct ttcgcacaac taaggaacgt caagagatac   7260
agaatccaaa ttttaccgca cctggtcaag aatttctgtc taaatctcat ttgtatgaac   7320
atctgacttt ggaaaaatct tcaagcaatt tagcagtttc aggacatcca ttttatcaag   7380
tttctgctac aagaaatgaa aaaatgagac acttgattac tacaggcaga ccaaccaaag   7440
```

```
tctttgttcc accttttaaa actaaatcac attttcacag agttgaacag tgtgttagga   7500
atattaactt ggaggaaaac agacaaaagc aaaacattga tggacatggc tctgatgata   7560
gtaaaaataa gattaatgac aatgagattc atcagtttaa caaaaacaac tccaatcaag   7620
cagcagctgt aactttcaca aagtgtgaag aagaaccttt agatttaatt acaagtcttc   7680
agaatgccag agatatacag gatatgcgaa ttaagaagaa acaaaggcaa cgcgtctttc   7740
cacagccagg cagtctgtat cttgcaaaaa catccactct gcctcgaatc tctctgaaag   7800
cagcagtagg aggccaagtt ccctctgcgt gttctcataa acagctgtat acgtatggcg   7860
tttctaaaca ttgcataaaa attaacagca aaaatgcaga gtcttttcag tttcacactg   7920
aagattattt tggtaaggaa agtttatgga ctggaaaagg aatacagttg gctgatggtg   7980
gatggctcat accctccaat gatggaaagg ctggaaaaga agaattttat agggctctgt   8040
gtgacactcc aggtgtggat ccaaagctta tttctagaat ttgggtttat aatcactata   8100
gatggatcat atggaaactg gcagctatgg aatgtgcctt tcctaaggaa tttgctaata   8160
gatgcctaag cccagaaagg gtgcttcttc aactaaaata cagatatgat acggaaattg   8220
atagaagcag aagatcggct ataaaaaaga taatggaaag ggatgacaca gctgcaaaaa   8280
cacttgttct ctgtgtttct gacataattt cattgagcgc aaatatatct gaaacttcta   8340
gcaataaaac tagtagtgca gatacccaaa aagtggccat tattgaactt acagatgggt   8400
ggtatgctgt taaggcccag ttagatcctc ccctcttagc tgtcttaaag aatggcagac   8460
tgacagttgg tcagaagatt attcttcatg gagcagaact ggtgggctct cctgatgcct   8520
gtacacctct tgaagcccca gaatctctta tgttaaagat ttctgctaac agtactcggc   8580
ctgctcgctg gtataccaaa cttggattct ttcctgaccc tagacctttt cctctgccct   8640
tatcatcgct tttcagtgat ggaggaaatg ttggttgtgt tgatgtaatt attcaaagag   8700
catacccctat acagtggatg gagaagacat catctggatt atacatattt cgcaatgaaa   8760
gagaggaaga aaaggaagca gcaaaatatg tggaggccca acaaaagaga ctagaagcct   8820
tattcactaa aattcaggag gaatttgaag aacatgaaga aaacacaaca aaaccatatt   8880
taccatcacg tgcactaaca agacagcaag ttcgtgcttt gcaagatggt gcagagcttt   8940
atgaagcagt gaagaatgca gcagacccag cttaccttga gggttatttc agtgaagagc   9000
agttaagagc cttgaataat cacaggcaaa tgttgaatga taagaaacaa gctcagatcc   9060
agttggaaat taggaaggcc atggaatctg ctgaacaaaa ggaacaaggt ttatcaaggg   9120
atgtcacaac cgtgtggaag ttgcgtattg taagctattc aaaaaaagaa aaagattcag   9180
ttatactgag tatttggcgt ccatcatcag atttatattc tctgttaaca gaaggaaaga   9240
gatacagaat ttatcatctt gcaacttcaa aatctaaaag taaatctgaa agagctaaca   9300
tacagttagc agcgacaaaa aaaactcagt atcaacaact accggtttca gatgaaattt   9360
tatttcagat ttaccagcca cgggagcccc ttcacttcag caaattttta gatccagact   9420
ttcagccatc ttgttctgag gtggacctaa taggatttgt cgtttctgtt gtgaaaaaaa   9480
caggacttgc ccctttcgtc tatttgtcag acgaatgtta caatttactg gcaataaagt   9540
tttggataga ccttaatgag gacattatta agcctcatat gttaattgct gcaagcaacc   9600
tccagtggcg accagaatcc aaatcaggcc ttcttacttt atttgctgga gatttttctg   9660
tgttttctgc tagtccaaaa gagggccact ttcaagagac attcaacaaa atgaaaaata   9720
ctgttgagaa tattgacata ctttgcaatg aagcagaaaa caagcttatg catatactgc   9780
atgcaaatga tcccaagtgg tccaccccaa ctaaagactg tacttcaggg ccgtacactg   9840
```

```
ctcaaatcat tcctggtaca ggaaacaagc ttctgatgtc ttctcctaat tgtgagatat   9900
attatcaaag tcctttatca ctttgtatgg ccaaaaggaa gtctgtttcc acacctgtct   9960
cagcccagat gacttcaaag tcttgtaaag gggagaaaga gattgatgac caaaagaact  10020
gcaaaaagag aagagccttg gatttcttga gtagactgcc tttacctcca cctgttagtc  10080
ccatttgtac atttgtttct ccggctgcac agaaggcatt tcagccacca aggagttgtg  10140
gcaccaaata cgaaacaccc ataaagaaaa aagaactgaa ttctcctcag atgactccat  10200
ttaaaaaatt caatgaaatt tctcttttgg aaagtaattc aatagctgac gaagaacttg  10260
cattgataaa tacccaagct cttttgtctg gttcaacagg agaaaaacaa tttatatctg  10320
tcagtgaatc cactaggact gctcccacca gttcagaaga ttatctcaga ctgaaacgac  10380
gttgtactac atctctgatc aaagaacagg agagttccca ggccagtacg gaagaatgtg  10440
agaaaaataa gcaggacaca attacaacta aaaaatatat ctaagcattt gcaaaggcga  10500
caataaatta ttgacgctta acctttccag tttataagac tggaatataa tttcaaacca  10560
cacattagta cttatgttgc acaatgagaa aagaaattag tttcaaattt acctcagcgt  10620
ttgtgtatcg ggcaaaaatc gttttgcccg attccgtatt ggtatacttt tgcttcagtt  10680
gcatatctta aaactaaatg taatttatta actaatcaag aaaaacatct ttggctgagc  10740
tcggtggctc atgcctgtaa tcccaacact ttgagaagct gaggtgggag gagtgcttga  10800
ggccaggagt tcaagaccag cctgggcaac atagggagac cccccatcttt acaaagaaaa  10860
aaaaaagggg aaaagaaaat cttttaaatc tttggatttg atcactacaa gtattatttt  10920
acaagtgaaa taaacatacc attttctttt agattgtgtc attaaatgga atgaggtctc  10980
ttagtacagt tattttgatg cagataattc cttttagttt agctactatt ttaggggatt  11040
ttttttagag gtaactcact atgaaatagt tctccttaat gcaaatatgt tggttctgct  11100
atagttccat cctgttcaaa agtcaggatg aatatgaaga gtggtgtttc cttttgagca  11160
attcttcatc cttaagtcag catgattata agaaaaatag aaccctcagt gtaactctaa  11220
ttccttttta ctattccagt gtgatctctg aaattaaatt acttcaacta aaaattcaaa  11280
tactttaaat cagaagattt catagttaat ttattttttt tttcaacaaa atggtcatcc  11340
aaactcaaac ttgagaaaat atcttgcttt caaattggca ctgatt                 11386
```

<210> SEQ ID NO 5
<211> LENGTH: 340
<212> TYPE: PRT
<213> ORGANISM: Homo sapiens

<400> SEQUENCE: 5

```
Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Thr Glu Ser Arg Ser
65                  70                  75                  80

Val Ala Arg Leu Glu Cys Asn Ser Val Ile Leu Val Tyr Cys Thr Leu
                85                  90                  95
```

```
Arg Leu Ser Gly Ser Ser Asp Ser Pro Ala Ser Ala Ser Arg Val Val
            100                 105                 110

Gly Thr Thr Gly Gly Ile Glu Thr Gly Ser Ile Thr Glu Met Phe Gly
        115                 120                 125

Glu Phe Arg Thr Gly Lys Thr Gln Ile Cys His Thr Leu Ala Val Thr
    130                 135                 140

Cys Gln Leu Pro Ile Asp Arg Gly Gly Gly Glu Gly Lys Ala Met Tyr
145                 150                 155                 160

Ile Asp Thr Glu Gly Thr Phe Arg Pro Glu Arg Leu Leu Ala Val Ala
                165                 170                 175

Glu Arg Tyr Gly Leu Ser Gly Ser Asp Val Leu Asp Asn Val Ala Tyr
            180                 185                 190

Ala Arg Ala Phe Asn Thr Asp His Gln Thr Gln Leu Leu Tyr Gln Ala
        195                 200                 205

Ser Ala Met Met Val Glu Ser Arg Tyr Ala Leu Leu Ile Val Asp Ser
    210                 215                 220

Ala Thr Ala Leu Tyr Arg Thr Asp Tyr Ser Gly Arg Gly Glu Leu Ser
225                 230                 235                 240

Ala Arg Gln Met His Leu Ala Arg Phe Leu Arg Met Leu Leu Arg Leu
                245                 250                 255

Ala Asp Glu Phe Gly Val Ala Val Val Ile Thr Asn Gln Val Val Ala
            260                 265                 270

Gln Val Asp Gly Ala Ala Met Phe Ala Ala Asp Pro Lys Lys Pro Ile
        275                 280                 285

Gly Gly Asn Ile Ile Ala His Ala Ser Thr Thr Arg Leu Tyr Leu Arg
    290                 295                 300

Lys Gly Arg Gly Glu Thr Arg Ile Cys Lys Ile Tyr Asp Ser Pro Cys
305                 310                 315                 320

Leu Pro Glu Ala Glu Ala Met Phe Ala Ile Asn Ala Asp Gly Val Gly
                325                 330                 335

Asp Ala Lys Asp
            340
```

<210> SEQ ID NO 6
<211> LENGTH: 2147
<212> TYPE: DNA
<213> ORGANISM: Homo sapiens

<400> SEQUENCE: 6

```
gaaagccgct ggcggaccgc gcgcagcggc cagagaccga gccctaagga gagtgcggcg     60

cttcccgagg cgtgcagctg ggaactgcaa ctcatctggg ttgtgcgcag aaggctgggg    120

caagcgagta gagaagtgga gctaatggca atgcagatgc agcttgaagc aaatgcagat    180

acttcagtgg aagaagaaag ctttggccca caacccattt cacggttaga gcagtgtggc    240

ataaatgcca acgatgtgaa gaaattggaa gaagctggat tccatactgt ggaggctgtt    300

gcctatgcgc caaagaagga gctaataaat attaagggaa ttagtgaagc caaagctgat    360

aaaattctga cggagtctcg ctctgttgcc aggctggagt gcaatagcgt gatcttggtc    420

tactgcaccc tccgcctctc aggttcaagt gattctcctg cctcagcctc ccgagtagtt    480

gggactacag gtggaattga gactggatct atcacagaaa tgtttggaga attccgaact    540

gggaagaccc agatctgtca tacgctagct gtcacctgcc agcttcccat tgaccggggt    600

ggaggtgaag gaaaggccat gtacattgac actgagggta cctttaggcc agaacggctg    660

ctggcagtgg ctgagaggta tggtctctct ggcagtgatg tcctggataa tgtagcatat    720
```

```
gctcgagcgt tcaacacaga ccaccagacc cagctccttt atcaagcatc agccatgatg    780

gtagaatcta ggtatgcact gcttattgta gacagtgcca ccgcccttta cagaacagac    840

tactcgggtc gaggtgagct ttcagccagg cagatgcact tggccaggtt tctgcggatg    900

cttctgcgac tcgctgatga gtttggtgta gcagtggtaa tcactaatca ggtggtagct    960

caagtggatg gagcagcgat gtttgctgct gatcccaaaa aacctattgg aggaaatatc   1020

atcgcccatg catcaacaac cagattgtat ctgaggaaag gaagagggga aaccagaatc   1080

tgcaaaatct acgactctcc ctgtcttcct gaagctgaag ctatgttcgc cattaatgca   1140

gatggagtgg gagatgccaa agactgaatc attgggtttt tcctctgtta aaaaccttaa   1200

gtgctgcagc ctaatgagag tgcactgctc cctggggttc tctacaggcc tcttcctgtt   1260

gtgactgcca ggataaagct tccgggaaaa cagctattat atcagctttt ctgatggtat   1320

aaacaggaga caggtcagta gtcacaaact gatctaaaat gtttattcct tctgtagtgt   1380

attaatctct gtgtgttttc tttggttttg gaggaggggt atgaagtatc tttgacatgg   1440

tgccttagga atgacttggg tttaacaagc tgtctactgg acaatcttat gtttccaaga   1500

gaactaaagc tggagagacc tgacccttct ctcacttcta aattaatggt aaaataaaat   1560

gcctcagcta tgtagcaaag ggaatgggtc tgcacagatt ctttttttct gtcagtaaaa   1620

ctctcaagca ggtttttaag ttgtctgtct gaatgatctt gtgtaaggtt ttggttatgg   1680

agtcttgtgc caaacctact aggccattag cccttcacca tctacctgct tggtctttca   1740

ttgctaagac taactcaaga taatcctaga gtcttaaagc atttcaggcc agtgtggtgt   1800

cttgcgcctg tactcccagc actttgggag gccgaggcag gtggatcgct tgagcccagg   1860

agttttaagt ccagcttggc caaggtggtg aaatcccatc tctacaaaaa atgcagaact   1920

taatctggac acactgttac acgtgcctgt agtcccagct actcgatagc ctgaggtggg   1980

agaatcactt aagcctggaa ggtggaagtt gcagtgagtc gagattgcac tgctgcattc   2040

cagccagggt gacagagtga gaccatgttt caaacaagaa acatttcaga gggtaagtaa   2100

acagatttga ttgtgaggct tctaataaag tagttattag tagtgaa                 2147
```

```
<210> SEQ ID NO 7
<211> LENGTH: 18
<212> TYPE: DNA
<213> ORGANISM: Unknown
<220> FEATURE:
<223> OTHER INFORMATION: Description of Unknown:
      I-SceI rare cutting endonuclease site sequence

<400> SEQUENCE: 7

tagggataac agggtaat                                                   18


<210> SEQ ID NO 8
<211> LENGTH: 15
<212> TYPE: DNA
<213> ORGANISM: Unknown
<220> FEATURE:
<223> OTHER INFORMATION: Description of Unknown:
      I-PpoI rare cutting endonuclease site sequence

<400> SEQUENCE: 8

ctctcttaag gtagc                                                      15


<210> SEQ ID NO 9
<211> LENGTH: 23
<212> TYPE: DNA
```

<213> ORGANISM: Escherichia coli

<400> SEQUENCE: 9
aattagtatg ttgtaactaa agt 23

<210> SEQ ID NO 10
<211> LENGTH: 23
<212> TYPE: DNA
<213> ORGANISM: Escherichia coli

<400> SEQUENCE: 10
aataagtatg ttgtaactaa agt 23

<210> SEQ ID NO 11
<211> LENGTH: 23
<212> TYPE: DNA
<213> ORGANISM: Escherichia coli

<400> SEQUENCE: 11
atataggatg ttgtaactaa tat 23

<210> SEQ ID NO 12
<211> LENGTH: 14
<212> TYPE: DNA
<213> ORGANISM: Escherichia coli
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 12
gnrngttgta ayka 14

<210> SEQ ID NO 13
<211> LENGTH: 23
<212> TYPE: DNA
<213> ORGANISM: Escherichia coli

<400> SEQUENCE: 13
cgatcgtatg ttgtaactat ctc 23

<210> SEQ ID NO 14
<211> LENGTH: 23
<212> TYPE: DNA
<213> ORGANISM: Escherichia coli

<400> SEQUENCE: 14
aacatggaag ttgtaactaa ccg 23

<210> SEQ ID NO 15
<211> LENGTH: 23
<212> TYPE: DNA
<213> ORGANISM: Escherichia coli

<400> SEQUENCE: 15
cattagtatg ttgtaactaa atg 23

<210> SEQ ID NO 16
<211> LENGTH: 23
<212> TYPE: DNA
<213> ORGANISM: Escherichia coli

<400> SEQUENCE: 16
gtcaaggatg ttgtaactaa cca 23

<210> SEQ ID NO 17
<211> LENGTH: 23
<212> TYPE: DNA
<213> ORGANISM: Escherichia coli

<400> SEQUENCE: 17
ttaaagtatg ttgtaactaa gca 23

<210> SEQ ID NO 18
<211> LENGTH: 23
<212> TYPE: DNA
<213> ORGANISM: Escherichia coli

<400> SEQUENCE: 18
cgattgagag ttgtaatgaa gtc 23

<210> SEQ ID NO 19
<211> LENGTH: 23
<212> TYPE: DNA
<213> ORGANISM: Escherichia coli

<400> SEQUENCE: 19
ccttcgtatg ttgtaacgac gat 23

<210> SEQ ID NO 20
<211> LENGTH: 23
<212> TYPE: DNA
<213> ORGANISM: Escherichia coli

<400> SEQUENCE: 20
acgcagtaag ttgtaactaa tgc 23

<210> SEQ ID NO 21
<211> LENGTH: 23
<212> TYPE: DNA
<213> ORGANISM: Escherichia coli

<400> SEQUENCE: 21
tatgggtacg ttgtaattag gga 23

<210> SEQ ID NO 22
<211> LENGTH: 23
<212> TYPE: DNA
<213> ORGANISM: Escherichia coli

<400> SEQUENCE: 22
gcactgggtg ttgtaatgac gca 23

<210> SEQ ID NO 23
<211> LENGTH: 23
<212> TYPE: DNA
<213> ORGANISM: Escherichia coli

<400> SEQUENCE: 23
tacccgcagg ttgtaacgag agc 23

<210> SEQ ID NO 24
<211> LENGTH: 309
<212> TYPE: PRT

<213> ORGANISM: Escherichia coli

<400> SEQUENCE: 24

```
Met Ala Arg Tyr Asp Leu Val Asp Arg Leu Asn Thr Thr Phe Arg Gln
1               5                   10                  15

Met Glu Gln Glu Leu Ala Ile Phe Ala Ala His Leu Glu Gln His Lys
            20                  25                  30

Leu Leu Val Ala Arg Val Phe Ser Leu Pro Glu Val Lys Lys Glu Asp
        35                  40                  45

Glu His Asn Pro Leu Asn Arg Ile Glu Val Lys Gln His Leu Gly Asn
    50                  55                  60

Asp Ala Gln Ser Leu Ala Leu Arg His Phe Arg His Leu Phe Ile Gln
65                  70                  75                  80

Gln Gln Ser Glu Asn Arg Ser Ser Lys Ala Ala Val Arg Leu Pro Gly
                85                  90                  95

Val Leu Cys Tyr Gln Val Asp Asn Leu Ser Gln Ala Ala Leu Val Ser
            100                 105                 110

His Ile Gln His Ile Asn Lys Leu Lys Thr Thr Phe Glu His Ile Val
        115                 120                 125

Thr Val Glu Ser Glu Leu Pro Thr Ala Ala Arg Phe Glu Trp Val His
    130                 135                 140

Arg His Leu Pro Gly Leu Ile Thr Leu Asn Ala Tyr Arg Thr Leu Thr
145                 150                 155                 160

Val Leu His Asp Pro Ala Thr Leu Arg Phe Gly Trp Ala Asn Lys His
                165                 170                 175

Ile Ile Lys Asn Leu His Arg Asp Glu Val Leu Ala Gln Leu Glu Lys
            180                 185                 190

Ser Leu Lys Ser Pro Arg Ser Val Ala Pro Trp Thr Arg Glu Glu Trp
        195                 200                 205

Gln Arg Lys Leu Glu Arg Glu Tyr Gln Asp Ile Ala Ala Leu Pro Gln
    210                 215                 220

Asn Ala Lys Leu Lys Ile Lys Arg Pro Val Lys Val Gln Pro Ile Ala
225                 230                 235                 240

Arg Val Trp Tyr Lys Gly Asp Gln Lys Gln Val Gln His Ala Cys Pro
                245                 250                 255

Thr Pro Leu Ile Ala Leu Ile Asn Arg Asp Asn Gly Ala Gly Val Pro
            260                 265                 270

Asp Val Gly Glu Leu Leu Asn Tyr Asp Ala Asp Asn Val Gln His Arg
        275                 280                 285

Tyr Lys Pro Gln Ala Gln Pro Leu Arg Leu Ile Ile Pro Arg Leu His
    290                 295                 300

Leu Tyr Val Ala Asp
305
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 25

```
catcaaggaa accctggact actg                                            24
```

<210> SEQ ID NO 26

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
cctcggctag gtaggggatc 20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ctgggtagtt tgtaagcatc c 21

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
caataaactg ctggtctcag gc 22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ggaaatggca acttgcctag 20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ctgcgagcag tcttcagaaa g 21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ttccgtggtg aaggagctt 19

<210> SEQ ID NO 32
<211> LENGTH: 18

<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tggctgcacg atcacaac 18

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gcctggacag aagacagca 19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cagtcccaca tcacaagacg 20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' FAM
<220> FEATURE:
<223> OTHER INFORMATION: 3' BHQ

<400> SEQUENCE: 35
cgctcaccca tgacacaggt gc 22

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' FAM
<220> FEATURE:
<223> OTHER INFORMATION: 3' BHQ

<400> SEQUENCE: 36
tgcacagctg cccaatatct ggg 23

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
atgagctgga gaggatgctg 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
ctgggcagtt gctgtcttct 20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ggtgctcatc tagttgtgat cg 22

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ctgtaccagg taggcatcca 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
agcctaggtg tccagctgtc 20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ctgcaatcac ctggcttagt t 21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
tctgccactg tgaaaaatgc 20

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tcaagctggg ctgaagatt 19

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gtgggacgac tggaatgagg 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 46 gcacctttg gtgtctctgg 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
ggatggacca tgcagcaaga 20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ccattcaaac cgaagggcg 19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 49

```
aggccagagg aatgcctgaa                                                20


<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

ccagtcatct ccatcctcta cc                                             22


<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

tggtcagaat tcaggttggc                                                20


<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

tttcaggacg tcagtcagcg                                                20


<210> SEQ ID NO 53
<211> LENGTH: 15438
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (382)..(382)
<223> OTHER INFORMATION: a, c, t, g, unknown or other

<400> SEQUENCE: 53

ccccgcggca ggccctccga gcgtggtgga gccgttctgt gagacagccg ggtacgagtc     60

gtgacgctgg aaggggcaag cgggtggtgg gcaggaatgc ggtccgccct gcagcaaccg    120

gagggggagg gagaagggag cggaaaagtc tccaccggac gcggccatgg ctcggggggg    180

ggggggcagc ggaggascgc ttccggccga cgtctcgtcg ctgattggct tyttttcctc    240

ccgccgtgtg tgaaaacaca aatggcgtgt tttggttggc gtaaggcgcc tgtcagttaa    300

cggcagccgg agtgcgcagc cgccggcagc ctcgctctgc ccactgggtg gggcgggagg    360

taggtggggt gaggcgagct gnacgtgcgg gcgcggtcgg cctctggcgg ggcgggggag    420

gggagggagg gtcagcgaaa gtagctcgcg cgcgagcggc cgcccaccct ccccttcctc    480

tgggggagtc gttttacccg ccgccggccg ggcctcgtcg tctgattggc tctcggggcc    540

cagaaaactg gcccttgcca ttggctcgtg ttcgtgcaag ttgagtccat ccgccggcca    600

gcgggggcgg cgaggaggcg ctcccaggtt ccggccctcc cctcggcccc gcgccgcaga    660

gtctggccgc gcgcccctgc gcaacgtggc aggaagcgcg cgctgggggc ggggacgggc    720
```

```
agtagggctg agcggctgcg gggcgggtgc aagcacgttt ccgacttgag ttgcctcaag    780
aggggcgtgc tgagccagac ctccatcgcg cactccgggg agtggaggga aggagcgagg    840
gctcagttgg gctgttttgg aggcaggaag cacttgctct cccaaagtcg ctctgagttg    900
ttatcagtaa gggagctgca gtggagtagg cggggagaag gccgcaccct tctccggagg    960
ggggagggga gtgttgcaat acctttctgg gagttctctg ctgcctcctg gcttctgagg   1020
accgccctgg gcctgggaga atcccttgcc ccctcttccc ctcgtgatct gcaactccag   1080
tctttctagc cttaattaag ggatctgtag ggcgcagtag tccagggttt ccttgatgat   1140
gtcatactta tcctgtccct tttttttcca cagctcgcgg ttgaggacaa actcttcgcg   1200
gtctttccag tggggatcga cggtatcgta gagtcgaggc cgctctagaa ctagtggatc   1260
taccatgacc gagtacaagc ccacggtgcg cctcgccacc cgcgacgacg tcccccgggc   1320
cgtacgcacc ctcgccgccg cgttcgccga ctaccccgcc acgcgccaca ccgtcgaccc   1380
ggaccgccac atcgagcggg tcaccgagct gcaagaactc ttcctcacgc gcgtcgggct   1440
cgacatcggc aaggtgtggg tcgcggacga cggcgccgcg gtggcggtct ggaccacgcc   1500
ggagagcgtc gaagcggggg cggtgttcgc cgagatcggc ccgcgcatgg ccgagttgag   1560
cggttcccgg ctggccgcgc agcaacagat ggaaggcctc ctggcgccgc accggcccaa   1620
ggagcccgcg tggttcctgg ccaccgtcgg cgtctcgccc gaccaccagg gcaagggtct   1680
gggcagcgcc gtcgtgctcc ccggagtgga ggcggccgag cgcgccgggg tgcccgcctt   1740
cctggagacc tccgcgcccc gcaacctccc cttctacgag cggctcggct tcaccgtcac   1800
cgccgacgtc gagtgcccga aggaccgcgc gacctggtgc atgacccgca agcccggtgc   1860
ctgactcgac cctaggggga ggctaactga aacacggaag gagacaatac cggaaggaac   1920
ccgcgctatg acggcaataa aaagacagaa taaaacgcac ggtgttgggt cgtttgttca   1980
taaacgcggg gttcggtccc agggctggca ctctgtcgat accccaccga gaccccattg   2040
gggccaatac gcccgcgttt cttccttttc cccaccccac cccccaagtt cgggtgaagg   2100
cccagggctc gcagccaacg tcggggcggc aggccctgcc atagcctcag gttactcgga   2160
tctcgacctc gaggggcccc cgcgggtggg gaagatctcg ggtgcccat cctggtcgag   2220
ctggacggcg acgtaaacgg ccacaagttc agcgtgtccg gcgagggcga gggcgatgcc   2280
acctacggca agctgaccct gaagttcatc tgcaccaccg gcaagctgcc cgtgccctgg   2340
cccaccctcg tgaccaccct gacctacggc gtgcagtgct tcagccgcta ccccgaccac   2400
atgaagcagc acgacttctt caagtccgcc atgcccgaag gctacgtcca ggagcgcacc   2460
atcttcttca aggacgacgg caactacaag acccgcgccg aggtgaagtt cgagggcgac   2520
accctggtga accgcatcga gctgaagggc atcgacttca aggaggacgg caacatcctg   2580
gggcacaagc tggagtacaa ctacaacagc cacaacgtct atatcatggc cgacaagcag   2640
aagaacggca tcaaggtgaa cttcaagatc cgccacaaca tcgaggacgg cagcgtgcag   2700
ctcgccgacc actaccagca gaacaccccc atcggcgacg gccccgtgct gctgcccgac   2760
aaccactacc tgagcaccca gtccgccctg agcaaagacc ccaacgagaa gcgcgatcac   2820
atggtcctgc tggagttcgt gaccgccgcc gggatcactc tcggcatgga cgagctgtac   2880
aagtaaagcg gccgcgactc tagatcataa tcagccatac cacatttgta gaggttttac   2940
ttgctttaaa aaacctccca cacctccccc tgaacctgaa acataaaatg aatgcaattg   3000
ttgttgttaa cttgtttatt gcagcttata atggttacaa ataaagcaat agcatcacaa   3060
```

```
atttcacaaa taaagcattt ttttcactgc attctagttg tggtttgtcc aaactcatca   3120
atgtcgggat cccgccaatt gtctagattt ctctaatcac ttttttttca aggcaatcag   3180
ggtatattat attgtacttc agcacagttt tagagaacaa ttgttataat taaatgataa   3240
ggtagaatat ttctgcatat aaattctggc tggcgtggaa atattcttat tggtagaaac   3300
aactacatcc tggtcatcat cctgcctttc tctttatggt tacaatgata tacactgttt   3360
gagatgagga taaaatactc tgagtccaaa ccgggcccct ctgctaacca tgttcatgcc   3420
ttcttctttt tcctacagga ctcctccctg caggacggcg agttcatcta caaggtgaag   3480
ctgcgcggca ccaacttccc ctccgacggc cccgtaatgc agaagaagac catgggctgg   3540
gaggcctcct ccgagcggat gtaccccgag gacggcgccc tgaagggcga gatcaagatg   3600
aggctgaagc tgaaggacgg tggccactac gacgccgagg tcaagaccac ctacatggcc   3660
aagaagcccg tgcagctgcc cggcgcctac aagaccgaca tcaagctgga catcacctcc   3720
cacaacgagg actacaccat cgtggaacag tacgagcgcg ccgagggccg ccactccacc   3780
ggcggtatgg atgaactcta taaataagca cgggccctat tctatagtgt cacctaaatg   3840
ctagagctcg ctgatcagcc tcgactgtgc cttctagttg ccagccatct gttgtttgcc   3900
cctcccccgt gccttccttg accctggaag gtgccactcc cactgtcctt tcctaataaa   3960
atgaggaaat tgcatcgcat tgtctgagta ggtgtcattc tattctgggg ggtggggtgg   4020
ggcaggacag caagggggag gattgggaag acaatagcag gcatgctggg gaggatctgt   4080
gtggaaagtc cccaggctcc ccaggcaggc agaagtatgc aaagcatgca tctcaattag   4140
tcagcaacca ggtgtggaaa gtccccaggc tccccagcag gcagaagtat gcaaagcatg   4200
catctcaatt agtcagcaac catagtcccg cccctaactc cgcccatccc gcccctaact   4260
ccgcccagtt ccgcccattc tccgccccat ggctgactaa ttttttttat ttatgcagag   4320
gccgaggccg cctctgcctc tgagctattc cagaagtagt gaggaggctt ttttggaggc   4380
ctaggctttt gcaaaaagct cccgggagct tgtatatcca ttttcggata agcttaacta   4440
aaccatggta tcaaaaggtg aagaaaacaa tatggcagtc atcaaggagt tcatgcgctt   4500
caaggtgcgc atggagggct ccgtgaacgg ccacgagttc gagatcgagg gcgagggcga   4560
gggccgcccc tacgagggca cccagaccgc caagctgaag gtgaccgagg gtggcccct   4620
gcccttcgcc tgggacatcc tgtcccctca gttcatgtac ggctccaagg cctacgtgaa   4680
gcaccccgcc gacatccccg actacttgaa gctgtccttc cccgagggct tcaagtggga   4740
gcgcgtgatg aacttcgagg acggcggcgt ggtgaccgtg acccaggtga gtttggggac   4800
ccttgattgt tctttctttt tcgctattgt aaaattcatg ttatatggag ggggcaaagt   4860
tttcagggtg ttgtttagaa tgggaagatg tcccttgtat caccatggac cctcatgata   4920
attttgtttc tttcactttc tactctgttg acaaccattg tctcctctta ttttcttttc   4980
attttctgta actttttcgt taaactttag cttgcatttg taacgaattt ttaaattcac   5040
ttttgtttat ttgtcagatt gtaagtaccg ggacccggaa ttctaccggg taggggaggc   5100
gcttttccca aggcagtctg gagcatgcgc tttagcagcc ccgctggcac ttggcgctac   5160
acaagtggcc tctggcctcg cacacattcc acatccaccg gtagcgccaa ccggctccgt   5220
tctttggtgg ccccttcgcg ccacttctac tcctccccta gtcaggaagt ttcccccagc   5280
aagctcgcgt cgtgcaggac gtgacaaatg gaagtagcac gtctcactag tctcgtgcag   5340
atggacagca ccgctgagca atggaagcgg gtaggccttt ggggcagcgg ccaatagcag   5400
ctttgttcct tcgctttctg ggctcagagg ctgggaaggg gtgggtccgg gggcgggctc   5460
```

```
aggggcgggc tcaggggcgg gcgggcgccc gaaggtcctc ccgaggcccg gcattctgca   5520
cgcttcaaaa gcgcacgtct gccgcgctgt tctcctcttc ctcatctccg ggcctttcga   5580
cctgcagccc aagctctagc gctaccggtc gccaccatgg tgagcaaggg cgaggagctg   5640
ttcaccgggg tggtgcccat cctggtcgag ctggacggcg acgtaaacgg ccacaagttc   5700
agcgtgtccg gcgagggcga gggcgatgcc acctacggca agctgaccct gaagttcatc   5760
tgcaccaccg gcaagctgcc cgtgccctgg cccaccctcg tgaccaccct gacctacggc   5820
gtgcagtgct tcagccgcta ccccgaccac atgaagcagc acgacttctt caagtccgcc   5880
atgcccgaag gctacgtcca ggagcgcacc atcttcttca aggacgacgg caactacaag   5940
acccgcgccg aggtgaagtt cgagggcgac accctggtga accgcatcga gctgaagggc   6000
atcgtaggga taacagggta atcaaggagg acggcaacat cctggggcac aagctggagt   6060
acaactacaa cagccacaac gtctatatca tggccgacaa gcagaagaac ggcatcaagg   6120
tgaacttcaa gatccgccac aacatcgagg acggcagcgt gcagctcgcc gaccactacc   6180
agcagaacac ccccatcggc gacggccccg tgctgctgcc cgacaaccac tacctgagca   6240
cccagtccgc cctgagcaaa gaccccaacg agaagcgcga tcacatggtc ctgctggagt   6300
tcgtgaccgc cgccgggatc actctcggca tggacgagct gtacaagtaa agcggccgcg   6360
actctagatc ataatcagcc ataccacatt tgtagaggtt ttacttgctt taaaaaacct   6420
cccacacctc cccctgaacc tgaaacataa aatgaatgca attgttgttg ttaacttgtt   6480
tattgcagct tataatggtt acaaataaag caatagcatc acaaatttca caaataaagc   6540
atttttttca ctgcattcta gttgtggttt gtccaaactc atcaatgtcg gatggccgcg   6600
ctggggatgc ggtgggctct atggcttatg aggcggaaag aaccagctgg ggctcgatcc   6660
tctagttggc gcgccggcta gaagatgggc gggagtcttc tgggcaggct taaaggctaa   6720
cctggtgtgt gggcgttgtc ctgcagggga attgaacagg tgtaaaattg gagggacaag   6780
acttcccaca gattttcggt tttgtcggga agttttttaa taggggcaaa taggaaaatg   6840
gaggatagga gtcatctggg gtttatgcag caaaactaca ggtatattgc ttgtatccgc   6900
ctcggagatt tccatgagga gataaagaca tgtcacccga gtttatactc tcctgcttag   6960
atcctactac agtatgaaat acagtgtygc gaggtagact atgtaagcag atttaatcat   7020
tttaaagagc ccagtacttc atatccattt ctcccgctcc ttctgcagcc ttatcaaaag   7080
gtatttagaa cactcatttt agccccattt tcatttatta tactggctta tccaacccct   7140
agacagagca ttggcatttt ccctttcctg atcttagaag tctgatgact catgaaacca   7200
gacagattag ttacatacac cacaaatcga ggctgtagct ggggcctcaa cactgcagtt   7260
cttttataac tccttagtac actttttgtt gatcctttgc cttgatcctt aattttcagt   7320
gtctatcacc tctcccgtca ggtggtgttc cacatttggg cctattctca gtccagggag   7380
ttttacaaca atagatgtat tgagaatcca acctaaagct taactttcca ctcccatgaa   7440
tgcctctctc ctttttctcc attataactg agctatwacc attaatggtt tcaggtggat   7500
gtctcctccc ccaatatacc tgatgtatct acatattgcc aggctgatat tttaagacat   7560
waaaggtata tttcattatt gagccacatg gtattgatta ctgctactaa aattttgtca   7620
ttgtacacat ctgtaaaagg tggttccttt tggaatgcaa agttcaggtg tttgttgtct   7680
ttcctgacct aaggtcttgt gagcttgtat tttttctatt taagcagtgc tttctcttgg   7740
actggcttga ctcatggcat tctacacgtt attgctggtc taaatgtgat tttgccaagc   7800
```

```
ttcttcagga cctataattt tgcttgactt gtagccaaac acaagtaaaa tgattaagca   7860
acaaatgtat ttgtgaagct tggtttttag gttgttgtgt tgtgtgtgct tgtgctctat   7920
aataatacta tccaggggct ggagaggtgg ctcggagttc aagagcacag actgctcttc   7980
cagaagtcct gagttcaatt cccagcaacc acatggtggc tcacaaccat ctgtaatggg   8040
atctgatgcc ctcttctggt gtgtctgaag accacaagtg tattcacatt aaataaataa   8100
tcctccttct tcttcttttt ttttttttaa agagaatwct gtctccagta gaattactga   8160
agtaatgaaa tactttgtgt ttgttccaat atggwagcca ataatcaaat actcttwagc   8220
actggaaatg taccaaggaa ctattttatt taagtgwact gtggacagag gagccataac   8280
tgcagacttg tgggatacag aagaccaatg cagacttaat gtcttttctc ttacactaag   8340
caataaagaa ataaaaattg aacttctagt atcctatttg ttaaactgct agctttacta   8400
acttttgtgc ttcatctata caaagctgaa agctaagtct gcagccatta ctaaacatga   8460
aagcaagtaa tgataatttt ggatttcaaa aatgtagggc cagagtttag ccagccagtg   8520
gtggtgcttg cctttatgcc ttaatcccag cactctggag gcagagacag gcagatctct   8580
gagtttgagc ccagcctggt ctacacatca agttctatct aggatagcca ggaatacaca   8640
cagaaaccct gttggggagg ggggctctga gatttcataa aattataatt gaagcattcc   8700
ctaatgagcc actatggatg tggctaaatc cgtctacctt tctgatgaga tttgggtatt   8760
attttttctg tctctgctgt tggttgggtc ttttgacact gtgggctttc ttaaagcctc   8820
cttccctgcc atgtggtctc ttgtttgcta ctaacttccc atggcttaaa tggcatggct   8880
ttttgccttc taagggcagc tgctgagwtt tgcagcctga tttccagggt ggggttggga   8940
aatctttcaa acactaaaat tgtcctttaa tttttttta aaaaatgggt tatataataa   9000
acctcataaa atagttatga ggagtgaggt ggactaatat taatgagtcc ctcccctata   9060
aaagagctat taaggctttt tgtcttatac taactttttt tttaaatgtg gtatctttag   9120
aaccaagggt cttagagttt tagtatacag aaactgttgc atcgcttaat cagattttct   9180
agtttcaaat ccagagaatc caaattcttc acagccaaag tcaaattaag aatttctgac   9240
tttaatgtta tttgctactg tgaatataaa atgatagctt ttcctgaggc agggtctcac   9300
tatgtatctc tgcctgatct gcaacaagat atgtagacta aagttctgcc tgcttttgtc   9360
tcctgaatac taaggttaaa atgtagtaat acttttggaa cttgcaggtc agattctttt   9420
ataggggaca cactaaggga gcttgggtga tagttggtaa atgtgtttaa gtgatgaaaa   9480
cttgaattat tatcaccgca acctactttt taaaaaaaaa agccaggcct gttagagcat   9540
gctaagggat ccctaggact tgctgagcac acaagagtag tacttggcag gctcctggtg   9600
agagcatatt tcaaaaaaca aggcagacaa ccaagaaact acagtaaggt tacctgtctt   9660
taaccatctg catatacaca gggatattaa aatattccaa ataatatttc attcaagttt   9720
tcccccatca aattgggaca tggatttctc cggtgaatag gcagagttgg aaactaaaca   9780
aatgttggtt ttgtgatttg tgaaattgtt ttcaagtgat agttaaagcc catgagatac   9840
agaacaaagc tgctatttcg aggtctcttg gttatactca gaagcacttc tttgggtttc   9900
cctgcactat cctgatcatg tgctaggcct wccttaggct gattgttgtt caaataactt   9960
aagtttcctg tcaggtgatg tcatatgatt tcatatatca aggcaaaaca tgttatatat   10020
gttaaacatt tgkacttaat gtgaaagtta ggtctttgtg ggttttgatt ttaatttcaa   10080
aacctgagct aaataagtca ttttacatgt cttacatttg gtgaattgta tattgtggtt   10140
tgcaggcaag actctctgac ctagtaaccc tcctatagag cactttgctg ggtcacaagt   10200
```

```
ctaggagtca agcatttcac cttgaagttg agacgttttg ttagtgtata ctagttatat  10260
gttggaggac atgtttatcc agaagatatt caggactatt tttgactggg ctaaggaatt  10320
gattctgatt agcactgtta gtgagcattg agtggccttt aggcttgaat tggagtcact  10380
tgtatatctc aaataatgct ggcctttttt waaaagccct tgttctttat caccctgttt  10440
tctacataat ttttgttcaa agaaatactt gtttggatct ccttttgaca acaatagcat  10500
gttttcaagc catatttttt ttcctttttt tttttttttt tggtttttcg agacagggtt  10560
tctctgtata gccctggctg tcctggaact cactttgtag accaggctgg cctcgaactc  10620
agaaatccgc ctgcctctgc ctcctgagtg ccgggattaa aggcgtgcac caccacgcct  10680
ggctaagttg gatattttgt atataactat aaccaatact aactccactg ggtggatttt  10740
taattcagtc agtagtctta agtggtcttt attggccctt attaaaatct actgttcact  10800
ctaacagagg ctgttggact agtggsacta agcaacttcc tacggatata ctagcagata  10860
agggtcaggg atagaaacta gtctagcgtt ttgtatacct accagcttat actaccttgt  10920
tctgatagaa atatttagga catctagctt atcgatccgt cgacggtatc gataagcttg  10980
atatcgaatt ctaccgggta ggggaggcgc ttttccaagg cagtctgagc atgcgcttag  11040
cagccccgct ggcacttggc gctacacaag tggcctytgg cctcgcacac attccacatc  11100
caccggtagg cgccaaccgg ctccgttctt tggtggcccc ttcgcgccac cttctwctcc  11160
tcccctagtc aggaagttcc cccccgcccc gcagctcgcg tcgtsaggac gtgacaaatg  11220
gaagtagcac gtctcactag tctcgtcaga tggacagcac cgctgagcaa tggaagcggg  11280
taggcctttg gggcagcggc caatagcagc tttgctcctt cgctttctgg gctcagaggc  11340
tgggaagggg tgggtccggg ggcgggctca ggggcgggct caggggcggg gcgggcgccc  11400
gaaggtcctc cggaggcccg gcattctgca cgcttcaaaa gcgcacgtct gccgcgctgt  11460
tctcctcttc ctcatctccg ggcctttcga cctgcaggtc ctcgccatgg atcctgatga  11520
tgttgttatt cttctaatct tttgtatgga aaacttttct tcgtaccacg ggactaaacc  11580
tggttatgta gattccattc aaaaaggtat acaaaagcca aaatctggta cacaaggaaa  11640
ttatgacgat gattggaaag ggttttatag taccgacaat aaatacgacg ctgcgggata  11700
ctctgtagat aatgaaaacc cgctctctgg aaaagctgga ggcgtggtca aagtgacgta  11760
tccaggactg acgaaggttc tcgcactaaa agtggataat gccgaaacta ttaagaaaga  11820
gttaggttta agtctcactg aaccgttgat ggagcaagtc ggaacggaag agtttatcaa  11880
aaggttcggt gatggtgctt cgcgtgtagt gctcagcctt cccttcgctg aggggagttc  11940
tagcgttgaa tatattaata actgggaaca ggcgaaagcg ttaagcgtag aacttgagat  12000
taattttgaa acccgtggaa aacgtggcca agatgcgatg tatgagtata tggctcaagc  12060
ctgtgcagga aatcgtgtca ggcgatctct ttgtgaagga accttacttc tgtggtgtga  12120
cataattgga caaactacct acagagattt aaagctctaa ggtaaatata aaatttttaa  12180
gtgtataatg tgttaaacta ctgattctaa ttgtttgtgt attttagatt ccaacctatg  12240
gaactgatga atgggagcag tggtggaatg cagatcctag agctcgctga tcagcctcga  12300
ctgtgccttc tagttgccag ccatctgttg tttgcccctc ccccgtgcct tccttgaccc  12360
tggaaggtgc cactcccact gtcctttcct aataaaatga ggaaattgca tcgcattgtc  12420
tgagtaggtg tcattctatt ctggggggtg gggtggggca ggacagcaag ggggaggatt  12480
gggaagacaa tagcaggcat gctggggatg cggtgggctc tatggcttct gaggcggaaa  12540
```

```
gaaccagctg ggctcgacc tcgaggggg gcccggtacc cagcttttgt tccctttagt  12600
gagggttaat tgcgcgcttg gcgtaatcat ggtcatagct gtttcctgtg tgaaattgtt  12660
atccgctcac aattccacac aacatacgag ccggaagcat aaagtgtaaa gcctggggtg  12720
cctaatgagt gagctaactc acattaattg cgttgcgctc actgcccgct ttccagtcgg  12780
gaaacctgtc gtgccagctg cattaatgaa tcggccaacg cgcgggaga ggcggtttgc  12840
gtattgggcg ctcttccgct tcctcgctca ctgactcgct gcgctcggtc gttcggctgc  12900
ggcgagcggt atcagctcac tcaaaggcgg taatacggtt atccacagaa tcaggggata  12960
acgcaggaaa gaacatgtga gcaaaaggcc agcaaaaggc caggaaccgt aaaaaggccg  13020
cgttgctggc gtttttccat aggctccgcc cccctgacga gcatcacaaa aatcgacgct  13080
caagtcagag gtggcgaaac ccgacaggac tataaagata ccaggcgttt ccccctggaa  13140
gctccctcgt gcgctctcct gttccgaccc tgccgcttac cggatacctg tccgcctttc  13200
tcccttcggg aagcgtggcg ctttctcata gctcacgctg taggtatctc agttcggtgt  13260
aggtcgttcg ctccaagctg ggctgtgtgc acgaaccccc cgttcagccc gaccgctgcg  13320
ccttatccgg taactatcgt cttgagtcca acccggtaag acacgactta tcgccactgg  13380
cagcagccac tggtaacagg attagcagag cgaggtatgt aggcggtgct acagagttct  13440
tgaagtggtg gcctaactac ggctacacta gaaggacagt atttggtatc tgcgctctgc  13500
tgaagccagt taccttcgga aaaagagttg gtagctcttg atccggcaaa caaaccaccg  13560
ctggtagcgg tggttttttt gtttgcaagc agcagattac gcgcagaaaa aaaggatctc  13620
aagaagatcc tttgatcttt tctacggggt ctgacgctca gtggaacgaa aactcacgtt  13680
aagggatttt ggtcatgaga ttatcaaaaa ggatcttcac ctagatcctt ttaaattaaa  13740
aatgaagttt taaatcaatc taaagtatat atgagtaaac ttggtctgac agttaccaat  13800
gcttaatcag tgaggcacct atctcagcga tctgtctatt tcgttcatcc atagttgcct  13860
gactccccgt cgtgtagata actacgatac gggagggctt accatctggc cccagtgctg  13920
caatgatacc gcgagaccca cgctcaccgg ctccagattt atcagcaata aaccagccag  13980
ccggaagggc cgagcgcaga agtggtcctg caactttatc cgcctccatc cagtctatta  14040
attgttgccg ggaagctaga gtaagtagtt cgccagttaa tagtttgcgc aacgttgttg  14100
ccattgctac aggcatcgtg gtgtcacgct cgtcgtttgg tatggcttca ttcagctccg  14160
gttcccaacg atcaaggcga gttacatgat cccccatgtt gtgcaaaaaa gcggttagct  14220
ccttcggtcc tccgatcgtt gtcagaagta agttggccgc agtgttatca ctcatggtta  14280
tggcagcact gcataattct cttactgtca tgccatccgt aagatgcttt tctgtgactg  14340
gtgagtactc aaccaagtca ttctgagaat agtgtatgcg gcgaccgagt tgctcttgcc  14400
cggcgtcaat acgggataat accgcgccac atagcagaac tttaaaagtg ctcatcattg  14460
gaaaacgttc ttcggggcga aaactctcaa ggatcttacc gctgttgaga tccagttcga  14520
tgtaacccac tcgtgcaccc aactgatctt cagcatcttt tactttcacc agcgtttctg  14580
ggtgagcaaa aacaggaagg caaaatgccg caaaaaaggg aataagggcg acacggaaat  14640
gttgaatact catactcttc ctttttcaat attattgaag catttatcag ggttattgtc  14700
tcatgagcgg atacatattt gaatgtattt agaaaaataa acaaataggg gttccgcgca  14760
catttccccg aaaagtgcca cctaaattgt aagcgttaat attttgttaa aattcgcgtt  14820
aaatttttgt taaatcagct cattttttaa ccaataggcc gaaatcggca aaatccctta  14880
taaatcaaaa gaatagaccg agatagggtt gagtgttgtt ccagtttgga acaagagtcc  14940
```

```
actattaaag aacgtggact ccaacgtcaa agggcgaaaa accgtctatc agggcgatgg  15000

cccactacgt gaaccatcac cctaatcaag ttttttgggg tcgaggtgcc gtaaagcact  15060

aaatcggaac cctaaaggga gcccccgatt tagagcttga cggggaaagc cggcgaacgt  15120

ggcgagaaag gaagggaaga aagcgaaagg agcgggcgct agggcgctgg caagtgtagc  15180

ggtcacgctg cgcgtaacca ccacacccgc cgcgcttaat gcgccgctac agggcgcgtc  15240

ccattcgcca ttcaggctgc gcaactgttg ggaagggcga tcggtgcggg cctcttcgct  15300

attacgccag ctggcgaaag ggggatgtgc tgcaaggcga ttaagttggg taacgccagg  15360

gttttcccag tcacgacgtt gtaaaacgac ggccagtgag cgcgcgtaat acgactcact  15420

atagggcgaa ttggagct                                                15438
```

```
<210> SEQ ID NO 54
<211> LENGTH: 7113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctagagtcg    900

atcctgagaa cttcagggtg agtttgggga cccttgattg ttctttcttt ttcgctattg    960

taaaattcat gttatatgga gggggcaaag ttttcagggt gttgtttaga atgggaagat   1020

gtcccttgta tcaccatgga ccctcatgat aattttgttt ctttcacttt ctactctgtt   1080

gacaaccatt gtctcctctt attttctttt cattttctgt aactttttcg ttaaacttta   1140

gcttgcattt gtaacgaatt tttaaattca cttttgttta tttgtcagat tgtaagtact   1200

ttctctaatc actttttttt caaggcaatc agggtatatt atattgtact tcagcacagt   1260

tttagagaac aattgttata attaaatgat aaggtagaat atttctgcat ataaattctg   1320

gctggcgtgg aaatattctt attggtagaa acaactacat cctggtcatc atcctgcctt   1380

tctctttatg gttacaatga tatacactgt ttgagatgag gataaaatac tctgagtcca   1440

aaccgggccc ctctgctaac catgttcatg ccttcttctt tttcctacag ctcctgggca   1500
```

```
acgtgctggt ttgtgctgtc gaccccaagc tggccgctcg agccaccatg gaacaaaagc   1560
tgatttctga agaagacttg gctagcgaac aaaagctgat ttctgaagaa gacttggaac   1620
aaaagctgat ttctgaagaa gacttgaccg gtatgccaaa aaagaagaga aaggtattag   1680
gatccatggc cagatacgac ctggtggaca ggctgaacac caccttcagg cagatggagc   1740
aggagctggc catcttcgcc gctcacctgg agcagcacaa gctgctggtg gcccgggtgt   1800
tctccctgcc tgaggtgaag aaggaggatg agcacaaccc actgaatcgc atcgaggtga   1860
agcagcacct gggcaacgat gctcagagcc tggctctgcg ccacttcagg cacctgttca   1920
tccagcagca gtccgagaac cgctcttcca aggccgctgt gaggctgcca ggagtgctgt   1980
gctaccaggt ggacaacctg tcccaggccg ccctggtgtc tcacatccag cacatcaaca   2040
agctgaagac cacattcgag cacatcgtga ccgtggagtc cgagctgcca accgcggccc   2100
ggttcgagtg ggtgcacaga cacctgccag gcctgatcac actgaacgct tacaggaccc   2160
tgaccgtgct gcacgatcct gctaccctga gatttggatg ggccaacaag cacatcatca   2220
agaacctgca cagagacgag gtgctggccc agctggagaa gagcctgaag agccccaggt   2280
ctgtggctcc ctggaccagg gaggagtggc agagaaagct ggagcgcgag taccaggaca   2340
tcgccgccct gccccagaac gccaagctga agatcaagag acctgtgaag gtgcagccaa   2400
tcgccagagt gtggtacaag ggcgaccaga agcaggtgca gcacgcctgc cccacaccac   2460
tgatcgccct gatcaatcgg gacaacggcg ccggagtgcc agacgtggga gagctgctga   2520
actacgacgc cgataatgtg cagcaccgct acaagcccca ggcccagccc ctgcggctga   2580
tcatcccacg gctgcacctg tacgtggctg actgatgaga attctgcaga tatccatcac   2640
actggcggcc ctagagggcc ctattctata gtgtcaccta aatgctagag ctcgctgatc   2700
agcctcgact gtgccttcta gttgccagcc atctgttgtt tgcccctccc ccgtgccttc   2760
cttgaccctg gaaggtgcca ctcccactgt cctttcctaa taaaatgagg aaattgcatc   2820
gcattgtctg agtaggtgtc attctattct ggggggtggg gtggggcagg acagcaaggg   2880
ggaggattgg gaagacaata gcaggcatgc tggggatgcg gtgggctcta tggcttctga   2940
ggcggaaaga accagctggg gctctagggg gtatccccac gcgccctgta gcggcgcatt   3000
aagcgcggcg ggtgtggtgg ttacgcgcag cgtgaccgct acacttgcca gcgccctagc   3060
gcccgctcct ttcgctttct tcccttcctt tctcgccacg ttcgccggct ttccccgtca   3120
agctctaaat cggggcatcc ctttagggtt ccgatttagt gctttacggc acctcgaccc   3180
caaaaaactt gattagggtg atggttcacg tagtgggcca tcgccctgat agacggtttt   3240
tcgccctttg acgttggagt ccacgttctt taatagtgga ctcttgttcc aaactggaac   3300
aacactcaac cctatctcgg tctattcttt tgatttataa gggattttgg ggatttcggc   3360
ctattggtta aaaaatgagc tgatttaaca aaaatttaac gcgaattaat tctgtggaat   3420
gtgtgtcagt tagggtgtgg aaagtcccca ggctccccag gcaggcagaa gtatgcaaag   3480
catgcatctc aattagtcag caaccaggtg tggaaagtcc ccaggctccc cagcaggcag   3540
aagtatgcaa agcatgcatc tcaattagtc agcaaccata gtcccgcccc taactccgcc   3600
catcccgccc ctaactccgc ccagttccgc ccattctccg ccccatggct gactaatttt   3660
ttttatttat gcagaggccg aggccgcctc tgcctctgag ctattccaga agtagtgagg   3720
aggctttttt ggaggcctag gcttttgcaa aaagctcccg ggagcttgta tatccatttt   3780
cggatctgat caagagacag gatgaggatc gtttcgcatg attgaacaag atggattgca   3840
```

-continued

```
cgcaggttct ccggccgctt gggtggagag gctattcggc tatgactggg cacaacagac   3900
aatcggctgc tctgatgccg ccgtgttccg gctgtcagcg caggggcgcc cggttctttt   3960
tgtcaagacc gacctgtccg gtgccctgaa tgaactgcag gacgaggcag cgcggctatc   4020
gtggctggcc acgacgggcg ttccttgcgc agctgtgctc gacgttgtca ctgaagcggg   4080
aagggactgg ctgctattgg gcgaagtgcc ggggcaggat ctcctgtcat ctcaccttgc   4140
tcctgccgag aaagtatcca tcatggctga tgcaatgcgg cggctgcata cgcttgatcc   4200
ggctacctgc ccattcgacc accaagcgaa acatcgcatc gagcgagcac gtactcggat   4260
ggaagccggt cttgtcgatc aggatgatct ggacgaagag catcaggggc tcgcgccagc   4320
cgaactgttc gccaggctca aggcgcgcat gcccgacggc gaggatctcg tcgtgaccca   4380
tggcgatgcc tgcttgccga atatcatggt ggaaaatggc cgcttttctg gattcatcga   4440
ctgtggccgg ctgggtgtgg cggaccgcta tcaggacata gcgttggcta cccgtgatat   4500
tgctgaagag cttggcggcg aatgggctga ccgcttcctc gtgctttacg gtatcgccgc   4560
tcccgattcg cagcgcatcg ccttctatcg ccttcttgac gagttcttct gagcgggact   4620
ctggggttcg aaatgaccga ccaagcgacg cccaacctgc catcacgaga tttcgattcc   4680
accgccgcct tctatgaaag gttgggcttc ggaatcgttt tccgggacgc cggctggatg   4740
atcctccagc gcggggatct catgctggag ttcttcgccc accccaactt gtttattgca   4800
gcttataatg gttacaaata aagcaatagc atcacaaatt tcacaaataa agcatttttt   4860
tcactgcatt ctagttgtgg tttgtccaaa ctcatcaatg tatcttatca tgtctgtata   4920
ccgtcgacct ctagctagag cttggcgtaa tcatggtcat agctgtttcc tgtgtgaaat   4980
tgttatccgc tcacaattcc acacaacata cgagccggaa gcataaagtg taaagcctgg   5040
ggtgcctaat gagtgagcta actcacatta attgcgttgc gctcactgcc cgctttccag   5100
tcgggaaacc tgtcgtgcca gctgcattaa tgaatcggcc aacgcgcggg gagaggcggt   5160
ttgcgtattg ggcgctcttc cgcttcctcg ctcactgact cgctgcgctc ggtcgttcgg   5220
ctgcggcgag cggtatcagc tcactcaaag gcggtaatac ggttatccac agaatcaggg   5280
gataacgcag gaaagaacat gtgagcaaaa ggccagcaaa aggccaggaa ccgtaaaaag   5340
gccgcgttgc tggcgttttt ccataggctc cgcccccctg acgagcatca caaaaatcga   5400
cgctcaagtc agaggtggcg aaacccgaca ggactataaa gataccaggc gtttccccct   5460
ggaagctccc tcgtgcgctc tcctgttccg accctgccgc ttaccggata cctgtccgcc   5520
tttctccctt cgggaagcgt ggcgctttct caatgctcac gctgtaggta tctcagttcg   5580
gtgtaggtcg ttcgctccaa gctgggctgt gtgcacgaac cccccgttca gcccgaccgc   5640
tgcgccttat ccggtaacta tcgtcttgag tccaacccgg taagacacga cttatcgcca   5700
ctggcagcag ccactggtaa caggattagc agagcgaggt atgtaggcgg tgctacagag   5760
ttcttgaagt ggtggcctaa ctacggctac actagaagga cagtatttgg tatctgcgct   5820
ctgctgaagc cagttacctt cggaaaaaga gttggtagct cttgatccgg caaacaaacc   5880
accgctggta gcggtggttt ttttgtttgc aagcagcaga ttacgcgcag aaaaaaagga   5940
tctcaagaag atcctttgat cttttctacg gggtctgacg ctcagtggaa cgaaaactca   6000
cgttaaggga ttttggtcat gagattatca aaaaggatct tcacctagat ccttttaaat   6060
taaaaatgaa gttttaaatc aatctaaagt atatatgagt aaacttggtc tgacagttac   6120
caatgcttaa tcagtgaggc acctatctca gcgatctgtc tatttcgttc atccatagtt   6180
gcctgactcc ccgtcgtgta gataactacg atacgggagg gcttaccatc tggccccagt   6240
```

```
gctgcaatga taccgcgaga cccacgctca ccggctccag atttatcagc aataaaccag   6300

ccagccggaa gggccgagcg cagaagtggt cctgcaactt tatccgcctc catccagtct   6360

attaattgtt gccgggaagc tagagtaagt agttcgccag ttaatagttt gcgcaacgtt   6420

gttgccattg ctacaggcat cgtggtgtca cgctcgtcgt ttggtatggc ttcattcagc   6480

tccggttccc aacgatcaag gcgagttaca tgatccccca tgttgtgcaa aaaagcggtt   6540

agctccttcg gtcctccgat cgttgtcaga agtaagttgg ccgcagtgtt atcactcatg   6600

gttatggcag cactgcataa ttctcttact gtcatgccat ccgtaagatg cttttctgtg   6660

actggtgagt actcaaccaa gtcattctga gaatagtgta tgcggcgacc gagttgctct   6720

tgcccggcgt caatacggga taataccgcg ccacatagca gaactttaaa agtgctcatc   6780

attggaaaac gttcttcggg gcgaaaactc tcaaggatct taccgctgtt gagatccagt   6840

tcgatgtaac ccactcgtgc acccaactga tcttcagcat cttttacttt caccagcgtt   6900

tctgggtgag caaaaacagg aaggcaaaat gccgcaaaaa agggaataag ggcgacacgg   6960

aaatgttgaa tactcatact cttccttttt caatattatt gaagcattta tcagggttat   7020

tgtctcatga gcggatacat atttgaatgt atttagaaaa ataaacaaat aggggttccg   7080

cgcacatttc cccgaaaagt gccacctgac gtc                                7113
```

<210> SEQ ID NO 55
<211> LENGTH: 16672
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (382)..(382)
<223> OTHER INFORMATION: a, c, t, g, unknown or other

<400> SEQUENCE: 55

```
ccccgcggca ggccctccga gcgtggtgga gccgttctgt gagacagccg ggtacgagtc     60

gtgacgctgg aaggggcaag cgggtggtgg gcaggaatgc ggtccgccct gcagcaaccg    120

gagggggagg gagaagggag cggaaaagtc tccaccggac gcggccatgg ctcggggggg    180

ggggggcagc ggaggascgc ttccggccga cgtctcgtcg ctgattggct tyttttcctc    240

ccgccgtgtg tgaaaacaca aatggcgtgt tttggttggc gtaaggcgcc tgtcagttaa    300

cggcagccgg agtgcgcagc cgccggcagc ctcgctctgc ccactgggtg gggcgggagg    360

taggtggggt gaggcgagct gnacgtgcgg gcgcggtcgg cctctggcgg ggcgggggag    420

gggagggagg gtcagcgaaa gtagctcgcg cgcgagcggc cgcccaccct ccccttcctc    480

tgggggagtc gttttacccg ccgccggccg ggcctcgtcg tctgattggc tctcggggcc    540

cagaaaactg gcccttgcca ttggctcgtg ttcgtgcaag ttgagtccat ccgccggcca    600

gcgggggcgg cgaggaggcg ctcccaggtt ccggccctcc cctcggcccc gcgccgcaga    660

gtctggccgc gcgcccctgc gcaacgtggc aggaagcgcg cgctgggggc ggggacgggc    720

agtagggctg agcggctgcg gggcgggtgc aagcacgttt ccgacttgag ttgcctcaag    780

aggggcgtgc tgagccagac ctccatcgcg cactccgggg agtggaggga aggagcgagg    840

gctcagttgg gctgttttgg aggcaggaag cacttgctct cccaaagtcg ctctgagttg    900

ttatcagtaa gggagctgca gtggagtagg cggggagaag gccgcaccct tctccggagg    960

ggggagggga gtgttgcaat acctttctgg gagttctctg ctgcctcctg gcttctgagg   1020
```

```
accgccctgg gcctgggaga atcccttgcc ccctcttccc ctcgtgatct gcaactccag   1080
tctttctagc cttaattaag ggatctgtag ggcgcagtag tccagggttt ccttgatgat   1140
gtcatactta tcctgtccct tttttttcca cagctcgcgg ttgaggacaa actcttcgcg   1200
gtctttccag tggggatcga cggtatcgta gagtcgaggc cgctctagaa ctagtggatc   1260
taccatgacc gagtacaagc ccacggtgcg cctcgccacc cgcgacgacg tcccccgggc   1320
cgtacgcacc ctcgccgccg cgttcgccga ctaccccgcc acgcgccaca ccgtcgaccc   1380
ggaccgccac atcgagcggg tcaccgagct gcaagaactc ttcctcacgc gcgtcgggct   1440
cgacatcggc aaggtgtggg tcgcggacga cggcgccgcg gtggcggtct ggaccacgcc   1500
ggagagcgtc gaagcggggg cggtgttcgc cgagatcggc ccgcgcatgg ccgagttgag   1560
cggttcccgg ctggccgcgc agcaacagat ggaaggcctc ctggcgccgc accggcccaa   1620
ggagcccgcg tggttcctgg ccaccgtcgg cgtctcgccc gaccaccagg gcaagggtct   1680
gggcagcgcc gtcgtgctcc ccggagtgga ggcggccgag cgcgccgggg tgcccgcctt   1740
cctggagacc tccgcgcccc gcaacctccc cttctacgag cggctcggct tcaccgtcac   1800
cgccgacgtc gagtgcccga aggaccgcgc gacctggtgc atgacccgca agcccggtgc   1860
ctgactcgac cctaggggga ggctaactga aacacggaag gagacaatac cggaaggaac   1920
ccgcgctatg acggcaataa aaagacagaa taaaacgcac ggtgttgggt cgtttgttca   1980
taaacgcggg gttcggtccc agggctggca ctctgtcgat accccaccga gaccccattg   2040
gggccaatac gcccgcgttt cttccttttc cccaccccac cccccaagtt cgggtgaagg   2100
cccagggctc gcagccaacg tcggggcggc aggccctgcc atagcctcag gttactcgga   2160
tctcgacctc gagacgcgtg cccccactcc acaatttcaa aaaaaagagt ggccacttgt   2220
ctttgtttat gggccccatt ggcgtggagc cccgtttaat tttcgggggt gttagagaca   2280
accagtggag tccgctgctg tcggcgtcca ctctctttcc ccttgttaca aatagagtgt   2340
aacaacatgg ttcacctgtc ttggtccctg cctgggacac atcttaataa ccccagtatc   2400
atattgcact aggattatgt gttgcccata gccataaatt cgtgtgagat ggacatccag   2460
tctttacggc ttgtccccac cccatggatt tctattgtta aagatattca gaatgtttca   2520
ttcctacact agtatttatt gcccaagggg tttgtgaggg ttatattggt gtcatagcac   2580
aatgccacca ctgaaccccc cgtccaaatt ttattctggg ggcgtcacct gaaaccttgt   2640
tttcgagcac ctcacataca ccttactgtt cacaactcag cagttattct attagctaaa   2700
cgaaggagaa tgaagaagca ggcgaagatt caggagagtt cactgcccgc tccttgatct   2760
tcagccactg cccttgtgac taaaatggtt cactaccctc gtggaatcct gaccccatgt   2820
aaataaaacc gtgacagctc atggggtggg agatatcgct gttccttagg accctttac    2880
taaccctaat tcgatagcat atgcttcccg ttgggtaaca tatgctattg aattagggtt   2940
agtctggata gtatatacta ctacccggga agcatatgct acccgtttag ggttaacaag   3000
ggggccttat aaacactatt gctaatgccc tcttgagggt ccgcttatcg gtagctacac   3060
aggcccctct gattgacgtt ggtgtagcct cccgtagtct tcctgggccc ctgggaggta   3120
catgtccccc agcattggtg taagagcttc agccaagagt tacacataaa ggtacgtacc   3180
agtcttcgaa agatctcggg gtgcccatcc tggtcgagct ggacggcgac gtaaacggcc   3240
acaagttcag cgtgtccggc gagggcgagg gcgatgccac ctacggcaag ctgaccctga   3300
agttcatctg caccaccggc aagctgcccg tgccctggcc caccctcgtg accaccctga   3360
```

```
cctacggcgt gcagtgcttc agccgctacc ccgaccacat gaagcagcac gacttcttca   3420
agtccgccat gcccgaaggc tacgtccagg agcgcaccat cttcttcaag gacgacggca   3480
actacaagac ccgcgccgag gtgaagttcg agggcgacac cctggtgaac cgcatcgagc   3540
tgaagggcat cgacttcaag gaggacggca acatcctggg gcacaagctg gagtacaact   3600
acaacagcca caacgtctat atcatggccg acaagcagaa gaacggcatc aaggtgaact   3660
tcaagatccg ccacaacatc gaggacggca gcgtgcagct cgccgaccac taccagcaga   3720
acacccccat cggcgacggc cccgtgctgc tgcccgacaa ccactacctg agcacccagt   3780
ccgccctgag caaagacccc aacgagaagc gcgatcacat ggtcctgctg gagttcgtga   3840
ccgccgccgg gatcactctc ggcatggacg agctgtacaa gtaaagcggc cgcgactcta   3900
gatcataatc agccatacca catttgtaga ggttttactt gctttaaaaa acctcccaca   3960
cctccccctg aacctgaaac ataaaatgaa tgcaattgtt gttgttaact tgtttattgc   4020
agcttataat ggttacaaat aaagcaatag catcacaaat ttcacaaata aagcattttt   4080
ttcactgcat tctagttgtg gtttgtccaa actcatcaat gtcgggatcc cgccaattgt   4140
ctagatttct ctaatcactt ttttttcaag gcaatcaggg tatattatat tgtacttcag   4200
cacagtttta gagaacaatt gttataatta aatgataagg tagaatattt ctgcatataa   4260
attctggctg gcgtggaaat attcttattg gtagaaacaa ctacatcctg gtcatcatcc   4320
tgcctttctc tttatggtta caatgatata cactgtttga gatgaggata aaatactctg   4380
agtccaaacc gggcccctct gctaaccatg ttcatgcctt cttctttttc ctacaggact   4440
cctccctgca ggacggcgag ttcatctaca aggtgaagct gcgcggcacc aacttcccct   4500
ccgacggccc cgtaatgcag aagaagacca tgggctggga ggcctcctcc gagcggatgt   4560
accccgagga cggcgccctg aagggcgaga tcaagatgag gctgaagctg aaggacggtg   4620
gccactacga cgccgaggtc aagaccacct acatggccaa gaagcccgtg cagctgcccg   4680
gcgcctacaa gaccgacatc aagctggaca tcacctccca caacgaggac tacaccatcg   4740
tggaacagta cgagcgcgcc gagggccgcc actccaccgg cggtatggat gaactctata   4800
aataagcacg ggccctattc tatagtgtca cctaaatgct agagctcgct gatcagcctc   4860
gactgtgcct tctagttgcc agccatctgt tgtttgcccc tcccccgtgc cttccttgac   4920
cctggaaggt gccactccca ctgtcctttc ctaataaaat gaggaaattg catcgcattg   4980
tctgagtagg tgtcattcta ttctgggggg tggggtgggg caggacagca agggggagga   5040
ttgggaagac aatagcaggc atgctgggga ggatctgtgt ggaaagtccc caggctcccc   5100
aggcaggcag aagtatgcaa agcatgcatc tcaattagtc agcaaccagg tgtggaaagt   5160
ccccaggctc cccagcaggc agaagtatgc aaagcatgca tctcaattag tcagcaacca   5220
tagtcccgcc cctaactccg cccatcccgc ccctaactcc gcccagttcc gcccattctc   5280
cgccccatgg ctgactaatt ttttttattt atgcagaggc cgaggccgcc tctgcctctg   5340
agctattcca gaagtagtga ggaggctttt ttggaggcct aggcttttgc aaaaagctcc   5400
cgggagcttg tatatccatt ttcggataag cttaactaaa ccatggtatc aaaaggtgaa   5460
gaaaacaata tggcagtcat caaggagttc atgcgcttca aggtgcgcat ggagggctcc   5520
gtgaacggcc acgagttcga gatcgagggc gagggcgagg gccgccccta cgagggcacc   5580
cagaccgcca agctgaaggt gaccgagggt ggcccccctgc ccttcgcctg ggacatcctg   5640
tcccctcagt tcatgtacgg ctccaaggcc tacgtgaagc accccgccga catccccgac   5700
tacttgaagc tgtccttccc cgagggcttc aagtgggagc gcgtgatgaa cttcgaggac   5760
```

```
ggcggcgtgg tgaccgtgac ccaggtgagt ttggggaccc ttgattgttc tttctttttc   5820
gctattgtaa aattcatgtt atatggaggg ggcaaagttt tcagggtgtt gtttagaatg   5880
ggaagatgtc ccttgtatca ccatggaccc tcatgataat tttgtttctt tcactttcta   5940
ctctgttgac aaccattgtc tcctcttatt ttcttttcat tttctgtaac tttttcgtta   6000
aactttagct tgcatttgta acgaattttt aaattcactt ttgtttattt gtcagattgt   6060
aagtaccggg acccggaatt ctaccgggta ggggaggcgc ttttcccaag gcagtctgga   6120
gcatgcgctt tagcagcccc gctggcactt ggcgctacac aagtggcctc tggcctcgca   6180
cacattccac atccaccggt agcgccaacc ggctccgttc tttggtggcc ccttcgcgcc   6240
acttctactc ctcccctagt caggaagttt cccccagcaa gctcgcgtcg tgcaggacgt   6300
gacaaatgga agtagcacgt ctcactagtc tcgtgcagat ggacagcacc gctgagcaat   6360
ggaagcgggt aggcctttgg ggcagcggcc aatagcagct ttgttccttc gctttctggg   6420
ctcagaggct gggaaggggt gggtccgggg gcgggctcag gggcgggctc aggggcgggc   6480
gggcgcccga aggtcctccc gaggcccggc attctgcacg cttcaaaagc gcacgtctgc   6540
cgcgctgttc tcctcttcct catctccggg cctttcgacc tgcagcccaa gctctagcgc   6600
taccggtcgc caccatggtg agcaagggcg aggagctgtt caccggggtg gtgcccatcc   6660
tggtcgagct ggacggcgac gtaaacggcc acaagttcag cgtgtccggc gagggcgagg   6720
gcgatgccac ctacggcaag ctgaccctga agttcatctg caccaccggc aagctgcccg   6780
tgccctggcc caccctcgtg accaccctga cctacggcgt gcagtgcttc agccgctacc   6840
ccgaccacat gaagcagcac gacttcttca agtccgccat gcccgaaggc tacgtccagg   6900
agcgcaccat cttcttcaag gacgacggca actacaagac ccgcgccgag gtgaagttcg   6960
agggcgacac cctggtgaac cgcatcgagc tgaagggcat cgtagggata acgctcatat   7020
atcgataata agtatgttgt aactaaagtc gtgaaataag tatgttgtaa ctaaagtctt   7080
acaataagta tgttgtaact aaagtgtata cctttccgga tagggataac gctcatatat   7140
cgataataag tatgttgtaa ctaaagtcgt gaaataagta tgttgtaact aaagtcttac   7200
aataagtatg ttgtaactaa agtgtatacc tttccggata gggataacag ggtaatcaag   7260
gaggacggca acatcctggg gcacaagctg gagtacaact acaacagcca caacgtctat   7320
atcatggccg acaagcagaa gaacggcatc aaggtgaact tcaagatccg ccacaacatc   7380
gaggacggca gcgtgcagct cgccgaccac taccagcaga acacccccat cggcgacggc   7440
cccgtgctgc tgcccgacaa ccactacctg agcacccagt ccgccctgag caaagacccc   7500
aacgagaagc gcgatcacat ggtcctgctg gagttcgtga ccgccgccgg gatcactctc   7560
ggcatggacg agctgtacaa gtaaagcggc cgcgactcta gatcataatc agccatacca   7620
catttgtaga ggttttactt gctttaaaaa acctcccaca cctccccctg aacctgaaac   7680
ataaaatgaa tgcaattgtt gttgttaact tgtttattgc agcttataat ggttacaaat   7740
aaagcaatag catcacaaat ttcacaaata aagcattttt ttcactgcat tctagttgtg   7800
gtttgtccaa actcatcaat gtcggatggc cgcgctgggg atgcggtggg ctctatggct   7860
tatgaggcgg aaagaaccag ctggggctcg atcctctagt tggcgcgccg gctagaagat   7920
gggcgggagt cttctgggca ggcttaaagg ctaacctggt gtgtgggcgt tgtcctgcag   7980
gggaattgaa caggtgtaaa attggaggga caagacttcc cacagatttt cggttttgtc   8040
gggaagtttt ttaatagggg caaataggaa aatggaggat aggagtcatc tggggtttat   8100
```

```
gcagcaaaac tacaggtata ttgcttgtat ccgcctcgga gatttccatg aggagataaa   8160
gacatgtcac ccgagtttat actctcctgc ttagatccta ctacagtatg aaatacagtg   8220
tygcgaggta gactatgtaa gcagatttaa tcattttaaa gagcccagta cttcatatcc   8280
atttctcccg ctccttctgc agccttatca aaaggtattt agaacactca ttttagcccc   8340
attttcattt attatactgg cttatccaac ccctagacag agcattggca ttttcccttt   8400
cctgatctta gaagtctgat gactcatgaa accagacaga ttagttacat acaccacaaa   8460
tcgaggctgt agctggggcc tcaacactgc agttctttta taactcctta gtacactttt   8520
tgttgatcct ttgccttgat ccttaatttt cagtgtctat cacctctccc gtcaggtggt   8580
gttccacatt tgggcctatt ctcagtccag ggagttttac aacaatagat gtattgagaa   8640
tccaacctaa agcttaactt tccactccca tgaatgcctc tctccttttt ctccattata   8700
actgagctat waccattaat ggtttcaggt ggatgtctcc tcccccaata tacctgatgt   8760
atctacatat tgccaggctg atattttaag acatwaaagg tatatttcat tattgagcca   8820
catggtattg attactgcta ctaaaatttt gtcattgtac acatctgtaa aaggtggttc   8880
cttttggaat gcaaagttca ggtgtttgtt gtctttcctg acctaaggtc ttgtgagctt   8940
gtatttttc tatttaagca gtgctttctc ttggactggc ttgactcatg gcattctaca   9000
cgttattgct ggtctaaatg tgattttgcc aagcttcttc aggacctata attttgcttg   9060
acttgtagcc aaacacaagt aaaatgatta agcaacaaat gtatttgtga agcttggttt   9120
ttaggttgtt gtgttgtgtg tgcttgtgct ctataataat actatccagg ggctggagag   9180
gtggctcgga gttcaagagc acagactgct cttccagaag tcctgagttc aattcccagc   9240
aaccacatgg tggctcacaa ccatctgtaa tgggatctga tgccctcttc tggtgtgtct   9300
gaagaccaca agtgtattca cattaaataa ataatcctcc ttcttcttct tttttttttt   9360
ttaaagagaa twctgtctcc agtagaatta ctgaagtaat gaaatacttt gtgtttgttc   9420
caatatggwa gccaataatc aaatactctt wagcactgga aatgtaccaa ggaactattt   9480
tatttaagtg wactgtggac agaggagcca taactgcaga cttgtgggat acagaagacc   9540
aatgcagact taatgtcttt tctcttacac taagcaataa agaaataaaa attgaacttc   9600
tagtatccta tttgttaaac tgctagcttt actaactttt gtgcttcatc tatacaaagc   9660
tgaaagctaa gtctgcagcc attactaaac atgaaagcaa gtaatgataa ttttggattt   9720
caaaaatgta gggccagagt ttagccagcc agtggtggtg cttgccttta tgccttaatc   9780
ccagcactct ggaggcagag acaggcagat ctctgagttt gagcccagcc tggtctacac   9840
atcaagttct atctaggata gccaggaata cacacagaaa ccctgttggg gagggggct   9900
ctgagatttc ataaaattat aattgaagca ttccctaatg agccactatg gatgtggcta   9960
aatccgtcta cctttctgat gagatttggg tattattttt tctgtctctg ctgttggttg  10020
ggtcttttga cactgtgggc tttcttaaag cctccttccc tgccatgtgg tctcttgttt  10080
gctactaact tcccatggct taaatggcat ggctttttgc cttctaaggg cagctgctga  10140
gwtttgcagc ctgatttcca gggtggggtt gggaaatctt tcaaacacta aaattgtcct  10200
ttaatttttt tttaaaaaat gggttatata ataaacctca taaaatagtt atgaggagtg  10260
aggtggacta atattaatga gtccctcccc tataaaagag ctattaaggc tttttgtctt  10320
atactaactt ttttttaaa tgtggtatct ttagaaccaa gggtcttaga gttttagtat  10380
acagaaactg ttgcatcgct taatcagatt ttctagtttc aaatccagag aatccaaatt  10440
cttcacagcc aaagtcaaat taagaatttc tgactttaat gttatttgct actgtgaata  10500
```

```
taaaatgata gcttttcctg aggcagggtc tcactatgta tctctgcctg atctgcaaca  10560
agatatgtag actaaagttc tgcctgcttt tgtctcctga atactaaggt taaaatgtag  10620
taatactttt ggaacttgca ggtcagattc ttttataggg gacacactaa gggagcttgg  10680
gtgatagttg gtaaatgtgt ttaagtgatg aaaacttgaa ttattatcac cgcaacctac  10740
tttttaaaaa aaaaagccag gcctgttaga gcatgctaag ggatccctag gacttgctga  10800
gcacacaaga gtagtacttg gcaggctcct ggtgagagca tatttcaaaa aacaaggcag  10860
acaaccaaga aactacagta aggttacctg tctttaacca tctgcatata cacagggata  10920
ttaaaatatt ccaaataata tttcattcaa gttttccccc atcaaattgg gacatggatt  10980
tctccggtga ataggcagag ttggaaacta aacaaatgtt ggttttgtga tttgtgaaat  11040
tgttttcaag tgatagttaa agcccatgag atacagaaca aagctgctat ttcgaggtct  11100
cttggttata ctcagaagca cttctttggg tttccctgca ctatcctgat catgtgctag  11160
gcctwcctta ggctgattgt tgttcaaata acttaagttt cctgtcaggt gatgtcatat  11220
gatttcatat atcaaggcaa aacatgttat atatgttaaa catttgkact taatgtgaaa  11280
gttaggtctt tgtgggtttt gattttaatt tcaaaacctg agctaaataa gtcattttac  11340
atgtcttaca tttggtgaat tgtatattgt ggtttgcagg caagactctc tgacctagta  11400
accctcctat agagcacttt gctgggtcac aagtctagga gtcaagcatt tcaccttgaa  11460
gttgagacgt tttgttagtg tatactagtt atatgttgga ggacatgttt atccagaaga  11520
tattcaggac tatttttgac tgggctaagg aattgattct gattagcact gttagtgagc  11580
attgagtggc ctttaggctt gaattggagt cacttgtata tctcaaataa tgctggcctt  11640
ttttwaaaag cccttgttct ttatcaccct gttttctaca taatttttgt tcaaagaaat  11700
acttgtttgg atctcctttt gacaacaata gcatgttttc aagccatatt ttttttcctt  11760
ttttttttt tttttggttt ttcgagacag ggtttctctg tatagccctg gctgtcctgg  11820
aactcacttt gtagaccagg ctggcctcga actcagaaat ccgcctgcct ctgcctcctg  11880
agtgccggga ttaaaggcgt gcaccaccac gcctggctaa gttggatatt ttgtatataa  11940
ctataaccaa tactaactcc actgggtgga tttttaattc agtcagtagt cttaagtggt  12000
ctttattggc ccttattaaa atctactgtt cactctaaca gaggctgttg gactagtggs  12060
actaagcaac ttcctacgga tatactagca gataagggtc agggatagaa actagtctag  12120
cgttttgtat acctaccagc ttatactacc ttgttctgat agaaatattt aggacatcta  12180
gcttatcgat ccgtcgacgg tatcgataag cttgatatcg aattctaccg ggtaggggag  12240
gcgcttttcc aaggcagtct gagcatgcgc ttagcagccc cgctggcact tggcgctaca  12300
caagtggcct ytggcctcgc acacattcca catccaccgg taggcgccaa ccggctccgt  12360
tctttggtgg ccccttcgcg ccaccttctw ctcctcccct agtcaggaag ttcccccccg  12420
ccccgcagct cgcgtcgtsa ggacgtgaca aatggaagta gcacgtctca ctagtctcgt  12480
cagatggaca gcaccgctga gcaatggaag cgggtaggcc tttggggcag cggccaatag  12540
cagctttgct ccttcgcttt ctgggctcag aggctgggaa ggggtgggtc cgggggcggg  12600
ctcaggggcg ggctcagggg cggggcgggc gcccgaaggt cctccggagg cccggcattc  12660
tgcacgcttc aaaagcgcac gtctgccgcg ctgttctcct cttcctcatc tccgggcctt  12720
tcgacctgca ggtcctcgcc atggatcctg atgatgttgt tattcttcta atcttttgta  12780
tggaaaactt ttcttcgtac cacgggacta aacctggtta tgtagattcc attcaaaaag  12840
```

```
gtatacaaaa gccaaaatct ggtacacaag gaaattatga cgatgattgg aaagggtttt  12900
atagtaccga caataaatac gacgctgcgg gatactctgt agataatgaa aacccgctct  12960
ctggaaaagc tggaggcgtg gtcaaagtga cgtatccagg actgacgaag gttctcgcac  13020
taaaagtgga taatgccgaa actattaaga aagagttagg tttaagtctc actgaaccgt  13080
tgatggagca agtcggaacg gaagagttta tcaaaaggtt cggtgatggt gcttcgcgtg  13140
tagtgctcag ccttcccttc gctgagggga gttctagcgt tgaatatatt aataactggg  13200
aacaggcgaa agcgttaagc gtagaacttg agattaattt tgaaacccgt ggaaaacgtg  13260
gccaagatgc gatgtatgag tatatggctc aagcctgtgc aggaaatcgt gtcaggcgat  13320
ctctttgtga aggaacctta cttctgtggt gtgacataat tggacaaact acctacagag  13380
atttaaagct ctaaggtaaa tataaaattt ttaagtgtat aatgtgttaa actactgatt  13440
ctaattgttt gtgtatttta gattccaacc tatggaactg atgaatggga gcagtggtgg  13500
aatgcagatc ctagagctcg ctgatcagcc tcgactgtgc cttctagttg ccagccatct  13560
gttgtttgcc cctcccccgt gccttccttg accctggaag gtgccactcc cactgtcctt  13620
tcctaataaa atgaggaaat tgcatcgcat tgtctgagta ggtgtcattc tattctgggg  13680
ggtggggtgg ggcaggacag caagggggag gattgggaag acaatagcag gcatgctggg  13740
gatgcggtgg gctctatggc ttctgaggcg gaaagaacca gctggggctc gacctcgagg  13800
gggggcccgg tacccagctt ttgttccctt tagtgagggt taattgcgcg cttggcgtaa  13860
tcatggtcat agctgtttcc tgtgtgaaat tgttatccgc tcacaattcc acacaacata  13920
cgagccggaa gcataaagtg taaagcctgg ggtgcctaat gagtgagcta actcacatta  13980
attgcgttgc gctcactgcc cgctttccag tcgggaaacc tgtcgtgcca gctgcattaa  14040
tgaatcggcc aacgcgcggg gagaggcggt ttgcgtattg ggcgctcttc cgcttcctcg  14100
ctcactgact cgctgcgctc ggtcgttcgg ctgcggcgag cggtatcagc tcactcaaag  14160
gcggtaatac ggttatccac agaatcaggg gataacgcag gaaagaacat gtgagcaaaa  14220
ggccagcaaa aggccaggaa ccgtaaaaag gccgcgttgc tggcgttttt ccataggctc  14280
cgcccccctg acgagcatca caaaaatcga cgctcaagtc agaggtggcg aaacccgaca  14340
ggactataaa gataccaggc gtttccccct ggaagctccc tcgtgcgctc tcctgttccg  14400
accctgccgc ttaccggata cctgtccgcc tttctccctt cgggaagcgt ggcgctttct  14460
catagctcac gctgtaggta tctcagttcg gtgtaggtcg ttcgctccaa gctgggctgt  14520
gtgcacgaac cccccgttca gcccgaccgc tgcgccttat ccggtaacta tcgtcttgag  14580
tccaacccgg taagacacga cttatcgcca ctggcagcag ccactggtaa caggattagc  14640
agagcgaggt atgtaggcgg tgctacagag ttcttgaagt ggtggcctaa ctacggctac  14700
actagaagga cagtatttgg tatctgcgct ctgctgaagc cagttacctt cggaaaaaga  14760
gttggtagct cttgatccgg caaacaaacc accgctggta gcggtggttt ttttgtttgc  14820
aagcagcaga ttacgcgcag aaaaaaagga tctcaagaag atcctttgat cttttctacg  14880
gggtctgacg ctcagtggaa cgaaaactca cgttaaggga ttttggtcat gagattatca  14940
aaaaggatct tcacctagat ccttttaaat taaaaatgaa gttttaaatc aatctaaagt  15000
atatatgagt aaacttggtc tgacagttac caatgcttaa tcagtgaggc acctatctca  15060
gcgatctgtc tatttcgttc atccatagtt gcctgactcc ccgtcgtgta gataactacg  15120
atacgggagg gcttaccatc tggccccagt gctgcaatga taccgcgaga cccacgctca  15180
ccggctccag atttatcagc aataaaccag ccagccggaa gggccgagcg cagaagtggt  15240
```

```
cctgcaactt tatccgcctc catccagtct attaattgtt gccgggaagc tagagtaagt  15300
agttcgccag ttaatagttt gcgcaacgtt gttgccattg ctacaggcat cgtggtgtca  15360
cgctcgtcgt ttggtatggc ttcattcagc tccggttccc aacgatcaag gcgagttaca  15420
tgatccccca tgttgtgcaa aaaagcggtt agctccttcg gtcctccgat cgttgtcaga  15480
agtaagttgg ccgcagtgtt atcactcatg gttatggcag cactgcataa ttctcttact  15540
gtcatgccat ccgtaagatg cttttctgtg actggtgagt actcaaccaa gtcattctga  15600
gaatagtgta tgcggcgacc gagttgctct tgcccggcgt caatacggga taataccgcg  15660
ccacatagca gaactttaaa agtgctcatc attggaaaac gttcttcggg gcgaaaactc  15720
tcaaggatct taccgctgtt gagatccagt tcgatgtaac ccactcgtgc acccaactga  15780
tcttcagcat cttttacttt caccagcgtt tctgggtgag caaaaacagg aaggcaaaat  15840
gccgcaaaaa agggaataag ggcgacacgg aaatgttgaa tactcatact cttccttttt  15900
caatattatt gaagcattta tcagggttat tgtctcatga gcggatacat atttgaatgt  15960
atttagaaaa ataaacaaat aggggttccg cgcacatttc cccgaaaagt gccacctaaa  16020
ttgtaagcgt taatattttg ttaaaattcg cgttaaattt ttgttaaatc agctcatttt  16080
ttaaccaata ggccgaaatc ggcaaaatcc cttataaatc aaaagaatag accgagatag  16140
ggttgagtgt tgttccagtt tggaacaaga gtccactatt aaagaacgtg gactccaacg  16200
tcaaagggcg aaaaaccgtc tatcagggcg atggcccact acgtgaacca tcaccctaat  16260
caagtttttt ggggtcgagg tgccgtaaag cactaaatcg gaaccctaaa gggagccccc  16320
gatttagagc ttgacgggga aagccggcga acgtggcgag aaaggaaggg aagaaagcga  16380
aaggagcggg cgctagggcg ctggcaagtg tagcggtcac gctgcgcgta accaccacac  16440
ccgccgcgct taatgcgccg ctacagggcg cgtcccattc gccattcagg ctgcgcaact  16500
gttgggaagg gcgatcggtg cgggcctctt cgctattacg ccagctggcg aaagggggat  16560
gtgctgcaag gcgattaagt tgggtaacgc cagggttttc ccagtcacga cgttgtaaaa  16620
cgacggccag tgagcgcgcg taatacgact cactataggg cgaattggag ct          16672
```

COMPOSITIONS AND METHODS FOR CHARACTERIZING A DNA REPAIR VARIANT POLYPEPTIDE

CROSS-REFERENCE TO RELATED APPLICATION

This application claims priority to and the benefit of U.S. Provisional Patent Application Ser. No. 62/080,875, filed Nov. 17, 2014, the entire contents of which is hereby incorporated by reference herein.

STATEMENT OF RIGHTS TO INVENTIONS MADE UNDER FEDERALLY SPONSORED RESEARCH

This invention was made with U.S. government support under Grant Nos: R01CA095175, R01GM073894 and R21CA144017, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 28, 2015, is named 366343.1002US1 (00007)_SL.txt and is 140,705 bytes in size.

BACKGROUND OF THE INVENTION

The major breast/ovarian cancer predisposition genes, BRCA1 and BRCA2, function in double strand break (DSB) repair and sister chromatid recombination (SCR), a potentially error-free pathway of homologous recombination (HR). Some BRCA1 missense mutations (encoding point mutant proteins) are known to be either neutral or pathogenic. However, most missense mutants—termed "variants of uncertain significance" (VUS)—are difficult to classify due to their scarcity in the human population. Therefore, if a woman carries a germ line BRCA1 VUS allele, her cancer risk is unknown. Methods of characterizing the functional significance of such variants are urgently required to distinguish variants that increase the risk of breast cancer from those that are not functionally significant.

SUMMARY OF THE INVENTION

As described below, the present invention provides quantitative homologous recombination assays developed to characterize the pathogenicity DNA repair polypeptides (e.g., BRCA1, BRCA2, Rad51) and provide urgently needed functional information on the significance of DNA repair variants of uncertain significance (VUS) alleles.

In one aspect, the invention provides a vector containing a promoter directing expression in a mammalian cell and a nucleic acid sequence containing one or more Ter sites.

In another aspect, the invention provides a homologous recombination reporter gene conversion vector comprising one or more Ter sites in a nucleic acid sequence encoding a reporter polypeptide or other detectable or selectable marker.

In another aspect, the invention provides a homologous recombination reporter of short and long tract gene conversion vector comprising a 5' truncated GFP encoding nucleic acid sequence positioned upstream of 5' and 3' RFP exons positioned upstream of one to six Ter sites positioned within a GFP encoding nucleic acid sequence.

In another aspect, the invention provides a cell containing the vector of any aspect of the invention.

In another aspect, the invention provides a mammalian cell containing or expressing a Tus polypeptide and a polynucleotide comprising one or more Ter sites (e.g., a vector of the invention, or portion thereof, is integrated as a single copy at a defined genomic locus).

In another aspect, the invention provides a cell containing a single copy of a polynucleotide containing a 5' truncated GFP encoding sequence positioned upstream of 5' and 3' RFP exons positioned upstream of one to six Ter sites positioned within a GFP encoding sequence, where the polynucleotide is integrated into the cell genome; and an expression vector encoding a wild-type Tus polypeptide.

In another aspect, the invention provides a method of characterizing the functional significance of a mutation in a DNA repair polypeptide, involving: expressing in a cell a DNA repair polypeptide having a mutation and a wild-type Tus polypeptide fused to a nuclear localization signal, where the cell contains a single genomic integrated copy of a polynucleotide containing a 5' truncated GFP encoding sequence positioned upstream of 5' and 3' RFP exons positioned upstream of one or more Ter sites positioned within a GFP encoding sequence comprising a rare cutting endonuclease site; and detecting long-tract gene conversion in the cell, where an increase in long tract gene conversion in the cell relative to a reference indicates that the mutation in the DNA repair polypeptide is functionally significant.

In another aspect, the invention provides a method of characterizing the functional significance of a mutation in a BRCA1, BRCA2, or Rad51 polypeptide, involving expressing in a cell one or more of a BRCA1, BRCA2, or Rad51 polypeptide comprising a mutation and a wild-type Tus polypeptide fused to a nuclear localization signal, where the cell contains a single genomic integrated copy of a polynucleotide containing a 5' truncated GFP encoding sequence positioned upstream of 5' and 3' RFP exons positioned upstream of one or more Ter sites positioned within a GFP encoding sequence comprising a rare cutting endonuclease site; and detecting long-tract gene conversion in the cell, where an increase in long tract gene conversion in the cell relative to a cell expressing a wild-type DNA repair polypeptide indicates that the mutation in the DNA repair polypeptide is functionally significant.

In another aspect, the invention provides a method of characterizing the functional significance of a mutation in a DNA repair polypeptide in a biological sample, involving sequencing a DNA repair gene in a biological sample derived from a subject, thereby identifying a mutation in the DNA repair gene; contacting a cell lacking the DNA repair polypeptide with each of an expression vector encoding a DNA repair polypeptide comprising the identified mutation; and an expression vector encoding a wild-type Tus polypeptide fused to a nuclear localization signal, where the cell contains a single genomic integrated copy of a polynucleotide containing a 5' truncated GFP encoding sequence positioned upstream of 5' and 3' RFP exons positioned upstream of one or more Ter sites positioned within a GFP encoding sequence containing a rare cutting endonuclease site; and detecting long-tract gene conversion in the cell, where an increase in long tract gene conversion in the cell relative to a reference cell expressing a wild-type DNA repair polypeptide indicates that the mutation in the DNA repair polypeptide is functionally significant.

In another aspect, the invention provides a method of selecting a treatment for a subject identified as having breast cancer, involving: sequencing a DNA repair gene in a biological sample derived from a patient, thereby identifying a mutation in the DNA repair gene; contacting a cell lacking the DNA repair polypeptide with each of: an expression vector encoding a DNA repair polypeptide comprising the identified mutation; and an expression vector encoding a wild-type Tus polypeptide fused to a nuclear localization signal; where the cell contains a single genomic integrated copy of a polynucleotide containing a 5' truncated GFP encoding sequence positioned upstream of 5' and 3' RFP exons positioned upstream of one or more Ter sites positioned within a GFP encoding sequence containing a rare cutting endonuclease site; and detecting long-tract gene conversion in the cell, where an increase in long tract gene conversion in the cell relative to a reference cell expressing a wild-type DNA repair polypeptide indicates that the mutation in the DNA repair polypeptide is functionally significant, thereby indicating that the patient should receive a PARP inhibitor or cisplatin. In various embodiments, the DNA repair polypeptide is BRCA1, BRCA2, and/or Rad51.

In one aspect, the invention provides a method of site-specific genome editing, involving contacting a genomic locus with two or more polypeptides that specifically bind two or more target nucleic acid sequences in the genomic locus and induce replication fork stalling, thereby producing error-free genome editing.

In another aspect, the invention provides a method of generating site specific recombination at a genomic locus, involving: inhibiting replication at the genomic locus, thereby generating site specific recombination at the genomic locus.

In another aspect, the invention provides a vector containing one or more Ter sites upstream of an origin of replication, which is upstream of a replication block.

In various embodiments of any of the aspects delineated herein, the origin of replication is an Epstein-Barr virus nuclear antigen 1 binding origin of replication and/or Epstein-Barr virus nuclear antigen 1-bound family of repeats. In various embodiments of any of the aspects delineated herein, the vector comprises more than one Ter sites. In particular embodiments, the vector contains one or more Ter sites upstream of an Epstein-Barr virus nuclear antigen 1 binding origin of replication and a replication block that is the Epstein-Barr virus nuclear antigen 1-bound family of repeats.

In a related aspect, the invention provides a cell containing a vector having one or more Ter sites upstream of an origin of replication. In various embodiments of any of the aspects delineated herein, the cell further contains a polynucleotide encoding a wild-type or variant Tus.

In another related aspect, the invention provides a cell containing a vector having one or more Ter sites upstream of an Epstein-Barr virus nuclear antigen 1 binding origin of replication and a replication block that is the Epstein-Barr virus nuclear antigen 1-bound family of repeats.

In another aspect, the invention provides a method of characterizing replication involving: contacting a cell that expresses EBNA1 with a vector comprising one or more Ter sites upstream of an Epstein-Barr virus nuclear antigen 1 binding origin of replication and a replication block that is the Epstein-Barr virus nuclear antigen 1-bound family of repeats and a vector encoding wild-type or variant Tus; and detecting long-tract gene conversion at Tus/Ter-stalled forks.

In various embodiments of any of the aspects delineated herein, the vector contains two, three, four, five, six or more Ter sites. In particular embodiments, the vector contains 6, 9, 12, 15, or 21 Ter sites. In various embodiments of any of the aspects delineated herein, the reporter polypeptide or other detectable or selectable marker is GFP, RFP, CFP, YFP, an antibiotic resistance marker, ampicillin-resistance, or cell surface marker selectable by antibody. In various embodiments of any of the aspects delineated herein, the vector is codon-optimized for mammalian expression. In various embodiments of any of the aspects delineated herein, the vector contains a rare cutting endonuclease site (e.g., targeted by I-SceI, I-PpoI, CRISPR/Cas9, TALEN, and/or Zinc finger nuclease).

In various embodiments of any of the aspects delineated herein, the polynucleotide is randomly integrated or targeted into the cell genome. In various embodiments of any of the aspects delineated herein, the Tus polypeptide is fused to a nuclear localization signal and/or an epitope tag. In various embodiments of any of the aspects delineated herein, the cell is a eukaryotic cell, mammalian cell, vertebrate cell, insect cell, chicken cell, mouse cell, or human cell.

In various embodiments of any of the aspects delineated herein, the reference is a cell expressing a wild-type DNA repair polypeptide. In various embodiments of any of the aspects delineated herein, the the DNA repair polypeptide is selected from one or more genes involved in homologous recombination. In specific embodiments, the the DNA repair polypeptide is one or more of BRCA1, BRCA2, BARD1, PALB2, RAD51, RAD51B, RAD51C, RAD51D, XRCC2, XRCC3, BLM, other RECQ helicases, MRE11, Rad50, NBS1, ATM, ATR, CTIP, Brip, RPA, and/or RPA-like polypeptide.

In various embodiments of any of the aspects delineated herein, long tract gene conversion is detected by detecting an alteration in fluorescence between the cell and the reference cell. In various embodiments, the fluorescence is detected using flow cytometry. In various embodiments of any of the aspects delineated herein, detection involves detecting $GFP^{+}RFP^{-}$; $GFP^{+}RFP^{+}$; and/or $GFP^{-}RFP^{+}$ in the cells.

In various embodiments of any of the aspects delineated herein, the functional significance of a mutation in a DNA repair polypeptide in a biological sample indicates the subject has or has a propensity to develop cancer. In various embodiments of any of the aspects delineated herein, the biological sample is a tumor sample or blood sample.

In various embodiments of any of the aspects delineated herein, replication is inhibited by contacting the genomic locus with a polypeptide or polypeptide complex that specifically binds a target nucleic acid sequence in the genomic locus. In various embodiments of any of the aspects delineated herein, the genomic locus is contacted with a plurality of polypeptides or polypeptide complexes. In various embodiments of any of the aspects delineated herein, the polypeptide or polypeptide complex comprises one or more of Cas9, Cas 9 null, guide nucleic acid, Tus, Zinc finger domain, Zinc finger nuclease, transcription activator-like effector (TALE) domain, and/or TALE nuclease. In various embodiments two or more polypeptides are Cas9, Cas9 null (i.e., catalytically inactive Cas9), Tus, Zinc finger domain, Zinc finger nuclease, transcription activator-like effector (TALE) domain, and/or TALE nucleases. In various embodiments of any of the aspects delineated herein, the genome editing or site specific recombination alters the DNA sequence of a disease gene at the genomic locus.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "biologic sample" is meant any tissue, cell, fluid, or other material derived from an organism.

By "BRCA1 polypeptide" is meant a protein having at least about 85% amino acid sequence identity to the sequence provided at Genbank accession no. AAC37594 or a fragment thereof and having DNA repair activity.

```
GenBank:
AAC37594.1 >gi|1698399|gb|AAC37594.1|BRCA1
[Homo sapiens]
MDLSALRVEEVQNVINAMQKILECPICLELIKEPVSTKCDHIFCKFCMLK
LLNQKKGPSQCPLCKNDITKRSLQESTRFSQLVEELLKIICAFQLDTGLE
YANSYNFAKKENNSPEHLKDEVSIIQSMGYRNRAKRLLQSEPENPSLQET
SLSVQLSNLGTVRTLRTKQRIQPQKTSVYIELGSDSSEDTVNKATYCSVG
DQELLQITPQGTRDEISLDSAKKAACEFSETDVTNTEHHQPSNNDLNTTE
KRAAERHPEKYQGSSVSNLHVEPCGTNTHASSLQHENSSLLLTKDRMNVE
KAEFCNKSKQPGLARSQHNRWAGSKETCNDRRTPSTEKKVDLNADPLCER
KEWNKQKLPCSENPRDTEDVPWITLNSSIQKVNEWFSRSDELLGSDDSHD
GESESNAKVADVLDVLNEVDEYSGSSEKIDLLASDPHEALICKSERVHSK
SVESNIEDKIFGKTYRKKASLPNLSHVTENLIIGAFVTEPQIIQERPLTN
KLKRKRRPTSGLHPEDFIKKADLAVQKTPEMINQGTNQTEQNGQVMNITN
SGHENKTKGDSIQNEKNPNPIESLEKESAFKTKAEPISSSISNMELELNI
HNSKAPKKNRLRRKSSTRHIHALELVVSRNLSPPNCTELQIDSCSSSEEI
KKKKYNQMPVRHSRNLQLMEGKEPATGAKKSNKPNEQTSKRHDSDTFPEL
```

-continued

```
KLTNAPGSFTKCSNTSELKEFVNPSLPREEKEEKLETVKVSNNAEDPKDL
MLSGERVLQTERSVESSSISLVPGTDYGTQESISLLEVSTLGKAKTEPNK
CVSQCAAFENPKGLIHGCSKDNRNDTEGFKYPLGHEVNHSRETSIEMEES
ELDAQYLQNTFKVSKRQSFAPFSNPGNAEEECATFSAHSGSLKKQSPKVT
FECEQKEENQGKNESNIKPVQTVNITAGFPVVGQKDKPVDNAKCSIKGGS
RFCLSSQFRGNETGLITPNKHGLLQNPYRIPPLFPIKSFVKTKCKKNLLE
ENFEEHSMSPEREMGNENIPSTVSTISRNNIRENVFKEASSSNINEVGSS
TNEVGSSINEIGSSDENIQAELGRNRGPKLNAMLRLGVLQPEVYKQSLPG
SNCKHPEIKKQEYEEVVQTVNTDFSPYLISDNLEQPMGSSHASQVCSETP
DDLLDDGEIKEDTSFAENDIKESSAVFSKSVQKGELSRSPSPFTHTHLAQ
GYRRGAKKLESSEENLSSEDEELPCFQHLLFGKVNNIPSQSTRHSTVATE
CLSKNTEENLLSLKNSLNDCSNQVILAKASQEHHLSEETKCSASLFSSQC
SELEDLTANTNTQDPFLIGSSKQMRHQSESQGVGLSDKELVSDDEERGTG
LEENNQEEQSMDSNLGEAASGCESETSVSEDCSGLSSQSDILTTQQRDTM
QHNLIKLQQEMAELEAVLEQHGSQPSNSYPSIISDSSALEDLRNPEQSTS
EKAVLTSQKSSEYPISQNPEGLSADKFEVSADSSTSKNKEPGVERSSPSK
CPSLDDRWYMHSCSGSLQNRNYPSQEELIKVVDVEEQQLEESGPHDLTET
SYLPRQDLEGTPYLESGISLFSDDPESDPSEDRAPESARVGNIPSSTSAL
KVPQLKVAESAQSPAAAHTTDTAGYNAMEESVSREKPELTASTERVNKRM
SMVVSGLTPEEFMLVYKFARKHHITLTNLITEETTHVVMKTDAEFVCERT
LKYFLGIAGGKWVVSYFWVTQSIKERKMLNEHDFEVRGDVVNGRNHQGPK
RARESQDRKIFRGLEICCYGPFTNMPTDQLEWMVQLCGASVVKELSSFTL
GTGVHPIVVVQPDAWTEDNGFHAIGQMCEAPVVTREWVLDSVALYQCQEL
DTYLIPQIPHSHY (SEQ ID NO: 1)
```

By "BRCA1 polynucleotide" is meant a nucleic acid molecule encoding a BRCA1 polypeptide. An exemplary polynucleotide sequence is provided at NCBI Ref. No. NM 007294, which is reproduced below:

```
  1 gtaccttgat ttcgtattct gagaggctgc tgcttagcgg tagccccttg gtttccgtgg
 61 caacggaaaa gcgcgggaat tacagataaa ttaaaactgc gactgcgcgg cgtgagctcg
121 ctgagacttc ctggacgggg gacaggctgt ggggtttctc agataactgg gcccctgcgc
181 tcaggaggcc ttcaccctct gctctgggta aagttcattg gaacagaaag aaatggattt
241 atctgctctt cgcgttgaag aagtacaaaa tgtcattaat gctatgcaga aaatcttaga
301 gtgtcccatc tgtctggagt tgatcaagga acctgtctcc acaaagtgtg accacatatt
361 ttgcaaattt tgcatgctga aacttctcaa ccagaagaaa gggccttcac agtgtccttt
421 atgtaagaat gatataacca aaaggagcct acaagaaagt acgagattta gtcaacttgt
481 tgaagagcta ttgaaaatca tttgtgcttt tcagcttgac acaggtttgg agtatgcaaa
541 cagctataat tttgcaaaaa aggaaaataa ctctcctgaa catctaaaag atgaagtttc
601 tatcatccaa agtatgggct acagaaaccg tgccaaaaga cttctacaga gtgaacccga
661 aaatccttcc ttgcaggaaa ccagtctcag tgtccaactc tctaaccttg gaactgtgag
721 aactctgagg acaaagcagc ggatacaacc tcaaaagacg tctgtctaca ttgaattggg
```

-continued

```
781 atctgattct tctgaagata ccgttaataa ggcaacttat tgcagtgtgg gagatcaaga
841 attgttacaa atcacccctc aaggaaccag ggatgaaatc agtttggatt ctgcaaaaaa
901 ggctgcttgt gaattttctg agacggatgt aacaaatact gaacatcatc aacccagtaa
961 taatgatttg aacaccactg agaagcgtgc agctgagagg catccagaaa agtatcaggg
1021 tagttctgtt tcaaacttgc atgtggagcc atgtggcaca aatactcatg ccagctcatt
1081 acagcatgag aacagcagtt tattactcac taaagacaga atgaatgtag aaaaggctga
1141 attctgtaat aaaagcaaac agcctggctt agcaaggagc caacataaca gatgggctgg
1201 aagtaaggaa acatgtaatg ataggcggac tcccagcaca gaaaaaaagg tagatctgaa
1261 tgctgatccc ctgtgtgaga gaaaagaatg gaataagcag aaactgccat gctcagagaa
1321 tcctagagat actgaagatg ttccttggat aacactaaat agcagcattc agaaagttaa
1381 tgagtggttt tccagaagtg atgaactgtt aggttctgat gactcacatg atggggagtc
1441 tgaatcaaat gccaaagtag ctgatgtatt ggacgttcta aatgaggtag atgaatattc
1501 tggttcttca gagaaaatag acttactggc cagtgatcct catgaggctt taatatgtaa
1561 aagtgaaaga gttcactcca aatcagtaga gagtaatatt gaagacaaaa tatttgggaa
1621 aacctatcgg aagaaggcaa gcctccccaa cttaagccat gtaactgaaa atctaattat
1681 aggagcattt gttactgagc cacagataat acaagagcgt cccctcacaa ataaattaaa
1741 gcgtaaaagg agacctacat caggccttca tcctgaggat tttatcaaga aagcagattt
1801 ggcagttcaa aagactcctg aaatgataaa tcagggaact aaccaaacgg agcagaatgg
1861 tcaagtgatg aatattacta atagtggtca tgagaataaa acaaaaggtg attctattca
1921 gaatgagaaa aatcctaacc caatagaatc actcgaaaaa gaatctgctt tcaaaacgaa
1981 agctgaacct ataagcagca gtataagcaa tatggaactc gaattaaata tccacaattc
2041 aaaagcacct aaaaagaata ggctgaggag gaagtcttct accaggcata ttcatgcgct
2101 tgaactagta gtcagtagaa atctaagccc acctaattgt actgaattgc aaattgatag
2161 ttgttctagc agtgaagaga taaagaaaaa aaagtacaac caaatgccag tcaggcacag
2221 cagaaaccta caactcatgg aaggtaaaga acctgcaact ggagccaaga agagtaacaa
2281 gccaaatgaa cagacaagta aaagacatga cagcgatact ttcccagagc tgaagttaac
2341 aaatgcacct ggttctttta ctaagtgttc aaataccagt gaacttaaag aatttgtcaa
2401 tcctagcctt ccaagagaag aaaaagaaga gaaactagaa acagttaaag tgtctaataa
2461 tgctgaagac cccaaagatc tcatgttaag tggagaaagg gttttgcaaa ctgaaagatc
2521 tgtagagagt agcagtattt cattggtacc tggtactgat tatggcactc aggaaagtat
2581 ctcgttactg gaagttagca ctctagggaa ggcaaaaaca gaaccaaata aatgtgtgag
2641 tcagtgtgca gcatttgaaa accccaaggg actaattcat ggttgttcca aagataatag
2701 aaatgacaca gaaggcttta agtatccatt gggacatgaa gttaaccaca gtcgggaaac
2761 aagcatagaa atggaagaaa gtgaacttga tgctcagtat ttgcagaata cattcaaggt
2821 ttcaaagcgc cagtcatttg ctccgttttc aaatccagga aatgcagaag aggaatgtgc
2881 aacattctct gcccactctg ggtccttaaa gaaacaaagt ccaaaagtca cttttgaatg
2941 tgaacaaaag gaagaaaatc aaggaaagaa tgagtctaat atcaagcctg tacagacagt
3001 taatatcact gcaggctttc ctgtggttgg tcagaaagat aagccagttg ataatgccaa
3061 atgtagtatc aaaggaggct ctaggttttg tctatcatct cagttcagag gcaacgaaac
3121 tggactcatt actccaaata aacatggact tttacaaaac ccatatcgta taccaccact
```

-continued

```
3181 ttttcccatc aagtcatttg ttaaaactaa atgtaagaaa aatctgctag aggaaaactt
3241 tgaggaacat tcaatgtcac ctgaaagaga aatgggaaat gagaacattc caagtacagt
3301 gagcacaatt agccgtaata acattagaga aaatgttttt aaagaagcca gctcaagcaa
3361 tattaatgaa gtaggttcca gtactaatga agtgggctcc agtattaatg aaataggttc
3421 cagtgatgaa aacattcaag cagaactagg tagaaacaga gggccaaaat tgaatgctat
3481 gcttagatta ggggttttgc aacctgaggt ctataaacaa agtcttcctg gaagtaattg
3541 taagcatcct gaaataaaaa agcaagaata tgaagaagta gttcagactg ttaatacaga
3601 tttctctcca tatctgattt cagataactt agaacagcct atgggaagta gtcatgcatc
3661 tcaggtttgt tctgagacac ctgatgacct gttagatgat ggtgaaataa aggaagatac
3721 tagttttgct gaaaatgaca ttaaggaaag ttctgctgtt tttagcaaaa gcgtccagaa
3781 aggagagctt agcaggagtc ctagcccttt cacccataca catttggctc agggttaccg
3841 aagaggggcc aagaaattag agtcctcaga agagaactta tctagtgagg atgaagagct
3901 tccctgcttc caacacttgt tatttggtaa agtaaacaat ataccttctc agtctactag
3961 gcatagcacc gttgctaccg agtgtctgtc taagaacaca gaggagaatt tattatcatt
4021 gaagaatagc ttaaatgact gcagtaacca ggtaatattg gcaaaggcat ctcaggaaca
4081 tcaccttagt gaggaaacaa aatgttctgc tagcttgttt tcttcacagt gcagtgaatt
4141 ggaagacttg actgcaaata caaacaccca ggatcctttc ttgattggtt cttccaaaca
4201 aatgaggcat cagtctgaaa gccagggagt tggtctgagt gacaaggaat tggtttcaga
4261 tgatgaagaa agaggaacgg gcttggaaga aaataatcaa gaagagcaaa gcatggattc
4321 aaacttaggt gaagcagcat ctgggtgtga gagtgaaaca agcgtctctg aagactgctc
4381 agggctatcc tctcagagtg acattttaac cactcagcag agggatacca tgcaacataa
4441 cctgataaag ctccagcagg aaatggctga actagaagct gtgttagaac agcatgggag
4501 ccagccttct aacagctacc cttccatcat aagtgactct tctgcccttg aggacctgcg
4561 aaatccagaa caaagcacat cagaaaaagc agtattaact tcacagaaaa gtagtgaata
4621 ccctataagc cagaatccag aaggcctttc tgctgacaag tttgaggtgt ctgcagatag
4681 ttctaccagt aaaaataaag aaccaggagt ggaaaggtca tccccttcta aatgcccatc
4741 attagatgat aggtggtaca tgcacagttg ctctgggagt cttcagaata gaaactaccc
4801 atctcaagag gagctcatta aggttgttga tgtggaggag caacagctgg aagagtctgg
4861 gccacacgat ttgacggaaa catcttactt gccaaggcaa gatctagagg gaacccctta
4921 cctggaatct ggaatcagcc tcttctctga tgaccctgaa tctgatcctt ctgaagacag
4981 agccccagag tcagctcgtg ttggcaacat accatcttca acctctgcat tgaaagttcc
5041 ccaattgaaa gttgcagaat ctgcccagag tccagctgct gctcatacta ctgatactgc
5101 tgggtataat gcaatggaag aaagtgtgag cagggagaag ccagaattga cagcttcaac
5161 agaaagggtc aacaaaagaa tgtccatggt ggtgtctggc ctgaccccag aagaatttat
5221 gctcgtgtac aagtttgcca gaaaacacca catcacttta actaatctaa ttactgaaga
5281 gactactcat gttgttatga aaacagatgc tgagtttgtg tgtgaacgga cactgaaata
5341 ttttctagga attgcgggag gaaaatgggt agttagctat ttctgggtga cccagtctat
5401 taaagaaaga aaaatgctga atgagcatga ttttgaagtc agaggagatg tggtcaatgg
5461 aagaaaccac caaggtccaa agcgagcaag agaatcccag gacagaaaga tcttcagggg
5521 gctagaaatc tgttgctatg ggcccttcac caacatgccc acagatcaac tggaatggat
5581 ggtacagctg tgtggtgctt ctgtggtgaa ggagctttca tcattcaccc ttggcacagg
```

-continued

```
5641 tgtccaccca attgtggttg tgcagccaga tgcctggaca gaggacaatg gcttccatgc
5701 aattgggcag atgtgtgagg cacctgtggt gacccgagag tgggtgttgg acagtgtagc
5761 actctaccag tgccaggagc tggacaccta cctgataccc cagatccccc acagccacta
5821 ctgactgcag ccagccacag gtacagagcc acaggacccc aagaatgagc ttacaaagtg
5881 gcctttccag gccctgggag ctcctctcac tcttcagtcc ttctactgtc ctggctacta
5941 aatattttat gtacatcagc ctgaaaagga cttctggcta tgcaagggtc ccttaaagat
6001 tttctgcttg aagtctccct tggaaatctg ccatgagcac aaaattatgg taatttttca
6061 cctgagaaga ttttaaaacc atttaaacgc caccaattga gcaagatgct gattcattat
6121 ttatcagccc tattctttct attcaggctg ttgttggctt agggctggaa gcacagagtg
6181 gcttggcctc aagagaatag ctggtttccc taagtttact tctctaaaac cctgtgttca
6241 caaaggcaga gagtcagacc cttcaatgga aggagagtgc ttgggatcga ttatgtgact
6301 taaagtcaga atagtccttg ggcagttctc aaatgttgga gtggaacatt ggggaggaaa
6361 ttctgaggca ggtattagaa atgaaaagga aacttgaaac ctgggcatgg tggctcacgc
6421 ctgtaatccc agcactttgg gaggccaagg tgggcagatc actggaggtc aggagttcga
6481 aaccagcctg gccaacatgg tgaaacccca tctctactaa aaatacagaa attagccggt
6541 catggtggtg gacacctgta atcccagcta ctcaggtggc taaggcagga gaatcacttc
6601 agcccgggag gtggaggttg cagtgagcca agatcatacc acggcactcc agcctgggtg
6661 acagtgagac tgtggctcaa aaaaaaaaaa aaaaaaagga aaatgaaact agaagagatt
6721 tctaaaagtc tgagatatat ttgctagatt tctaaagaat gtgttctaaa acagcagaag
6781 attttcaaga accggtttcc aaagacagtc ttctaattcc tcattagtaa taagtaaaat
6841 gtttattgtt gtagctctgg tatataatcc attcctctta aaatataaga cctctggcat
6901 gaatatttca tatctataaa atgacagatc ccaccaggaa ggaagctgtt gctttctttg
6961 aggtgatttt tttcctttgc tccctgttgc tgaaaccata cagcttcata aataattttg
7021 cttgctgaag gaagaaaaag tgtttttcat aaacccatta tccaggactg tttatagctg
7081 ttggaaggac taggtcttcc ctagcccccc cagtgtgcaa gggcagtgaa gacttgattg
7141 tacaaaatac gttttgtaaa tgttgtgctg ttaacactgc aaataaactt ggtagcaaac
7201 acttccaaaa aaaaaaaaaa aaaa (SEQ ID NO: 2)
```

By “BRCA2 polypeptide” is meant a protein having at least about 85% amino acid sequence identity to GenBank Accession No: AAB07223 or a fragment thereof having DNA repair activity. The amino acid sequence of an exemplary BRCA2 polypeptide is provided below:

```
GenBank: AAB07223.1
>gi|1161384|gb|AAB07223.1|BRCA2 [Homo sapiens]
MPIGSKERPTFFEIFKTRCNKADLGPISLNWFEELSSEAPPYNSEPAEES
EHKNNNYEPNLFKTPQRKPSYNQLASTPIIFKEQGLTLPLYQSPVKELDK
FKLDLGRNVPNSRHKSLRTVKTKMDQADDVSCPLLNSCLSESPVVLQCTH
VTPQRDKSVVCGSLFHTPKFVKGRQTPKHISESLGAEVDPDMSWSSSLAT
PPTLSSTVLIVRNEEASETVFPHDTTANVKSYFSNHDESLKKNDRFIASV
TDSENTNQREAASHGFGKTSGNSFKVNSCKDHIGKSMPNVLEDEVYETVV
DTSEEDSFSLCFSKCRTKNLQKVRTSKTRKKIFHEANADECEKSKNQVKE
```

-continued

```
KYSFVSEVEPNDTDPLDSNVAHQKPFESGSDKISKEVVPSLACEWSQLTL
SGLNGAQMEKIPLLHISSCDQNISEKDLLDTENKRKKDFLTSENSLPRIS
SLPKSEKPLNEETVVNKRDEEQHLESHTDCILAVKQAISGTSPVASSFQG
IKKSIFRIRESPKETFNASFSGHMTDPNFKKETEASESGLEIHTVCSQKE
DSLCPNLIDNGSWPATTTQNSVALKNAGLISTLKKKTNKFIYAIHDETFY
KGKKIPKDQKSELINCSAQFEANAFEAPLTFANADSGLLHSSVKRSCSQN
DSEEPTLSLTSSFGTILRKCSRNETCSNNTVISQDLDYKEAKCNKEKLQL
FITPEADSLSCLQEGQCENDPKSKKVSDIKEEVLAAACHPVQHSKVEYSD
TDFQSQKSLLYDHENASTLILTPTSKDVLSNLVMISRGKESYKMSDKLKG
NNYESDVELTKNIPMEKNQDVCALNENYKNVELLPPEKYMRVASPSRKVQ
FNQNTNLRVIQKNQEETTSISKITVNPDSEELFSDNENNFVFQVANERNN
LALGNTKELHETDLTCVNEPIFKNSTMVLYGDTGDKQATQVSIKKDLVYV
```

-continued

```
LAEENKNSVKQHIKMTLGQDLKSDISLNIDKIPEKNNDYMNKWAGLLGPI
SNHSFGGSFRTASNKEIKLSEHNIKKSKMFFKDIEEQYPTSLACVEIVNT
LALDNQKKLSKPQSINTVSAHLQSSVVVSDCKNSHITPQMLFSKQDFNSN
HNLTPSQKAEITELSTILEESGSQFEFTQFRKPSYILQKSTFEVPENQMT
ILKTTSEECRDADLHVIMNAPSIGQVDSSKQFEGTVEIKRKFAGLLKNDC
NKSASGYLTDENEVGFRGFYSAHGTKLNVSTEALQKAVKLFSDIENISEE
TSAEVHPISLSSSKCHDSVVSMFKIENHNDKTVSEKNNKCQLILQNNIEM
TTGTFVEEITENYKRNTENEDNKYTAASRNSHNLEFDGSDSSKNDTVCIH
KDETDLLFTDQHNICLKLSGQFMKEGNTQIKEDLSDLTFLEVAKAQEACH
GNTSNKEQLTATKTEQNIKDFETSDTFFQTASGKNISVAKESFNKIVNFF
DQKPEELHNFSLNSELHSDIRKNKMDILSYEETDIVKHKILKESVPVGTG
NQLVTFQGQPERDEKIKEPTLLGFHTASGKKVKIAKESLDKVKNLFDEKE
QGTSEITSFSHQWAKTLKYREACKDLELACETIEITAAPKCKEMQNSLNN
DKNLVSIETVVPPKLLSDNLCRQTENLKTSKSIFLKVKVHENVEKETAKS
PATCYTNQSPYSVIENSALAFYTSCSRKTSVSQTSLLEAKKWLREGIFDG
QPERINTADYVGNYLYENNSNSTIAENDKNHLSEKQDTYLSNSSMSNSYS
YHSDEVYNDSGYLSKNKLDSGIEPVLKNVEDQKNTSFSKVISNVKDANAY
PQTVNEDICVEELVTSSSPCKNKNAAIKLSISNSNNFEVGPPAFRIASGK
IVCVSHETIKKVKDIFTDSFSKVIKENNENKSKICQTKIMAGCYEALDDS
EDILHNSLDNDECSTHSHKVFADIQSEEILQHNQNMSGLEKVSKISPCDV
SLETSDICKCSIGKLHKSVSSANTCGIFSTASGKSVQVSDASLQNARQVF
SEIEDSTKQVFSKVLFKSNEHSDQLTREENTAIRTPEHLISQKGFSYNVV
NSSAFSGFSTASGKQVSILESSLHKVKGVLEEFDLIRTEHSLHYSPTSRQ
NVSKILPRVDKRNPEHCVNSEMEKTCSKEFKLSNNLNVEGGSSENNHSIK
VSPYLSQFQQDKQQLVLGTKVSLVENIHVLGKEQASPKNVKMEIGKTETF
SDVPVKTNIEVCSTYSKDSENYFETEAVEIAKAFMEDDELTDSKLPSHAT
```

-continued

```
HSLFTCPENEEMVLSNSRIGKRRGEPLILVGEPSIKRNLLNEFDRIIENQ
EKSLKASKSTPDGTIKDRRLFMHHVSLEPITCVPFRTTKERQEIQNPNFT
APGQEFLSKSHLYEHLTLEKSSSNLAVSGHPFYQVSATRNEKMRHLITTG
RPTKVFVPPFKTKSHFHRVEQCVRNINLEENRQKQNIDGHGSDDSKNKIN
DNEIHQFNKNNSNQAAAVTFTKCEEEPLDLITSLQNARDIQDMRIKKKQR
QRVFPQPGSLYLAKTSTLPRISLKAAVGGQVPSACSHKQLYTYGVSKHCI
KINSKNAESFQFHTEDYFGKESLWTGKGIQLADGGWLIPSNDGKAGKEEF
YRALCDTPGVDPKLISRIWVYNHYRWIIWKLAAMECAFPKEFANRCLSPE
RVLLQLKYRYDTEIDRSRRSAIKKIMERDDTAAKTLVLCVSDIISLSANI
SETSSNKTSSADTQKVAIIELTDGWYAVKAQLDPPLLAVLKNGRLTVGQK
IILHGAELVGSPDACTPLEAPESLMLKISANSTRPARWYTKLGFFPDPRP
FPLPLSSLFSDGGNVGCVDVIIQRAYPIQWMEKTSSGLYIFRNEREEEKE
AAKYVEAQQKRLEALFTKIQEEFEEHEENTTKPYLPSRALTRQQVRALQD
GAELYEAVKNAADPAYLEGYFSEEQLRALNNHRQMLNDKKQAQIQLEIRK
AMESAEQKEQGLSRDVTTVWKLRIVSYSKKEKDSVILSIWRPSSDLYSLL
TEGKRYRIYHLATSKSKSKSERANIQLAATKKTQYQQLPVSDEILFQIYQ
PREPLHFSKFLDPDFQPSCSEVDLIGFVVSVVKKTGLAPFVYLSDECYNL
LAIKFWIDLNEDIIKPHMLIAASNLQWRPESKSGLLTLFAGDFSVFSASP
KEGHFQETFNKMKNTVENIDILCNEAENKLMHILHANDPKWSTPTKDCTS
GPYTAQIIPGTGNKLLMSSPNCEIYYQSPLSLCMAKRKSVSTPVSAQMTS
KSCKGEKEIDDQKNCKKRRALDFLSRLPLPPPVSPICTFVSPAAQKAFQP
PRSCGTKYETPIKKKELNSPQMTPFKKFNEISLLESNSIADEELALINTQ
ALLSGSTGEKQFISVSESTRTAPTSSEDYLRLKRRCTTSLIKEQESSQAS
TEECEKNKQDTITTKKYI (SEQ ID NO: 3)
```

By "BRCA2 polynucleotide" is meant a nucleic acid molecule encoding a BRCA2 polypeptide. An exemplary BRCA2 polynucleotide is provided at NM_000059, which is reproduced below:

```
  1 gtggcgcgag cttctgaaac taggcggcag aggcggagcc gctgtggcac tgctgcgcct
 61 ctgctgcgcc tcgggtgtct tttgcggcgg tgggtcgccg ccgggagaag cgtgagggga
121 cagatttgtg accggcgcgg tttttgtcag cttactccgg ccaaaaaaga actgcacctc
181 tggagcggac ttatttacca agcattggag gaatatcgta ggtaaaaatg cctattggat
241 ccaaagagag gccaacattt tttgaaattt ttaagacacg ctgcaacaaa gcagatttag
301 gaccaataag tcttaattgg tttgaagaac tttcttcaga agctccaccc tataattctg
361 aacctgcaga agaatctgaa cataaaaaca acaattacga accaaaccta tttaaaactc
421 cacaaaggaa accatcttat aatcagctgg cttcaactcc aataatattc aaagagcaag
481 ggctgactct gccgctgtac caatctcctg taaaagaatt agataaattc aaattagact
541 taggaaggaa tgttcccaat agtagacata aaagtcttcg cacagtgaaa actaaaatgg
601 atcaagcaga tgatgtttcc tgtccacttc taaattcttg tcttagtgaa agtcctgttg
661 ttctacaatg tacacatgta acaccacaaa gagataagtc agtggtatgt gggagtttgt
721 ttcatacacc aaagtttgtg aagggtcgtc agacaccaaa acatatttct gaaagtctag
```

-continued 781 gagctgaggt ggatcctgat atgtcttggt caagttcttt agctacacca cccaccctta 841 gttctactgt gctcatagtc agaaatgaag aagcatctga aactgtattt cctcatgata 901 ctactgctaa tgtgaaaagc tatttttcca atcatgatga aagtctgaag aaaaatgata 961 gatttatcgc ttctgtgaca gacagtgaaa acacaaatca aagagaagct gcaagtcatg 1021 gatttggaaa aacatcaggg aattcattta aagtaaatag ctgcaaagac cacattggaa 1081 agtcaatgcc aaatgtccta gaagatgaag tatatgaaac agttgtagat acctctgaag 1141 aagatagttt ttcattatgt ttttctaaat gtagaacaaa aaatctacaa aaagtaagaa 1201 ctagcaagac taggaaaaaa attttccatg aagcaaacgc tgatgaatgt gaaaaatcta 1261 aaaaccaagt gaaagaaaaa tactcatttg tatctgaagt ggaaccaaat gatactgatc 1321 cattagattc aaatgtagca aatcagaagc cctttgagag tggaagtgac aaaatctcca 1381 aggaagttgt accgtctttg gcctgtgaat ggtctcaact aaccctttca ggtctaaatg 1441 gagcccagat ggagaaaata cccctattgc atatttcttc atgtgaccaa aatatttcag 1501 aaaaagacct attagacaca gagaacaaaa gaaagaaaga ttttcttact tcagagaatt 1561 ctttgccacg tatttctagc ctaccaaaat cagagaagcc attaaatgag gaaacagtgg 1621 taaataagag agatgaagag cagcatcttg aatctcatac agactgcatt cttgcagtaa 1681 agcaggcaat atctggaact tctccagtgg cttcttcatt tcagggtatc aaaaagtcta 1741 tattcagaat aagagaatca cctaaagaga ctttcaatgc aagtttttca ggtcatatga 1801 ctgatccaaa ctttaaaaaa gaaactgaag cctctgaaag tggactggaa atacatactg 1861 tttgctcaca gaaggaggac tccttatgtc caaatttaat tgataatgga agctggccag 1921 ccaccaccac acagaattct gtagctttga agaatgcagg tttaatatcc actttgaaaa 1981 agaaaacaaa taagtttatt tatgctatac atgatgaaac atcttataaa ggaaaaaaaa 2041 taccgaaaga ccaaaaatca gaactaatta actgttcagc ccagtttgaa gcaaatgctt 2101 ttgaagcacc acttacattt gcaaatgctg attcaggttt attgcattct tctgtgaaaa 2161 gaagctgttc acagaatgat tctgaagaac caactttgtc cttaactagc tcttttggga 2221 caattctgag gaaatgttct agaaatgaaa catgttctaa taatacagta atctctcagg 2281 atcttgatta taaagaagca aaatgtaata aggaaaaact acagttattt attaccccag 2341 aagctgattc tctgtcatgc ctgcaggaag gacagtgtga aaatgatcca aaaagcaaaa 2401 aagtttcaga tataaaagaa gaggtcttgg ctgcagcatg tcacccagta caacattcaa 2461 aagtggaata cagtgatact gactttcaat cccagaaaag tcttttatat gatcatgaaa 2521 atgccagcac tcttatttta actcctactt ccaaggatgt tctgtcaaac ctagtcatga 2581 tttctagagg caaagaatca tacaaaatgt cagacaagct caaaggtaac aattatgaat 2641 ctgatgttga attaaccaaa aatattccca tggaaaagaa tcaagatgta tgtgctttaa 2701 atgaaaatta taaaaacgtt gagctgttgc cacctgaaaa atacatgaga gtagcatcac 2761 cttcaagaaa ggtacaattc aaccaaaaca caaatctaag agtaatccaa aaaaatcaag 2821 aagaaactac ttcaatttca aaaataactg tcaatccaga ctctgaagaa cttttctcag 2881 acaatgagaa taattttgtc ttccaagtag ctaatgaaag gaataatctt gctttaggaa 2941 atactaagga acttcatgaa acagacttga cttgtgtaaa cgaacccatt ttcaagaact 3001 ctaccatggt tttatatgga gacacaggtg ataaacaagc aacccaagtg tcaattaaaa 3061 aagatttggt ttatgttctt gcagaggaga acaaaaatag tgtaaagcag catataaaaa 3121 tgactctagg tcaagattta aaatcggaca tctccttgaa tatagataaa ataccagaaa -continued

```
3181 aaaataatga ttacatgaac aaatgggcag gactcttagg tccaatttca aatcacagtt
3241 ttggaggtag cttcagaaca gcttcaaata aggaaatcaa gctctctgaa cataacatta
3301 agaagagcaa aatgttcttc aaagatattg aagaacaata tcctactagt ttagcttgtg
3361 ttgaaattgt aaataccttg gcattagata atcaaaagaa actgagcaag cctcagtcaa
3421 ttaatactgt atctgcacat ttacagagta gtgtagttgt ttctgattgt aaaaatagtc
3481 atataacccc tcagatgtta ttttccaagc aggattttaa ttcaaaccat aatttaacac
3541 ctagccaaaa ggcagaaatt acagaacttt ctactatatt agaagaatca ggaagtcagt
3601 ttgaatttac tcagtttaga aaaccaagct acatattgca gaagagtaca tttgaagtgc
3661 ctgaaaacca gatgactatc ttaaagacca cttctgagga atgcagagat gctgatcttc
3721 atgtcataat gaatgcccca tcgattggtc aggtagacag cagcaagcaa tttgaaggta
3781 cagttgaaat taaacggaag tttgctggcc tgttgaaaaa tgactgtaac aaaagtgctt
3841 ctggttattt aacagatgaa aatgaagtgg ggtttagggg cttttattct gctcatggca
3901 caaaactgaa tgtttctact gaagctctgc aaaaagctgt gaaactgttt agtgatattg
3961 agaatattag tgaggaaact tctgcagagg tacatccaat aagtttatct tcaagtaaat
4021 gtcatgattc tgttgtttca atgtttaaga tagaaaatca taatgataaa actgtaagtg
4081 aaaaaaataa taaatgccaa ctgatattac aaaataatat tgaaatgact actggcactt
4141 ttgttgaaga aattactgaa aattacaaga gaaatactga aaatgaagat aacaaatata
4201 ctgctgccag tagaaattct cataacttag aatttgatgg cagtgattca agtaaaaatg
4261 atactgtttg tattcataaa gatgaaacgg acttgctatt tactgatcag cacaacatat
4321 gtcttaaatt atctggccag tttatgaagg agggaaacac tcagattaaa gaagatttgt
4381 cagatttaac tttttggaa gttgcgaaag ctcaagaagc atgtcatggt aatacttcaa
4441 ataaagaaca gttaactgct actaaaacgg agcaaaatat aaaagatttt gagacttctg
4501 atacattttt tcagactgca agtgggaaaa atattagtgt cgccaaagag tcatttaata
4561 aaattgtaaa tttctttgat cagaaaccag aagaattgca taacttttcc ttaaattctg
4621 aattacattc tgacataaga aagaacaaaa tggacattct aagttatgag gaaacagaca
4681 tagttaaaca caaaatactg aaagaaagtg tcccagttgg tactggaaat caactagtga
4741 ccttccaggg acaacccgaa cgtgatgaaa agatcaaaga acctactcta ttgggtttttc
4801 atacagctag cgggaaaaaa gttaaaattg caaaggaatc tttggacaaa gtgaaaaacc
4861 tttttgatga aaaagagcaa ggtactagtg aaatcaccag ttttagccat caatgggcaa
4921 agaccctaaa gtacagagag gcctgtaaag accttgaatt agcatgtgag accattgaga
4981 tcacagctgc cccaaagtgt aaagaaatgc agaattctct caataatgat aaaaaccttg
5041 tttctattga gactgtggtg ccacctaagc tcttaagtga taatttatgt agacaaactg
5101 aaaatctcaa aacatcaaaa agtatctttt tgaaagttaa agtacatgaa aatgtagaaa
5161 aagaaacagc aaaaagtcct gcaacttgtt acacaaatca gtccccttat tcagtcattg
5221 aaaattcagc cttagctttt tacacaagtt gtagtagaaa aacttctgtg agtcagactt
5281 cattacttga agcaaaaaaa tggcttagag aaggaatatt tgatggtcaa ccagaaagaa
5341 taaatactgc agattatgta ggaaattatt tgtatgaaaa taattcaaac agtactatag
5401 ctgaaaatga caaaaatcat ctctccgaaa aacaagatac ttatttaagt aacagtagca
5461 tgtctaacag ctattcctac cattctgatg aggtatataa tgattcagga tatctctcaa
5521 aaaataaact tgattctggt attgagccag tattgaagaa tgttgaagat caaaaaaaca
5581 ctagtttttc caaagtaata tccaatgtaa aagatgcaaa tgcataccca caaactgtaa
```

-continued

```
5641 atgaagatat ttgcgttgag gaacttgtga ctagctcttc accctgcaaa aataaaaatg
5701 cagccattaa attgtccata tctaatagta ataattttga ggtagggcca cctgcattta
5761 ggatagccag tggtaaaatc gtttgtgttt cacatgaaac aattaaaaaa gtgaaagaca
5821 tatttacaga cagtttcagt aaagtaatta aggaaaacaa cgagaataaa tcaaaaattt
5881 gccaaacgaa aattatggca ggttgttacg aggcattgga tgattcagag gatattcttc
5941 ataactctct agataatgat gaatgtagca cgcattcaca taaggttttt gctgacattc
6001 agagtgaaga aattttacaa cataaccaaa atatgtctgg attggagaaa gtttctaaaa
6061 tatcaccttg tgatgttagt ttggaaactt cagatatatg taaatgtagt atagggaagc
6121 ttcataagtc agtctcatct gcaaatactt gtgggatttt tagcacagca agtggaaaat
6181 ctgtccaggt atcagatgct tcattacaaa acgcaagaca agtgtttttct gaaatagaag
6241 atagtaccaa gcaagtcttt tccaaagtat tgtttaaaag taacgaacat tcagaccagc
6301 tcacaagaga agaaaatact gctatacgta ctccagaaca tttaatatcc caaaaaggct
6361 tttcatataa tgtggtaaat tcatctgctt tctctggatt tagtacagca agtggaaagc
6421 aagtttccat tttagaaagt tccttacaca aagttaaggg agtgttagag gaatttgatt
6481 taatcagaac tgagcatagt cttcactatt cacctacgtc tagacaaaat gtatcaaaaa
6541 tacttcctcg tgttgataag agaaacccag agcactgtgt aaactcagaa atggaaaaaa
6601 cctgcagtaa agaatttaaa ttatcaaata acttaaatgt tgaaggtggt tcttcagaaa
6661 ataatcactc tattaaagtt tctccatatc tctctcaatt tcaacaagac aaacaacagt
6721 tggtattagg aaccaaagtg tcacttgttg agaacattca tgttttggga aaagaacagg
6781 cttcacctaa aaacgtaaaa atggaaattg gtaaaactga aacttttttct gatgttcctg
6841 tgaaaacaaa tatagaagtt tgttctactt actccaaaga ttcagaaaac tactttgaaa
6901 cagaagcagt agaaattgct aaagctttta tggaagatga tgaactgaca gattctaaac
6961 tgccaagtca tgccacacat tctcttttta catgtcccga aaatgaggaa atggttttgt
7021 caaattcaag aattggaaaa agaagaggag agccccttat cttagtggga gaaccctcaa
7081 tcaaaagaaa cttattaaat gaatttgaca ggataataga aaatcaagaa aaatccttaa
7141 aggcttcaaa aagcactcca gatggcacaa taaaagatcg aagattgttt atgcatcatg
7201 tttctttaga gccgattacc tgtgtaccct ttcgcacaac taaggaacgt caagagatac
7261 agaatccaaa ttttaccgca cctggtcaag aatttctgtc taaatctcat ttgtatgaac
7321 atctgacttt ggaaaaatct tcaagcaatt tagcagtttc aggacatcca ttttatcaag
7381 tttctgctac aagaaatgaa aaaatgagac acttgattac tacaggcaga ccaaccaaag
7441 tctttgttcc accttttaaa actaaatcac attttcacag agttgaacag tgtgttagga
7501 atattaactt ggaggaaaac agacaaaagc aaaacattga tggacatggc tctgatgata
7561 gtaaaaataa gattaatgac aatgagattc atcagtttaa caaaaacaac tccaatcaag
7621 cagcagctgt aactttcaca aagtgtgaag aagaaccttt agatttaatt acaagtcttc
7681 agaatgccag agatatacag gatatgcgaa ttaagaagaa acaaaggcaa cgcgtctttc
7741 cacagccagg cagtctgtat cttgcaaaaa catccactct gcctcgaatc tctctgaaag
7801 cagcagtagg aggccaagtt ccctctgcgt gttctcataa acagctgtat acgtatggcg
7861 tttctaaaca ttgcataaaa attaacagca aaaatgcaga gtcttttcag tttcacactg
7921 aagattattt tggtaaggaa agtttatgga ctggaaaagg aatacagttg gctgatggtg
7981 gatggctcat accctccaat gatggaaagg ctggaaaaga agaattttat agggctctgt
```

-continued

```
8041 gtgacactcc aggtgtggat ccaaagctta tttctagaat ttgggtttat aatcactata
8101 gatggatcat atggaaactg gcagctatgg aatgtgcctt tcctaaggaa tttgctaata
8161 gatgcctaag cccagaaagg gtgcttcttc aactaaaata cagatatgat acggaaattg
8221 atagaagcag aagatcggct ataaaaaaga taatggaaag ggatgacaca gctgcaaaaa
8281 cacttgttct ctgtgtttct gacataattt cattgagcgc aaatatatct gaaacttcta
8341 gcaataaaac tagtagtgca gatacccaaa aagtggccat tattgaactt acagatgggt
8401 ggtatgctgt taaggcccag ttagatcctc ccctcttagc tgtcttaaag aatggcagac
8461 tgacagttgg tcagaagatt attcttcatg gagcagaact ggtgggctct cctgatgcct
8521 gtacacctct tgaagcccca gaatctctta tgttaaagat ttctgctaac agtactcggc
8581 ctgctcgctg gtataccaaa cttggattct ttcctgaccc tagacctttt cctctgccct
8641 tatcatcgct tttcagtgat ggaggaaatg ttggttgtgt tgatgtaatt attcaaagag
8701 catacctat acagtggatg gagaagacat catctggatt atacatattt cgcaatgaaa
8761 gagaggaaga aaaggaagca gcaaaatatg tggaggccca acaaaagaga ctagaagcct
8821 tattcactaa aattcaggag gaatttgaag aacatgaaga aaacacaaca aaaccatatt
8881 taccatcacg tgcactaaca agacagcaag ttcgtgcttt gcaagatggt gcagagcttt
8941 atgaagcagt gaagaatgca gcagacccag cttaccttga gggttatttc agtgaagagc
9001 agttaagagc cttgaataat cacaggcaaa tgttgaatga taagaaacaa gctcagatcc
9061 agttggaaat taggaaggcc atggaatctg ctgaacaaaa ggaacaaggt ttatcaaggg
9121 atgtcacaac cgtgtggaag ttgcgtattg taagctattc aaaaaaagaa aaagattcag
9181 ttatactgag tatttggcgt ccatcatcag atttatattc tctgttaaca gaaggaaaga
9241 gatacagaat ttatcatctt gcaacttcaa aatctaaaag taaatctgaa agagctaaca
9301 tacagttagc agcgacaaaa aaaactcagt atcaacaact accggtttca gatgaaattt
9361 tatttcagat ttaccagcca cgggagcccc ttcacttcag caaattttta gatccagact
9421 ttcagccatc ttgttctgag gtggacctaa taggatttgt cgtttctgtt gtgaaaaaaa
9481 caggacttgc ccctttcgtc tatttgtcag acgaatgtta caatttactg gcaataaagt
9541 tttggataga ccttaatgag gacattatta agcctcatat gttaattgct gcaagcaacc
9601 tccagtggcg accagaatcc aaatcaggcc ttcttacttt atttgctgga gatttttctg
9661 tgttttctgc tagtccaaaa gagggccact ttcaagagac attcaacaaa atgaaaaata
9721 ctgttgagaa tattgacata ctttgcaatg aagcagaaaa caagcttatg catatactgc
9781 atgcaaatga tcccaagtgg tccaccccaa ctaaagactg tacttcaggg ccgtacactg
9841 ctcaaatcat tcctggtaca ggaaacaagc ttctgatgtc ttctcctaat tgtgagatat
9901 attatcaaag tcctttatca ctttgtatgg ccaaaaggaa gtctgtttcc acacctgtct
9961 cagcccagat gacttcaaag tcttgtaaag gggagaaaga gattgatgac caaaagaact
10021 gcaaaaagag aagagccttg gatttcttga gtagactgcc tttacctcca cctgttagtc
10081 ccatttgtac atttgtttct ccggctgcac agaaggcatt tcagccacca aggagttgtg
10141 gcaccaaata cgaaacaccc ataaagaaaa aagaactgaa ttctcctcag atgactccat
10201 ttaaaaaatt caatgaaatt tctcttttgg aaagtaattc aatagctgac gaagaacttg
10261 cattgataaa tacccaagct cttttgtctg gttcaacagg agaaaaacaa tttatatctg
10321 tcagtgaatc cactaggact gctcccacca gttcagaaga ttatctcaga ctgaaacgac
10381 gttgtactac atctctgatc aaagaacagg agagttccca ggccagtacg gaagaatgtg
10441 agaaaaataa gcaggacaca attacaacta aaaaatatat ctaagcattt gcaaaggcga
```

-continued

```
10501 caataaatta ttgacgctta acctttccag tttataagac tggaatataa tttcaaacca

10561 cacattagta cttatgttgc acaatgagaa aagaaattag tttcaaattt acctcagcgt

10621 ttgtgtatcg ggcaaaaatc gttttgcccg attccgtatt ggtatacttt tgcttcagtt

10681 gcatatctta aaactaaatg taatttatta actaatcaag aaaaacatct ttggctgagc

10741 tcggtggctc atgcctgtaa tcccaacact ttgagaagct gaggtgggag gagtgcttga

10801 ggccaggagt tcaagaccag cctgggcaac atagggagac cccatcttt acaaagaaaa

10861 aaaaaagggg aaaagaaaat cttttaaatc tttggatttg atcactacaa gtattatttt

10921 acaagtgaaa taaacatacc attttctttt agattgtgtc attaaatgga atgaggtctc

10981 ttagtacagt tattttgatg cagataattc cttttagttt agctactatt ttaggggatt

11041 ttttttagag gtaactcact atgaaatagt tctccttaat gcaaatatgt tggttctgct

11101 atagttccat cctgttcaaa agtcaggatg aatatgaaga gtggtgtttc cttttgagca

11161 attcttcatc cttaagtcag catgattata agaaaaatag aaccctcagt gtaactctaa

11221 ttccttttta ctattccagt gtgatctctg aaattaaatt acttcaacta aaaattcaaa

11281 tactttaaat cagaagattt catagttaat ttattttttt tttcaacaaa atggtcatcc

11341 aaactcaaac ttgagaaaat atcttgcttt caaattggca ctgatt (SEQ ID NO: 4)
```

In this disclosure, “comprises,” “comprising,” “containing” and “having” and the like can have the meaning ascribed to them in U.S. Patent law and can mean “includes,” “including,” and the like; “consisting essentially of” or “consists essentially” likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

“Detect” refers to identifying the presence, absence or amount of the analyte to be detected.

By “detectable or selectable marker” is meant a composition that when linked to a molecule of interest renders the latter detectable, via spectroscopic, photochemical, biochemical, immunochemical, or chemical means or genetically selectable (e.g., when expressed in a cell). For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. Genetically selectable markers include antibiotic resistance, inducible, cell surface expression, auxotrophic complementation, and the like.

By “diagnostic” is meant any method that identifies the presence of a pathologic condition or characterizes the nature of a pathologic condition (e.g., a neoplasia). Diagnostic methods differ in their sensitivity and specificity. While a particular diagnostic method may not provide a definitive diagnosis of a condition, it suffices if the method provides a positive indication that aids in diagnosis.

By “disease” is meant any condition or disorder that damages or interferes with the normal function of a cell, tissue, or organ. Examples of diseases include cancer, including breast and ovarian cancer associated with defects in a DNA repair polypeptide.

By “increases” is meant a positive alteration of at least 10%, 25%, 50%, 75%, or 100%.

The terms “isolated,” “purified,” or “biologically pure” refer to material that is free to varying degrees from components which normally accompany it as found in its native state. “Isolate” denotes a degree of separation from original source or surroundings. “Purify” denotes a degree of separation that is higher than isolation. A “purified” or “biologically pure” protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term “purified” can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By “isolated polynucleotide” is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an “isolated polypeptide” is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder. Exemplary markers of breast or ovarian cancer include polypeptides that function in DNA repair, including but not limited to, BRCA1, BRCA2, BARD, PALB2, RAD51, RAD51B, RAD51C, RAD51D, XRCC2, XRCC3, BLM, RECQ helicase, MRE11, Rad50, NBS1, ATM, ATR, CTIP, Brip, RPA and RPA-like polypeptide.

By "mutation" is meant a variation in a nucleic acid sequence relative to a wild-type reference sequence. In particular embodiments, a mutation is an insertion, deletion, substitution (e.g., missense mutation), or any other alteration known in the art. A DNA repair variant polypeptide comprises an amino acid sequence that varies from the sequence of a wild-type reference DNA repair polypeptide. Such variations may be functionally significant. DNA repair variant polypeptides are characterized according to the methods of the invention.

By "nuclear localization signal (NLS)" is meant any amino acid sequence sufficient to direct a polypeptide into the nucleus. In various embodiments, an NLS comprises one or more short sequences of positively charged lysines or arginines exposed on the protein surface. Exemplary nuclear localization signals include the C-myc NLS, SV40 Large T-antigen NLS, and nucleoplasmin NLS.

By "Rad51 polypeptide" having at least about 85% identity to NCBI Accession No. NP_001157741. An exemplary Rad51 polypeptide sequence is provided below:

```
  1 mamqmqlean adtsveeesf gpqpisrleq cginandvkk leeagfhtve avayapkkel
 61 inikgiseak adkiltesrs varlecnsvi lvyctlrlsg ssdspasasr vvgttggiet
121 gsitemfgef rtgktqicht lavtcqlpid rgggegkamy idtegtfrpe rllavaeryg
181 lsgsdvldnv ayarafntdh qtqllyqasa mmvesryall ivdsatalyr tdysgrgels
241 arqmhlarfl rmllrladef gvavvitnqv vaqvdgaamf aadpkkpigg niiahasttr
301 lylrkgrget rickiydspc lpeaeamfai nadgvgdakd (SEQ ID NO: 5)
```

By a "Rad51 polynucleotide" is meant a nucleic acid sequence encoding a Rad51 polypeptide. An exemplary polynucleotide sequence is provided at NCBI Accession No. NM_001164269, which is reproduced below:

```
   1 gaaagccgct ggcggaccgc gcgcagcggc cagagaccga gccctaagga gagtgcggcg
  61 cttcccgagg cgtgcagctg ggaactgcaa ctcatctggg ttgtgcgcag aaggctgggg
 121 caagcgagta gagaagtgga gctaatggca atgcagatgc agcttgaagc aaatgcagat
 181 acttcagtgg aagaagaaag ctttggccca caacccattt cacggttaga gcagtgtggc
 241 ataaatgcca acgatgtgaa gaaattggaa gaagctggat tccatactgt ggaggctgtt
 301 gcctatgcgc caaagaagga gctaataaat attaagggaa ttagtgaagc caaagctgat
 361 aaaattctga cggagtctcg ctctgttgcc aggctggagt gcaatagcgt gatcttggtc
 421 tactgcaccc tccgcctctc aggttcaagt gattctcctg cctcagcctc ccgagtagtt
 481 gggactacag gtggaattga gactggatct atcacagaaa tgtttggaga attccgaact
 541 gggaagaccc agatctgtca tacgctagct gtcacctgcc agcttcccat tgaccggggt
 601 ggaggtgaag gaaaggccat gtacattgac actgagggta cctttaggcc agaacggctg
 661 ctggcagtgg ctgagaggta tggtctctct ggcagtgatg tcctggataa tgtagcatat
 721 gctcgagcgt tcaacacaga ccaccagacc cagctccttt atcaagcatc agccatgatg
 781 gtagaatcta ggtatgcact gcttattgta gacagtgcca ccgcccttta cagaacagac
 841 tactcgggtc gaggtgagct ttcagccagg cagatgcact tggccaggtt tctgcggatg
 901 cttctgcgac tcgctgatga gtttggtgta gcagtggtaa tcactaatca ggtggtagct
 961 caagtggatg gagcagcgat gtttgctgct gatcccaaaa aacctattgg aggaaatatc
1021 atcgcccatg catcaacaac cagattgtat ctgaggaaag gaagagggga aaccagaatc
```

-continued

```
1081 tgcaaaatct acgactctcc ctgtcttcct gaagctgaag ctatgttcgc cattaatgca

1141 gatggagtgg gagatgccaa agactgaatc attgggtttt tcctctgtta aaaaccttaa

1201 gtgctgcagc ctaatgagag tgcactgctc cctggggttc tctacaggcc tcttcctgtt

1261 gtgactgcca ggataaagct tccgggaaaa cagctattat atcagctttt ctgatggtat

1321 aaacaggaga caggtcagta gtcacaaact gatctaaaat gtttattcct tctgtagtgt

1381 attaatctct gtgtgttttc tttggttttg gaggaggggt atgaagtatc tttgacatgg

1441 tgccttagga atgacttggg tttaacaagc tgtctactgg acaatcttat gtttccaaga

1501 gaactaaagc tggagagacc tgacccttct ctcacttcta aattaatggt aaaataaaat

1561 gcctcagcta tgtagcaaag ggaatgggtc tgcacagatt cttttttct gtcagtaaaa

1621 ctctcaagca ggtttttaag ttgtctgtct gaatgatctt gtgtaaggtt ttggttatgg

1681 agtcttgtgc caaacctact aggccattag cccttcacca tctacctgct tggtctttca

1741 ttgctaagac taactcaaga taatcctaga gtcttaaagc atttcaggcc agtgtggtgt

1801 cttgcgcctg tactcccagc actttgggag gccgaggcag gtggatcgct tgagcccagg

1861 agttttaagt ccagcttggc caaggtggtg aaatcccatc tctacaaaaa atgcagaact

1921 taatctggac acactgttac acgtgcctgt agtcccagct actcgatagc ctgaggtggg

1981 agaatcactt aagcctggaa ggtggaagtt gcagtgagtc gagattgcac tgctgcattc

2041 cagccagggt gacagagtga gaccatgttt caaacaagaa acatttcaga gggtaagtaa

2101 acagatttga ttgtgaggct tctaataaag tagttattag tagtgaa (SEQ ID NO: 6)
```

By "rare cutting endonuclease" is meant a nuclease that cuts about once or less in a wild-type mammalian genome. I-SceI is an exemplary rare cutting endonuclease that recognizes an 18-base pair nucleic acid sequence TAGGGATAACAGGGTAAT (SEQ ID NO: 7). I-PpoI is an exemplary rare cutting endonuclease that recognizes an 15-base pair nucleic acid sequence CTCTCTTAAGGTAGC (SEQ ID NO: 8).

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous nucleic acid sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous nucleic acid sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "Ter site" is meant a nucleic acid sequence having at least about 85% sequence identity to AATTAGTATGTTGTAACTAAAGT (SEQ ID NO: 9) (TerA), AATAAGTATGTTGTAACTAAAGT (SEQ ID NO: 10) (TerB), ATATAGGATGTTGTAACTAATAT (SEQ ID NO: 11) (TerC) and/or variants thereof capable of binding a Tus polypeptide. In certain embodiments, Ter sequences are 23 base-pairs in length. In specific embodiments, Ter sites have a consensus sequence: GNRNGTTGTAAYKA (SEQ ID NO: 12). Exemplary Ter sequences are provided below:

```
TerH CGATCGTATGTTGTAACTATCTC      (SEQ ID NO: 13)
TerI AACATGGAAGTTGTAACTAACCG      (SEQ ID NO: 14)
TerD CATTAGTATGTTGTAACTAAATG      (SEQ ID NO: 15)
TerA AATTAGTATGTTGTAACTAAAGT      (SEQ ID NO: 9)
TerC ATATAGGATGTTGTAACTAATAT      (SEQ ID NO: 11)
TerB AATAAGTATGTTGTAACTAAAGT      (SEQ ID NO: 10)
TerG GTCAAGGATGTTGTAACTAACCA      (SEQ ID NO: 16)
pTerE TTAAAGTATGTTGTAACTAAGCA     (SEQ ID NO: 17)
pTerK CGATTGAGAGTTGTAATGAAGTC     (SEQ ID NO: 18)
pTerF CCTTCGTATGTTGTAACGACGAT     (SEQ ID NO: 19)
pTerJ ACGCAGTAAGTTGTAACTAATGC     (SEQ ID NO: 20)
pTerY TATGGGTACGTTGTAATTAGGGA     (SEQ ID NO: 21)
pTerL GCACTGGGTGTTGTAATGACGCA     (SEQ ID NO: 22)
pTerZ TACCCGCAGGTTGTAACGAGAGC     (SEQ ID NO: 23)
```

By "Tus (Terminus utilization substance) polypeptide" is meant a protein having at least about 85% amino acid sequence identity to the sequence provided at Genbank accession no. WP_001310846 or a fragment thereof and having DNA binding activity (e.g., to a Ter site) and/or DNA replication inhibitor activity (e.g., replication fork arrest; replication fork stalling; counter-helicase activity). An exemplary Tus polypeptide sequence is provided below:

```
>sp|P16525|TUS_ECOLI DNA replication terminus
site-binding protein
MARYDLVDRLNTTFRQMEQELAIFAAHLEQHKLLVARVFSLPEVKKEDEH

NPLNRIEVKQHLGNDAQSLALRHFRHLFIQQQSENRSSKAAVRLPGVLCY

QVDNLSQAALVSHIQHINKLKTTFEHIVTVESELPTAARFEWVHRHLPGL

ITLNAYRTLTVLHDPATLRFGWANKHIIKNLHRDEVLAQLEKSLKSPRSV

APWTREEWQRKLEREYQDIAALPQNAKLKIKRPVKVQPIARVWYKGDQKQ

VQHACPTPLIALINRDNGAGVPDVGELLNYDADNVQHRYKPQAQPLRLII

PRLHLYVAD (SEQ ID NO: 24)
```

By a "Tus polynucleotide" is meant a nucleic acid sequence encoding a Tus polypeptide.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a schematic showing EBNA1-driven plasmid replication. Ori, EBNA1-binding origin of replication. EBNA1-binding FR repeats impeded the anticlockwise fork. Red triangle indicates the 6×Ter array (vertex, non-permissive end). Location of Southern blotting probe shown in black. FIG. 1B has two images depicting plasmid replication intermediates in 293E cells transiently transfected with 6×Ter-containing plasmids or 'no Ter' control, co-transfected with empty vector (EV), TusH144A or Tus. Samples from one experiment of DNA digested with XmnI plus SnaBI and analyzed by two-dimensional gel electrophoresis/Southern blotting. 6×REVTer: clockwise fork encountered permissive end of Ter. Arc A, replication fork. Spot B, Tus/Ter-stalled clockwise fork. Spot C, bidirectional fork arrest (double Y) at Tus/6×Ter, reflecting incomplete replication block at FR20. FIG. 1C is a graph showing stall spot B quantification, n=5 (see FIG. 2A). Error bars represent s.e.m. For Student's t-test 6×Ter wild-type Tus versus any other, P<0.01; 6×REVTer wild-type Tus versus any other, P<0.01. 6×Ter TusH144A versus 6×Ter EV, P<0.03. FIG. 1D is an immunoblot showing upper panel, anti-myc immunoblot of 293E cells expressing empty vector (EV), Tus(WT) or TusH144A (H). Lower panel shows beta-tubulin loading control.

FIG. 2A has two images showing phosphorimager quantification of spot B. One of five independent experiments that contributed to FIG. 2C. Four areas were quantified for each sample using ImageJ 1.48p software, as shown by cartoon. A, area containing a portion of replication fork arc A. B, area containing replication fork stall spot B (same shape/size as A). F, largest area of replication fork arc that was accessible to quantification in every sample. G, same shape as F, used to quantify background signal on membrane. Stall spot B intensity was calculated as: (B−A)/(F−G)×100%. Note, this value does not correspond to the probability of stalling at the Tus/Ter block, but is used to illustrate the relatively weaker arrest produced by 6×REVTer. FIG. 2B is a schematic diagram illustrating the same plasmid elements as in FIG. 1A. MluI/XmnI digested plasmid yields a linear fragment of 5.4 kb. Probe for Southern blotting is indicated by the black bar. FIG. 2C shows two images of plasmid replication intermediates extracted from 293E cells transiently transfected with 6×Ter-containing plasmids or no Ter control, co-transfected with empty vector (EV), TusH144A or Tus as shown. All samples are from one experiment. Plasmid DNA extracted from 293E cells was digested with XmnI and MluI and analyzed by neutral/neutral two-dimensional gel-electrophoresis and Southern blotting. Replication intermediates as described in FIG. 2A. FIG. 2D is a schematic showing predicted replication intermediates generated by Tus/Ter-induced replication fork stalling with or without effective FR/EBNA1 replication fork block. Diagrams below plasmid maps show shape of the major Tus/Ter-dependent fork arrest species. Green dotted line shows predicted additional branch of double Y structure formed by stalling of anticlockwise fork at Tus/6×Ter when FR/EBNA1 replication block fails. The length of the additional branch is shown in each diagram. Note that the relationship between spots B and C will vary according to the length of this additional branch. FIG. 2E depicts two images showing plasmid replication intermediates extracted from 293E cells transiently transfected with 6×Ter containing plasmids and co-transfected with empty vector (EV) or wild-type Tus as shown. Restriction digests of extracted plasmids are as shown. All samples are from one experiment. Note: replication fork size and position of stall spot B in relation to replication arc A varied with restriction digest. For example, spot B in KpnI/MluI was close to the 2n linear position, since the Tus/Ter-stall site was only approximately 680 bp from the KpnI site. For the same reason, spots B and C were closely placed in the KpnI/MluI-digested sample. Note: the relatively weak spot C in the KpnI/MluI digest, which was consistent across multiple experiments, might reflect a proportionately large contribution of ssDNA (reflecting processed lagging strand DNA) to the approximately 680 bp lagging strand of the stalled anticlockwise fork.

FIG. 3A is a schematic showing that Tus/Ter-mediated replication stall structures responsible for spots B and C. The relative abundance of the single stall spot B and the double Y stall spot C can be used to calculate the efficiency of the FR/EBNA1 replication fork barrier. FIG. 3B shows four images and one graph depicting phosphorimager analysis of twelve independent Southern blot experiments (method described in FIG. 1B). Areas B, B', C and C' were the same shape and size within each experiment, but varied between experiments. B, stall spot B. B', background gel signal of same area as B. C, stall spot C. C', background gel signal of same area as C. Relative intensity of spot B/(B+C) estimated the stalling efficiency at FR/EBNA1 and was calculated as: (B−B')/(B+C−B'−C')×100%. The stalling efficiency at FR/EBNA1 was therefore 70±0.2% (s.e.m.). Relative intensity of spot C was calculated as: (C−C')/(B+C−B'−C')×100%. FIG. 3C is a schematic showing the structure of p6×Ter-2Ori plasmid. Stalled replication intermediates depicted different combinations of FR/EBNA1 block/bypass and Tus/6×Ter block/bypass. Spots B and B2 were defined as in the diagram. Spots C and C2 resulted from FR/EBNA1 bypass. Spot C2 required successful arrest at both of the 6×Ter arrays. Spot C results from bypass of one of the two 6×Ter arrays. FIG. 3D shows three images and one graph providing one of three independent experiments performed with p6×Ter-2Ori. Methods as in FIG. 1B. Note presence of four stall spots in p6×Ter-2Ori replicating in presence of Tus. Double Y stall spots C and C2 and background signal C' were quantified. Note that the shape and size of each area was identical within an individual experiment, but varied between experiments. By considering only double Y stall spots (that is, in which FR/EBNA1 bypass had occurred), the relative abundance of the double Y stall spots C and C2 were used to estimate the efficiency of the Tus/6×Ter replication fork barrier. Let a=probability of the 6×Ter array blocking the fork and b=probability of 6×Ter bypass. Then a+b=1. The probability of the two 6×Ter arrays blocking each fork on one p6×Ter-2Ori plasmid (generating spot C2) is $a^2$. The probability of one 6×Ter array being blocked and the second array being bypassed (generating spot C) is 2ab. Relative densitometry of spots C and C2 (each with subtraction of background C') shows that spot C contributed 49.6% and C2 contributed 50.4% (s.e.m. 5.6%). Therefore $0.496a^2=0.0.504\times 2ab$. Solving this, a=0.67 Therefore the estimated efficiency of the Tus/6××Ter replication fork block within the replicating plasmid is 67%. Note that the efficiency of the Tus/6×Ter replication fork block within the chromosome is unknown.

FIG. 4A is a cartoon showing a 6×Ter-HR reporter and major HR products (assuming two-ended breaks). STGC and short-tract gene conversion; LTGC, long-tract gene conversion. LTGC generated wild-type RFP expression through RNA splicing. Grey boxes, mutant GFP. Green box, wild-type GFP. Circles A and B represent 5' and 3' artificial RFP exons. Tr-GFP, 5' truncated GFP. Red triangle indicates 6×Ter array adjacent to I-SceI site. B, BglII; GFP-hybridizing fragment sizes in kilobases. Bidirectional fork stalling triggered SCR. Green arrow, strand exchange. FIG. 4B shows five graphs depicting FACS data of $Brca1^{fl/BRCT}$ 6×Ter-HR cells transfected with empty vector (EV), I-SceI, Tus or TusH144A. No Ter reporter, $Brca1^{fl/BRCT}$ cells carrying the ROSA26-targeted HR reporter lacking the Ter array. FIG. 4C depicts three graphs showing that I-SceI- and Tus-induced HR (blue diamonds and orange circles, respectively) in three independent $Brca1^{fl/BRCT}$ clones. Mean of triplicate samples, n=3. Error bars represent s.e.m. Student's t-test LTGC/total HR, I-SceI versus Tus: P=0.0186. FIG. 4D shows two blots depicting a Southern blot analysis of Tus- and I-SceI-induced HR in $Brca1^{fl/BRCT}$ 6×Ter-HR cells (GFP probe). P, parental reporter; B, BglII digest; BI, BglII plus I-SceI digest.

FIG. 5A is a schematic showing that bidirectional fork arrest would provide two DNA ends for sister chromatid recombination. Termination by annealing generated STGC products of a fixed size. Recombining GFP elements and HR reporter features other than Tus/Ter are not shown. Black strands represent parental DNA. Grey strands represent newly synthesized DNA. Arrowheads on DNA strands represent DNA synthesis. Blue/grey hexagons, Tus monomers. Red triangles, Ter sites. Green line, invading DNA strand. Green dotted line, nascent strand extension. FIG. 5B is a schematic showing that unidirectional fork arrest would provide only one DNA end for sister chromatid recombination. Following one-ended invasion of the neighboring sister chromatid, any STGC products could not be terminated by annealing, as there was no homologous second end. Termination by non-canonical mechanisms would generate STGCs of unpredictable/variable size. DNA and protein elements labelled as in panel FIG. 5A. LTGC was not considered in this analysis, as the mechanisms of termination of the major LTGC products were not accessible from the current data. Each model invoked a hypothetical DSB intermediate. Tus/Ter-induced HR could be initiated by a template switching mechanism (that is, without the formation of an initiating DSB intermediate). However, the requirement for a homologous second end was not altered by consideration of a template switch model and this second end had to be provided by the processing of a second arrested fork (the right-hand fork in panel a).

FIG. 6A depicts three graphs with primary data from FIG. 4C, showing directly measured frequencies of background HR, Tus-induced HR and I-SceI-induced HR in three independent $Brca1^{fl/BRCT}$ 6×Ter/HR reporter clones. Cells were transfected with empty vector (EV, grey squares), myc-NLS-I-SceI (I-SceI, blue diamonds), or myc-NLS-Tus expression vectors (Tus, orange circles). Each point represents the mean of triplicate samples from three independent experiments (that is, n=3). Error bars represent s.e.m. Student's t-test of Tus versus EV: STGC P<0.0001; LTGC P<0.0001. Student's t-test of I-SceI versus EV: STGC P<0.0001; LTGC P<0.0001. Student's t-test of Tus versus I-SceI: STGC P<0.0001; LTGC P=0.0018; LTGC/Total HR P=0.0186. FIG. 6B shows three graphs of primary data comparing a single ROSA26 targeted $Brca1^{fl/BRCT}$ 6×Ter/HR clone with three independently derived clones, each harboring a single intact 6×Ter/HR reporter randomly integrated at an unknown locus. Filled symbols, ROSA26-targeted clone (as in panel a). Open symbols, data from randomly integrated 6×Ter/HR reporter clones. Each point represents the mean of six independent experiments, triplicate replicates for each experiment (that is, n=6). Error bars represent s.e.m. Student's t-test of pooled random integrants Tus versus EV: STGC P<0.0001; LTGC P<0.0001. Student's t-test of pooled random integrants I-SceI versus EV: STGC P<0.0001; LTGC P<0.0001. Student's t-test of pooled random integrants Tus versus I-SceI: STGC P<0.0001; LTGC P=0 P=0.3620; LTGC/total HR P=0.00012. FIG. 6C depicts a graph showing primary data of STGC products observed in $Brca1^{fl/BRCT}$ 6×Ter/HR cells transfected with empty vector (EV), wild-type Tus, DNA binding defective TusH144A, lock defective TusF140A or I-SceI. All expression vectors are codon-optimized for mammalian expression and encode N-terminal myc epitope and NLS sequences. Each column represents the mean of six independent experiments (that is, n=6). Error bars represent s.e.m. Student's t-test of Tus versus EV: P=0.0002; Tus versus TusH144A: P=0.0004; Tus versus TusF140A: P=0.0042; Tus versus I-SceI: P=0.0139; TusH144A versus EV: P=0.4406; TusF140A versus EV: P<0.0001; TusF140A versus TusH144A: P<0.0001; TusF140A versus I-SceI: P=0.0888. FIG. 6D is a blot showing Myc-tagged protein abundance in transfected $Brca1^{fl/BRCT}$ 6×Ter-HR cells. EV, empty vector. Other lanes as marked. Lower panel, beta-tubulin loading control. FIG. 6E shows six cartoons of the Ter/HR reporter constructs assayed in FIG. 6F. FIG. 6F depicts two graphs showing frequencies of Tus-induced STGC in $Brca1^{fl/BRCT}$ cells carrying single copy ROSA26-targeted Ter/HR reporters shown in panel 6E. Left, HR in 6×Ter, 3×Ter, 2×Ter and 1×Ter HR reporters, as shown. Right, HR in three independently derived clones carrying single copy, ROSA26-targeted 6×REVTer HR reporters. Each column represents the mean of three independent experiments (that is, n=3). Error bars represent s.e.m. Student's t-test of 6×Ter versus 3×Ter#1: P=0.2604; 6×Ter versus 3×Ter#2: P=0.5192; 6×Ter versus 2×Ter#1: P=0.0547; 6×Ter versus 2×Ter#2: P=0.0524; 6×Ter versus 1×Ter#1: P=0.0507; 6×Ter versus 1×Ter#2: P=0.0507; 3×Ter#1 versus 3×Ter#2: P=0.8291; 3×Ter#1 versus 2×Ter#1: P=0.0650; 3×Ter#1 versus 2×Ter#2: P=0.0606; 3×Ter#1 versus 1×Ter#1: P=0.0576; 3×Ter#1 versus 1×Ter#2: P=0.0574; 3×Ter#2 versus 2×Ter#1: P=0.1832; 3×Ter#2 versus 2×Ter#2: P=0.1748; 3×Ter#2 versus 1×Ter#1: P=0.1677; 3×Ter#2 versus 1×Ter#2: P=0.1697. By one-way ANOVA (analysis of variance) test used to compare more than three sets of data, the trend in HR from 6× to 1×, P=0.0012.

FIG. 7A depicts two graphs showing frequencies of STGC in Brca1$^{fl/BRCT}$ 6×Ter-HR cells co-transfected with Tus (orange) or I-SceI (blue) and with either control Luciferase siRNA(siLuc), Slx4 SMARTpool (siSlx4), Slx1 SMARTpool (siSlx1), Slx1 and Slx4 SMARTpools (siSlx1 siSlx4), Eme1 SMARTpool (siEme1), Eme1 and Slx4 SMARTpools (siEme1 siSlx4), Xpf SMARTpool (siXpf), Xpf and Slx4 SMARTpools (siXpf siSlx4). Each column represents the mean of triplicate samples from four independent experiments for each clone (that is, n=4). Error bars represent s.e.m. Tus-induced HR: Student's t-test of siSlx4 versus siLuc: P=0.0219; siSlx4 versus siSlx1: P=0.0012; siSlx4 versus siSlx4+Slx1: P=0.5983; siSlx4 versus siEme1: P=0.0171; siSlx4 versus siSlx4+siEme1: P=0.8721; siSlx4 versus siXpf: P=0.0098; siSlx4 versus siSlx4+siXpf: P=0.4711; siSlx1 versus siLuc: P=0.9332; siEme1 versus siLuc: P=0.4631; siXpf versus siLuc: P=0.7818; siSlx4+siSlx1 versus siLuc: P=0.0155; siSlx4+siEme1 versus siLuc: P=0.0215; siSlx4+siXpf versus siLuc: P=0.0305. I-SceI-induced HR: Student's t-test of siSlx4 versus siLuc: P=0.0907; siSlx4 versus siSlx1: P=0.0195; siSlx4 versus siSlx41siSlx1: P=0.4897; siSlx4 versus siEme1: P=0.0568; siSlx4 versus siSlx4+siEme1: P=0.3411; siSlx4 versus siXpf: P=0.0745; siSlx4 versus siSlx4+siXpf: P=0.2726; siSlx1 versus siLuc: P=0.9198; siEme1 versus siLuc: P=0.3349; siXpf versus siLuc: P=0.9217; siSlx4+siSlx1 versus siLuc: P=0.1521; siSlx4+siEme1 versus siLuc: P=0.2864; siSlx4 1 siXpf versus siLuc: P=0.2063. FIG. 7B depicts four graphs showing a qRT-PCR analysis of mRNA exon boundaries for Slx4, Slx1, Eme1 and Xpf mRNA in siRNA-SMARTpool-treated cells used in panel a.

FIG. 8A depicts two cartoons showing the Brca1 gene in Brca1$^{BRCT}$ ES cells. Brca1$^{BRCT}$ encodes a truncated protein. Cre converted Brca" to the exon 22-24-deleted Brca1$^{\Delta}$ allele. Grey boxes, Brca1 exons; black triangles, loxP sites; pA, polyadenylation signal; SA, splice acceptor; neo: neomycin resistance gene; pgk, phosphoglycerate kinase promoter. FIG. 8B depicts 6 graphs showing that Tus- and I-SceI-induced HR in Brca1$^{fl/BRCT}$ and Brca1$^{\Delta/BRCT}$ 6×Ter-HR cells (three independent clones each). Mean of triplicate samples, n=4. Error bars represent s.e.m. Student's t-test Brca1$^{fl/BRCT}$ versus Brca1$^{\Delta/BRCT}$ in all 6 panels P<0.05. FIG. 8C shows an immunoblot: upper panel, endogenous Brca1 immunoblot in Brca1$^{fl/BRCT}$ and Brca1$^{\Delta/BRCT}$ ES cells. Asterisk indicates a background band. Lower panel, beta-actin loading control. FIG. 8D is a graph showing a quantitative polymerase chain reaction with reverse transcription (qRT-PCR) for Brca1 mRNA. Exon 22-23 was deleted in Brca1$^{\Delta/BRCT}$ cells.

FIG. 9A is a cartoon showing the structure of the 6×Ter/HR parental reporter, and major STGC or LTGC HR products (assuming two-ended breaks). Elements as shown in FIG. 4A. FIG. 9B depicts five blots showing a Southern blot analysis of Tus-induced and I-SceI induced HR products in Brca1$^{\Delta/BRCT}$ 6×Ter-HR cells. P, un-rearranged reporter; STGC and LTGC as shown. SN, STGC accompanied non-disjunction with retention of parental donor reporter; LN, LTGC accompanied non-disjunction with retention of parental donor reporter. B, BglII digest. BI, BglII1I-SceI digest. Membranes probed with full length GFP cDNA. Panels underneath two SN events and one LN event show that re-cloning did not separate the two reporters, confirming that the cell contained two copies of the reporter (consistent with non-disjunction).

FIG. 10A depicts six graphs showing frequencies of Tus-induced and I-SceI-induced HR in Brca1$^{fl/BRCT}$ and Brca1$^{\Delta/BRCT}$ 6×Ter/HR cells transiently co-transfected with Tus or I-SceI and with either control Luciferase siRNA (siLuc) or Brca1 SMARTpool (siBrca1). Each column represents the mean of triplicate samples for each independent clone from seven independent experiments (that is, n=7). Error bars represent s.e.m. Tus induced HR, Brca1$^{fl/BRCT}$ cells, Student's t-test siBrca1 versus siLuc: STGC: P=0.0013; LTGC: P=0.0206; LTGC/total HR: P=0.0003; Brca1$^{\Delta/BRCT}$ cells, siBrca1 versus siLuc: STGC: P=0.0016; LTGC: P=0.4558; LTGC/total HR: P<0.0001. I-SceI-induced HR, Brca1$^{fl/BRCT}$ cells, Student's t-test siBrca1 versus siLuc: STGC: P<0.0001; LTGC: P=0.0033; LTGC/total HR: P=0.9214; Brca1$^{\Delta/BRCT}$ cells, siBrca1 versus siLuc: STGC: P=0.0013; LTGC: P=0.2348; LTGC/total HR: P=0.0071. FIG. 10B is a blot showing Brca1 protein levels and beta-actin loading control in Brca1$^{fl/BRCT}$ and Brca1$^{\Delta/BRCT}$ in siRNA-treated cells as shown. FIG. 10C is a graph showing a qRT-PCR analysis of Brca1 mRNA in siRNA-treated cells as shown.

FIG. 11A is a cartoon of the Brca1 gene in Brca1$^{fl/Exon11}$ ES cells. The Brca1$^{Exon11}$ encodes the Δexon11 product. Cre converts Brca1$^{fl}$ to exon11-deleted Brca1$^{\Delta}$ allele. Symbols as in FIG. 8. PCR primers a, b and d shown. FIG. 11B depicts 6 graphs showing Tus- and I-SceI-induced HR in Brca1$^{fl/Exon11}$ and Brca1$^{\Delta/Exon11}$ 6×Ter-HR cells (three independent clones each). Mean of triplicate samples, n=4. Error bars represent s.e.m. Student's t-test Brca1$^{fl/Exon11}$ versus Brca1$^{\Delta/Exon11}$ in all 6 panels P<0.005. FIG. 11C is an immunoblot, Upper panel, endogenous Brca1 immunoblot in Brca1$^{fl/Exon11}$ and Brca1$^{\Delta/Exon11}$ ES cells. The asterisk denotes a background band. The lower panel denotes a beta-actin loading control. FIG. 11D depicts two gels showing PCR genotyping of Brca1$^{fl/Exon11}$ and Brca1$^{D/Exon11}$ clones from panel b. P, untargeted Brca1$^{fl/Exon11}$. E, empty (no DNA) control. Brca1$^{fl}$ product, 531 bp; Brca1$^{\Delta}$ product, 621 bp.

FIG. 12A depicts three graphs showing frequencies of Tus-induced and I-SceI-induced HR in Brca1$^{fl/BRCT}$ and Brca1$^{\Delta/BRCT}$ 6×Ter/HR cells transiently co-transfected with Tus, or I-SceI and with either control Luciferase siRNA (siLuc) or Brca2 SMARTpool (siBrca2). Each column represents the mean of triplicate samples for each independent clone from five independent experiments (that is, n=5). Error bars represent s.e.m. Tus induced HR, Brca1$^{fl/BRCT}$ cells, Student's t-test siBrca2 v versus siLuc: STGC: P=0.0031; LTGC: P=0.0007; LTGC/total HR: P=0.0042; Brca1$^{\Delta/BRCT}$ cells, siBrca2 versus siLuc: STGC: P=0.0040; LTGC: P=0.0013; LTGC/total HR: P=0.0006. I-SceI-induced HR, Brca1$^{fl/BRCT}$ cells, Student's t-test siBrca2 versus siLuc: STGC: P=0.0028; LTGC: P=0.0456; LTGC/total HR: P=0.7945; Brca1$^{\Delta/BRCT}$ cells, siBrca2 versus siLuc: STGC: P=0.0010; LTGC: P=0.2926; LTGC/total HR: P=0.0316. b, qRT-PCR analysis of Brca2 mRNA in siRNA-treated cells as shown.

FIG. 13A depicts six graphs showing the frequencies of Tus-induced and I-SceI-induced HR in $Brca1^{fl/BRCT}$ and $Brca1^{\Delta/BRCT}$ 6×Ter/HR cells transiently co-transfected with Tus, or I-SceI and with either control Luciferase siRNA (siLuc) or Rad51 SMARTpool (siRad51). Each column represents the mean of triplicate samples for each independent clone from seven independent experiments for $Brca1^{fl/BRCT}$ (that is, n=7) and four independent experiments for $Brca1^{\Delta/BRCT}$ cells (that is, n=4). Error bars represent s.e.m. Tus-induced HR, $Brca1^{fl/BRCT}$ cells, Student's t-test siRad51 versus siLuc: STGC: P<0.0001; LTGC: P=0.1578; LTGC/total HR: P=0.0002; $Brca1^{\Delta/BRCT}$ cells, siRad51 versus siLuc: STGC: P=0.0010; LTGC: P=0.0676; LTGC/total HR: P<0.0001. I-SceI-induced HR, $Brca1^{fl/BRCT}$ cells, Student's t-test siRad51 versus siLuc: STGC: P=0.0014; LTGC: P=0.0002; LTGC/total HR: P=0.6216; $Brca1^{\Delta/BRCT}$ cells, siRad51 versus siLuc: STGC: P=0.0068; LTGC: P=0.2064; LTGC/total HR: P=0.0186. FIG. 13B depicts an immunoblot of Rad51 protein levels and beta-tubulin loading control in $Brca1^{fl/BRCT}$ and $Brca1^{\Delta/BRCT}$ siRNA treated cells as shown.

FIG. 14A depicts six graphs showing frequencies of Tus-induced and I-SceI induced HR in $Brca1^{fl/BRCT}$ and $Brca1^{\Delta/BRCT}$ 6×Ter/HR cells transiently co-transfected with Tus or I-SceI expression vectors and with either F53BP1 D1521R fragment (D1521R; non-chromatin-binding negative control for 'dominant-negative' 53BP1 fragment) or 'dominant-negative' F53BP1 wt fragment (F53BP1 wt). Each column represents the mean of triplicate samples for each independent clone from five independent experiments (that is, n=5). Error bars represent s.e.m. Tus-induced HR, $Brca1^{fl/BRCT}$ cells, Student's t-test D1521R versus F53BP1 wt: STGC: P=0.1818; LTGC: P=0.9005; LTGC/total HR: P=0.3570; $Brca1^{D/BRCT}$ cells, Student's t-test D1521R versus F53BP1 wt: STGC: P=0.5008; LTGC: P=0.5375; LTGC/total HR: P=0.4921. I-SceI induced HR, $Brca1^{fl/BRCT}$ cells, Student's t-test D1521R versus F53BP1 wt: STGC: P=0.0442; LTGC: P=0.5739; LTGC/total HR: P=0.2250; $Brca1^{\Delta/BRCT}$ cells, Student's t-test D1521R versus F53BP1 wt: STGC: P=0.0086; LTGC: P=0.6888; LTGC/total HR: P=0.0328. Tus-induced LTGC/total HR, $Brca1^{fl/BRCT}$ versus $Brca1^{\Delta/BRCT}$ cells, Student's t-test F53BP1 wt: 0.0064; $Brca1^{fl/BRCT}$ versus $Brca1^{\Delta/BRCT}$ cells, Student's t-test D1521R: 0.0014; I-SceI-induced LTGC/total HR, $Brca1^{fl/BRCT}$ versus $Brca1^{\Delta/BRCT}$ cells, Student's t-test F53BP1 wt: 0.1556; $Brca1^{fl/BRCT}$ versus $Brca1^{\Delta/BRCT}$ cells, Student's t-test D1521R: 0.0208. FIG. 14B depicts an immunoblot showing abundance of 53BP1 fragments, and beta-tubulin (loading control) in treated $Brca1^{fl/BRCT}$ and $Brca1^{\Delta/BRCT}$ 6×Ter/HR reporter ES cells in FIG. 14A.

FIGS. 18A-18F depict the DNA sequence of an LTGC reporter vector comprising an I-SceI restriction enzyme site.

FIGS. 19A-19C depict the DNA sequence of a Tus expression vector.

FIGS. 20A-20G depict the DNA sequence of a Ter array (6×Ter) reporter plasmid..

FIG. 21A depicts an enzymatically active Cas9 nuclease (red oval) binding to the cognate target of a CRISPR guide RNA (yellow). In addition, all endonucleases used for targeted gene editing generate "off-target" mutagenic effects. Binding also occurs at off-target loci that interact with the same guide RNA (sgRNA). FIG. 21B depicts a model in which an array of enzymatically inactive CRISPR/Cas9 complexes (dark gray ovals) formed at the target locus provokes site-specific replication fork arrest only at the target locus. Without being bound to theory, the results described herein indicate multiplexed copies of CRISPR/Cas9 bound in an array at the target locus are able to stall the replication fork and induce HR-mediated gene editing. Notably, the likelihood of off-target binding of individual CRISPR/Cas9 complexes to form a tandem array of stalling complexes is low or greatly minimized. Additionally, the likehood that a single CRISPR/Cas9 would provoke replication arrest, and unintended repair response would be negligible Thus, the multiplexed nature of the stalling complex has the potential to address the problem of "off-target" effects.

FIG. 22A depicts a model of sister chromatid recombination induced at a Tus/Ter replication fork block. Replication fork stalling triggers breakage of the stalled fork by endogenous stalled fork processing enzymes. The double strand break (DSBs) produced are repaired by HR using the intact sister chromatid as donor template. FIG. 22B depicts a model of gene targeting involving recombination with an exogenous plasmid at a Tus/Ter replication fork block. A Tus/Ter block is established while a homologous plasmid is present. Without being bound to theory, DSBs produced at the arrested fork are primarily repaired by HR using the exogenous plasmid as the donor template. The excess of donor plasmid should favor its use in the repair process rather than the sister chromatid.

FIG. 23A is a schematic of a recombination assay used to detect repair of an inactive mutant GFP at a Tus/Ter-mediated replication block. A single copy reporter containing one mutant copy of GFP is targeted to the ROSA26 locus of mouse ES cells. The mutant copy of GFP ("6×Ter-I-SceI") contains an array of 6×Ter sites and a cleavage site for the rare-cutting homing endonuclease I-SceI. Arrows indicate promoter to drive GFP expression at the ROSA26 locus. Red triangle: 6×Ter array, with neighboring I-SceI site. Without being bound to theory, replication arrest and fork breakage generates double strand break (DSBs) for recombination. The donor plasmid contains a 5' truncated copy of GFP ("Tr-GFP"), which recombines with the broken chromosomal copy of GFP to generate wt GFP. FIG. 23B depicts representative FACS readouts of gene targeting triggered by Tus or by positive control I-SceI. Green cells represent $GFP^+$ cells, indicating successful gene targeting/gene editing. Note absence of $GFP^+$ products in the negative control that received empty vector in the presence of the donor plasmid. FIG. 23C depicts graphs showing quantitation of gene targeting. Cells received either Tus, I-SceI or empty vector (for background level of $GFP^+$, consistently zero), together with donor plasmid containing Tr-GFP at increasing concentrations (0, 50, 100 or 150 ng). Total DNA transfected per sample was normalized as needed with addition of further empty vector. Note titratable induction of $GFP^+$ cells with increasing amount of donor vector.

DETAILED DESCRIPTION OF THE INVENTION

Figure 1A:
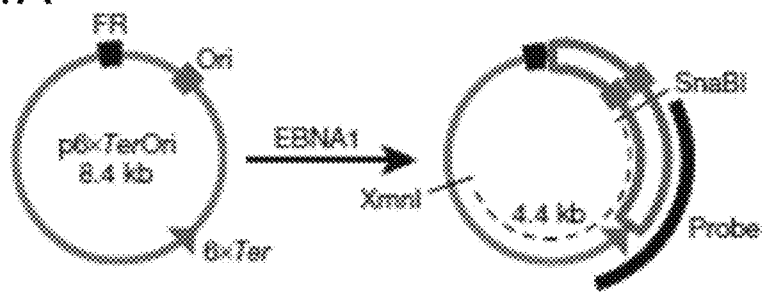
FIGS. 1A-1D show Tus/Ter-induced replication fork stalling in mammalian cells.

As described below, the present invention provides quantitative homologous recombination assays developed to characterize the pathogenicity of DNA repair polypeptides (e.g., BRCA1, BRCA2, Rad51) and provide urgently needed functional information on the significance of DNA repair variants of uncertain significance (VUS) alleles.

The invention is based, at least in part, on the discovery that replication fork stalling can promote genomic instability, predisposing to cancer and other diseases. Stalled replication forks may be processed by sister chromatid recombination (SCR), generating error-free or error-prone homologous recombination (HR)outcomes. In mammalian cells, a long-standing hypothesis proposes that the major hereditary breast/ovarian cancer predisposition gene products, BRCA1 and BRCA2, control HR/SCR at stalled replication forks. Although BRCA1 and BRCA2 affect replication fork processing, direct evidence that BRCA gene products regulate homologous recombination at stalled chromosomal replication forks is lacking, due to a dearth of tools for studying this process. As reported herein below, the *Escherichia coli* Tus/Ter complex can be engineered to induce site-specific replication fork stalling and chromosomal HR/SCR in mouse cells.

Tus/Ter-induced homologous recombination entails processing of bidirectionally arrested forks. As reported herein, the Brca1 carboxy (C)-terminal tandem BRCT repeat and regions of Brca1 encoded by exon 11—two Brca1 elements implicated in tumour suppression—control Tus/Ter-induced homologous recombination. Inactivation of either Brca1 or Brca2 increases the absolute frequency of 'long tract' gene conversions at Tus/Ter-stalled forks, an outcome not observed in response to a site-specific endonuclease-mediated chromosomal double-strand break. Therefore, homologous recombination at stalled forks is regulated differently from homologous recombination at double-strand breaks arising independently of a replication fork. These findings have significance for genome editing, which relies on inducing double stranded breaks to repair or replace deleterious genes. In particular, the invention provides for error-free homologous recombination. Aberrant long-tract homologous recombination at stalled replication forks contributes to genomic instability and breast/ovarian cancer predisposition in BRCA mutant cells.

Accordingly, the invention provides methods for characterizing the functional significance of a DNA repair polypeptide variant, homologous recombination reporter gene conversion vectors, homologous recombination reporter of short and long tract gene conversion vectors, cells comprising such vectors, and methods of characterizing the functional significance of a mutation in a DNA repair polypeptide derived from a biological sample obtained from a patient. Furthermore, the invention provides methods for identifying subjects with a propensity to develop cancer or whose cells have a propensity for genomic instability to occur.

Types of Biological Samples

The present invention provides a method to characterize the functional significance of a mutation in a DNA repair polypeptide (e.g., including but not limited to BRCA1, BRCA2, BARD, PALB2, RAD51, RAD51B, RAD51C, RAD51D, XRCC2, XRCC3, BLM, other RECQ helicases, MRE11, Rad50, NBS1, ATM, ATR, CTIP, Brip, RPA and RPA-like polypeptide). These polynucleotides may be extracted from different types of biologic samples. In one embodiment, the biologic sample is a tissue sample that includes cells of a tissue or organ (e.g., breast or ovarian cancer cells). Breast or ovarian cancer cell tissue is obtained, for example, from a biopsy of the affected organ or a metastasis thereof. In another embodiment, the biologic sample is a biologic fluid sample. Biological fluid samples include blood, blood serum, plasma, urine, or any other biological fluid useful in the methods of the invention.

Detection of Defects in DNA Repair Pathways

Defects in a polynucleotide encoding a DNA repair polypeptide are detected using routine methods known in the art. DNA sequencing remains the "gold standard" for identifying specific nucleotide variations. Such sequencing includes not only traditional sequencing methods (e.g., the Sanger method), but also next-generation sequencing (NGS) technologies capable of sequencing millions of DNA templates in parallel. Methods for characterizing polynucleotides are known in the art and typically focus on allele-specific and sequence-scanning detection methods.

Primer extension (Piggee et al., J Chromatogr A. 1997; 781:367-375), allele-specific amplification (Struewing et al. New Engl J Med. 1997; 336:1401-1408), allele-specific oligonucleotide hybridization (Hacia et al. Nat Genet. 1996; 14:441-447) and oligonucleotide ligation (Iannone et al. Cytometry. 2000; 39:131-140) are specific mutation detection methods that are currently used. The aforementioned publications are incorporated herein by reference for all that they teach relating to these methods.

Other methods for detecting nucleotide variations include heteroduplex analysis (HDA; Gerrard and Dean Single-strand conformation polymorphism and heteroduplex analysis. In: Cotton RGH, Edkins E, Forrest S, editors. Mutation detection—a practical approach. New York: Oxford University Press; 1998. pp. 25-33), single-strand conformation polymorphism (SSCP; Nataraj et al. Electrophoresis. 1999; 20:1177-1185), denaturing gradient gel electrophoresis (DGGE; De Santis and Azzi J Virol Methods. 2000; 85:101-108), temperature gradient gel electrophoresis (TGGE; Toliat et al. Electrophoresis. 2000; 21:541-544), denaturing high-performance liquid chromatography (DHPLC; Nucleic Acids Res. 1998; 26:1396-1400), RNase cleavage (Faudoa et al. Hum Mutat. 2000; 15:474-478), and methods using either DNA repair enzymes or resolvases for the detection of mismatches (Hsu et al. Carcinogenesis. 1994; 15:1657-1662) represent sequence-scanning (or nonspecific) approaches to mutation detection.

Defects in polypeptide biomarkers (e.g., polypeptides that function in DNA repair) can be detected by any suitable method. The methods described herein can be used individually or in combination for a more accurate detection of the biomarkers (e.g., immunoassay, mass spectrometry, and the like).

In particular embodiments, biomarkers of the invention (e.g., DNA repair pathway polypeptides) are measured by immunoassay using an antibody that detects a mutant version of the protein. This invention contemplates traditional immunoassays including, for example, Western blot, sandwich immunoassays including ELISA and other enzyme immunoassays, fluorescence-based immunoassays, chemiluminescence. Nephelometry is an assay done in liquid phase, in which antibodies are in solution. Binding of the antigen to the antibody results in changes in absorbance, which is measured. Other forms of immunoassay include magnetic immunoassay, radioimmunoassay, and real-time immunoquantitative PCR (iqPCR).

Immunoassays can be carried out on solid substrates (e.g., chips, beads, microfluidic platforms, membranes) or on any other forms that supports binding of the antibody to the marker and subsequent detection. A single marker may be detected at a time or a multiplex format may be used. Multiplex immunoanalysis may involve planar microarrays (protein chips) and bead-based microarrays (suspension arrays).

Polynucleotide Vectors of the Invention

The invention provides a number of vectors for characterizing the functional significance of a variation in the sequence of a DNA repair pathway polypeptide. Vectors of the invention encode, for example, a Tus polypeptide (e.g., wild-type). In various embodiments, the Tus polypeptide can have additions and alterations designed to improve function (e.g., addition of an epitope tag, a nuclear localization sequence, codon optimization for use in mammalian cells). In a particular embodiment, the Tus polypeptide is a variant with a point mutation, such as Tus F140A, to increase the affinity of Tus for its binding site Ter. Vectors of the invention encode, for example, a wild-type DNA repair polypeptide, a DNA repair polypeptide comprising a mutation (e.g., a variant DNA repair polypeptide), and one or more detectable proteins (e.g., GFP, RFP). Also, nucleic acid sequences encoding a rare cutting endonuclease may optionally be included in vectors of the invention. Exemplary rare cutting endonucleases include I-SceI. Vectors of the invention also comprise one or more Ter sites (e.g., in an array). In various embodiments, vectors of the invention comprise one, two, three, four, five, six, or more Ter sites. In various specific embodiments, vectors of the invention comprise 6, 9, 12, 15, 21 Ter sites, which are functional for replication fork stalling. Typically, recombinant polypeptides are produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a eukaryotic host (e.g., mammalian cells, e.g., NIH 3T3, HeLa, COS cells). Other cell types that may be used include without limitation vertebrate cells, insect cells, chicken cells, and mouse cells. Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Selection of a Treatment Method

After a subject is diagnosed as having a neoplasia (e.g., breast or ovarian cancer) a method of treatment is selected. In breast or ovarian cancer, for example, a number of standard treatment regimens are available. The presence of a defect in a DNA repair pathway suggests that the subject could be treated, for example, with a PARP inhibitor, cross-linking agents such as cisplatin and other agents that exploit the specific DNA repair defect of the tumor cells. Such a therapy can be combined, for example, with one or more of the following therapies: mastectomy, ovarectomy, radiation therapy (e.g., external beam and brachytherapy), hormone therapy, and chemotherapy. Additionally, prior to the diagnosis of cancer, a patient may opt to have treatments that reduce the risk of cancer based on the characterization of a DNA repair polypeptide. Examples include mastectomy and/or oophrectomy to reduce the risk of breast or ovarian cancer, respectively. The assays proposed might be useful prior to the onset of cancer in certain individuals with high cancer risk.

Kits

The invention also provides kits methods for characterizing the functional significance of a DNA repair pathway mutation to determine whether the patient has or has a propensity to develop breast or ovarian cancer in a biological sample obtained from a subject. The assay currently identifies mutations as high risk and/or distinguishes high risk mutations from those that do not elevate risk. In various embodiments, the kit includes one or more vectors of the invention. Preferably, such vectors include a homologous recombination reporter of short and long tract gene conversion vector comprising one to six Ter sites. In yet other embodiments, the kit comprises a sterile container which contains the primer or probe; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a neoplasia (e.g., breast/ovarian cancer). Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

Genome Editing

Therapeutic gene editing is a major focus of biomedical research, embracing the interface between basic and clinical science. A large number of different recessive hereditary human disease syndromes are caused by inheritance of biallelic inactivating point mutations of disease genes. In one embodiment, if it were possible to safely reverse the disease-causing point mutation in cells cultured from the patient and to reconstitute the tissues of the patient's body with these corrected cells, this could lead to a cure for the disease or, at least, significant alleviation of the dysfunction.

Substantial progress towards this goal has been made with the advent of technologies for inducing pluripotency in cells derived from patients and with the remarkable development of novel "gene editing" tools. Broadly, gene editing requires the ability to manipulate the DNA sequence of a cell at a specific chromosomal locus, without introducing mutations at other sites of the genome. This technology effectively enables the researcher to manipulate the genome of the patient's cells in vitro, to effect a reversion of a deleterious genotype and to then reintroduce these cells into the patient. Successful development of gene editing has the potential to impact a large number of patients carrying known, defined genetic mutations and could have additional benefits in other diseases.

In one embodiment, gene editing involves targeting an endonuclease (an enzyme that causes DNA breaks internally within a DNA molecule) to a specific site of the genome and thereby triggering formation of a chromosomal double strand break (DSB) at the chosen site. If, concomitant with the introduction of the chromosome breaks, a donor DNA molecule is introduced (for example, by plasmid or oligonucleotide introduction), interactions between the broken chromosome and the introduced DNA can occur, especially if the two sequences share homology. In this instance, a process termed "gene targeting" can occur, in which the DNA ends of the chromosome invade homologous sequences of the donor DNA by homologous recombination (HR). By using the donor plasmid sequence as a template for HR, a seamless repair of the chromosomal DSB can be accomplished. Importantly, if the donor DNA molecule differs slightly in sequence from the chromosomal sequence, HR-mediated DSB repair will introduce the donor sequence into the chromosome, resulting in gene conversion/gene correction of the chromosomal locus. In the context of therapeutic gene targeting, the altered sequence chosen would be an active or functional fragment (e.g., wild type, normal) of the disease gene of interest. By targeting the nuclease to a genomic site that contains the disease-causing point mutation, the concept is to use DSB formation to stimulate HR and to thereby replace the mutant disease sequence with wild-type sequence (gene correction). The advantage of the HR pathway is that it has the potential to generate seamlessly a wild type copy of the gene in place of the previous mutant allele.

Current genome editing tools use the induction of double strand breaks (DSBs) to enhance gene manipulation of cells. Such methods include zinc finger nucleases (ZFNs; described for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, and U.S. Pat. Publ. Nos. 20030232410 and US2009020314, which are incorporated herein by reference), Transcription Activator-Like Effector Nucleases (TALENs; described for example in U.S. Pat. Nos. 8,440,431, 8,440,432, 8,450,471, 8,586,363, and 8,697,853, and U.S. Pat. Publ. Nos. 20110145940, 20120178131, 20120178169, 20120214228, 20130122581, 20140335592, and 20140335618, which are incorporated herein by reference), and the CRISPR (Clustered Regularly Interspaced Short Palindromic Repeats)/Cas9 system (described for example in U.S. Pat. Nos. 8,697,359, 8,771,945, 8,795,965, 8,871,445, 8,889,356, 8,906,616, 8,932,814, 8,945,839, 8,993,233, and 8,999,641, and U.S. Pat. Publ. Nos. 20140170753, 20140227787, 20140179006, 20140189896, 20140273231, 20140242664, 20140273232, 20150184139, 20150203872, 20150031134, 20150079681, 20150232882, and 20150247150, which are incorporated herein by reference). For example, ZFN DNA sequence recognition capabilities and specificity can be unpredictable. Similarly, TALENs and CRISPR/Cas9 cleave not only at the desired site, but often at other "off-target" sites, as well. These methods have significant issues connected with off-target double-stranded break induction and the potential for deleterious mutations, including indels, genomic rearrangements, and chromosomal rearrangements, associated with these off-target effects. ZFNs and TALENs entail use of modular sequence-specific DNA binding proteins to generate specificity for ~18 bp sequences in the genome. The more recently developed, CRISPR/Cas9, adapts an RNA-guided bacterial host defense system and uses engineered RNA-DNA pairing to achieve target specificity. However, all current gene editing methods including CRISPR/Cas9, TALENs and ZFNs are plagued by "off-target" mutagenic effects, related to off-target binding of the gene editing nuclease to additional unintentionally specified sites (shown for CRISPR/Cas9 in FIG. 21A). Unfortunately, off-target effects are commonly observed with all of these methods, registering as "indels"—small insertions or deletions that indicate sites of off-target action of the endonuclease with repair by error-prone mechanisms such as non-homologous end joining (NHEJ). Clearly, if an off-target indel were to disrupt a functional gene in the patient's cell, this could be dangerous. For example, off-target inactivation of one allele of a tumor suppressor gene, such as TP53 or RB, could set the "gene corrected" cells on the path to cancer. Efforts to minimize such off-target effects have included the use of "nickases"—mutants of the endonuclease that inactivate one active site and leave the enzyme capable of inducing "nicks" (single stranded interruption of the sugar-phosphate backbone) in the genomic DNA. By combining two nickases to attack each DNA strand at the target site, the idea is to focus DSBs preferentially at the target locus. Although off-target effects may be reduced by this maneuver, there is no indication that it will abolish off-target indel formation altogether. There are good theoretical reasons why this is the case. Nicked DNA, if encountered during replication, can generate DSBs and, hence, promote indel formation or other types of mutation.

Figure 21A:
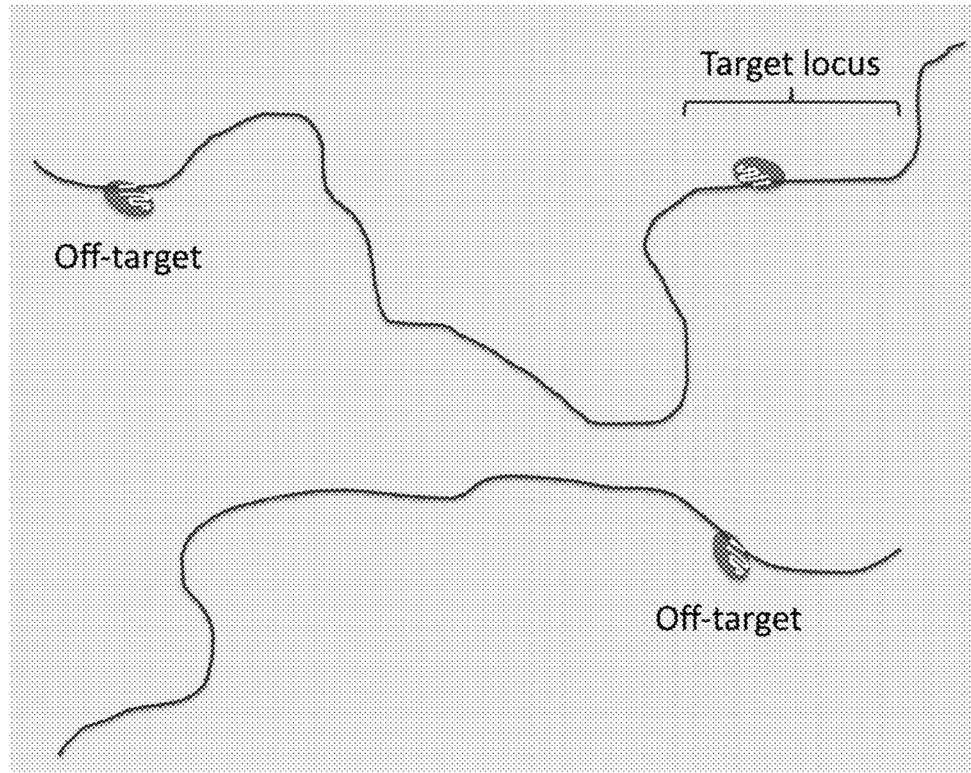
FIGS. 21A and 21B depict a model in which enzymatically inactive CRISPR/Cas9 arrays are used to stall replication in a site-specific manner at a single locus targeted for gene editing.
Figure 21B:
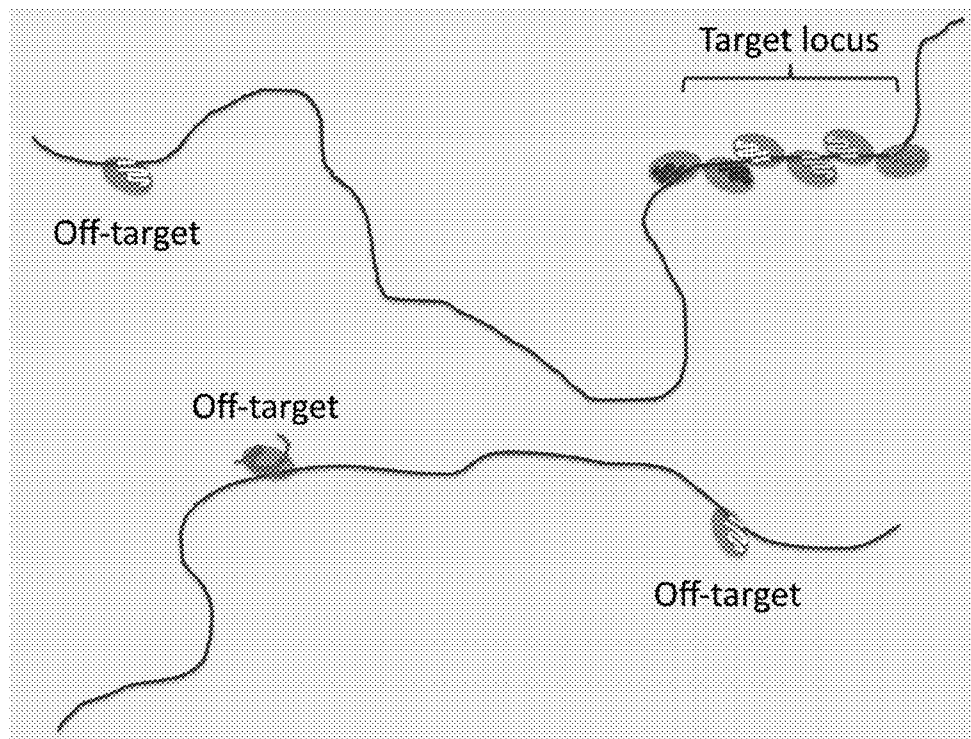

A new adaptation of existing gene editing tools is proposed to address the problem of off-target mutagenesis. This is accomplished by using an array of nuclease dead CRISPR/Cas9 complexes, arrayed in tight succession, side-by-side, at the target locus, to provoke site-specific replication fork stalling and limit gene targeting/gene editing specifically to the target locus (FIG. 21B). Because the stimulus to gene editing (a site-specific replication fork block) will only occur where the editing complexes are clustered/multiplexed in an array at the target locus, off-target binding of individual nuclease dead CRISPR/Cas9 complexes will not provoke replication fork arrest or chromosome breakage. In other words, by making the stimulus to DNA breakage a product of multiplexed CRISPR/Cas9 complex binding, the potential for off-target mutation is reduced to a negligible level. As described herein, experiments with a defined site-specific replication fork arrest tool indicate the potential for this approach to eradicate one of the obstacles to therapeutic gene editing (i.e., off-target mutagenesis) and to accelerate progress towards its safe clinical use. Although this description focuses on CRISPR/Cas9, it is envisioned that this method may be adapted to other gene editing tools (TALENs, ZFNs) in search of the optimal technology.

In one aspect, the invention provides methods of increasing replication fork stalling (e.g., Tus/Ter system), which could be used to induce error free double stranded breaks with fewer off-target effects. In various embodiments, one or more DNA binding proteins can be used to induce replication fork stalling. In one embodiment, the invention provides a GFP cDNA containing an array of Ter sites. A Tus expression vector is co-transfected together with a donor mutant GFP sequence (see e.g., FIGS. 19 and 20), and detection of whether Tus/Ter triggers conversion of the integrated GFP copy to wild type is assayed. Production of $GFP^{+}$ cells marks those that have undergone successful gene targeting. In this way, the ability of Tus/Ter to stimulate gene targeting is assayed. In other various embodiments, one or more of the following DNA binding proteins is used: Cas9, Cas9 null (i.e., catalytically inactive Cas9), Tus, Zinc finger domain, Zinc finger nuclease, transcription activator-like effector (TALE) domain, and/or TALE nucleases.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1B:
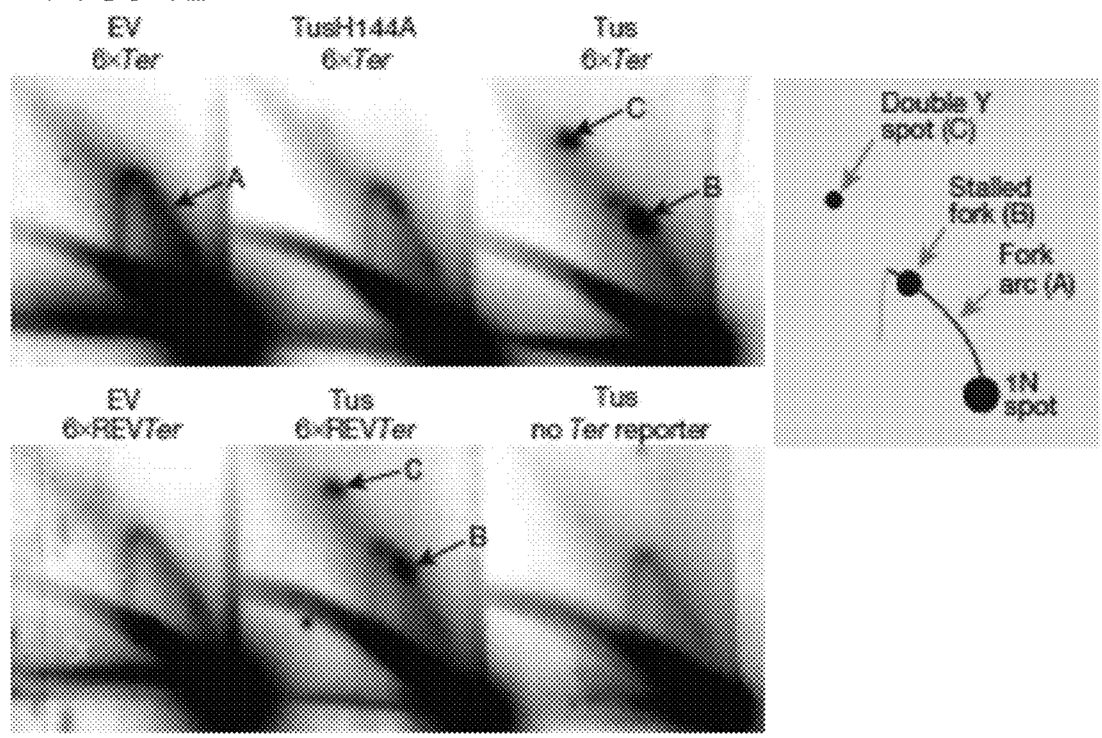
Figure 1C:
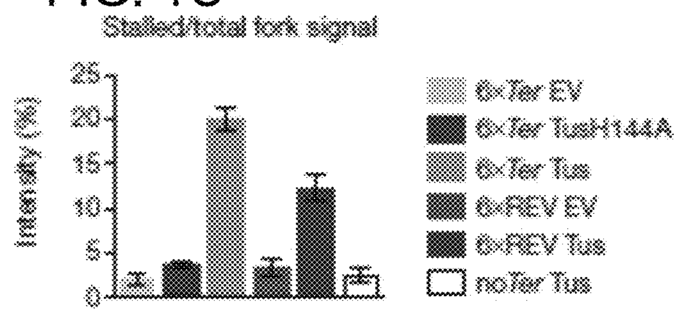
Figure 1D:
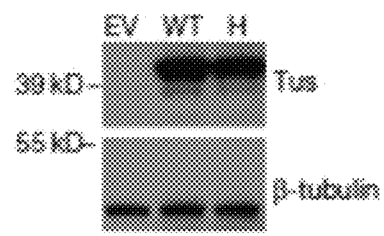
Figure 2A:
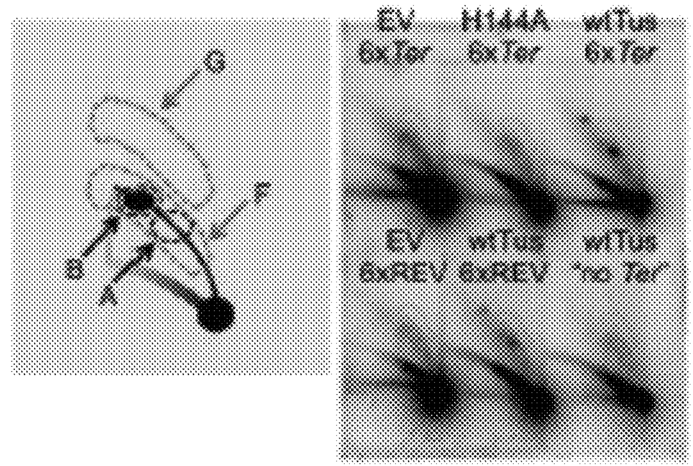
FIGS. 2A-2E show Tus/Ter-induced replication fork stalling visualized by additional restriction digests.
Figure 2B:
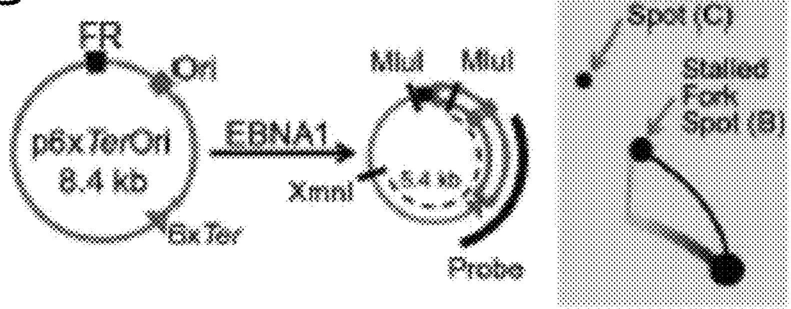
Figure 2C:
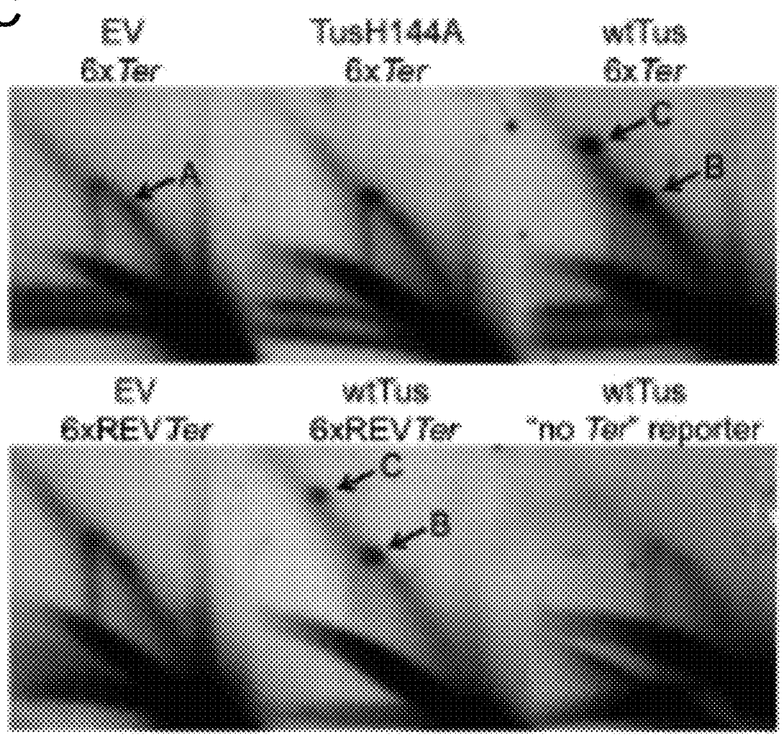
Figure 2D:
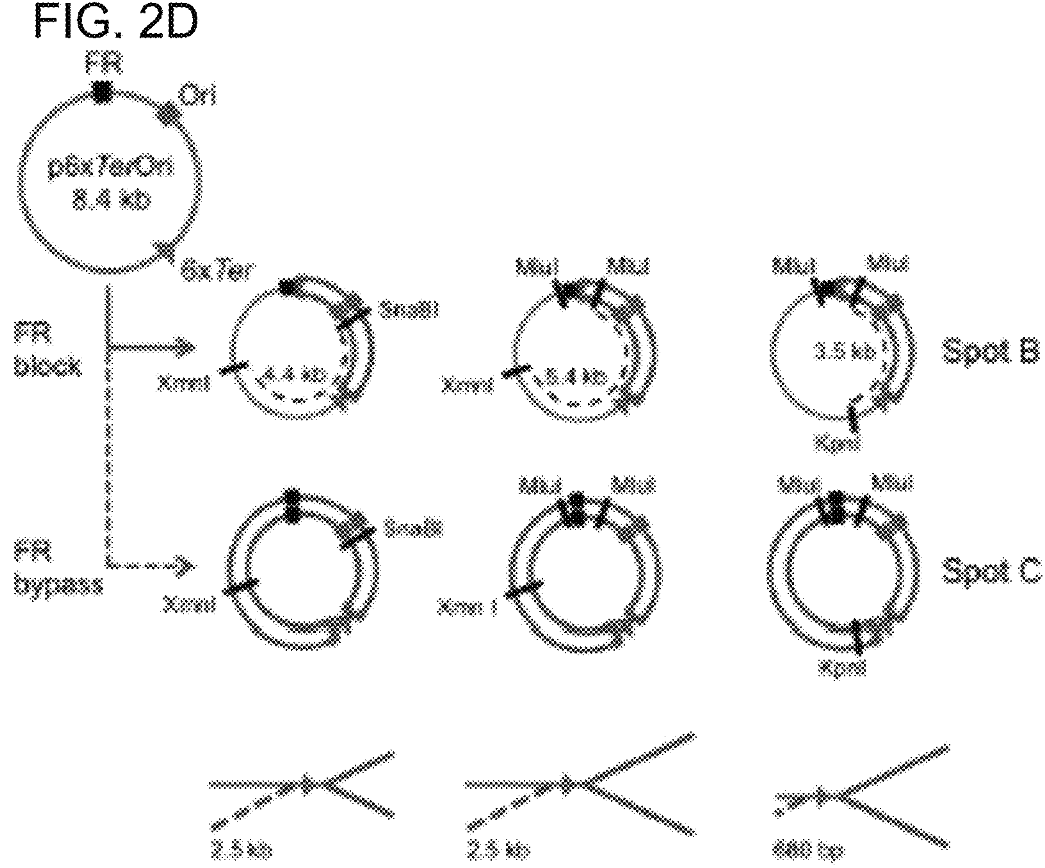
Figure 2E:
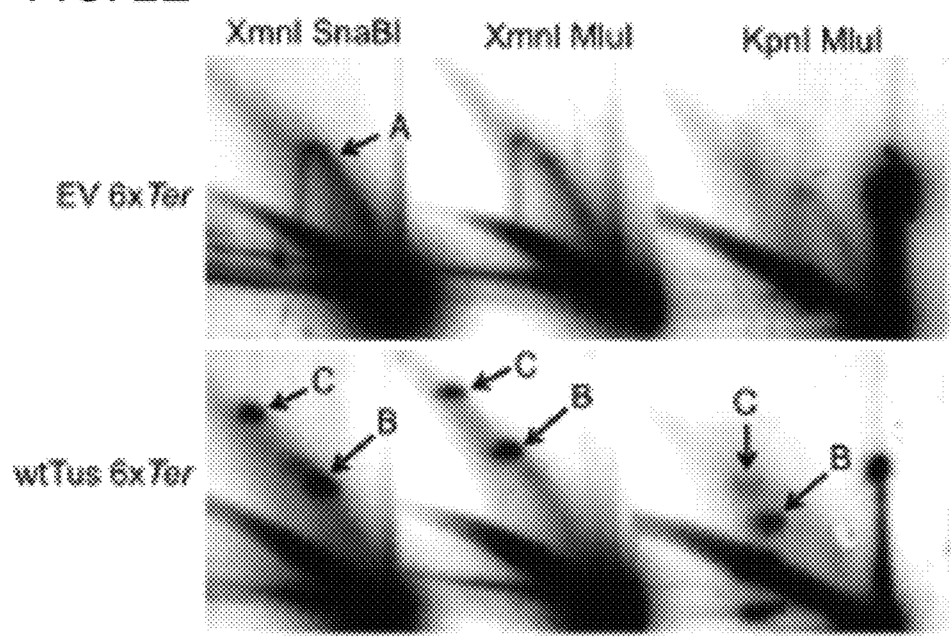
Figure 3A:
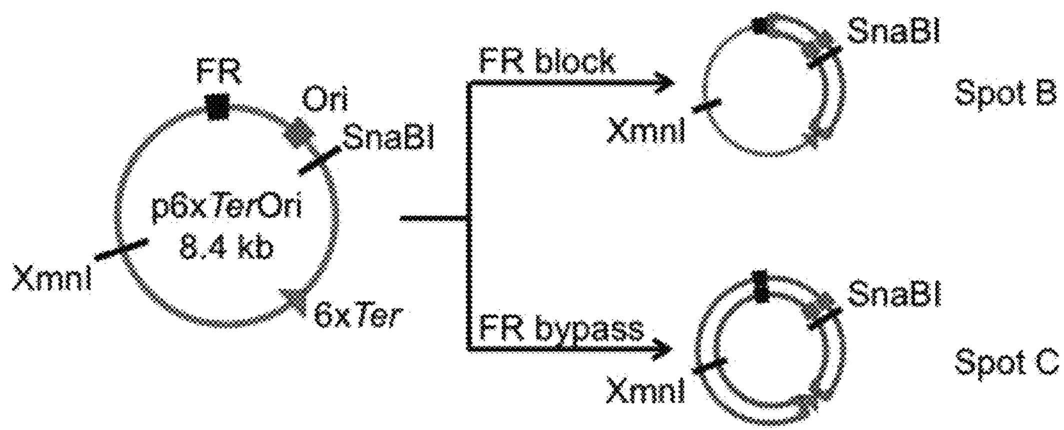
FIGS. 3A-3D show an estimation of efficiencies of the FR/EBNA1 and Tus/6×Ter replication fork barriers.
Figure 3B:
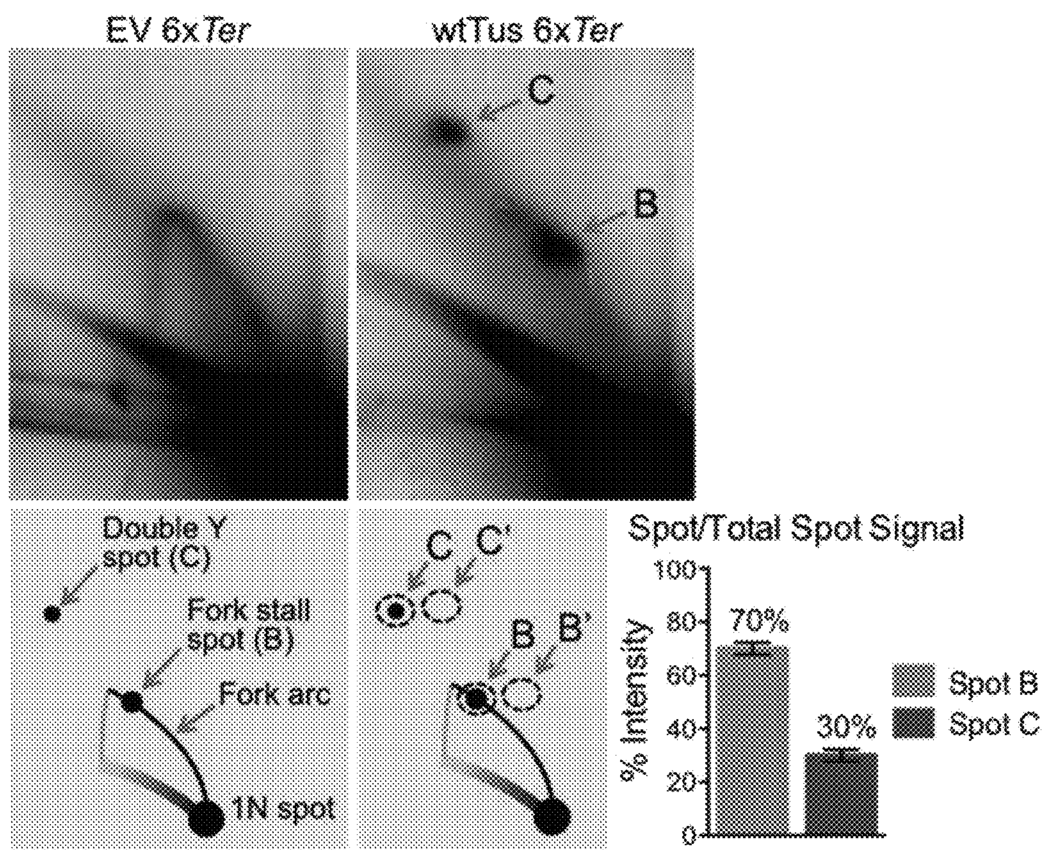
Figure 3C:
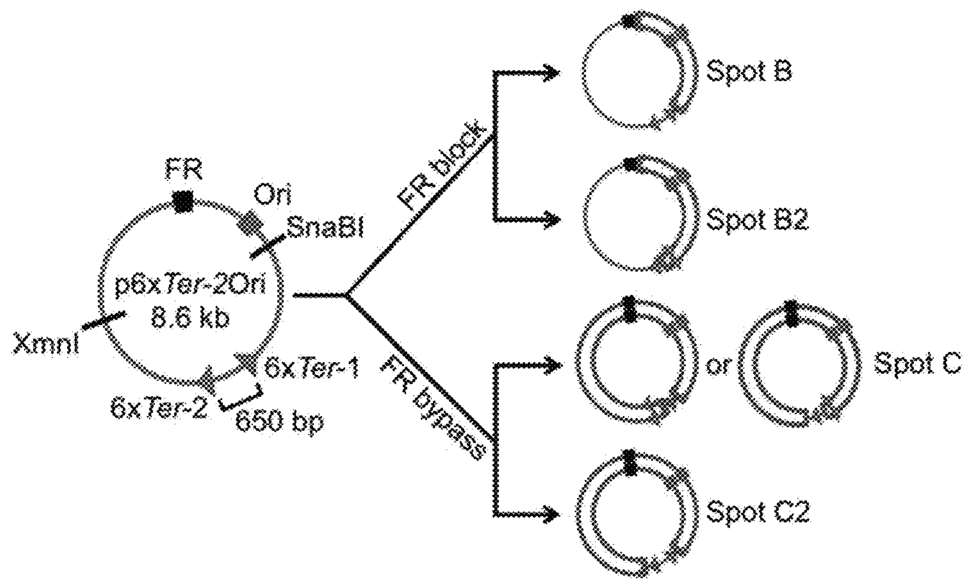
Figure 3D:
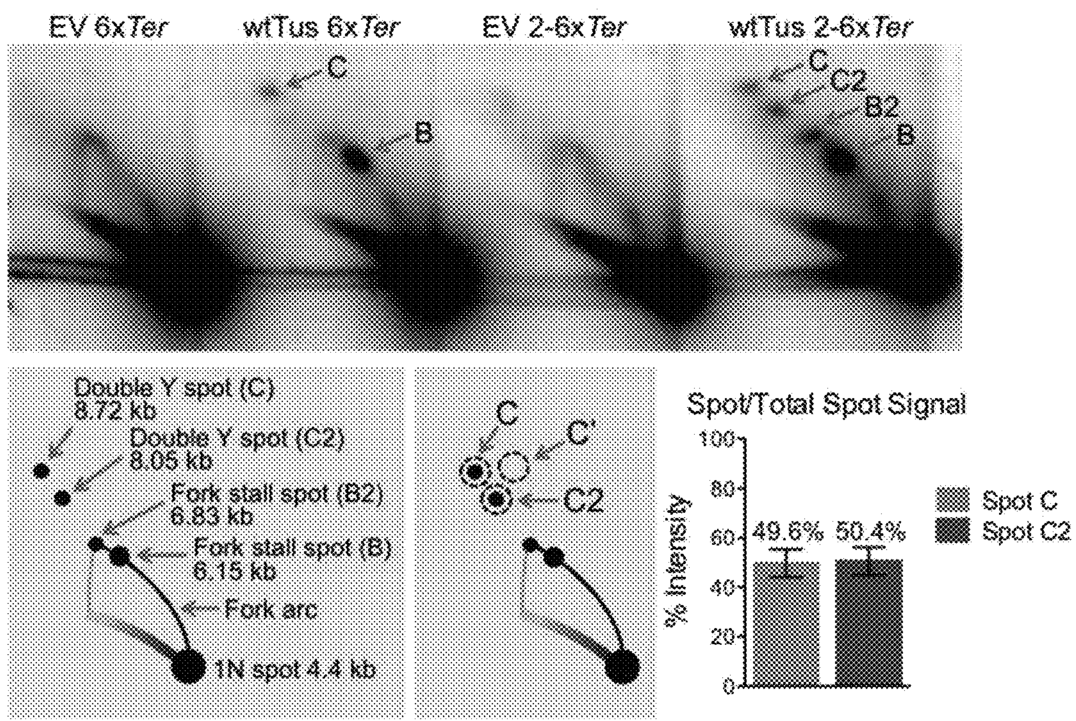

Example 1: Loss of BRCA1/BRCA2/Rad51-Dependent Suppression of LTGC at Stalled Replication Forks Contributes to Breast/Ovarian Cancer Predisposition Tus binds the 23 base pair (bp) Ter site to induce polar replication fork arrest in *E. coli*. To determine whether Tus/Ter can arrest mammalian replisomes, six TerB sites were introduced into a plasmid containing the Epstein-Barr virus nuclear antigen 1 (EBNA1)-binding origin of replication (p6×TerOri, FIG. 1A). EBNA1 recruits mammalian replication factors, mediating predominantly unidirectional plasmid replication, due to a replication block at EBNA1-bound FR (family of repeats). In p6×TerOri, the major clockwise fork approaches the 'non-permissive' (fork-stalling) face of Tus/Ter (FIG. 1A). Two-dimensional DNA gel electrophoresis with Southern blotting was used to visualize replication through Ter. Transfection of 293E cells, which express EBNA1, with p6×TerOri and control empty vector revealed plasmid replication intermediates (arc A, FIG. 1B). Co-transfection of p6×TerOri and myc-tagged Tus revealed site-specific stalling of the clockwise fork (spot B, FIGS. 1B, 1C, 1D and FIGS. 2A-2E). TusH144A, a Ter-binding-impaired mutant, induced minimal fork stalling. Reversal of 6×Ter to the 'permissive' orientation (6×REVTer, FIG. 1B) also supported Tus-dependent stalling of the clockwise fork, albeit less efficiently than non-permissive 6×Ter (FIGS. 1B and 1C). The FR/EBNA1 replication block is incomplete. A weaker Tus/Ter-dependent double-Y spot (C, FIG. 1B and FIGS. 2A-2E) reflects bidirectional fork arrest at 6×Ter. The FR/EBNA1 and Tus/6×Ter replication block efficiencies were estimated as, 70% (FIGS. 3A-3D). Thus, Tus/Ter mediates bidirectional site-specific arrest of mammalian replication forks.

Figure 4A:
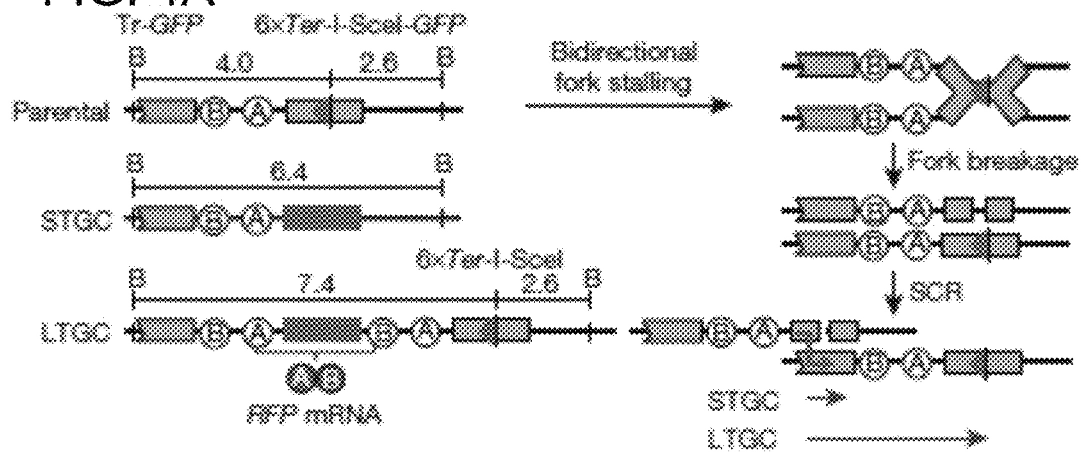
FIGS. 4A-4D show Tus/Ter-induced homologous recombination in mammalian cells.
Figure 4B:
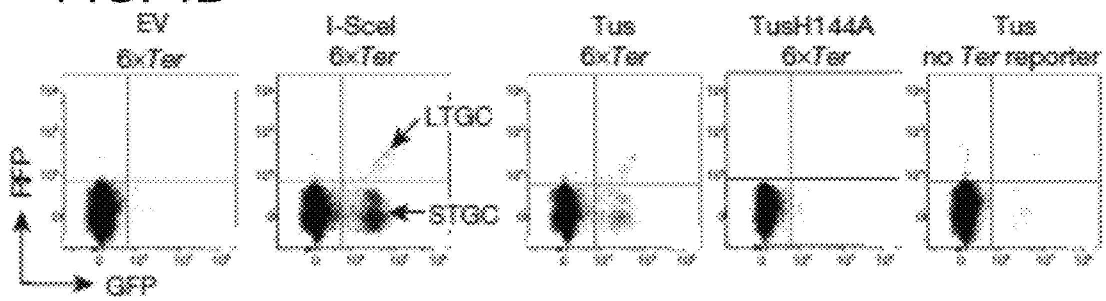
Figure 4C:
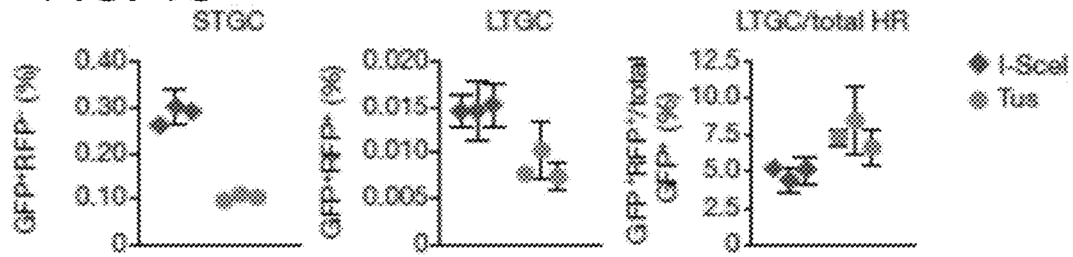
Figure 5A:
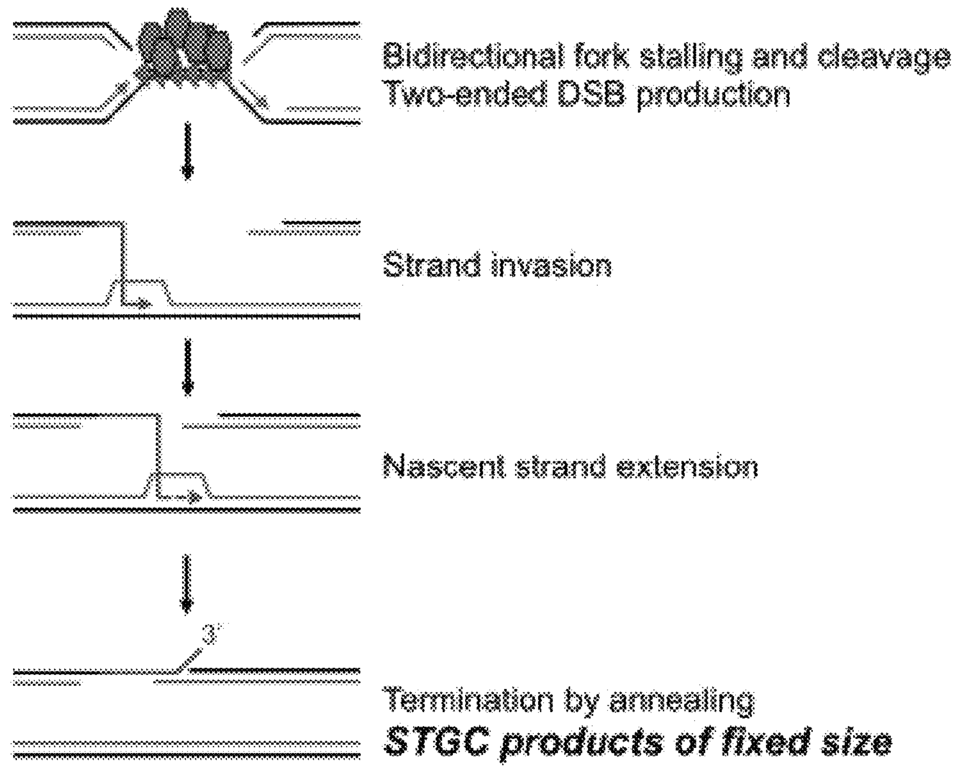
FIGS. 5A and 5B show two-ended versus one-ended break repair models of Tus/Ter-induced homologous recombination.
Figure 5B:
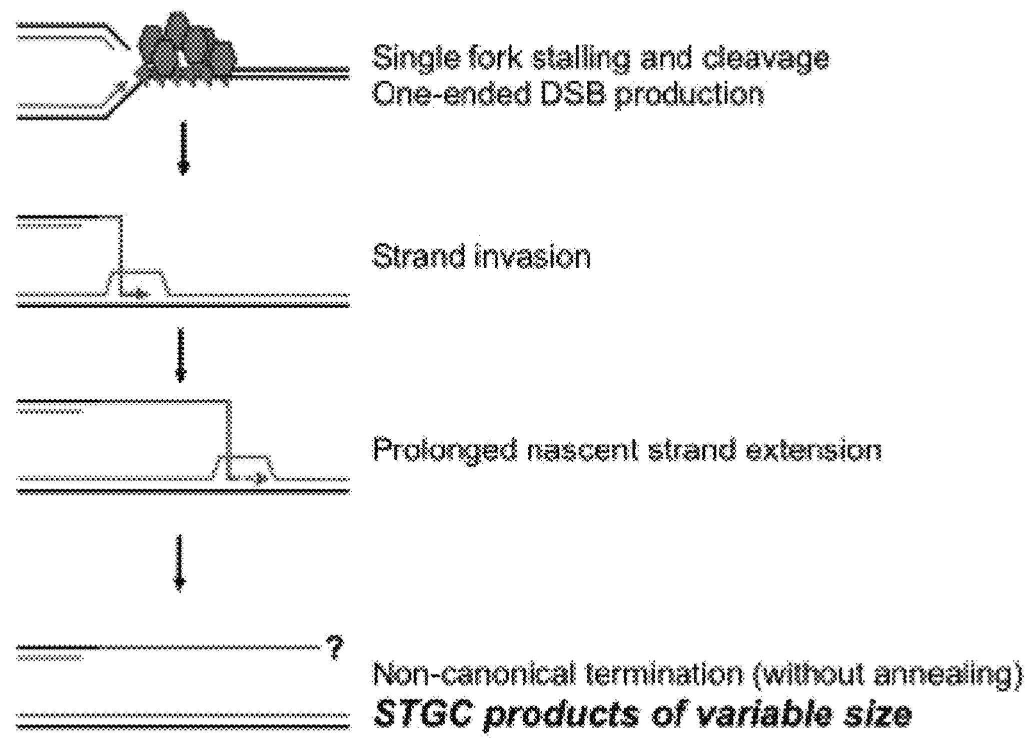
Figure 6A:
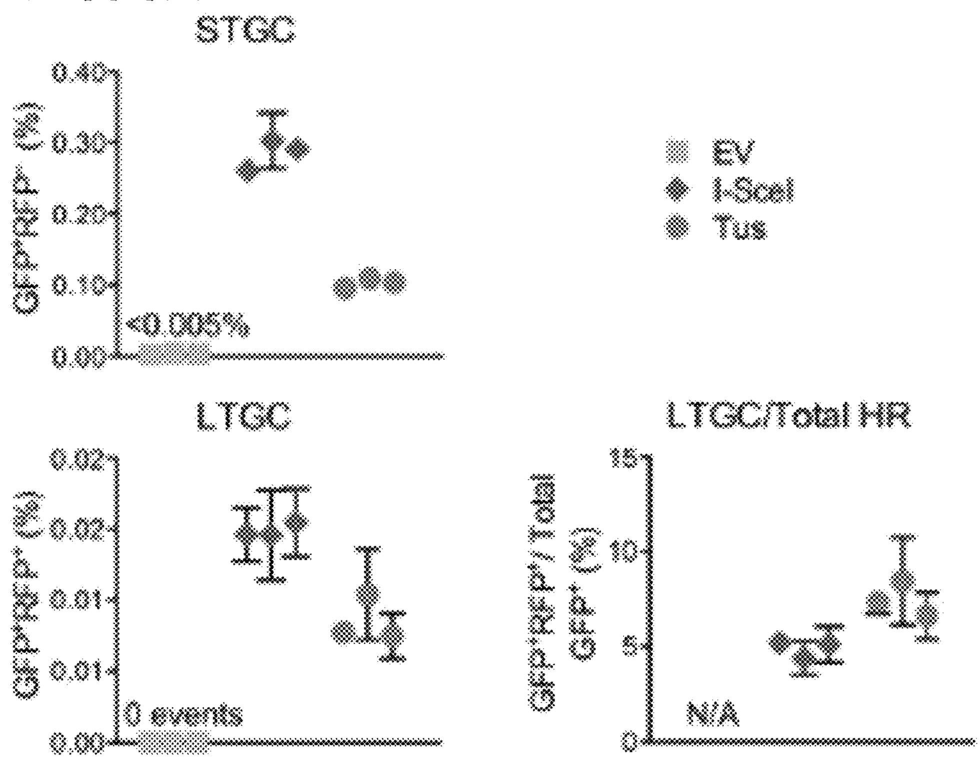
FIGS. 6A-6F show that Tus/Ter-induced homologous recombination in $Brca1^{fl/BRCT}$ 6×Ter/HR cells conformed to an affinity/avidity model.
Figure 6B:
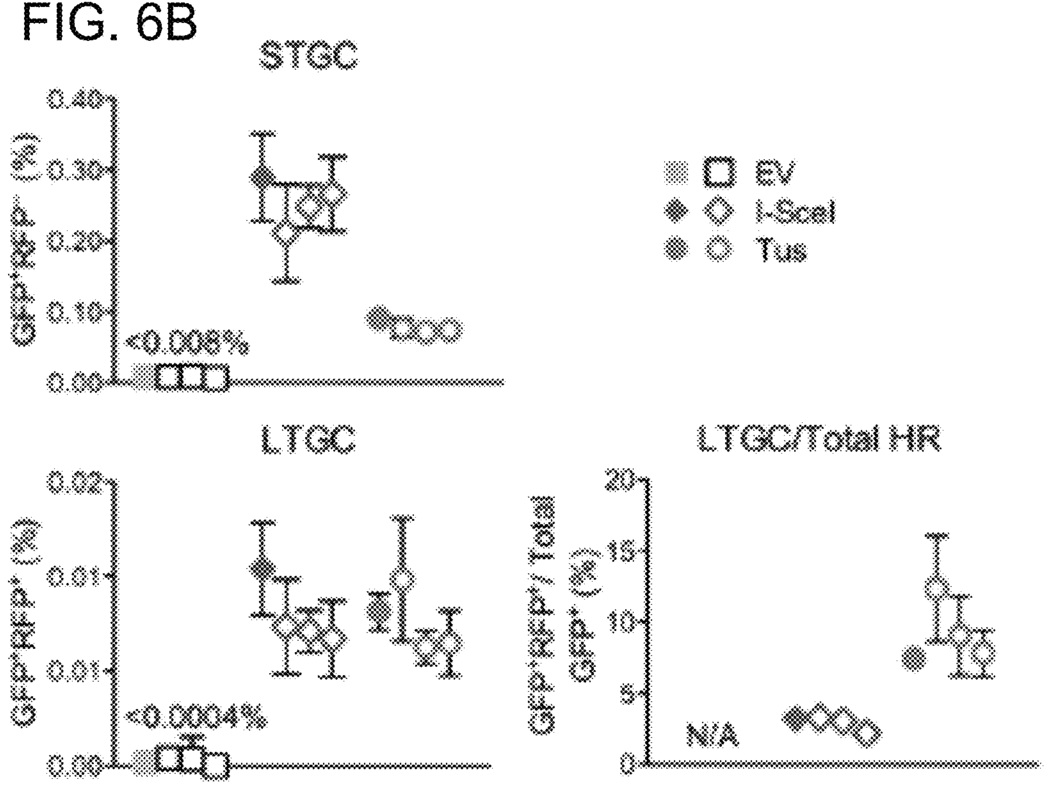

To determine whether Tus/Ter induces HR/SCR at a defined chromosomal locus in mammalian cells, 6×Ter was placed in a homologous recombination reporter of short- and long-tract gene conversion (termed STGC and LTGC, respectively) between sister chromatids. Duplication of a red fluorescent protein (RFP) cassette distinguished LTGC (length>1252 bp; $GFP^{+}RFP^{-}$) from STGC (length<1,252 bp; $GFP^{+}RFP^{-}$ FIG. 2A). 6×Ter abuts an I-SceI site, interrupting an enhanced green fluorescent protein gene (6×Ter-I-SceI-GFP, FIG. 4A). Recombination of the stalled left-hand fork (FIG. 4A) with the 59-truncated GFP copy (Tr-GFP) of the sister chromatid generated wild-type GFP. If chromosomal fork arrest were bidirectional, this could produce a two-ended break, generating predominantly STGCs (FIGS. 4A and 5A). In contrast, unidirectional fork arrest with one-ended breaks would favour LTGC, and any STGCs arising from one-ended breaks would necessarily be terminated by non-canonical mechanisms (FIG. 5B). The 6×Ter/HR reporter was targeted as a single copy to the ROSA26 locus of mouse embryonic stem (ES) cell line 11CO/47T ($Brca1^{fl/BRCT}$). $Brca1^{BRCT}$ encodes a C-terminal truncated protein; the BRCT-encoding elements of $Brca1^{fl}$ can be conditionally deleted (generating $Brca1^{\Delta}$). Indeed, Tus, but not TusH144A, induced HR within 63 Ter/HR$Brca1^{fl/BRCT}$ cells, the major HR product being STGC(FIG. 4B). Tus failed to induce HR in $Brca1^{fl/BRCT}$ cells containing a ROSA26-targeted HR reporter lacking the Ter array (FIG. 4B). Thus, Tus/Ter-induced chromosomal HR requires cognate Tus-Ter binding. The ratio LTGC/total HR, a measure of the probability that HR resolves as LTGC, was approximately 7% in three independent Tus-transfected clones (FIGS. 4C and 6A). Three additional independent clones of $Brca1^{fl/BRCT}$ ES cells, each containing a single-copy randomly integrated chromosomal 6×Ter/HR reporter, behaved similarly (FIG. 6B). The predominance of STGC and the consistent results at different loci suggested that Tus/Ter-induced HR entails bidirectional fork arrest (FIG. 5A). This was resolved definitively by Southern blot analysis of Tus/Ter-induced STGCs. Unidirectional fork arrest/breakage (FIG. 5B) could produce a one-ended break, generating STGC products of variable size.

Figure 4D:
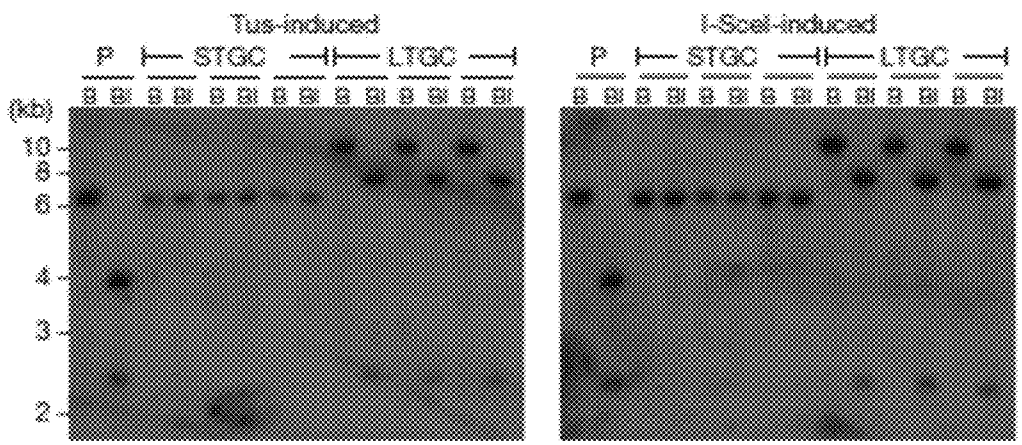
Figure 6C:
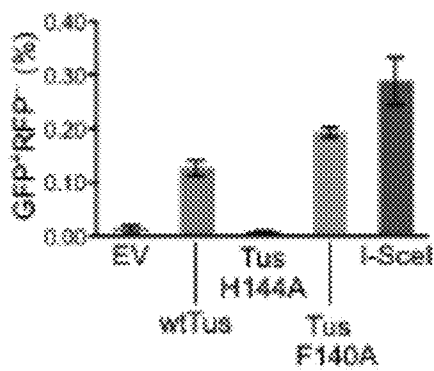
Figure 6D:
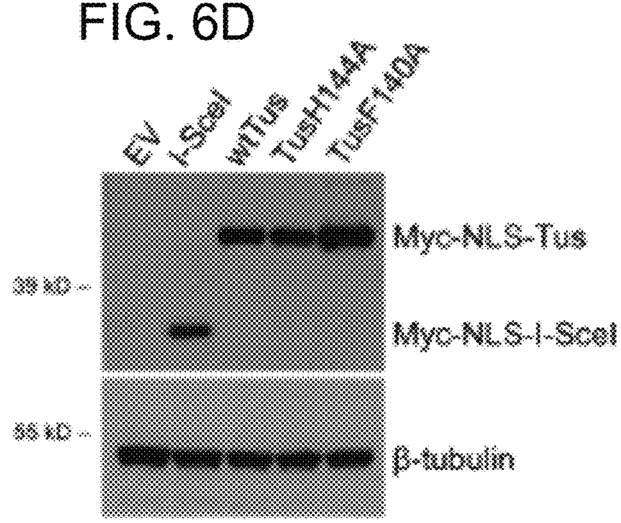
Figure 6E:
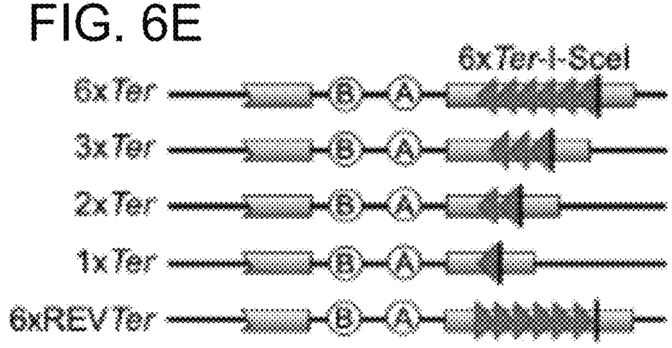
Figure 6F:
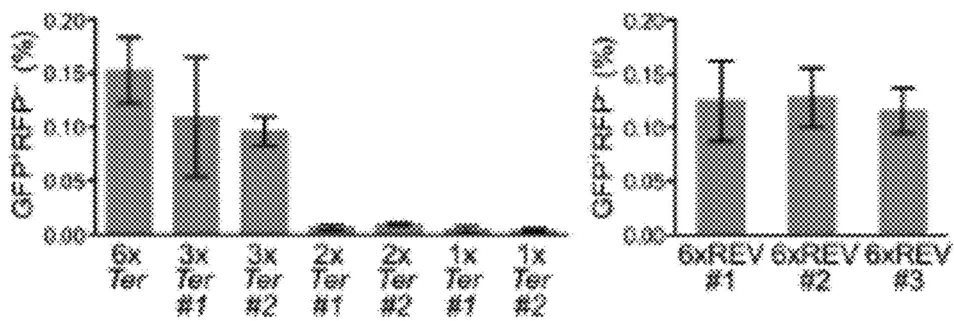

In contrast, bidirectional fork arrest (FIGS. 4A and 5A) could produce a two-ended break, with STGC termination by annealing. This would generate STGC products of fixed size, resembling the parental reporter, but lacking the 6×Ter array or I-SceI site (FIG. 4A). Indeed, 44/44Tus/Ter-induced STGCs in 6×Ter/HR reporter Brca1$^{fl/BRCT}$ cells revealed this latter structure (FIG. 4D). As expected, I-SceI-induced HR behaved similarly (FIG. 4D). A second arrested fork (right-hand fork, FIG. 4A) must provide the homologous second end during Tus/Ter induced STGC. Therefore, Tus/Ter-induced STGC is the product of bidirectional replication fork arrest. Overall, I-SceI-induced HR in Brca1$^{fl/BRCT}$ 6×Ter/HR reporter cells was approximately 20% of that in isogenic ROSA26-targeted Brca1$^{fl/BRCT}$HR reporter cells, which lack a 6×Ter array. To investigate further the non-polar behaviour of Tus/Ter in mammalian HR, the Tus mutant F140A that binds duplex Ter with higher affinity than Tus, but is defective for the Ter C-6 base-flipping 'locking' mechanism that contributes to polar fork arrest in *E. coli* was studied. Tus F140A induced higher levels of HR than Tus in 6×Ter/HR Brca1$^{fl/BRCT}$ cells (FIGS. 6C and 6D), showing that the C-6 'lock' is dispensable for Tus/Ter-induced HR in mammalian cells. This might be explained by the different polarities of the *E. coli* DnaB and vertebrate MCM replicative helicases. Ter C-6 is located on the leading strand of the fork approaching the non-permissive end of Ter. Unlike DnaB, which translocates along the lagging strand, the MCM helicase translocated along the leading strand and might occlude Ter C-6 within its barrel, thereby denying Tus access to the C-6 lock mechanism. To determine the minimal number of Tus/Ter complexes needed for HR induction, reporters containing 3, 2 or 1 Ter sites were generated (FIG. 6E). Each, was targeted in parallel, as a single copy to the ROSA26 locus of Brca1$^{fl/BRCT}$ ES cells and it was found that a minimum of 3 Ter sites was required for robust Tus-induced HR (FIG. 6F). The 6×Ter array orientation was inverted to generate a 6×REVTer/HR reporter. When targeted as a single copy to the ROSA26 locus of Brca1$^{fl/BRCT}$ ES cells, this reporter supported Tus-induced HR as robustly as the 6×Ter/HR reporter (FIG. 6F). These findings do not exclude a polar component to Tus/Ter-induced fork stalling on a mammalian chromosome but this polarity, if present, is relative and not absolute.

In summary, it was discovered that Tus/Ter-induced HR: requires cognate binding of Tus to the Ter array; is independent of Ter site orientation; is dependent on Ter site number (requires at least 3×Ter; optimal is 6×Ter); occurs equally efficiently at different random chromosomal sites; is a product of bidirectional replication fork arrest (shown by Southern blot analysis of HR products); and is regulated differently from HR in response to a "generic" chromosomal DSB induced by the rare-cutting homing endonuclease I-SceI. Furthermore, Tus/Ter-induced HR was observed in human somatic cells, and is therefore not restricted to a specific cell type.

Figure 7A:
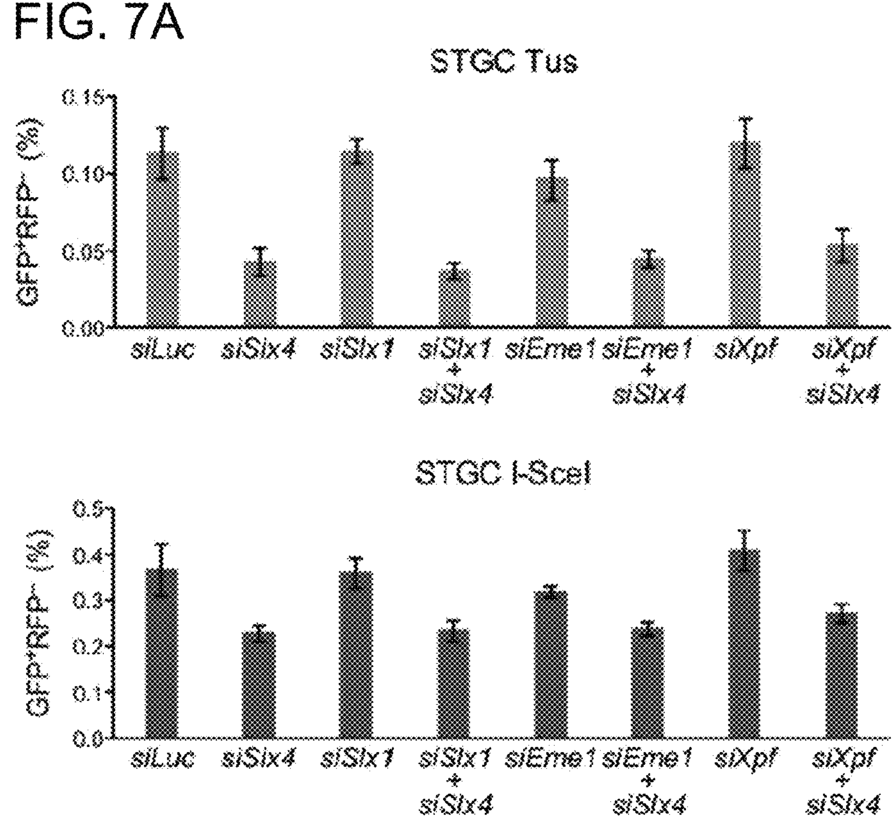
FIGS. 7A and 7B show Slx4/FancP depletion suppressed Tus/Ter induced HR.
Figure 7B:
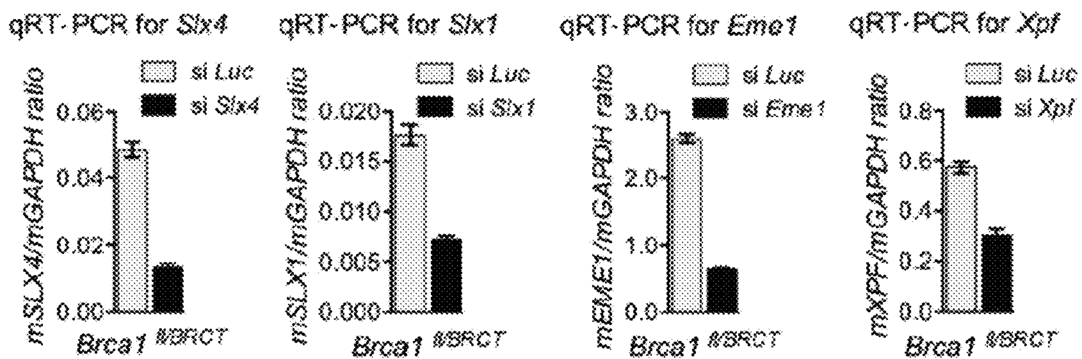

Interstrand DNAcrosslink repair of plasmids replicating in *Xenopus laevis* egg extracts entailed endonucleolytic attack of bidirectionally stalled forks. Interestingly, Tus/Ter-induced HR was suppressed by depletion of the endonuclease scaffold Slx4/FancP to a greater extent than I-SceI-induced HR (FIGS. 7A and 7B), indicating that Slx4 contributes specifically to Tus/Ter-induced HR. However, it was not clear whether Slx4 mediates endonucleolytic attack of stalled forks during Tus/Ter-induced HR. Work in *Schizosaccharomyces pombe* suggested that alternative mechanisms, such as template switching, could mediate HR at stalled mammalian forks.

Figure 8A:
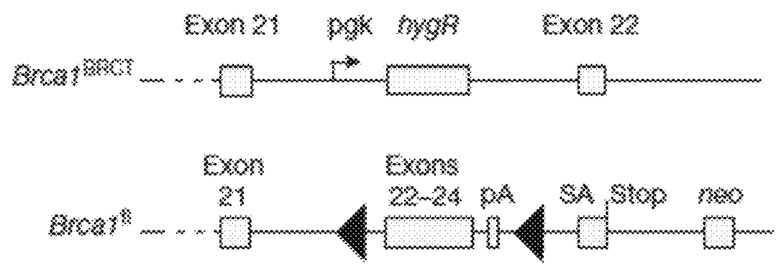
FIGS. 8A-8D show the Brca1 tandem BRCT repeat regulates Tus/Ter-induced homologous recombination.
Figure 8B:
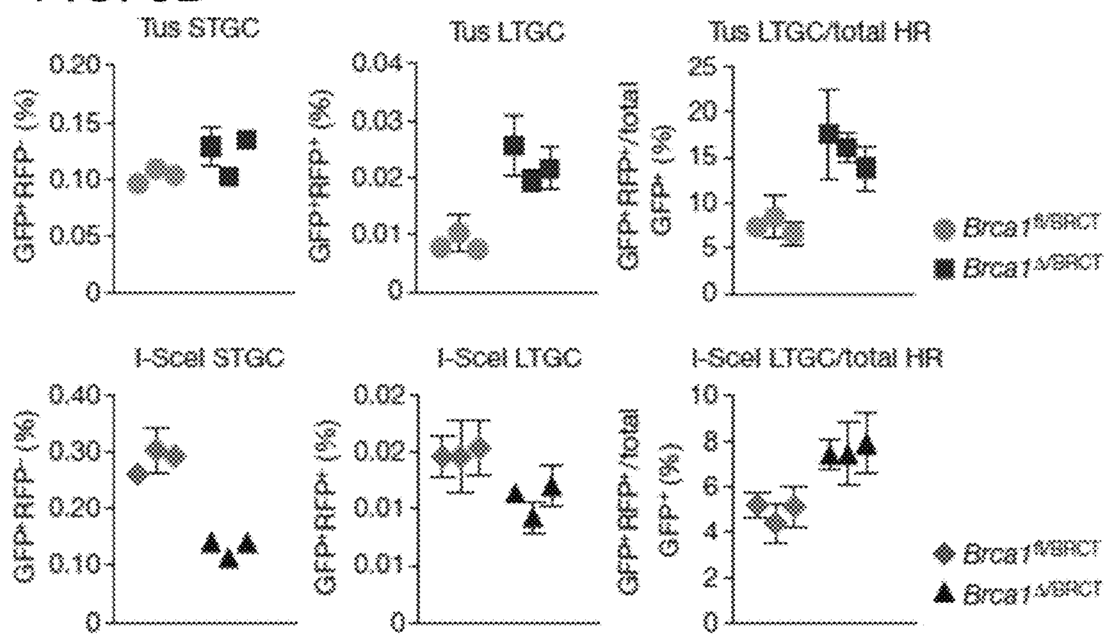
Figure 8C:
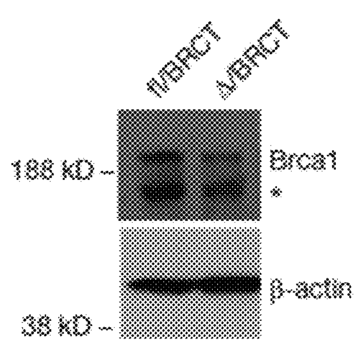
Figure 8D:
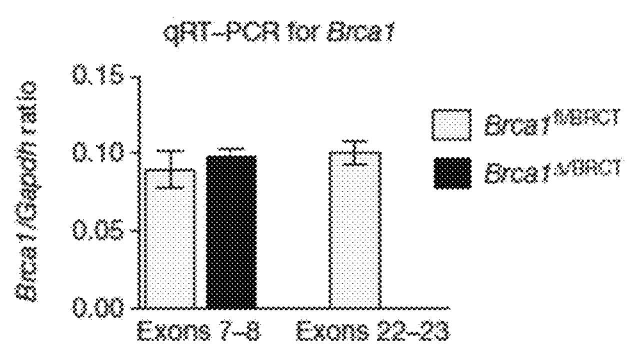
Figure 9A:
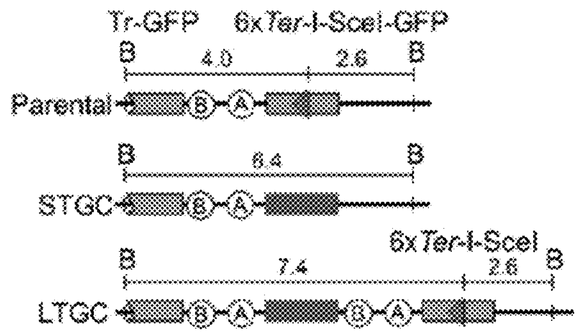
FIGS. 9A and 9B show a Southern blot analysis of Tus/Ter- and I-SceI induced HR products in Brca1$^{\Delta/BRCT}$ 6×Ter/HR cells.
Figure 9B:
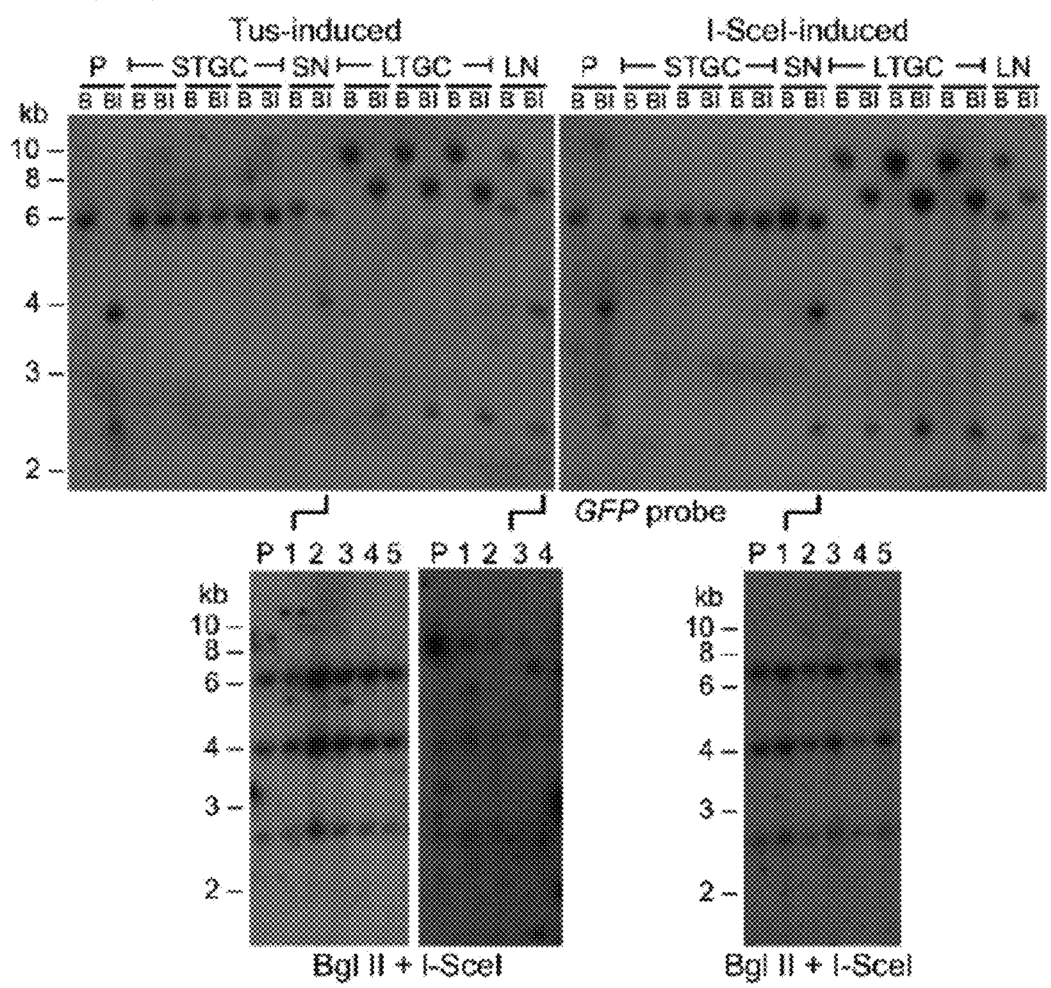

To determine whether BRCA1 regulates HR at stalled replication forks, 6×Ter/HR Brca1$^{fl/BRCT}$ cells were transduced with adeno-Cre and screened for Brca1 loss (FIGS. 8A-8D). The resulting Brca1$^{\Delta/BRCT}$ cells were viable hypomorphs with growth characteristics similar to Brca1$^{fl/BRCT}$ cells21. Tus-induced HR in three independent Cre-treated clones of each genotype were studied (FIGS. 8A and 8B). Surprisingly, Tus-induced STGC in 6×Ter/HR Brca1$^{\Delta/BRCT}$ cells showed no reduction compared to Brca1$^{\Delta/BRCT}$ cells, but LTGC was elevated twofold (FIG. 8B). Correspondingly, the probability of engaging LTGC during Tus/Ter-induced HR was doubled to, 15% (FIG. 8B). Consistent with recent findings, I-SceI-induced HR in 6×Ter/HR Brca1$^{D/BRCT}$ cells was diminished and biased in favour of LTGC (FIG. 8B). Southern blot analysis of Tus/Ter-induced STGC and LTGC products in 6×Ter/HR Brca1$^{\Delta/BRCT}$ cells revealed patterns similar to Brca1$^{fl/BRCT}$ cells (FIGS. 9A and 9B). However, in Brca1$^{\Delta/BRCT}$ cells, 6/41 (15%) Tus/Ter-induced STGC and 3/15 (20%) LTGC clones retained an additional copy of the parental reporter (FIGS. 9A and 9B). This was not separable by recloning, suggesting that it was retained by non-disjunction. A total of 4/41 (9.8%) I-SceI-induced STGC Brca1$^{D/BRCT}$ clones revealed non-disjunction; thus, non-disjunction is not specific to Tus/Ter-induced HR. The fact that the donor sister was unaltered during LTGC excludes crossing-over as a cause of the LTGC outcome in these clones.

Figure 10A:
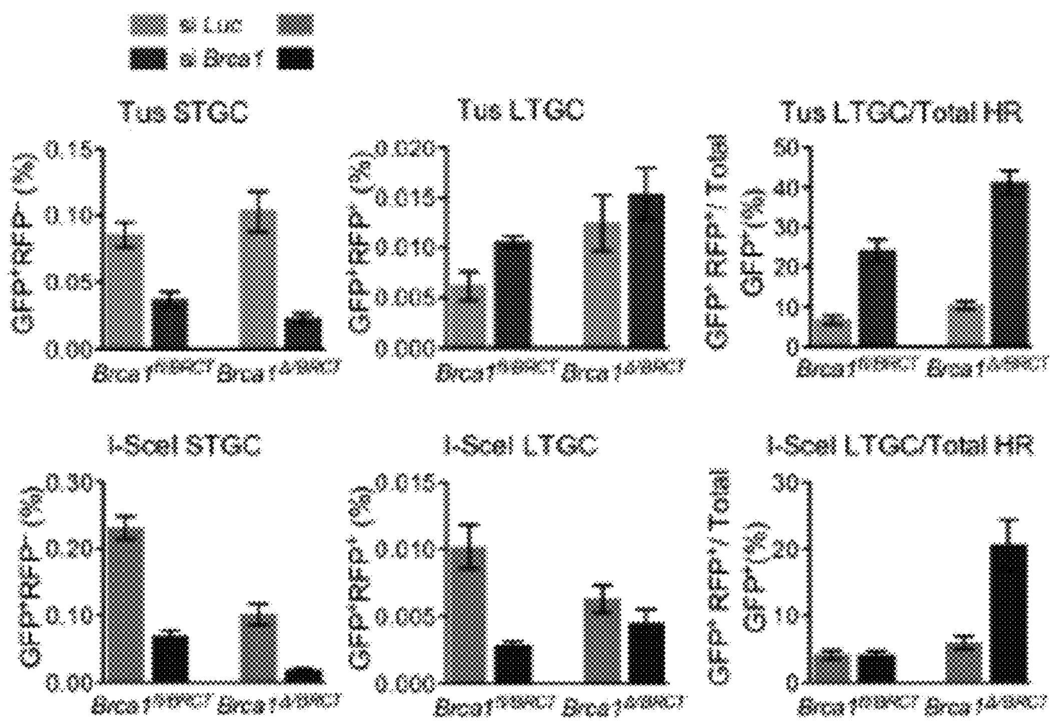
FIGS. 10A-10C show that Brca1 contributed quantitatively and qualitatively to homologous recombination at stalled replication forks.
Figure 10B:
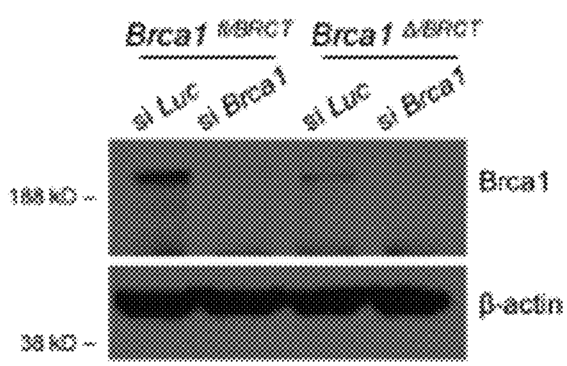
Figure 10C:
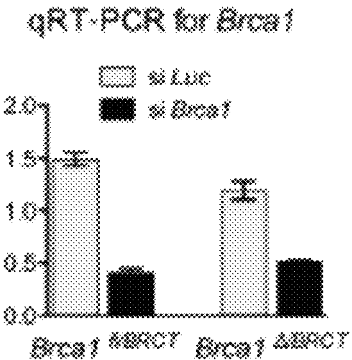

Next it was studied whether Brca1 domains additional to the BRCT repeat regulate Tus/Ter-induced HR. Indeed, short interfering (siRNA)-mediated Brca1 depletion suppressed STGC, but increased LTGC in both Brca$^{1fl/BRCT}$ and Brca1$^{\Delta/BRCT}$ cells (FIGS. 10A-10C). In Brca1-depleted Brca1$^{\Delta/BRCT}$ cells, 40% of all HR products were LTGCs. More than half of the BRCA1 polypeptide is encoded by exon 11, which is a target of inactivating germline mutations in hereditary breast/ovarian cancer; exon 11 is also alternatively spliced, generating an in-frame nuclear Δexon11 gene product that retains an N-terminal RING domain and C-terminal BRCT functions.

Figure 11A:
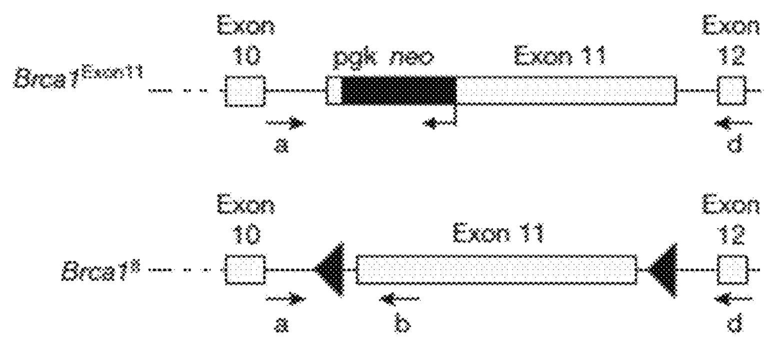
FIGS. 11A-11D show that Brca1 Exon11 regulates Tus/Ter-induced homologous recombination.
Figure 11B:
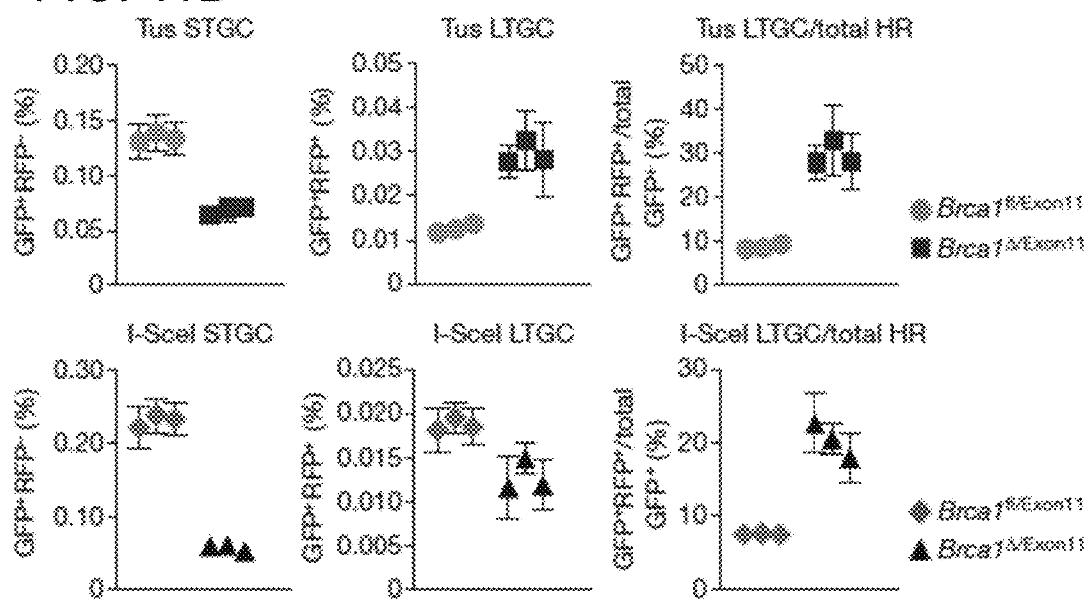
Figure 11C:
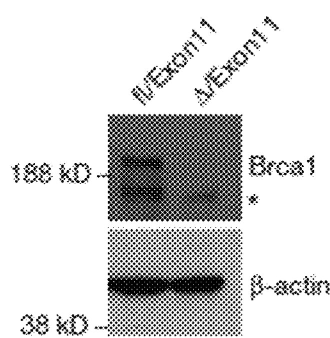
Figure 11D:
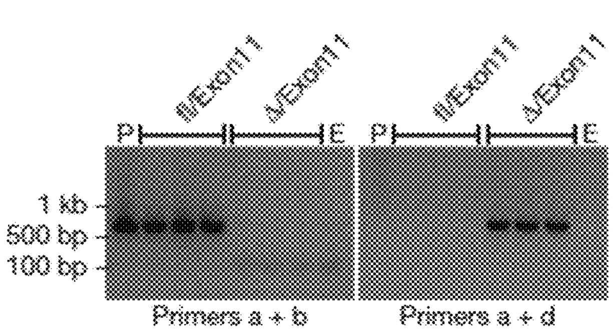
Figure 12A:
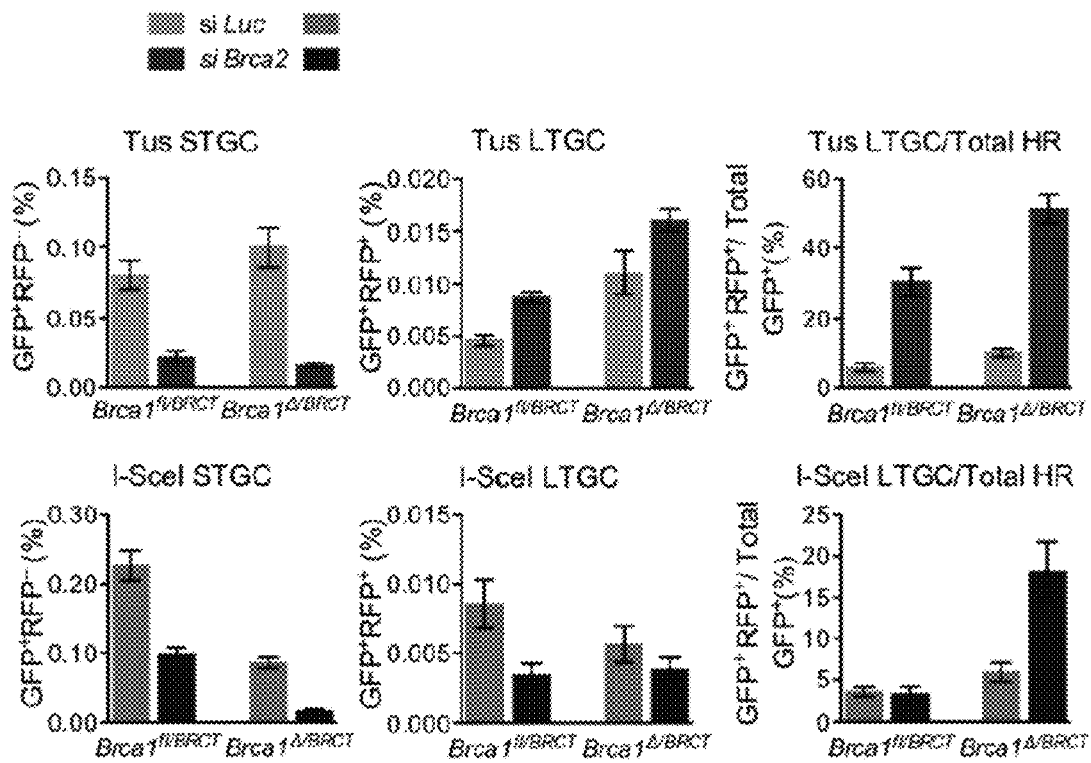
FIGS. 12A and 12B show that Brca2 contributed quantitatively and qualitatively to homologous recombination at stalled replication forks.
Figure 12B:
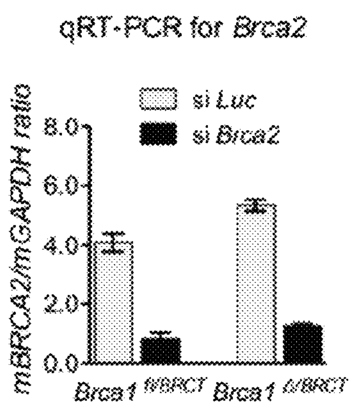
Figure 13A:
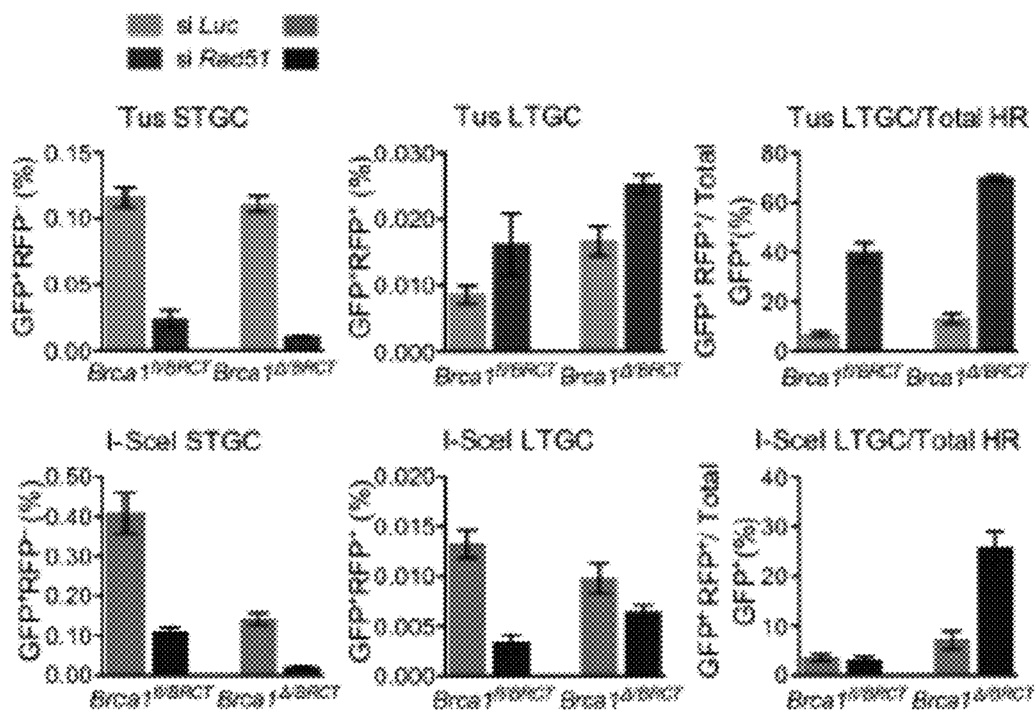
FIGS. 13A and 13B show that Rad51 contributes quantitatively and qualitatively to homologous recombination at stalled replication forks.
Figure 13B:
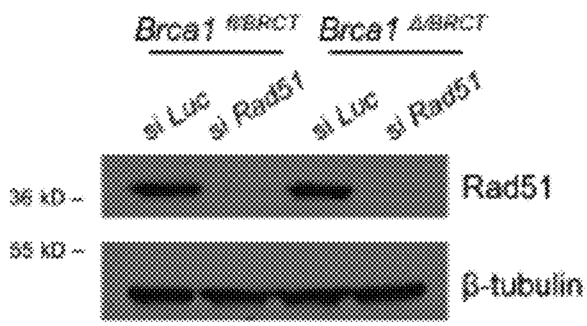
Figure 14A:
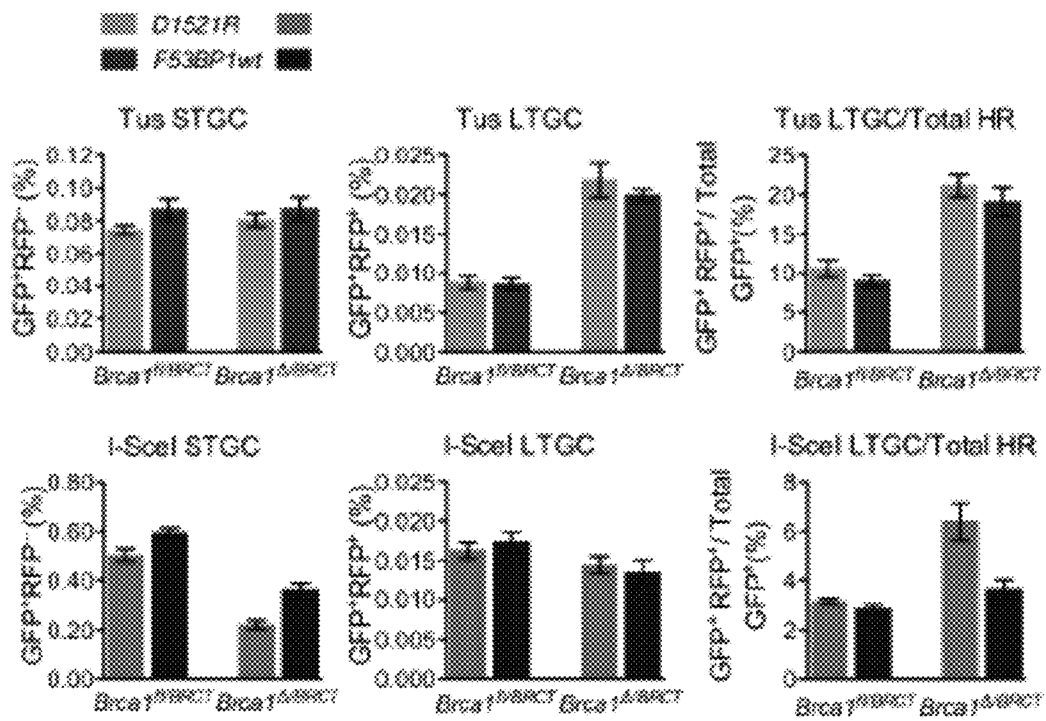
FIGS. 14A and 14B show the effect of 53BP1 inhibition on Tus/Ter-induced homologous recombination.
Figure 14B:
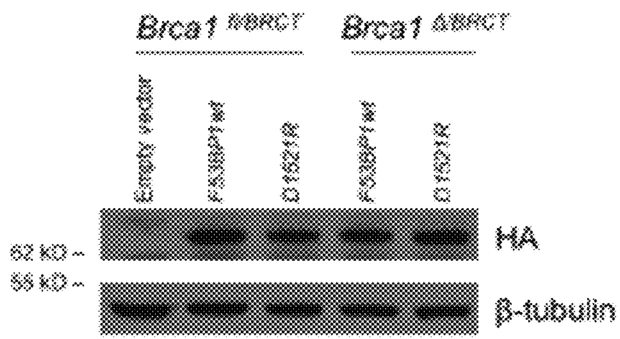

To test whether Brca1 exon 11 regulates Tus/Ter-induced HR, a single copy of the 6×Ter/HR reporter was targeted to the ROSA26 locus of mouse Brca1$^{fl/Exon11}$ ES cells (FIG. 11A-11D). The Brca1$^{Exon11}$ allele lacks exon 11; exon 11 of Brca1$^{fl}$ can be conditionally deleted to generate Brca1$^{\Delta}$ (FIG. 11A). Note that Brca1$^{fl}$ and Brca1$^{\Delta}$ denote distinct Brca1 alleles in the two Brca1 conditional systems described here. Following adeno-Cre treatment, 6×Ter/HR Brca1$^{fl/Exon11}$ and 6×Ter/HR Brca1$^{\Delta/Exon11}$ clones were retrieved. Each of three independent 6×Ter/HR Brca1$^{\Delta/Exon11}$ clones revealed reduced Tus/Ter-induced STGC but increased absolute frequencies of LTGC in comparison with three independent 6×Ter/HR Brca1$^{fl/Exon11}$ clones (FIG. 11B). Deletion of Brca1 exon 11 increased the probability of engaging Tus/Ter-induced LTGC approximately 4-fold to approximately 30% (FIGS. 11B-11D). In contrast, the absolute frequency of I-SceI-induced LTGC was reduced in Brca1$^{\Delta/Exon11}$ cells and approximately 20% of HR products were LTGCs (FIG. 11B). Thus, Brca1 exon 11 contributes to Tus/Ter-induced HR both quantitatively and qualitatively. To determine whether BRCA2/Rad51 regulates Tus/Ter-induced HR, siRNA to deplete Brca2 or Rad51 during HR induction was used. Depletion of Brca2 suppressed Tus/Ter-induced STGC but elevated LTGC frequencies in both Brca1$^{fl/BRCT}$ and Brca1$^{\Delta/BRCT}$ cells (FIGS. 12A and 12B). In Brca1$^{fl/BRCT}$ and Brca1$^{\Delta/BRCT}$ cells depleted of Brca2, approximately 30% and approximately 50% respectively of all Tus/Ter-induced HR products were LTGCs, whereas the equivalent probabilities for Rad51-depleted cells were approximately 40% and approximately 70% (FIGS. 13A and 13B). Thus, suppression of LTGC at stalled forks is a shared function of BRCA1, BRCA2 and Rad51. Inhibition of 53BP1 partially reversed defective I-SceI-induced HR in Brca1$^{\Delta/BRCT}$ cells, as expected, but did not affect Tus/Ter-induced HR in either Brca1$^{fl/BRCT}$ or Brca1$^{\Delta/BRCT}$ cells (FIGS. 14A and 14B). This suggests that BRCA1's functions in Tus/Ter-induced and SceI-induced HR are, in part, distinct. LTGC at stalled forks may include pathological responses analogous to break-induced replication in yeast. The present results identified loss of BRCA1/BRCA2/Rad51-dependent suppression of LTGC at stalled replication forks as contributing to breast/ovarian cancer predisposition.

Example 2: Assay for Analysis of Large Numbers of BRCA1 Variants

Figures 15, 15B:
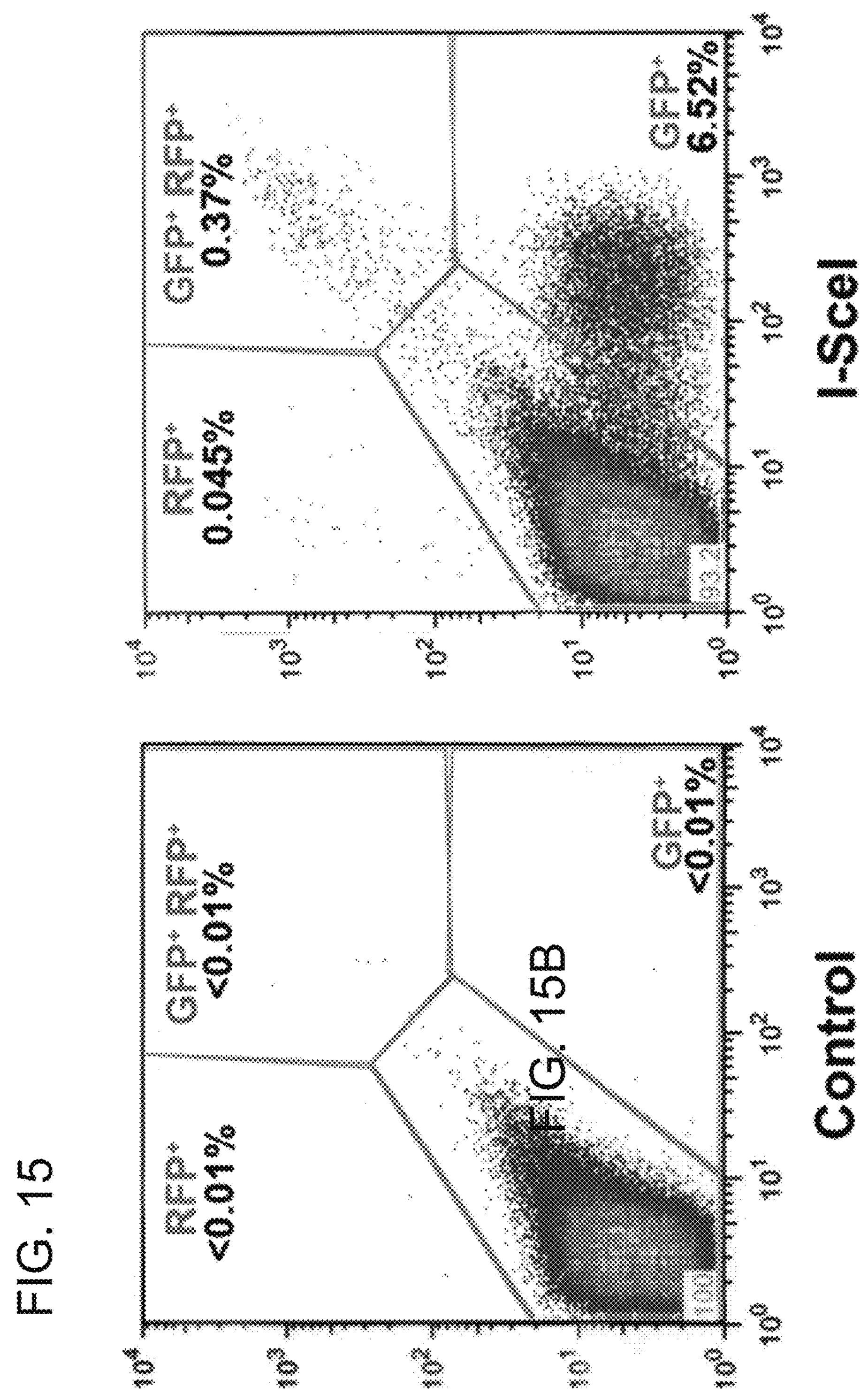
FIG. 15 depicts two graphs showing induction of $GFP^+$ and $RFP^+$ HR products by ISceI. RFP-SCR reporter U2OS cells received control (upper panel) or I-SceI-encoding adenovirus (lower panel). Note ISceI-induced STGC ($GFP^+$ $RFP^-$), LTGC ($GFP^+RFP^+$) and "mutagenic" LTGC ($GFP^-$ $RFP^+$). Probability of HR resolving as LTGC=$GFP^+RFP^+$/total $GFP^+$=5.4%. Probability of "mutagenic" LTGC=$GFP^-$ $RFP^+$/total $RFP^+$=10.8%.

BRCA1 mediates error-free STGC and suppresses LTGC. The invention provides a reporter for quantifying short tract gene conversion (STGC) vs. long tract gene conversion (LTGC) in response to a DSB induced by the rare-cutting meganuclease, I-SceI. A new "RFP-SCR" reporter was developed in which STGC (an error-free HR pathway) was scored by conversion of mutant enhanced green fluorescent protein (GFP) allele to wild type and LTGC (an error-prone pathway) by production of red fluorescent protein (RFP) (see e.g., the vector in FIG. 18, which contains the target I-SceI site and into which a Ter array can be inserted, designed to be targeted to the ROSA26 locus of the mouse genome). STGC ($GFP^{+}RFP^{-}$) and LTGC ($GFP^{+}RFP^{+}$) were scored rapidly and simultaneously by flow cytometry (FACS) (FIG. 15). The ratio of I-SceI induced $GFP^{+}RFP^{+}$: Total $GFP^{+}$ estimated the probability that an HR event will resolve as LTGC. A single copy of the RFP-SCR reporter was targeted to the ROSA26 locus of mouse embryonic stem (ES) cells that contain one hypomorphic mutant allele of Brca1 ("Brca1$^{BRCT}$" encoding a gene product lacking functional BRCT repeats) and one "foxed" conditional Brca1 allele ("Brca1$^{fl}$", deletable by Cre-mediated recombination to "Brca1$^{\Delta}$").

Brca1$^{\Delta/BRCT}$ ES cells have growth characteristics similar to Brca1$^{fl/BRCT}$ ES cells. Deletion of wt Brca1 reduced overall HR as expected. However, Brca1$^{\Delta/BRCT}$ cells also revealed a bias towards LTGC—revealed as an increased ratio of LTGC: total HR. siRNA-mediated depletion of BRCA1 in human osteosarcoma U2OS cells also skewed HR towards LTGC. Identical observations were made in mouse ES RFP-SCR cells lacking Brca1 exon 11. Thus, "LTGC suppression" is a general function of BRCA1. Potential relationship of "LTGC suppression" to BRCA1 tumor suppression: Expression of wild type (wt) human (h)BRCA1 in Brca1$^{\Delta/BRCT}$ cells restored overall HR and suppressed the LTGC bias. In contrast, four pathogenic BRCA1 missense alleles that disable either the BRCT or RING domains failed to restore overall HR or to suppress the LTGC bias. This survey of a small number of BRCA1 variants suggested that BRCA1 might perform a tumor suppressor function in "LTGC suppression".

Figure 16:
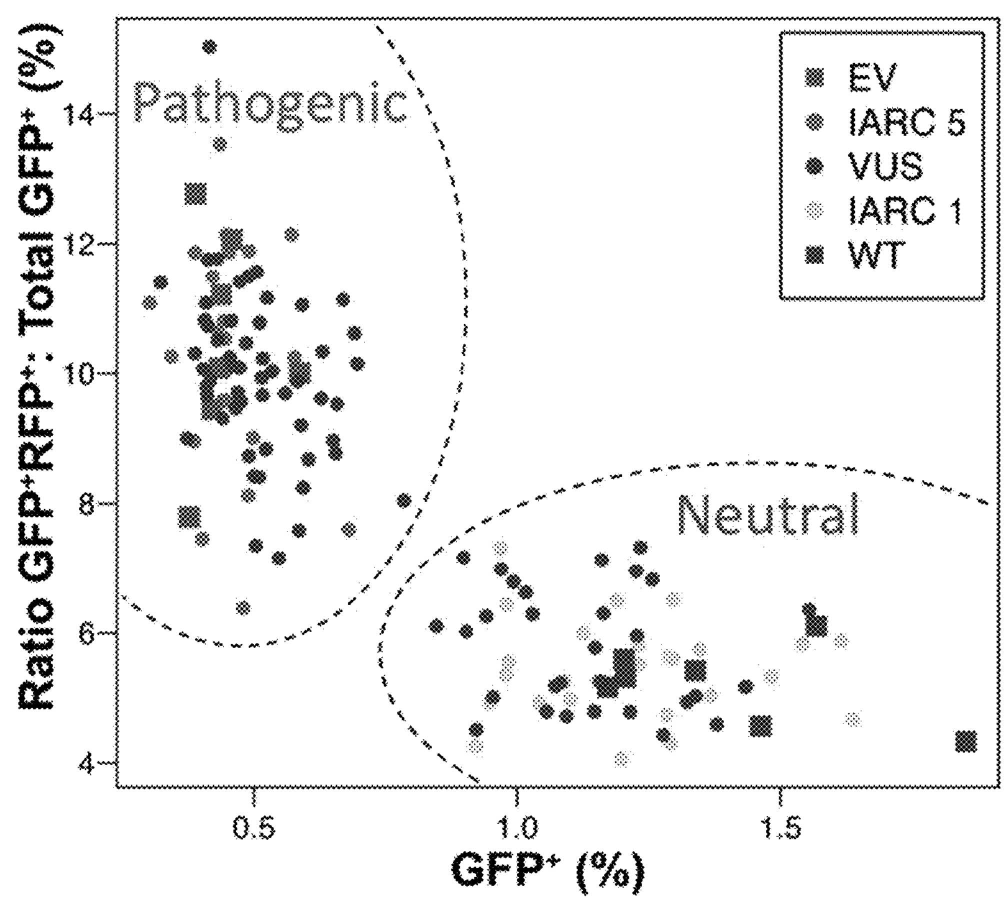
FIG. 16 is a graph showing raw data on 28 BRCA1 variants in HR. Each data point represents the mean value for one variant in one of 7 experiments. No batch correction. EV: empty vector. WT: wt BRCA1. Note apparent segregation into two populations. Neutral (IARC 1) and Pathogenic (IARC 5) variants are mutually exclusive.

A rapid assay of full-length BRCA1 tumor suppressor function in HR and LTGC suppression. The RFP-SCR reporter to the ROSA26 locus of Brca1$^{fl/Exon11}$ ES cells was targeted and Cre-deleted Brca1$^{\Delta/Exon11}$ cells were generated (i.e., deleted for exon 11. Note: "fl" and "Δ" denote distinct Brca1 alleles in the two genetic systems described). As noted above, Brca1 exon 11 deletion reduced overall HR (I-SceI-induced $GFP^{+}$) but elevated the probability of LTGC (ratio of $GFP^{+}RFP^{+}$:Total $GFP^{+}$). A rapid assay of full-length BRCA1 function in HR and LTGC suppression was developed. This entailed receipt of plasmids from Dr. Jonkers for expression of BRCA1. Brca1$^{\Delta/Exon11}$ ES RFP-SCR cells with BRCA1 variants (Bowman et al., Cancer Discovery 3(10):1142-1155, 2013) and I-SceI nuclease were transiently co-transfected. In seven experiments, overall HR ($GFP^{+}$) and probability of LTGC (ratio of $GFP^{+}RFP^{+}$:Total $GFP^{+}$) of 28 hBRCA1 variants was assayed. The variants included 5 known neutral variants (i.e., IARC class 1; missense amino acid substitution given)—Y105C, T826K, Y856H, R866C and G1706A; 5 known pathogenic variants (i.e., IARC class 5)—C61G, R1699W, A1708E and the common pathogenic frame-shift alleles 185delAG and 5382insC. 18 BRCA1 VUS alleles (each missense mutations) were studied: S4F, R841Q, M1400V, L1407P, M1411T, R1699Q, T16911, E1735K, H1746Q, R1753T, V1736A, 51651P, 51651F, G1706E, S1655F, L1746P and G1770V, as well as BRCA1 exon 11 del (strictly a VUS allele). Consistent with results reported herein above, each variant appeared to segregate into one of two classes, suggesting a two component model (FIG. 16):

| | | |
|---|---|---|
| Neutral (N) | IARC 1 | high $GFP^{+}$; low ratio |
| Pathogenic (P) | IARC 5 | low $GFP^{+}$, high ratio |

Figure 17:
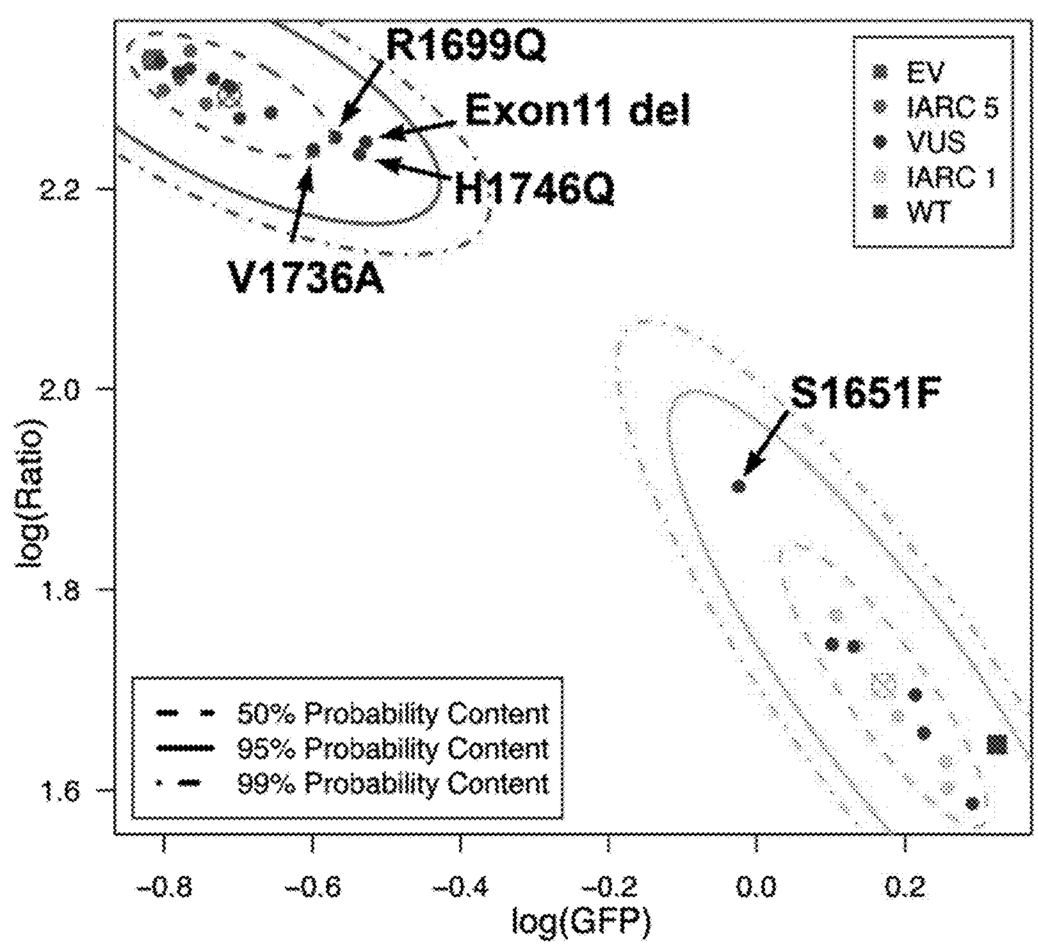
FIG. 17 is a graph providing analysis results of 28 BRCA1 variants. Results of Bayesian bivariate analysis of seven experiments, with 50%, 95% and 99% confidence intervals shown. Neutral (N): green ellipses. Pathogenic (P): red ellipses. 5/5 IARC 1 variants and 6/18 VUS alleles segregate with wtBRCA1 (WT) as N. 5/5 IARC 5 variants and 12/18 VUS alleles segregate with empty vector (EV) as P. Potential "outlier" VUS alleles are indicated.

Importantly, the raw data (FIG. 16) segregated known IARC 1 (N) or IARC 5 (P) alleles in 100% concordance with their IARC classification. These conclusions concur with other functional analyses of some of these VUS alleles. FIG. 17 shows 100% concordance with known IARC classifications. Thus, the present data fully validates this novel, rapid assay of full-length BRCA1 in HR and LTGC suppression. Test results from this assay provide a means to distinguish neutral and pathogenic or potentially pathogenic DNA repair polypeptide variant alleles, thus informing patient monitoring and treatment selection.

A number of hereditary breast/ovarian cancer predisposition genes are known to play important roles in homologous recombination. For example, if a woman inherits one defective copy of either BRCA1 or BRCA2, she will have a greatly elevated risk of breast or ovarian cancer across her lifetime. Full sequencing of the BRCA1 or BRCA2 genes is now used routinely to screen individuals for cancer-predisposing variants of the genes. In many cases, BRCA gene sequencing reveals two wild type copies of the relevant gene, indicating no increase in cancer risk attributable to the BRCA gene in question. However, if sequencing reveals that a woman carries a defective ("pathogenic") variant of the BRCA gene, this indicates that her risk of breast/ovarian cancer is elevated ~10-fold. In this circumstance, a physician might recommend that the woman consider bilateral mastectomy and/or oophorectomy, so as to definitively reduce her risk of breast/ovarian cancer. A third possibility is that gene sequencing reveals a variation in the BRCA gene that alters the encoded protein (for example, a single amino acid substitution), but this specific alteration is too infrequent in the human population for there to be statistical clarity about its associated disease risk. These "variants of uncertain significance" (VUS) are individually rare in the human population, but the number of such alleles is large. Estimates of the frequency of BRCA VUS alleles in the human population vary, but in some estimates ~1% of the population might carry a VUS allele. Currently, if a woman carries a BRCA VUS allele in her germ line, the physician cannot accurately advise the women about whether mastectomy and/or oophorectomy might help her to live a longer, healthier life. Thus, VUS alleles pose a significant burden on the human population.

In an effort to provide information about disease risk associated with specific VUS alleles, the invention provides a rapid test for the homologous recombination functions of individual BRCA1 alleles that is able to differentiate between functionally wild type alleles ("neutral" variants) and "pathogenic" (cancer predisposing) variants. This assay therefore provides a way to predict disease risk attributable to specific BRCA1 missense mutations. This assay could be modified so as to assess disease risk of VUS alleles of other homologous recombination genes implicated in hereditary cancer predisposition. Accordingly, the invention provides for the analysis of large numbers of BRCA1 variants.

Example 3: Tus/Ter-Mediated Replication Fork Stalling was Used to Stimulate Gene Targeting at the Site of Replication Arrest One major obstacle to the use of gene editing in human disease is the existence of "off-target" loci that are cleaved by the endonuclease (FIG. 21A). Systematic studies have shown that no currently existing nuclease-mediated gene editing method has yet avoided the problem of off-target indel formation. This represents a formidable barrier to clinical application of therapeutic gene editing.

The present invention addresses this problem by the use of a fundamentally different mechanism for achieving site-specific gene targeting—a site-specific replication block. The invention is based at least in part from discoveries relating to the development of novel tools for provoking site-specific replication fork arrest on a mammalian chromosome which involved adapting a natural replication terminator complex from *Escherichia coli* called Tus/Ter for use in mammalian cells. In mammalian cells, Tus/Ter is able to block mammalian replication forks' progression and to induce chromosomal homologous recombination (HR). Mechanistic analysis shows that the competence of the Tus/Ter complex to arrest a mammalian replisome is a simple function of affinity/avidity interactions between Tus and Ter. This raises the possibility that other DNA-protein complexes, if present in high enough affinity and in arrays containing multiple copies of the DNA-protein complex, might also mediate site-specific replisome arrest and HR within the chromosome.

Figure 22A:
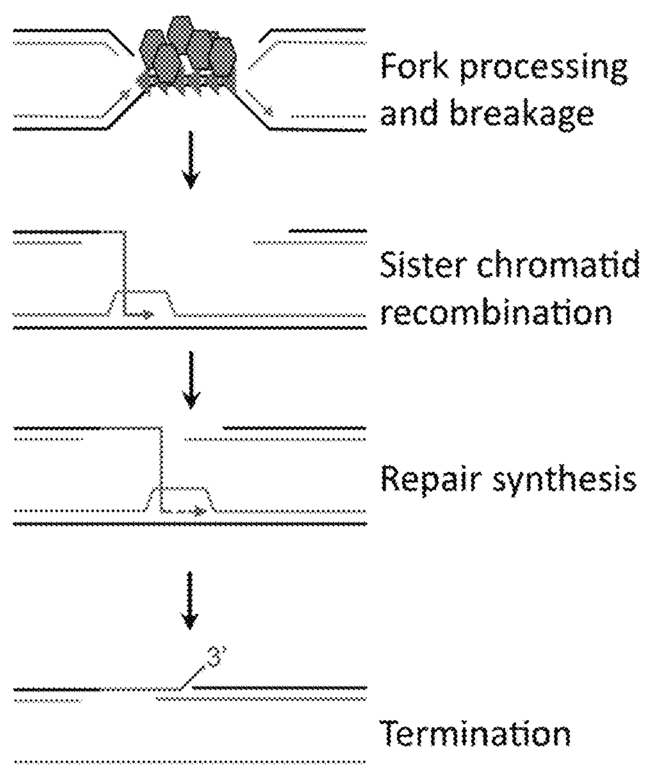
FIGS. 22A and 22B depict models of homologous recombination (HR) induced at a Tus/Ter replication fork block. Red triangles: Ter array. Blue hexagons: Tus protein monomers.
Figure 22B:
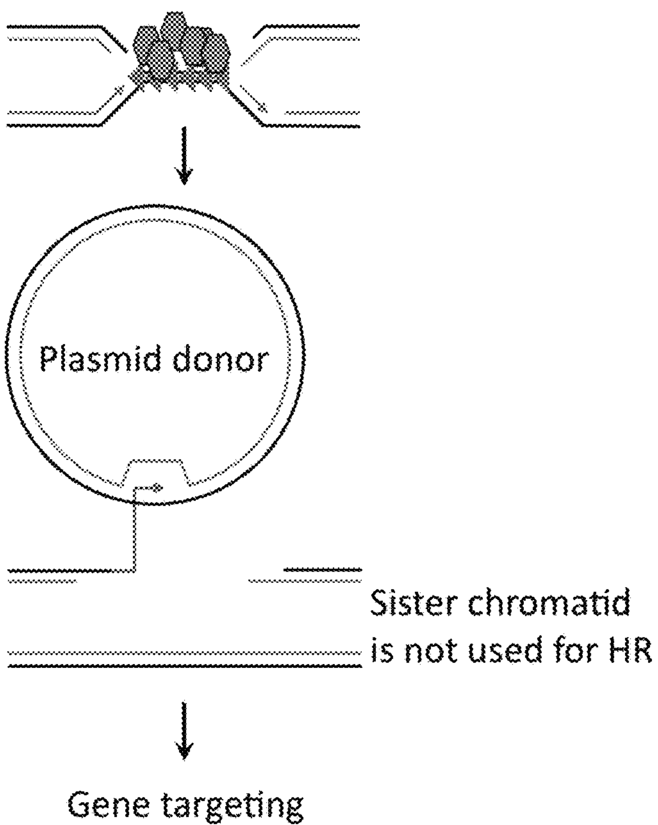
Figure 23A:
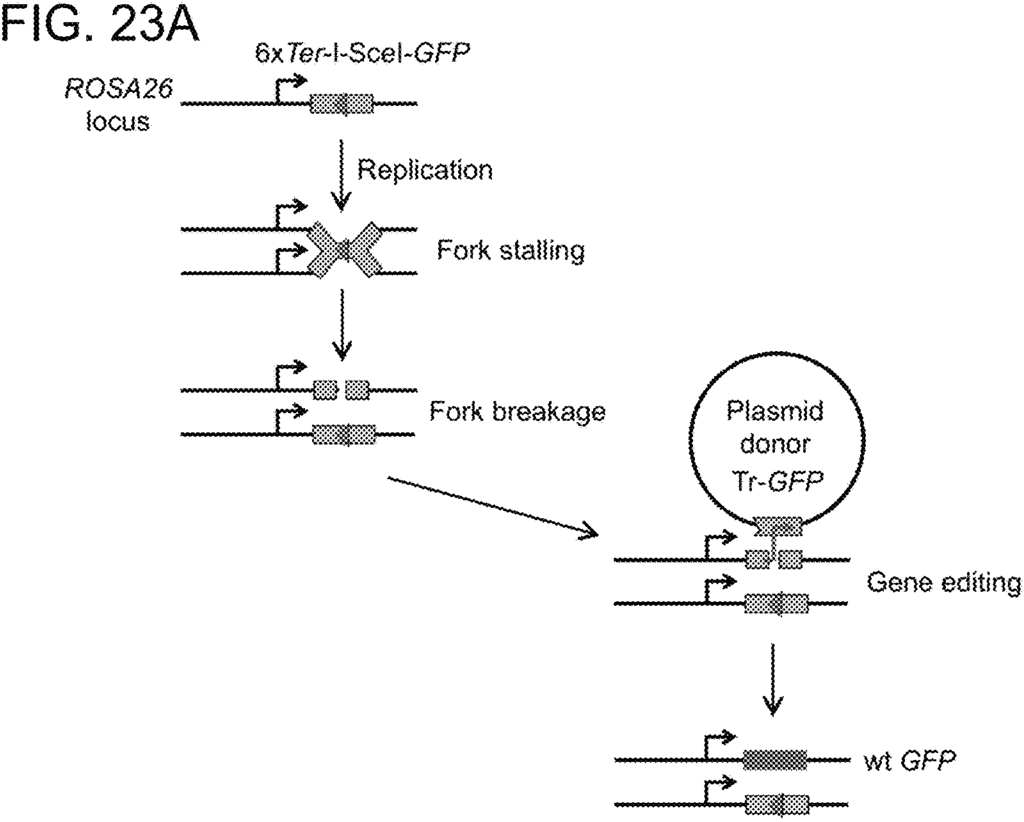
FIGS. 23A-23C depict gene editing involving a Tus/Ter-mediated replication block.
Figure 23B:
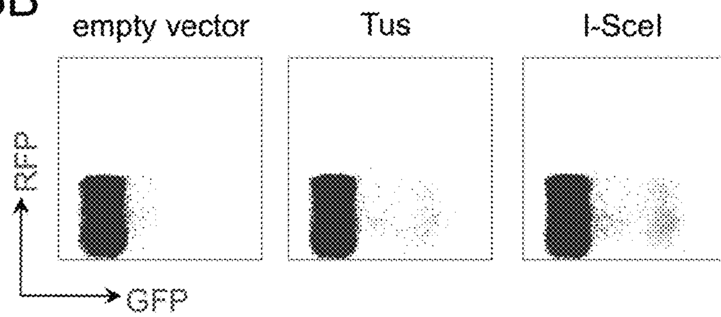
Figure 23C:
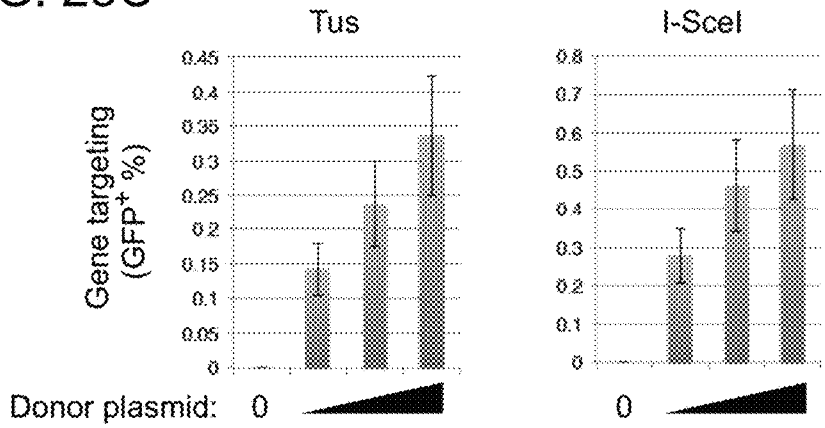

Without being bound to theory, Tus/Ter stimulates HR at the site of replication fork stalling and double strand break (DSBs) are formed at the site of Tus/Ter-induced replication arrest—for example as a result of endogenous nucleases acting at the stalled fork (FIG. 22A). Consistent with this model, homologous recombination might not be limited to the neighboring sister chromatid, but might also engage an exogenous DNA sequence for gene targeting (FIG. 22B). This was tested by targeting a simplified reporter to the ROSA26 locus of mouse ES cells (FIGS. 23A-23C). Briefly, this reporter contains only one copy of the cDNA encoding the enhanced green fluorescent protein ("GFP"), disrupted by an array of 6×Ter sites and a cleavage site for the rare-cutting homing endonuclease I-SceI. I-SceI provides a positive control for nuclease-induced HR. There is no opportunity to generate wt GFP by recombination with chromosomal elements. Donor sequences needed for GFP gene correction were supplied on a co-transfected plasmid, which contained a nonfunctional, 5' truncated copy of GFP ("Tr-GFP", FIG. 23A). This truncation guarantees that the donor plasmid alone also cannot generate wt GFP. If the Tus/Ter-stalled fork were to recombine with the donor plasmid, this would correct the endogenous copy of GFP to wild type and convert the cell to $GFP^+$. Indeed, it was found that Tus induces gene targeting/gene correction to wt GFP almost as efficiently as the I-SceI control (FIGS. 23B and 23C). This establishes that a replication fork blocking complex (e.g., Tus/Ter) that has no innate nuclease function, can guide site-specific gene editing in mammalian cells.

These results indicate that site-specific replication arrest can be used to stimulate gene targeting/gene editing in mammalian cells. This system may offer advantages over current methods of gene editing, by reducing unwanted and potentially hazardous off-target mutations.

The results set forth in Example 1 were obtained using the following methods and materials.

Molecular Biology, siRNAs and Antibodies.

The vector for mammalian expression of myc epitope-tagged, nuclear localized, codon-optimized wild-type Tus (pCMVbeta myc-NLS-Tus), vectors p6×TerOri and p6×REVTerOri and the Ter HR reporters were constructed by conventional cloning methods using a previously described RFP-SCR reporter (Chandramouly et al., Nature Communications. 4, 2404, 2013). Ter-containing plasmids were cultivated in JJC33 (Tus2) strains of *E. coli*. siRNA SMART pools were purchased from Dharmacon. Cells were lysed in RIPA buffer (50 mM Tris-HCl, pH 8.0, 250 mM NaCl, 0.1% sodium dodecyl sulphate, 1% NP-40 containing protease and phosphatase inhibitors PMSF and Roche complete protease inhibitor tablet). Extracted protein was resolved by 4-12% bis-Tris SDS-PAGE (Invitrogen) and analysed by immunoblotting using the following antibodies; Brca1 (a gift of the Baer laboratory, 1:100), beta-tubulin (Abcam ab6046, 1:4,000), beta-actin(Abcam ab8226, 1:10, 000), Myc (Abeam ab9106, 1:10,000), hRad51 (aliquot B32, 1:500), and HA (Santa Cruz sc-805, 1:200).

Cell Lines and Cell Culture.

Mouse embryonic stem (ES) cells were grown in ES medium on either MEF feeders or gelatinized plates as described previously (Chandramouly et al., Nature Communications. 4, 2404, 2013, Xie. et al., Molecular Cell 28, 1045-1057, 2007, Xie et al., Molecular. Cell 16, 1017-1025, 2004).). A total of 10 mg of the 6×Ter HR reporter ROSA26 targeting plasmid was linearized by KpnI digest and introduced by electroporation to $1\times10^7$ to $2\times10^7$ cells and subsequently seeded on 6-cm plates with puromycin-resistant feeders. Plates were supplemented with puromycin (4 μg $ml^{-1}$) 24 hr later and colonies were picked 5-10 days later. ROSA26 targeted lines were screened for by PCR and verified by Southern blotting (Chandramouly et al., Nature Communications. 4, 2404, 2013). Multiple Brca1-deficient ES clones were generated by transient adenovirus-mediated Cre expression. ROSA26 genotyping primers: ROSA26-sense: CA TCAAGGAAACCCTGGACTACTG (SEQ ID NO: 25); TerB36 HR reporter antisense: CCTCGG CTAG-GTAGGGGATC (SEQ ID NO: 26). The Brca1 exon11 status was determined by PCR. Brca1 5' sense: CTGGG-TAGTTTGTAAGCATCC (SEQ ID NO: 27); Brca1 exon11 antisense: CAATAA ACTGCTGGTCTCAGGC (SEQ ID NO: 28); Brca1 exon11 sense: GGAAATGGCAACTT-GCCT AG (SEQ ID NO: 29); Brca1 3' antisense: CTGC-GAGCAGTCTTCAGAAAG (SEQ ID NO: 30).

Recombination Assays.

A total of $1.6\times10^5$ cells were transfected in suspension with 0.5 μg pcDNA3beta-myc NLS-I-SceI (Puget et al., DNA Repair 4, 149-161, 2005), pcDNA3beta-mycNLS-Tus, pcDNA3beta-myc NLS-TusH144A, pcDNA3beta-myc NLS-TusF140A, or control vector using Lipofectamine 2000 (Invitrogen). $GFP^+$ and $GFP^+RFP^+$ frequencies were scored 3 days after transfection by flow cytometry using a Becton Dickinson 5 Laser LSRII in triplicate and values presented corrected for background events and transfection efficiency. Transfection efficiency was measured by parallel transfection with 0.05 μg of wild-type GFP expression vector and 0.45 control vector. Typically $6\times10^5$ total events were scored per sample. Tus or I-SceI expression vector transfection efficiencies were typically between 50% and 75%, and background levels of HR products typically less than 0.005% for $GFP^+RFP^-$ and less than 0.001% for $GFP^+RFP^+$ (for example, FIGS. 6A and 6B).

Statistical Methods.

Each figure legend reports the sample size in terms of number of replicates per experiment and number of experiments that were analysed to generate the data shown. For statistical analysis of HR values, the arithmetic mean of triplicate samples was calculated for each independent experiment (that is, experiments performed on different days) and these single data points for each experiment were used to calculate the mean and standard deviation between experiments. The standard error of the mean (s.e.m.) was calculated as standard deviation/in, where n=number of experiments (not number of replicates). For example, if triplicate samples in four different independent experiments were measured, then n=4. Differences between groups were analysed by Student's two-tailed unpaired t-test, assuming unknown variance, using GraphPad Prism v5.0d software. P values are given in the figure legends. Densitometry of two-dimensional gel data was also analysed by calculation of arithmetic mean and s.e.m. and analysis by Student's t-test. Analysis of trend in FIG. 6F was performed by ANOVA using GraphPad Prism v5.0d software, in addition to the t-test as described above.

qRT-PCRanalysis.

RNA from transfected ES cells was extracted by Qiagen RNeasy Mini Kit (Qiagen Sciences) 2 days post-transfection. First-strand cDNA analysis was performed on an ABI 7300 Real time PCR System using Power SYBR Green RNA-to CT 1-Step Kit (Applied Biosystems). TaqMan probe and primer sets to genotype for Brca1 were: Brca1 Exon 22-23 sense: TTCCGTGGTGAAGGAGCTT (SEQ ID NO: 31); Brca1 Exon 22-23 antisense: TGGCTGCACGATCACAAC (SEQ ID NO: 32); Brca1 Exon 23-24 sense: GCCTGGACAGAAGACAGCA (SEQ ID NO: 33); Brca1 Exon 23-24 antisense: CAGTCCCACA TCACAAGACG (SEQ ID NO: 34); Brca1 Exon 22-23 TaqMan probe FAM-CGCTCACCCATGA CACAGGTGC-BHQ (SEQ ID NO: 35); Brca1 Exon 23-24 TaqMan probe-FAM-TGCACAGCT GCCCAATATCTGGG-BHQ (SEQ ID NO: 36). Conventional SYBR green qRT-PCR assays of Gapdh and siRNA-targeted gene was performed. The NIH NCI Nucleotide utility to Primer 3 software (Whitehead Institute, MIT) was used to generate gene-specific primer sequences for mouse Brca1 and Gapdh. The NIH NCI Nucleotide utility was used to generate gene-specific primer sequences for mouse Slx4, Slx1, Eme1 and Xpf (also known as Ercc4). Primers for RT-PCR were Brca1-exon 21-22 sense: ATG AGCTGGAGAGGATGCTG (SEQ ID NO: 37); Brca1 exon 21-22 antisense: CTGGGCAGTTGCT GTCTTCT (SEQ ID NO: 38); Brca1 exon 22-23 sense: GGTGCTCATCTAGTTGTGATCG (SEQ ID NO: 39); Brca1 exon 22-23 antisense: CTGTACCAGGTAGGCATCCA (SEQ ID NO: 40); Brca1 exon 7-8 sense: AGCCTAGGTGTCCAGCTGTC (SEQ ID NO: 41); Brca1 exon 7-8-antisense: CTGCAATCACC TGGCTTAGTT (SEQ ID NO: 42); Brca2 sense: TCTGCCACTGTGAAAAATGC (SEQ ID NO: 43); Brca2 antisense: TCAAGCTGGGCTGAAGATT (SEQ ID NO: 44); Slx4 sense: GTGGGACGACTGGAATGAGG (SEQ ID NO: 45); Slx4 antisense: GCACCTTTTGGTGTCTCTGG (SEQ ID NO: 46); Slx1 sense: GGATGGACCAT GCAGCAAGA (SEQ ID NO: 47); Slx1 antisense: CCATTCAAACCGAAGGGCG (SEQ ID NO: 48); Eme1 sense: AG GCCAGAGGAATGCCTGAA (SEQ ID NO: 49); Eme1 antisense: CCAGTCATCTCCATCCTCT ACC (SEQ ID NO: 50); Xpf sense: TGGTCAGAATTCAGGTTGGC (SEQ ID NO: 51); Xpf antisense: TTTCAGGAC GTCAGTCAGCG (SEQ ID NO: 52). The mRNA was measured in triplicates with a standard curve generated for each gene using cDNA obtained from each sample. The expression level of target genes was normalized to internal Gapdh.

293 Cell Transfection and Episome Two-Dimensional Gel Electrophoresis.

A total of $12\times10^6$ 293E (ATCCCRL-10852) cells were plated per 15-cm dish 1 day before transfection. Cells were transfected with 4.5 μg pOri plasmids and 1 μg of control empty vector or pcDNA3beta-mycNLS-Tus in antibiotic free media using Lipofectamine2000 reagent, and media changed 24 hr after transfection. Then 40 hr after transfection, plates were rinsed with 1×PBS and cells washed off the plate with ice-cold PBS, washed again with ice-cold PBS and HIRT extracted as described below. Purified DNA was restriction digested 8-16 hr and run on a 14×16 cm 0.4% agar 0.1 μg $ml^{-1}$ ethidium bromide 0.53TBE gel 13 hr in the dark at 40 V. First dimension gel slabs were cut out and embedded in the second dimension slab gel (20×25 cm 1% agar, 0.5×TBE, 1 μg $ml^{-1}$ ethidium bromide) and run at 160 V for 7.5 hr in the cold room at 4° C.

HIRT Episome Extraction from 293 Cells.

The plasmid was extracted as published (Follonier et al., Methods Molecular. Biology 1094, 209-219, 2014). Briefly, PBS-washed 293HEK or 293E cells were lysed in 2.25 ml 0.6% sodium dodecyl sulphate 33 mM Tris-HCl, 6 mM EDTA, 66 μg $ml^{-1}$ RNase followed by digestion with 0.5 μg proteinase K for 90 min at 37° C. Samples were subject to brief, 20 s, base extraction with 0.75 ml 0.1 M NaOH and proteins precipitated by addition of 1 ml 4.2 M Gu-HCl, 0.9 M potassium acetate pH 4.8. Cell debris was pelleted at 39,000 g and supernatant loaded onto a Qiagen Miniprep spin column (Qiagen Sciences, Maryland). Columns were washed with 0.5 ml Qiagen Buffer PB (5 M Gu-HCl, 30% ethanol, adding 10 mM Tris-HCl pH 6.6) and 0.75 ml Qiagen Buffer PE (10 mM Tris-HCl pH 7.5, 80% ethanol) and plasmid DNA eluted using two volumes of 40 μl Qiagen EB buffer.

Southern Blotting.

Southern blotting of genomic DNA was performed using GFP cDNA or ROSA26 5' probes as described previously (Xie. et al., Molecular. Cell 16, 1017-1025, 2004, Puget et al., DNA Repair 4, 149-161, 2005). For all experiments, including mouse ES cells containing a randomly integrated reporter not at ROSA26, clones containing only one intact copy of the reporter were used. Genomic DNA was extracted from confluent ES cells on 6-well plates (approximately $5\times10^6$ to $10\times10^6$ cells) using a Puregene DNA Isolation Kit (Gentra Systems). Episomal plasmid DNA was extracted by HIRT extraction described above and Southern blotting performed using random labelled probe produced from the KpnI/HindIII restriction fragment of p6×TerOri.

Statistical Methods i) Bayesian two component model: each BRCA1 variant (including VUS alleles) is assumed to be truly either N or P.

ii) Bivariate model uses log-transformed data of two variables: overall HR ($GFP^+$) and ratio of LTGC: Total HR.

iii) Batch corrections are incorporated into the analysis.

iv) Assumed prior probabilities of pathogenicity (i.e., the starting assumptions of the computer model) are:

IARC 1: known to be N p=0.0

IARC 5 known to be P p=1.0

VUS alleles: unknown p=0.5

(arbitrarily chosen)

The VarCall program uses an iterative procedure to calculate the best fit for each VUS allele. It generated these posterior probabilities ofpathogenicity:

p<0.002: predicted neutral variants: S4F, R841Q, M1400V, L1407P, M1411T, S1651F.

p>0.998: predicted pathogenic variants: R1699Q, T1691I, E1735K, H1746Q, R1753T, V1736A, S1651P, G1706E, S1655F, L1746P, G1770V, and Exon 11 del.

These conclusions concur with other functional analyses of some of these VUS alleles. FIG. 17 shows 100% concordance with known IARC classifications. Thus, the present data fully validates this novel, rapid assay of full-length BRCA1 in HR and LTGC suppression.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of characterizing the functional significance of a mutation in a DNA repair polypeptide, the method comprising:

(a) expressing in a mammalian cell a DNA repair polypeptide comprising a mutation and a wild-type Tus polypeptide fused to a nuclear localization signal, wherein the cell comprises a single genomic integrated copy of a polynucleotide comprising, from 5' to 3': a promoter directing expression in the mammalian cell, a 5' truncated green fluorescent protein (GFP)-encoding sequence, a 3' red fluorescent protein (RFP) exon, a 5' RFP exon, and mutated GFP encoding sequence comprising one to six Ter sites adjacent to a rare cutting endonuclease site; and (b) detecting long-tract gene conversion in the cell, wherein an increase in long tract gene conversion in the cell relative to a reference indicates that the mutation in the DNA repair polypeptide is functionally significant.

2. The method of claim 1, wherein the DNA repair polypeptide is BRCA1, BRCA2, BARD1, PALB2, RAD51, RAD51B, RAD51C, RAD51D, XRCC2, XRCC3, BLM, RecQ helicase, MRE11, Rad50, NBS1, ATM, ATR, CTIP, Brip, RPA, RPA-like polypeptide, and combinations thereof.

3. A method of characterizing the functional significance of a mutation in a DNA repair polypeptide in a biological sample, the method comprising (a) sequencing a DNA repair gene in a biological sample derived from a subject, thereby identifying a mutation in the DNA repair gene;

(b) contacting a mammalian cell lacking a DNA repair polypeptide and comprising a single genomic integrated copy of a polynucleotide comprising, from 5' to 3', a promoter directing expression in the mammalian cell, a 5' truncated green fluorescent protein (GFP)-encoding sequence, a 3' red fluorescent protein (RFP) exon, a 5' RFP exon, and a mutated GFP encoding sequence comprising one to six Ter sites adjacent to a rare cutting endonuclease site, with each of:

a vector encoding a DNA repair polypeptide comprising the identified mutation of step (a), and a vector encoding a wild-type Tus polypeptide fused to a nuclear localization signal; and (c) detecting long-tract gene conversion in the cell, wherein an increase in long tract gene conversion in the cell relative to a reference cell expressing a wild-type DNA repair polypeptide indicates that the mutation in the DNA repair polypeptide is functionally significant.

4. The method of claim 3, wherein the DNA repair polypeptide is BRCA1, BRCA2, BARD1, PALB2, RAD51, RAD51B, RAD51C, RAD51D, XRCC2, XRCC3, BLM, RecQ helicase, MRE11, Rad50, NBS1, ATM, ATR, CTIP, Brip, RPA, RPA-like polypeptide, and combinations thereof.

5. The method of claim 3, wherein long tract gene conversion is detected by detecting an alteration in fluorescence between the cell and the reference cell.

6. The method of claim 5, wherein the functional significance of a mutation in a DNA repair polypeptide in a biological sample indicates the subject has or has a propensity to develop cancer.

* * * * *